(12) United States Patent
Gao et al.

(10) Patent No.: US 12,371,434 B2
(45) Date of Patent: Jul. 29, 2025

(54) MLL1 INHIBITORS AND ANTI-CANCER AGENTS

(71) Applicant: NOVARTIS AG, Basel (CH)

(72) Inventors: Zhenting Gao, Shanghai (CN); Haibing Guo, Shanghai (CN); Ming Li, Shanghai (CN); Kun Chin Liu, Shanghai (CN); Chunliang Lu, Shanghai (CN); Zhuming Sun, Shanghai (CN); Yihui Zhu, Warren, NJ (US)

(73) Assignee: CHINA NOVARTIS INSTITUTES FOR BIOMEDICAL RESEARCH CO., LTD., Shanghai (CN)

( * ) Notice: Subject to any disclaimer, the term of this patent is extended or adjusted under 35 U.S.C. 154(b) by 763 days.

(21) Appl. No.: 17/772,888

(22) PCT Filed: May 27, 2021

(86) PCT No.: PCT/CN2021/096539
§ 371 (c)(1),
(2) Date: Apr. 28, 2022

(87) PCT Pub. No.: WO2021/239077
PCT Pub. Date: Dec. 2, 2021

(65) Prior Publication Data
US 2023/0121768 A1 Apr. 20, 2023

(30) Foreign Application Priority Data
May 28, 2020 (WO) ................ PCT/CN2020/092801

(51) Int. Cl.
| | |
|---|---|
| *C07D 473/34* | (2006.01) |
| *A61K 31/437* | (2006.01) |
| *A61K 31/52* | (2006.01) |
| *A61K 31/53* | (2006.01) |
| *A61P 35/02* | (2006.01) |
| *C07D 471/04* | (2006.01) |
| *C07D 487/04* | (2006.01) |

(52) U.S. Cl.
CPC .......... *C07D 473/34* (2013.01); *A61K 31/437* (2013.01); *A61K 31/52* (2013.01); *A61K 31/53* (2013.01); *A61P 35/02* (2018.01); *C07D 471/04* (2013.01); *C07D 487/04* (2013.01)

(58) Field of Classification Search
CPC .. C07D 473/34; C07D 471/04; C07D 487/04; A61P 35/02; A61K 31/437; A61K 31/52; A61K 31/53
See application file for complete search history.

(56) References Cited

U.S. PATENT DOCUMENTS

2012/0295283 A1   11/2012   Barrett et al.

FOREIGN PATENT DOCUMENTS

| CN | 105188705 A | 12/2015 |
|---|---|---|
| CN | 110325533 A | 10/2019 |
| JP | 2005-502643 A | 1/2005 |
| JP | 2022-519374 A | 3/2022 |
| JP | 2022-521473 A | 4/2022 |
| WO | 2003/013540 A1 | 2/2003 |
| WO | 2007/034817 A1 | 3/2007 |
| WO | 2007/034917 A1 | 3/2007 |
| WO | 2008/114817 A1 | 9/2008 |
| WO | 2013/183578 A1 | 12/2013 |
| WO | 2016/081732 A1 | 5/2016 |

OTHER PUBLICATIONS

Chern et al., "Discovery of Potent Small-Molecule Inhibitors of MLL Methyltransferase," *ACS Med. Chem. Lett.* 11:1348-1352 (2020).

*Primary Examiner* — Joseph K McKane
*Assistant Examiner* — Quincy McKoy
(74) *Attorney, Agent, or Firm* — Seed IP Law Group LLP

(57) ABSTRACT

The present invention provides a compound of Formula (I): or an enantiomer, an enantiomeric mixture, or a pharmaceutically acceptable salt thereof; wherein the variables are as defined herein. The present invention further provides pharmaceutical compositions comprising such compounds; and methods of using such compounds for treating a disease or condition mediated by mixed lineage leukemia 1 (MLL1).

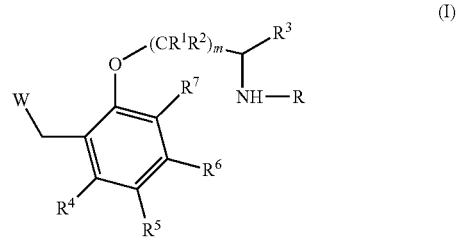

19 Claims, No Drawings

MLL1 INHIBITORS AND ANTI-CANCER AGENTS

FIELD OF THE INVENTION

The present invention relates to compounds, compositions and methods for inhibiting mixed lineage leukemia 1 (MLL1).

BACKGROUND OF THE INVENTION

Chromatin is the main repository of genetic information in the eukaryotic nucleus, comprising DNA compacted into structures called nucleosomes by a set of small basic histones and non-histone chromosomal proteins. Histones can be enzymatically modified by the addition of acetyl, methyl, or phosphate groups. Histone-lysine N-methyltransferase 2 (KMT2) family proteins methylate lysine 4 on the histone H3 tail (H3K4) at important regulatory regions in the genome, and thereby impart crucial functions through modulating chromatin structures and DNA accessibility.

KMT2 family mutations are among the most frequent alterations in human cancer (Kandoth et al., Nature 502: 333-339 (2013)). The most prominent example is mixed lineage leukemia (MLL or MLL-r), which presents a heterogeneous group of AML (acute myeloid leukemia) and ALL (acute lymphoblastic leukemia) bearing features. The hallmark of this type of disease is the chromosomal rearrangement of MLL1 gene (also known as KMT2A, MLL, ALL-1 and HRX) (Krivtsov et al., Nature Rev. Cancer 7:823-833 (2007); Liedtke et al., Blood 113:6061-6068 (2009).

In MLL1 rearranged leukemia, reciprocal translocation of MLL1 gene results in in-frame fusion of the 5'-end MLL1 with the 3'-end of the fusion partner gene, which may recruit other factors aberrantly such as Dot1L. A common feature of MLL1 abnormality in MLL-r leukemia is the preservation of one wild-type MLL1 allele. It has been reported that MLL1-AF9 induced leukemogenesis requires co-expression of the wild type MLL1 allele, since genetic deletion of MLL1 in MLL1-AF9 murine leukemia cells reduced clonogenic potential and leukemia progression. Mutations in the MLL1 region are also prevalent in a large range of solid tumors, including for example, colon, lung, bladder, endometrial and breast cancers (Ding et al., Nature 455:1069-1075 (2008); Wood et al., Science 318:1108-1113 (2007); Giu et al., Genetics 43:875-878 (2011); Kandoth et al., Nature 497:67-73 (2013)).

MLL1 is a promising therapeutic target for MLL-r AML, ALL and other cancers; and there remains a need for selective inhibitors of MLL1.

SUMMARY OF THE INVENTION

The present invention provides novel compounds that inhibit MLL1; and compositions and methods for treating or preventing a disease or condition mediated by MLL1.

In one aspect, the invention provides a compound of Formula (I):

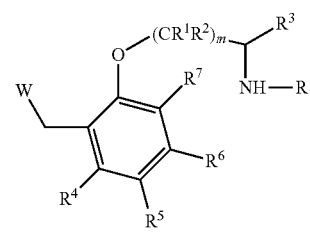

or an enantiomer, an enantiomeric mixture, or a pharmaceutically acceptable salt thereof;
wherein W is selected from:

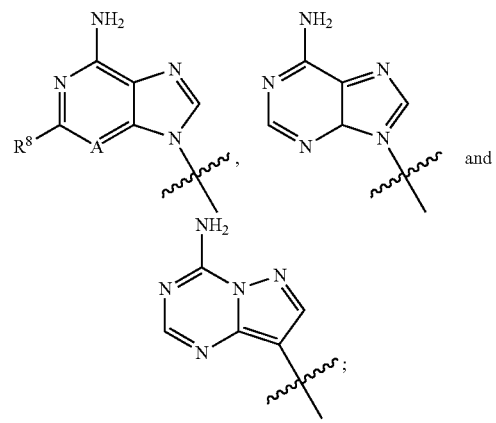

A is N or $CR^9$ wherein $R^9$ is hydrogen or halo;
R, $R^1$ and $R^2$ are independently H or $C_{1-4}$ alkyl;
$R^3$ is hydrogen or selected from the group consisting of:
(i) —$C_{1-6}$ alkyl, -halo$C_{1-6}$ alkyl, -hydroxy$C_{1-6}$ alkyl, —$C_{1-6}$alkoxy$C_{1-6}$alkyl, —$C_{3-8}$ cycloalkoxy ($C_{1-6}$ alkyl), cyano, -cyano$C_{1-6}$ alkyl, —$C_{1-6}$ alkylthio$C_{1-6}$alkyl, —$C_{2-6}$ alkenyl, -halo$C_{2-6}$ alkenyl, —$C_{2-6}$ alkynyl, —$C_{1-4}$ alkyl-S—$C_{1-4}$alkyl, —$C_{1-4}$ alkylSO$_2$C$_{1-4}$alkyl, —SO$_2$(C$_{1-4}$ alkyl), or —C((C$_{1-4}$ alkyl)=N—O(C$_{1-4}$ alkyl);
(ii) —$C_{1-4}$alkylcarbonyl, —$(CR^aR^b)_p$—C(═O)—OR$^{10a}$, or —C(═O)—$(CR^aR^b)_q$R$^{11}$;
wherein $R^{11}$ is —$C_{3-7}$ cycloalkyl, 5-6 membered heterocyclyl or 5-6 membered heteroaryl, each of which is independently unsubstituted or substituted with —$C_{1-6}$ alkyl or —$C_{1-6}$ alkoxy; and said 5-6 membered heterocyclyl or 5-6 membered heteroaryl independently comprises 1-3 heteroatoms selected from nitrogen, oxygen and sulfur;
(iii) —$(CR^aR^b)_r$—C(═O)—NR$^{12}$R$^{13}$, —$(CR^aR^b)_s$—NR$^{12}$R$^{13}$, —$(CR^aR^b)_{1-4}$—O—$(CR^aR^b)_{1-4}$—OR$^{10a}$ or —$(CR^aR^b)_{1-4}$—O—$(CR^aR^b)_{1-4}$—C(═O)—NR$^{12}$R$^{13}$.
wherein $R^{12}$ is hydrogen or —$C_{1-6}$ alkyl;
$R^{13}$ is hydrogen, —$C_{1-6}$ alkyl, —$C_{1-6}$alkoxy$C_{1-6}$alkyl, -cyano$C_{1-6}$ alkyl; —$C_{0-4}$ alkylSO$_2$R$^{10b}$ wherein R$^{10b}$ is —$C_{1-6}$ alkyl or phenyl; $C_{3-10}$ monocyclic or bicyclic cycloalkylC$_{0-6}$alkyl, phenyl, 5-10 membered monocyclic or bicyclic heterocyclic ring or 5-9 membered heteroarylC$_{0-6}$alkyl;
said 5-10 membered monocyclic or bicyclic heterocyclic ring or 5-9 membered heteroaryl radical independently comprises 1-4 heteroatoms selected from nitrogen, oxygen and sulfur; and said $C_{3-10}$ monocyclic or bicyclic cycloalkyl, phenyl, 5-10 membered monocyclic or bicyclic heterocyclic ring or 5-9 membered heteroaryl radical are independently unsubstituted or substituted with 1-2 —$C_{1-4}$ alkyl, -hydroxy$C_{1-6}$ alkyl, —$C_{1-4}$ alkoxy, halo, hydroxyl, phenyl or —S($C_{1-4}$ alkyl);

or $R^{12}$ and $R^{13}$ together form a 5-10 membered monocyclic or bicyclic heterocyclic ring comprising 1-4 heteroatoms selected from nitrogen, oxygen and sulfur; and is unsubstituted or substituted with —$C_{1-4}$ alkyl, hydroxyl, cyano, -cyano$C_{1-6}$ alkyl, —$SO_2$ or —$C_{2-4}$alkenylcarbonyl;

(v) 5-6 membered heterocyclyl$C_{0-6}$alkyl or 5-6 membered heterocyclyl(halo$C_{1-4}$ alkyl), wherein each said heterocyclyl radical is unsubstituted or substituted with oxo; and wherein each said heterocyclyl radical comprises 1-3 heteroatoms selected from nitrogen, oxygen and sulfur; and (vi) phenyl, 5-9 membered heteroaryl$C_{0-6}$alkyl or 5-9 membered heteroaryl(halo$C_{1-4}$alkyl), wherein each said phenyl or heteroaryl radical is independently unsubstituted or substituted by —$C_{1-4}$ alkyl, -halo$C_{1-4}$ alkyl, -hydroxy$C_{1-4}$ alkyl, —$C_{1-4}$ alkoxy, -halo$C_{1-4}$ alkoxy, halo, hydroxy, cyano, oxido, amino, —$C_{1-4}$ alkylamino, —$C_{1-4}$ dialkylamino, -aminocarbonyl $C_{0-6}$alkyl, —$C_{1-4}$alkylaminocarbonyl$C_{0-6}$alkyl, -di$C_{1-4}$alkylaminocarbonyl$C_{0-6}$alkyl or $C_{3-7}$ cycloalkyl;

wherein each said heteroaryl radical comprises 1-4 heteroatoms selected from nitrogen, oxygen and sulfur;

$R^4$, $R^5$, $R^6$ and $R^7$ are independently hydrogen, halo, —$C_{1-4}$ alkyl, -halo$C_{1-6}$ alkyl, -hydroxy$C_{1-6}$ alkyl, cyano, -cyano$C_{1-6}$ alkyl, —$C_{2-6}$ alkenyl, —$C_{2-6}$ alkynyl, —$C_{1-6}$ alkylthio, —$(CR^aR^b)_{1-4}$—$NR^{14}R^{15}$, —$(CR^aR^b)_{1-4}$—$NR^{14}$—$C(O)$—$OR^{15}$, —$(CR^aR^b)_{1-4}$—$OR^{16}$, $C_{3-8}$ cycloalkyl, phenyl or 5-6 membered heteroaryl comprising 1-3 heteroatoms selected from nitrogen, oxygen and sulfur; wherein said $C_{3-8}$ cycloalkyl, phenyl or 5-6 membered heteroaryl is independently substituted with 1-2 $R^{17}$;

alternatively, $R^4$ and $R^5$, $R^5$ and $R^6$, and $R^6$ and $R^7$ together with the phenyl ring to which they are attached form a 9-10 membered benzo-fused carbocycle or benzo-fused heterocycle comprising 1-3 heteroatoms selected from nitrogen, oxygen and sulfur; wherein said benzo-fused carbocycle or benzo-fused heterocycle is independently unsubstituted or substituted with 1-2 halo or $C_{1-4}$ alkyl;

$R^8$ is hydrogen, —$C_{1-4}$ alkyl or —$C_{1-4}$ alkoxy;

$R^a$, $R^b$, $R^c$, $R^{10a}$ and $R^{14}$ are independently hydrogen or —$C_{1-4}$ alkyl;

$R^{15}$ is hydrogen, —$C_{1-4}$ alkyl, -halo$C_{1-6}$ alkyl or —$C_{3-6}$ cycloalkyl;

alternatively, $R^{14}$ and $R^{15}$ together with N in the —$NR^{14}R^{15}$ moiety form a 4-10 membered monocyclic or bicyclic heterocyclic ring comprising 1-3 heteroatoms selected from nitrogen, oxygen and sulfur; wherein said 4-10 membered monocyclic or bicyclic heterocyclic ring is unsubstituted or substituted with 1-2 halo or —$C_{1-4}$ alkyl;

$R^{16}$ is hydrogen, —$C_{1-4}$ alkyl, -halo$C_{1-6}$ alkyl, —$C_{3-6}$ cycloalkyl, phenyl, 5-6 membered heterocyclyl or 5-6 membered heteroaryl; wherein said 5-6 membered heterocyclyl or 5-6 membered heteroaryl independently comprises 1-3 heteroatoms selected from nitrogen, oxygen and sulfur;

$R^{17}$ is —$C_{1-4}$ alkyl, halo or —$C_{3-6}$ cycloalkyl; or two $R^{20}$ together form a 5-6 membered ring;

m is 1, 2, 3 or 4; and p, q, r and s are independently 0, 1, 2, 3 or 4.

In another aspect, the invention provides a pharmaceutical composition comprising a therapeutically effective amount of a compound of Formula (I) or sub-formulae thereof, or a pharmaceutically acceptable salt thereof; and one or more pharmaceutically acceptable carriers.

In yet another aspect, the invention provides a combination, in particular a pharmaceutical combination, comprising a therapeutically effective amount of a compound of Formula (I) or sub-formulae thereof, or a pharmaceutically acceptable salt thereof; and one or more therapeutically active agent(s).

The compounds of the invention, alone or in combination with one or more therapeutically active agent(s), can be used for treating or preventing a disease or condition mediated by MLL1; and more particularly wherein the disease or condition is characterized by overexpression or undesired upregulation of MLL1.

DETAILED DESCRIPTION OF THE INVENTION

The present invention provides compositions and methods for treating or preventing a disease or condition mediated by MLL1.

Definitions

For purposes of interpreting this specification, the following definitions will apply and whenever appropriate, terms used in the singular will also include the plural and vice versa.

As used herein, the term "—$C_{1-6}$alkyl" refers to a straight or branched hydrocarbon chain radical consisting solely of carbon and hydrogen atoms, containing no unsaturation, having from one to six carbon atoms, and which is attached to the rest of the molecule by a single bond. The term "$C_{1-4}$alkyl" is to be construed accordingly. Examples of $C_{1-6}$alkyl include, but are not limited to, methyl, ethyl, n-propyl, 1-methylethyl (iso-propyl), n-butyl, n-pentyl and 1,1-dimethylethyl (t-butyl).

As used herein, the term "—$C_{2-6}$alkenyl" refers to a straight or branched hydrocarbon chain radical group consisting solely of carbon and hydrogen atoms, containing at least one double bond, having from two to six carbon atoms, which is attached to the rest of the molecule by a single bond. The term "$C_{2-4}$alkenyl" is to be construed accordingly. Examples of $C_{2-6}$alkenyl include, but are not limited to, ethenyl, prop-1-enyl, but-1-enyl, pent-1-enyl, pent-4-enyl and penta-1,4-dienyl.

As used herein, the term "—$C_{2-6}$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_{2-4}$alkynyl" is to be construed accordingly. Examples of $C_{2-6}$alkynyl include, but are not limited to, ethynyl, prop-1-ynyl, but-1-ynyl, pent-1-ynyl, pent-4-ynyl and penta-1,4-diynyl.

As used herein, the term "—$C_{1-6}$alkoxy" refers to a radical of the formula —$OR_a$ where $R_a$ is a $C_{1-6}$alkyl radical as generally defined above. Examples of $C_{1-6}$alkoxy include, but are not limited to, methoxy, ethoxy, propoxy, iso-propoxy, butoxy, isobutoxy, pentoxy, and hexoxy.

As used herein, the term "—$C_{1-6}$alkoxy$C_{1-6}$alkyl" refers to a radical of the formula —$R_a$—O—$R_a$ where each $R_a$ is independently a $C_{1-6}$alkyl radical as defined above. The oxygen atom may be bonded to any carbon atom in either alkyl radical. Examples of $C_{1-6}$alkoxy $C_{1-6}$alkyl include, but are not limited to, methoxy-methyl, methoxy-ethyl, ethoxy-ethyl, 1-ethoxy-propyl and 2-methoxy-butyl.

As used herein, the term "—$C_{1-4}$alkylcarbonyl" refers to a radical of the formula —C(=O)—$R_a$ where $R_a$ is a $C_{1-4}$alkyl radical as defined above.

As used herein, the term "—$C_{1-6}$alkylthio$C_{1-6}$alkyl" refers to a radical of the formula —$R_a$—S—$R_a$, where each $R_a$ is independently a $C_{1-4}$ alkyl radical as defined above.

As used herein, the term "-hydroxy$C_{1-6}$alkyl" refers to a $C_{1-6}$alkyl radical as defined above, wherein one of the hydrogen atoms of the $C_{1-6}$alkyl radical is replaced by OH. Examples of hydroxy$C_{1-6}$alkyl include, but are not limited to, ethan-1-olyl, 2-methylpropan-1-olyl, hydroxy-methyl, 2-hydroxy-ethyl, 2-hydroxy-propyl, 3-hydroxy-propyl and 5-hydroxy-pentyl.

As used herein, the term "-aminocarbonyl$C_{0-6}$alkyl" refers to a radical of the formula —$R_a$—C(=O)—NH$_2$, wherein $R_a$ is a single bond or a $C_{1-6}$alkyl radical as defined above.

As used herein, the term "—$C_{1-4}$alkylaminocarbonyl $C_{0-6}$alkyl" refers to a radical of the formula —$R_{a1}$—C(=O)—NH—$R_{a2}$, where $R_{a1}$ is a single bond or a $C_{1-6}$ alkyl radical as defined above; and $R_{a2}$ is a $C_{1-6}$alkyl radical as defined above.

As used herein, the term "-di$C_{1-4}$alkylaminocarbonyl $C_{0-6}$alkyl" refers to a radical of the formula —$R_{a1}$—C(=O)—N($R_{a2}$)—$R_{a2}$ where $R_{a1}$ is a single bond or a $C_{1-6}$alkyl radical as defined above; and each $R_{a2}$ is a $C_{1-4}$alkyl radical as defined above, and may be the same or different.

As used herein, the term "—$C_{3-10}$ monocyclic or bicyclic cycloalkyl$C_{0-6}$alkyl" refers to a stable monocyclic or bicyclic saturated hydrocarbon radical consisting solely of carbon and hydrogen atoms, having from three to ten carbon atoms, and which is attached to the rest of the molecule by a single bond (i.e., $C_{3-8}$cycloalkyl) or by a $C_{1-6}$alkyl radical as defined above. The terms "$C_{3-7}$cycloalkyl" and "$C_{3-6}$cycloalkyl" are to be construed accordingly. Examples include, for example, cyclopropyl, cyclopropyl-methyl, cyclobutyl, cyclobutyl-ethyl, cyclopentyl, cyclopentyl-propyl, cyclohexyl, cyclohepty and cyclooctyl.

As used herein, the term "—$C_{3-8}$cycloalkoxy$C_{1-6}$alkyl" refers to a radical of the formula —$R_a$—O—$R_b$ wherein $R_a$ is independently a $C_{1-6}$alkyl radical as defined above and $R_b$ is a $C_{3-8}$cycloalkyl as defined above. Examples of $C_{3-8}$cycloalkoxy$C_{1-6}$alkyl include but are not limited to cyclopropoxymethyl and cyclobutoxymethyl.

"Halo" refers to bromo, chloro, fluoro or iodo.

As used herein, the term "-halo$C_{1-6}$alkyl" refers to a $C_{1-6}$alkyl radical, as defined above, substituted by one or more halo radicals, as defined above. Examples of halo$C_{1-6}$alkyl include, but are not limited to, trifluoromethyl, difluoromethyl, fluoromethyl, trichloromethyl, 2,2,2-trifluoroethyl, 1,3-dibromopropan-2-yl, 3-bromo-2-fluoropropyl and 1,4,4-trifluorobutan-2-yl.

The term "halo$C_{1-4}$alkyl" is to be construed accordingly.

As used herein, the term "-cyano$C_{1-6}$ alkyl" refers to a radical of the formula —$R_a$—CN, where $R_a$ is a $C_{1-4}$alkyl radical as defined above.

As used herein, the term "-halo$C_{2-6}$alkenyl" refers to a $C_{2-6}$alkenyl radical, as defined above, substituted by one or more halo radicals, as defined above.

As used herein, the term "heterocyclyl" or "heterocyclic" refers to a stable 4-7 membered non-aromatic monocyclic ring radical comprising 1, 2, or 3, heteroatoms individually selected from nitrogen, oxygen and sulfur. The heterocyclyl radical may be bonded via a carbon atom or heteroatom. The term "5-6 membered heterocyclyl" is to be construed accordingly. Examples of heterocyclyl include, but are not limited to, azetidinyl, oxetanyl, pyrrolinyl, pyrrolidyl, tetrahydrofuryl, tetrahydrothienyl, piperidyl, piperazinyl, tetrahydropyranyl or morpholinyl or perhydroazepinyl.

As used herein, the term "heterocyclyl$C_{0-6}$alkyl" refers to a heterocyclic ring as defined above which is attached to the rest of the molecule by a single bond or by a $C_{1-6}$alkyl radical as defined above.

As used herein, the term "heteroaryl" refers to a 5-9 membered aromatic monocyclic or fused ring radical comprising 1, 2, 3 or 4 heteroatoms individually selected from nitrogen, oxygen and sulfur. The heteroaryl radical may be bonded via a carbon atom or heteroatom. The term "5-6 membered heteroaryl" is to be construed accordingly. Examples of 5-6 membered monocyclic heteroaryls include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl. Examples of fused heteroaryls include but are not limited to 9-membered heteroaryls such as benzofuranyl; 2,3-dihydrobenzofuranyl, 1,3-dihydroisobenzofuranyl; benzo[d][1,3]dioxol-5-yl; imidazo[1,2-a]pyridinyl; pyrazolo[1,5-a]pyridinoyl; 1H-indazolyl and 1H-benzo[d]-imidazolyl.

As used herein, the term "heteroaryl$C_{0-6}$alkyl" refers to a heteroaryl ring as defined above which is attached to the rest of the molecule by a single bond or by a $C_{1-6}$alkyl radical as defined above.

As used herein, the term "heteroaryl(halo$C_{1-4}$alkyl)" refers to a heteroaryl ring as defined above which is attached to the rest of the molecule by a halo$C_{1-4}$alkyl as defined above. An illustrative example of an heteroaryl(halo$C_{1-4}$alkyl) is fluoro(pyridin-2-yl)methyl.

As used herein, the term "IC$_{50}$" refers to the molar concentration of an inhibitor or modulator that produces 50% inhibition.

As used herein, the term "protected derivatives" refers to derivatives of inhibitors in which a reactive site or sites are blocked with protecting groups. Protected derivatives are useful in the preparation of inhibitors or in themselves may be active as inhibitors. Examples of protected group includes, but are not limited to, acetyl, tetrahydropyran, methoxymethyl ether, 0-methoxyethoxymethyl ether, ρ-methoxybenzyl, methylthiomethyl ether, pivaloyl, silyl ether, carbobenzyloxy, benzyl, tert-butoxycarbonyl, ρ-methoxyphenyl, 9-fluorenylmethyloxycarbonyl, acetals, ketals, acylals, dithianes, methylesters, benzyl esters, tert-butyl esters, and silyl esters. A comprehensive list of suitable protecting groups can be found in T. W. Greene, *Protecting Groups in Organic Synthesis,* 3rd edition, John Wiley & Sons, Inc. 1999.

As used herein, the term "subject" refers to mammals, primates (e.g., humans, male or female), dogs, rabbits, guinea pigs, pigs, rats and mice. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder As used herein, a subject is "in need of" a treatment if such subject would benefit biologically, medically or in quality of life from such treatment.

As used herein, the term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc.

As used herein, the term "anti-cancer agent" or antineoplastic agent, refers to a therapeutic agent that is useful for treating or controlling the growth of cancerous cells.

As used herein, the term "anti-inflammatory agent" refers to a therapeutic agent that reduces inflammation (redness, swelling and/or pain) in the body. Anti-inflammatory agents block certain substances in the body that cause inflammation.

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22$^{nd}$ Ed. Pharmaceutical Press, 2013, pp. 1049-1070).

As used herein, the term "a," "an," "the" and similar terms used in the context of the present invention (especially in the context of the claims) are to be construed to cover both the singular and plural unless otherwise indicated herein or clearly contradicted by the context.

DESCRIPTION OF PREFERRED EMBODIMENTS

The present invention provides novel compounds that inhibit MLL1; and compositions and methods for treating or preventing a condition mediated by MLL1.

Various enumerated embodiments of the invention are described herein. Features specified in each embodiment may be combined with other specified features to provide further embodiments of the present invention.

Embodiment 1. A compound of Formula (I), or an enantiomer, an enantiomeric mixture, or a pharmaceutically acceptable salt thereof; as described above.

Embodiment 2. A compound according to Embodiment 1, wherein said compound is of Formula (II):

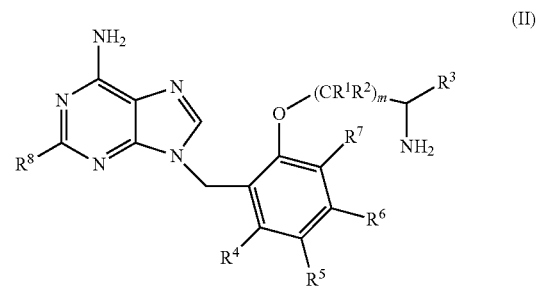

or an enantiomer, an enantiomeric mixture, or a pharmaceutically acceptable salt thereof.

Embodiment 3. A compound according to Embodiment 1, wherein said compound is of Formula (III):

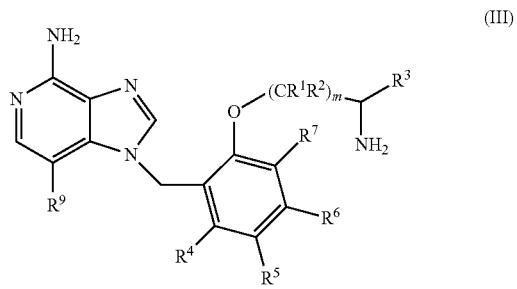

or an enantiomer, an enantiomeric mixture, or a pharmaceutically acceptable salt thereof.

Embodiment 4. A compound according to Embodiment 1, wherein said compound is of Formula (IV):

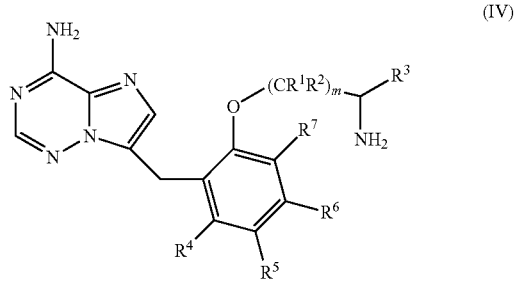

or an enantiomer, an enantiomeric mixture, or a pharmaceutically acceptable salt thereof.

Embodiment 5. A compound according to Embodiment 1, wherein said compound is of Formula (V):

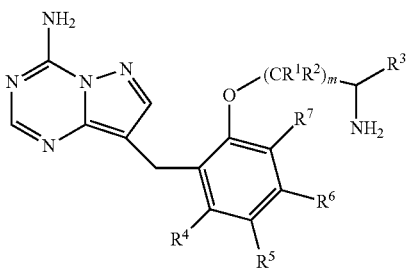

(V)

or an enantiomer, an enantiomeric mixture, or a pharmaceutically acceptable salt thereof.

Embodiment 6. A compound according to any one of Embodiments 1-5, or an enantiomer, an enantiomeric mixture, or a pharmaceutically acceptable salt thereof;
wherein $R^3$ is hydrogen, -hydroxyC$_{1-6}$ alkyl, —C$_{1-6}$alkoxyC$_{1-6}$alkyl, —C$_{1-4}$ alkyl-S—C$_{1-4}$alkyl, —C(=O)—OR$^{10a}$, —C(=O)—NR$^{12}$R$^{13}$, —(CR$^a$R$^b$)—NR$^{12}$R$^{13}$, —(CR$^a$R$^b$)—O—(CR$^a$R$^b$)$_2$—O—C$_{1-6}$alkyl or 5-9 membered heteroarylC$_{0-6}$alkyl wherein said heteroaryl radical is unsubstituted or substituted by —C$_{1-4}$ alkyl;
$R^a$, $R^b$, $R^{10a}$ and $R^{12}$ are independently hydrogen or C$_{1-4}$ alkyl;
$R^{13}$ is hydrogen, —C$_{1-6}$ alkyl, —C$_{1-6}$alkoxyC$_{1-6}$alkyl, —SO$_2$—(C$_{1-4}$ alkyl) or -cyclopropyl; and
m is 1, 2, 3 or 4.

Embodiment 7. A compound according to any one of Embodiments 1-5, or an enantiomer, an enantiomeric mixture, or a pharmaceutically acceptable salt thereof;
wherein $R^3$ is —C$_{1-6}$alkoxyC$_{1-6}$alkyl, —C(=O)—OR$^{10a}$, —C(=O)—NR$^{12}$R$^{13}$, triazolyl or thiadiazolyl unsubstituted or substituted by —C$_{1-4}$ alkyl;
$R^{10a}$ and $R^{12}$ are independently hydrogen or C$_{1-4}$ alkyl;
$R^{13}$ is hydrogen, —C$_{1-6}$alkoxyC$_{1-6}$alkyl, —SO$_2$—(C$_{1-4}$ alkyl) or -cyclopropyl; and
m is 1, 2 or 3.

Embodiment 8. A compound according to any one of Embodiments 1-7, or an enantiomer, an enantiomeric mixture, or a pharmaceutically acceptable salt thereof; wherein:
$R^4$ and $R^5$ are halo; and
$R^6$ and $R^7$ are hydrogen.

Embodiment 9. A compound according to any one of Embodiments 1-7, or an enantiomer, an enantiomeric mixture, or a pharmaceutically acceptable salt thereof; wherein:
$R^4$ is halo or —C$_{1-4}$ alkyl;
$R^6$ is halo; and
$R^5$ and $R^7$ are hydrogen.

Embodiment 10. A compound according to any one of Embodiments 1-7, or an enantiomer, an enantiomeric mixture, or a pharmaceutically acceptable salt thereof, wherein $R^4$ and $R^5$ together with the phenyl ring to which they are attached form a 9-10 membered benzo-fused carbocycle; wherein said benzo-fused carbocycle is unsubstituted or substituted with halo; and
$R^6$ and $R^7$ are hydrogen.

Embodiment 11. A compound according to any one of Embodiments 1-7, or an enantiomer, an enantiomeric mixture, or a pharmaceutically acceptable salt thereof, wherein:
$R^4$ and $R^7$ are hydrogen; and
$R^5$ and $R^6$ together with the phenyl ring to which they are attached form a 9-10 membered benzo-fused carbocycle.

Embodiment 12. A compound according to any one of Embodiments 1-7, or an enantiomer, an enantiomeric mixture, or a pharmaceutically acceptable salt thereof, wherein $R^4$, $R^5$, $R^6$ and $R^7$ are hydrogen; or wherein one of $R^4$, $R^5$, $R^6$ and $R^7$ is halo and the others are hydrogen.

Embodiment 13. The compound according to any one of Embodiments 1-12, wherein said compound is in the (R) configuration, (S) configuration, or a mixture thereof.

Embodiment 14. A compound according to Embodiment 1, wherein said compound is selected from a compound in Table 1, or a pharmaceutically acceptable salt thereof.

Embodiment 15. The compound according to Embodiment 1, wherein said compound is selected from:
(R)-9-(6-((4-amino-5-methoxypentyl)oxy)-2,3-dichlorobenzyl)-9H-purin-6-amine;
(S)-9-((2-(2-amino-3-methoxypropoxy)naphthalen-1-yl)methyl)-9H-purin-6-amine;
(R)-9-((2-((4-amino-5-methoxypentyl)oxy)-6-bromonaphthalen-1-yl)methyl)-9H-purin-6-amine;
(R)-2-amino-5-(2-((6-amino-9H-purin-9-yl)methyl)-3,4-dichlorophenoxy)pentanoic acid;
Ethyl (R)-2-amino-5-(2-((6-amino-9H-purin-9-yl)methyl)-3,4-dichlorophenoxy)pentanoate;
Ethyl (2R)-2-amino-5-(2-((6-amino-9H-purin-9-yl)methyl)-3,4-dichlorophenoxy)hexanoate;
Methyl 2-amino-5-(2-((4-amino-7-chloro-1H-imidazo[4,5-c]pyridin-1-yl)methyl)-3,5-dichloro phenoxy)pentanoate;
Ethyl (R)-2-amino-5-(2-((6-amino-9H-purin-9-yl)methyl)-3,5-dichlorophenoxy)pentanoate;
Methyl (R)-2-amino-5-(2-((6-amino-9H-purin-9-yl)methyl)-3,4-dichlorophenoxy)pentanoate;
Methyl (R)-2-amino-5-(2-((4-aminoimidazo[2,1-f][1,2,4]triazin-7-yl)methyl)-3,4-dichlorophenoxy)pentanoate;
(R)-2-amino-5-(2-((4-aminoimidazo[2,1-f][1,2,4]triazin-7-yl)methyl)-3,4-dichlorophenoxy)-N-cyclopropylpentanamide;
(R)-2-amino-5-(2-((6-amino-9H-purin-9-yl)methyl)-3,4-dichlorophenoxy)pentanamide;
(R)-2-amino-5-(2-((6-amino-9H-purin-9-yl)methyl)-3,4-dichlorophenoxy)-N-(2-methoxyethyl) pentanamide;
(R)-2-amino-5-(2-((6-amino-9H-purin-9-yl)methyl)-3,4-dichlorophenoxy)-N-cyclopropylpentanamide;
(R)-2-amino-5-(2-((6-amino-9H-purin-9-yl)methyl)-3,4-dichlorophenoxy)-N-(methylsulfonyl)pentanamide;
(R)-9-(6-(4-amino-4-(1H-1,2,4-triazol-3-yl)butoxy)-2,3-dichlorobenzyl)-9H-purin-6-amine;
(R)-9-(6-((4-amino-5-(1H-pyrazol-1-yl)pentyl)oxy)-2,3-dichlorobenzyl)-9H-purin-6-amine;
(R)-9-(6-(4-amino-4-(5-methyl-1,3,4-thiadiazol-2-yl)butoxy)-2,3-dichlorobenzyl)-9H-purin-6-amine;
or a pharmaceutically acceptable salt thereof.

Embodiment 16. A pharmaceutical composition comprising a compound according to any one of Embodiments 1-15 and one or more pharmaceutically acceptable carrier.

Embodiment 17. A combination comprising a compound according to any one of Embodiments 1-15 and one or more additional therapeutically active agent.

Embodiment 18. The combination according to Embodiment 17, wherein said one or more additional therapeutically active agent is an anti-cancer agent, an analgesic, an anti-inflammatory agent, or a combination thereof.

Embodiment 19. A compound according to any one of Embodiments 1-15 and optionally in combination with a second therapeutic agent, for use in treating a disease or condition mediated by mixed lineage leukemia 1 (MLL1).

Embodiment 20. The compound according to Embodiment 19, wherein said second therapeutic agent is an anti-cancer agent, an analgesic, an anti-inflammatory agent or a combination thereof.

Embodiment 21. Use of a compound according to any one of Embodiments 1-15 and optionally in combination with a second therapeutic agent, in the manufacture of a medicament for a disease or condition mediated by mixed lineage leukemia 1 (MLL1).

Embodiment 22. A method for treating a disease or condition mediated by mixed lineage leukemia 1 (MLL1), comprising administering to a subject in need thereof, a therapeutically effective amount of a compound according to any one of Embodiments 1-15 and optionally in combination with a second therapeutic agent; thereby treating said disease or condition mediated by MLL1.

Embodiment 23. A method for treating a disease or condition that benefit from or is treatable by inhibition of mixed lineage leukemia 1 (MLL1), comprising administering to a subject in need thereof, a therapeutically effective amount of a compound according to any one of Embodiments 1-15 and optionally in combination with a second therapeutic agent; thereby treating said disease or condition that benefit from or is treatable by inhibition by MLL1.

Embodiment 24. The use of a compound according to Embodiment 21, or the method according to Embodiment 22 or 23, wherein said disease or condition mediated by MLL1, or said disease or condition that benefit from or is treatable by inhibition of MLL1, is breast cancer, cervical cancer, skin cancer, ovarian cancer, gastric cancer, prostate cancer, pancreatic cancer, lung cancer, hepatocellular carcinoma, head and neck cancer, peripheral nerve sheath tumor, osteosarcoma, myeloma, neuroblastoma, leukemia, lymphoma, or pulmonary arterial hypertension.

Embodiment 25. The use of a compound according to Embodiment 24, or the method according to Embodiment 24, wherein said disease or condition mediated by MLL1, or said disease or condition that benefit from or is treatable by inhibition of MLL1, is leukemia.

Embodiment 26. The use of a compound according to Embodiment 25, or the method according to Embodiment 25, wherein said leukemia is acute lymphoblastic leukemia (ALL), acute myeloid leukemia (AML), chronic myeloid leukemia (CML) or chronic myelomonocytic leukemia (CMML).

Embodiment 27. The use of a compound according to Embodiment 24, or the method according to Embodiment 24, wherein said disease or condition mediated by MLL1, or said disease or condition that benefit from or is treatable by inhibition of MLL1, is breast cancer.

Embodiment 28. The use of a compound according to Embodiment 24, or the method according to Embodiment 24, wherein said disease or condition mediated by MLL1, or said disease or condition that benefit from or is treatable by inhibition of MLL1, is lung cancer.

Embodiment 29. The use of a compound according to Embodiment 28, or the method according to Embodiment 28, wherein said lung cancer is small cell or non-small cell lung cancer.

Embodiment 30. The use of a compound according to Embodiment 24, or the method according to Embodiment 24, wherein said disease or condition mediated by MLL1, or said disease or condition that benefit from or is treatable by inhibition of MLL1, is skin cancer.

Embodiment 31. The use of a compound according to Embodiment 30, or the method according to Embodiment 30, wherein said skin cancer is melanoma, basal cell carcinoma or squamous cell carcinoma.

Embodiment 32. The use of a compound according to Embodiment 24, or the method according to Embodiment 24, wherein said disease or condition mediated by MLL1, or said disease or condition that benefit from or is treatable by inhibition of MLL1, is lymphoma.

Embodiment 33. The use of a compound according to Embodiment 32, or the method according to Embodiment 32, wherein said lymphoma is Hodgkin's lymphoma or non-Hodgkin's lymphoma.

Embodiment 34. The use of a compound according to Embodiment 32, or the method according to Embodiment 32, wherein said lymphoma is mantle cell lymphoma or diffuse large B cell lymphoma.

Embodiment 35. The use of a compound according to Embodiment 24, or the method according to Embodiment 24, wherein said disease or condition mediated by MLL1, or said disease or condition that benefit from or is treatable by inhibition of MLL1, is multiple myeloma.

Embodiment 36. A method according to any one of Embodiment 22-35, wherein said compound is administered orally.

Unless specified otherwise, the term "compounds of the present invention" or "compound of the present invention" refers to compounds of Formula (I) subformulae thereof, and exemplified compounds, and salts thereof, as well as all stereoisomers (including diastereoisomers and enantiomers), rotamers, tautomers and isotopically labeled compounds (including deuterium substitutions), as well as inherently formed moieties.

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-stereoisomers may be prepared using chiral synthons or chiral reagents, or resolved using conventional techniques. Substituents at atoms with unsaturated double bonds may, if possible, be present in cis-(Z)- or trans-(E)-form. If the compound contains a disubstituted cycloalkyl, the cycloalkyl substituent may have a cis- or trans-configuration.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present invention or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds of the present invention or racemic intermediates can also be resolved by chiral chromatography, e.g., high pressure liquid chromatography (HPLC) using a chiral adsorbent.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of Formula (I) or sub-formulae thereof. The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as $^3$H, $^{11}$C, $^{13}$C, $^{14}$C, $^5$N, $^{18}$F $^{31}$P, $^{32}$P, $^{35}$S, $^{36}$Cl, $^{123}$I, $^{124}$I, $^{125}$I respectively. Accordingly it should be understood that the invention includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of Formula (I) or sub-formulae thereof can generally be prepared by conventional techniques known to those skilled in the art or by processes analogous to those described in the accompanying examples using an appropriate isotopically-labeled reagent in place of the non-labeled reagent previously employed.

The compounds of the present invention are either obtained in the free form, as a salt thereof. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of the present invention in acetate, ascorbate, adipate, aspartate, benzoate, besylate, bromide/hydrobromide, bicarbonate/carbonate, bisulfate/sulfate, camphorsulfonate, caprate, chloride/hydrochloride, chlorotheophyllinate, citrate, ethanedisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Processes for Making Compounds of the Invention

All methods described herein can be performed in any suitable order, unless otherwise indicated or otherwise clearly contradicted by context.

Scheme 1

Under Scheme 1, OH in compound A was first protected as diethylcarbamate B. After -deprotonation and alkylation with DMF, it was followed by hydrolysis with NaOH to yield compound C. Free OH of compound C was again protected as allyl ether and the aldehyde was reduced to give compound D. Mitsunobu reaction with intermediate E resulted in compound F, which was subjected to PhSiH$_3$/Pd (PPh$_3$)$_4$ yielding compound G. Subsequent alkylation of the free OH of G and manipulation of the side chain followed by removal of NBoc protective groups afforded products H.

Scheme 2

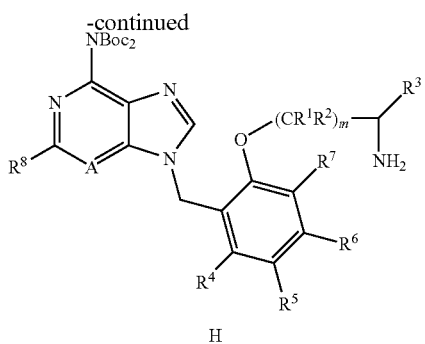

Alternatively, in some cases, compounds of the present invention may be prepared in accordance with Scheme 2. Free OH in compound C was first alkylated with a side chain to give compound I, which was reduced to yield compound J. Mitsunobu reaction with E resulted in intermediates which could be further transformed at the side chain moieties if needed. Subsequent deprotection of NHBoc groups afforded final compound H.

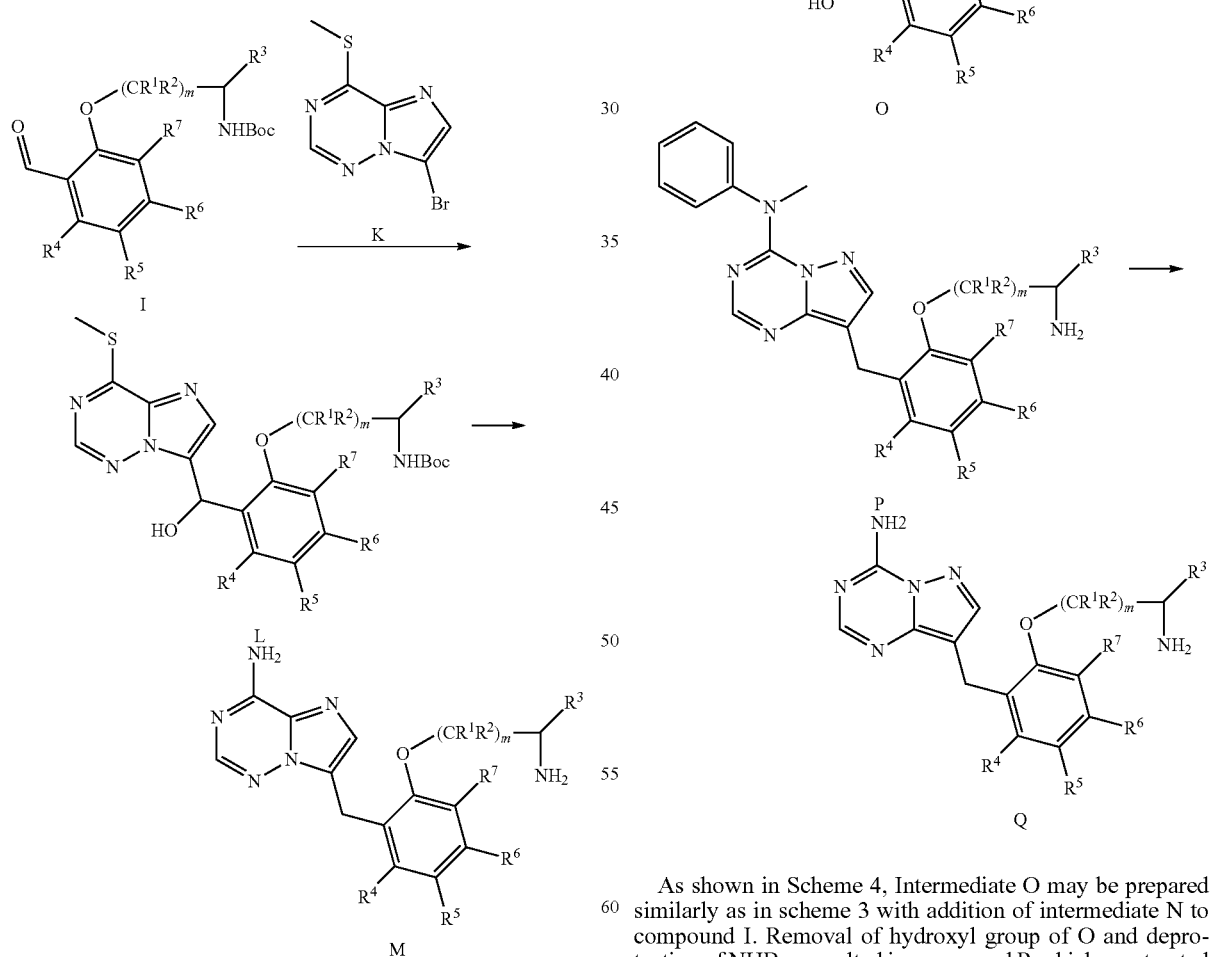

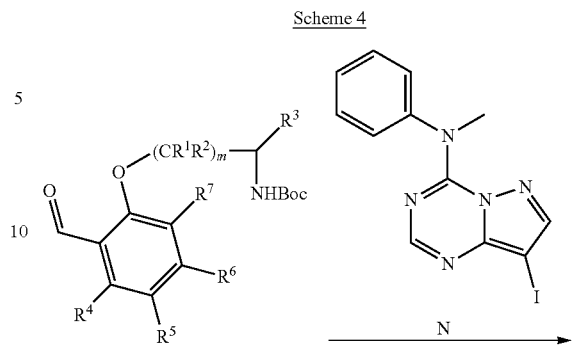

In Scheme 3, addition of intermediate K to aldehyde of compound I yield compound L. Removal of hydroxyl group of compound L followed by deprotection afforded final compound M.

As shown in Scheme 4, Intermediate O may be prepared similarly as in scheme 3 with addition of intermediate N to compound I. Removal of hydroxyl group of O and deprotection of NHBoc resulted in compound P, which was treated with $NH_3$ to yield final compound Q.

The invention further includes any variant of the present processes; for example, wherein an intermediate product obtainable at any stage thereof is used as starting material and the remaining steps are carried out; wherein starting materials are formed in situ under the reaction conditions; or wherein the reaction components are used in the form of their salts or optically pure material. Compounds of the invention and intermediates can also be converted into each other according to methods generally known to those skilled in the art.

Pharmacology and Utility

In one aspect, the invention provides compounds of Formula (I) or subformulae thereof, or a pharmaceutically acceptable salt thereof, that are useful for therapy; particularly, for treating or preventing a disease or condition that is mediated by MLL1.

In another aspect, the invention provides the use of a compound of Formula (I) or subformulae thereof, or a pharmaceutically acceptable salt thereof, for treating a disease or condition that benefit from or is treatable by inhibition of MLL1; and for the manufacture of a medicament for treating a disease or condition that is treatable by inhibition of MLL1.

Examples of diseases or conditions that are mediated by MLL1, or that benefit from or are treatable by inhibition of MLL1, include but is not limited to breast cancer, cervical cancer, skin cancer (particularly skin squamous cell carcinoma), ovarian cancer, gastric cancer, prostate cancer, pancreatic cancer, lung cancer, hepatocellular carcinoma, head and neck cancer, peripheral nerve sheath tumor, osteosarcoma, multiple myeloma, neuroblastoma, leukemia (particularly acute lymphoblastic leukemia), non-Hodgkin's lymphoma (particularly mantle cell lymphoma), and pulmonary arterial hypertension.

Pharmaceutical Compositions, Dosage and Administration

In another aspect, the present invention provides a pharmaceutical composition comprising a compound of the present invention, or a pharmaceutically acceptable salt thereof, and a pharmaceutically acceptable carrier.

In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired
 d) disintegrants, e.g., starches, agar, alginic acid or its sodium salt, or effervescent mixtures; and
 e) absorbents, colorants, flavors and sweeteners.

In another aspect, the compounds of the present invention are combined with other therapeutic agents, such as other anti-cancer agents, anti-allergic agents, anti-nausea agents (or anti-emetics), pain relievers, cytoprotective agents, and combinations thereof.

In one embodiment, the other therapeutic agent is an anti-cancer agent or chemo-therapeutic agent. Examples of anti-cancer agents considered for use in combination therapies of the invention include but are not limited erlotinib, bortezomib, fulvestrant, sunitib imatinib mesylate, letrozole, finasunate, platins such as oxaliplatin, carboplatin, and cisplatin, finasunate, fluorouracil, rapamycin, leucovorin, lapatinib, lonafamib, sorafenib, gefitinib, camptothecin, topotecan, bryostatin, adozelesin, anthracycline, carzelesin, bizelesin, dolastatin, auristatins, duocarmycin, eleutherobin, taxols such as paclitaxel or docetaxel, cyclophosphamide, doxorubicin, vincristine, prednisone or prednisolone, other alkylating agents such as mechlorethamine, chlorambucil, and ifosfamide, antimetabolites such as azathioprine or mercaptopurine, other microtubule inhibitors (vinca alkaloids like vincristine, vinblastine, vinorelbine and vindesine, as well as taxanes), podophyllotoxins (etoposide, teniposide, etoposide phosphate, and epipodophyllotoxins), topoisomerase inhibitors, other cytotoxins such as actinomycin, daunorubicin, valrubicin, idarubicin, edrecolomab, epirubicin, bleomycin, plicamycin, mitomycin, as well as other anticancer antibodies (cetuximab, bevacizumab, ibritumomab, abagovomab, adecatumumab, afutuzumab, alacizumab, alemtuzumab, anatumomab, apolizumab, bavituximab, belimumab, bivatuzumab mertansine, blinatumomab, brentuximab vedotin, cantuzumab mertansine, catumazomab, cetuximab, citatuzumab bogatox, cixutumumab, clivatuzumab tetraxetan, conatumumab, dacetuzumab, daclizumab, detumomab, ecromeximab, edrecolomab, elotuzumab, epratuzumab, ertumaxomab, etaracizumab, farletuzumab, figitumumab, fresolimumab, galiximab, gembatumumab vedotin, gemtuzumab, ibritumomab tiuxetan, inotuzumab ozogamicin, intetumumab, ipilimumab, iratumumab, labetuzumab, lexatumumab, lintuzumab, lucatumumab, lumilisimab, mapatumumab, matuzumab, milatuzumab, mitumomab, nacolomab tafenatox, naptumomab estafenatox, necitumumab, nimotuzumab, ofatumumab, olaratumab, oportuzumab monatox, oregovomab, panitumumab, pemtumomab, pertuzumab, pintumomab, pritumumab, ramucirumab, rilotumumab, robatumumab, rituximab, sibrotuzumab, tacatuzumab tetraxetan, taplitumomab paptox, tenatumomab, ticilimumab, tigatuzumab, tositumomab or $^{131}$I-tositumomab, trastuzumab, tremelimumab, tuocotuzumab celmoleukin, veltuzumab, visilizumab, volocixumab, votumumab, zalutumumab, zanolimumab, IGN-101, MDX-010, ABX-EGR, EMD72000, ior-t1, MDX-220, MRA, H-11 scFv, huJ591, TriGem, TriAb, R3, MT-201, G-250, ACA-125, Onyvax-105, CD:-960, CeaVac, BrevaRex AR54, IMC-1C11, GlioMab-H, ING-1, anti-LCG MAbs, MT-103, KSB-303, Therex, KW2871, anti-HMl.24, Anti-PTHrP, 2C$_4$ antibody, SGN-30, TRAIL-RI MAb, Prostate Cancer antibody, H22xKi-r, ABX-Mai, Imuteran, Monopharm-C), and antibody-drug conjugates comprising any of the above agents (especially auristatins MMAE and MMAF, maytansinoids like DM-1, calicheamycins, or various cytotoxins).

In another embodiment, the compounds of the invention are combined with another therapeutic agent selected from anastrozole (ARIMIDEX®), bicalutamide (CASODEX®), bleomycin sulfate (BLENOXANE®), busulfan (MYLERAN®), busulfan injection (BUSULFEX®), capecitabine (XELODA®), N4-pentoxycarbonyl-5-deoxy-5-fluorocytidine, carboplatin (PARAPLATIN®), carmustine (BiCNU®), chlorambucil (LEUKERAN®), cisplatin (PLA- TINOL®), cladribine (LEUSTATIN®), cyclophosphamide (CYTOXAN® or NEOSAR®), cytarabine, cytosine arabinoside (CYTOSAR-U®), cytarabine liposome injection (DEPOCYT®), dacarbazine (DTIC-Dome®), dactinomycin (actinomycin D, COSMEGAN®), daunorubicin hydrochloride (CERUBIDINE®), daunorubicin citrate liposome injection (DAUNOXOME®), dexamethasone, docetaxel (TAXOTERE®), doxorubicin hydrochloride (ADRIAMYCIN®, RUBEX®), etoposide (VEPESID®), fludarabine phosphate (FLUDARA®), 5-fluorouracil (ADRUCIL®, EFUDEX®), flutamide (EULEXIN®), tezacitibine, gemcitabine (difluorodeoxycitidine), hydroxyurea (HYDREA®), idarubicin (IDAMYCIN®), ifosfamide (IFEX®), irinotecan (CAMPTOSAR®), L-asparaginase (ELSPAR®), leucovorin calcium, melphalan (ALKERAN®), 6-mercaptopurine (PURINETHOL®), methotrexate (FOLEX®), mitoxantrone (NOVANTRONE®), gemtuzumab ozogamicin (MYLOTARG™), paclitaxel (TAXOL®), nab-paclitaxel (ABRAXANE®), phoenix (Yttrium90/MX-DTPA), pentostatin, polifeprosan 20 with carmustine implant (GLIADEL®), tamoxifen citrate (NOLVADEX®), teniposide (VUMON®), 6-thioguanine, thiotepa, tirapazamine (TIRAZONE®), topotecan hydrochloride for injection (HYCAMPTIN®), vinblastine (VELBAN®), vincristine (ONCOVIN®), and vinorelbine (NAVELBINE®).

In another embodiment, the compounds of the present invention are combined with another therapeutic agent capable of inhibiting BRAF, MEK, CDK4/6, SHP-2, HDAC, EGFR, MET, mTOR, PI3K or AKT, or a combination thereof. In a particular embodiment, the compounds of the present invention are combined with another therapeutic agent selected from vemurafinib, debrafinib, LGX818, trametinib, MEK162, LEE011, PD-0332991, panobinostat, verinostat, romidepsin, cetuximab, gefitinib, erlotinib, lapatinib, panitumumab, vandetanib, INC280, everolimus, simolimus, BMK120, BYL719 or CLR457, or a combination thereof.

In another embodiment, the therapeutic agent for use with the compounds of the present invention is selected based on the disease or condition that is being treated. For example, in the treatment of melanoma, the other therapeutic agent may be selected from aldesleukin (e.g., PROLEUKIN®), dabrafenib (e.g., TAFINLAR®), dacarbazine, recombinant interferon alfa-2b (e.g., INTRON® A), ipilimumab, trametinib (e.g., MEKINIST®), peginterferon alfa-2b (e.g., PEGINTRON®, SYLATRON™), vemurafenib (e.g., ZELBORAF®)), and ipilimumab (e.g., YERVOY®).

For the treatment of ovarian cancer, the other therapeutic agent may be selected from doxorubicin hydrochloride (Adriamycin®), carboplatin (PARAPLATIN®), cyclophosphamide (CYTOXAN®, NEOSAR®), cisplatin (PLATINOL®, PLATINOL-AQ®), doxorubicin hydrochloride liposome (DOXIL®, DOX-SL®, EVACET®, LIPODOX®), gemcitabine hydrochloride (GEMZAR®), topotecan hydrochloride (HYCAMTIN®), and paclitaxel (TAXOL®).

For the treatment of thyroid cancer, the other therapeutic agent may be selected from doxorubicin hydrochloride (Adriamycin®), cabozantinib-S-malate (COMETRIQ®), and vandetanib (CAPRELSA®).

For the treatment of colon cancer, the other therapeutic may be selected from fluorouracil (e.g., ADRUCIL®, EFUDEX®, FLUOROPLEX®), bevacizumab (AVASTIN®), irinotecan hydrochloride (CAMPTOSAR®), capecitabine (XELODA®), cetuximab (ERBITUX®), oxaliplatin (ELOXATIN®), leucovorin calcium (WELLCOVORIN®), regorafenib (STIVARGA®), panitumumab (VECTIBIX®), and ziv-aflibercept (ZALTRAP®).

For the treatment of lung cancer, the other therapeutic may be selected from methotrexate, methotrexate LPF (e.g., FOLEX®, FOLEX PFS®, Abitrexate®, MEXATE®, MEXATE-AQ®), paclitaxel (TAXOL®), paclitaxel albumin-stabilized nanoparticle formulation (ABRAXANE®), afatinib dimaleate (GILOTRIF®), pemetrexed disodium (ALIMTA®), bevacizumab (AVASTIN®), carboplatin (PARAPLATIN®), cisplatin (PLATINOL®, PLATINOL-AQ®), crizotinib (XALKORI®), erlotinib hydrochloride (TARCEVA®), gefitinib (IRESSA®) and gemcitabine hydrochloride (GEMZAR®).

For the treatment of pancreatic cancer, the other therapeutic agent may be selected from fluorouracil (ADRUCIL®, EFUDEX®, FLUOROPLEX®), erlotinib hydrochloride (TARCEVA®), gemcitabine hydrochloride (GEMZAR®), and mitomycin or mitomycin C (MITOZYTREX™, MUTAMYCIN®).

For the treatment of cervical cancer, the other therapeutic agent may be selected from bleomycin (BLENOXANE®), cisplatin (PLATINOL®, PLATINOL-AQ®) and topotecan hydrochloride (HYCAMTIN®).

For the treatment of head and neck cancer, the other therapeutic agent may be selected from methotrexate, methotrexate LPF (e.g., FOLEX®, FOLEX PFS®, Abitrexate®, MEXATE®, MEXATE-AQ®), fluorouracil (ADRUCIL®, EFUDEX®, FLUOROPLEX®), bleomycin (BLENOXANE®), cetuximab (ERBITUX®), cisplatin (PLATINOL®, PLATINOL-AQ®) and docetaxel (TAXOTERE®).

For the treatment of leukemia, including chronic myelomonocytic leukemia (CMML), the other therapeutic agent can be selected from bosutinib (BOSULIF®), cyclophosphamide (CYTOXAN®, NEOSAR®), cytarabine (CYTOSAR-U®, TARABINE PFS®), dasatinib (SPRYCEL®), imatinib mesylate (GLEEVEC®), ponatinib (ICLUSIG®), nilotinib (TASIGNA®) and omacetaxine mepesuccinate (SYNRIBO®).

In another aspect, the present invention provides pharmaceutical compositions comprising at least one compound of the present invention (e.g., a compound of Formula (I) or a sub-formulae thereof) or a pharmaceutically acceptable salt thereof, together with a pharmaceutically acceptable carrier suitable for administration to a human or animal subject, either alone or together with other anti-cancer agents.

In combination therapies, compositions will either be formulated together as a combination therapeutic, or as separate compositions. The compound of the invention and the other therapeutic agent may be manufactured and/or formulated by the same or different manufacturers. The structure of therapeutic agents identified by code numbers, generic or trade names may be taken from the actual edition of the standard compendium "The Merck Index" or from databases, e.g. Patents International (e.g. IMS World Publications). The other therapeutic agents, which can be used in combination with a compound of the present invention, can be prepared and administered as described in the art, such as in the documents cited above.

Optionally, the pharmaceutical composition may comprise a pharmaceutically acceptable carrier, as described above. The pharmaceutical composition or combination of the present invention may, for example, be in unit dosage of about 0.5 mg to 1000 mg of active ingredient(s) for a subject of about 50-70 kg.

In another aspect, the present invention provides methods of treating human or animal subjects suffering from a cellular proliferative disease, such as cancer, comprising administering to the subject a therapeutically effective amount of a compound of the present invention or a pharmaceutically acceptable salt thereof, either alone or in combination with other anti-cancer agents. In combination therapy, the compound of the present invention and other anti-cancer agent(s) may be administered either simultaneously, concurrently or sequentially with no specific time limits, wherein such administration provides therapeutically effective levels of the two compounds in the body of the patient. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

In one embodiment, the compound of the present invention and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In yet another aspect, compounds of the present invention may be combined with other anti-cancer agents, anti-allergic agents, anti-nausea agents (or anti-emetics), pain relievers, cytoprotective agents, and combinations thereof.

In some instances, patients may experience allergic reactions to the compounds of the present invention and/or other anti-cancer agent(s) during or after administration. Therefore, anti-allergic agents may be administered to minimize the risk of an allergic reaction. Suitable anti-allergic agents include corticosteroids, such as dexamethasone (e.g., DECADRON®), beclomethasone (e.g., BECLOVENT®), hydrocortisone (also known as cortisone, hydrocortisone sodium succinate, hydrocortisone sodium phosphate; e.g., ALA-CORT®, hydrocortisone phosphate, Solu-CORTEF®, HYDROCORT Acetate® and LANACORT®), prednisolone (e.g., DELTA-Cortel®, ORAPRED®, PEDIAPRED® and PRELONE®), prednisone (e.g., DELTASONE®, LIQUID RED®, METICORTEN® and ORASONE®), methylprednisolone (also known as 6-methylprednisolone, methylprednisolone acetate, methylprednisolone sodium succinate; e.g., DURALONE®, MEDRALONE®, MEDROL®, M-PREDNISOL® and SOLU-MEDROL®); antihistamines, such as diphenhydramine (e.g., BENADRYL®), hydroxyzine, and cyproheptadine; and bronchodilators, such as the beta-adrenergic receptor agonists, albuterol (e.g., PROVENTIL®), and terbutaline (BRETHINE®).

In other instances, patients may experience nausea during and after administration of the compound of the present invention and/or other anti-cancer agent(s). Therefore, anti-emetics may be administered in preventing nausea (upper stomach) and vomiting. Suitable anti-emetics include aprepitant (EMEND®), ondansetron (ZOFRAN®), granisetron HCl (KYTRIL®), lorazepam (ATIVAN®. dexamethasone (DECADRON®), prochlorperazine (COMPAZINE®), casopitant (REZONIC® and Zunrisa®), and combinations thereof.

In yet other instances, medication to alleviate the pain experienced during the treatment period is prescribed to make the patient more comfortable. Common over-the-counter analgesics, such TYLENOL®, are often used. Opioid analgesic drugs such as hydrocodone/paracetamol or hydrocodone/acetaminophen (e.g., VICODIN®), morphine (e.g., ASTRAMORPH® or AVINZA®), oxycodone (e.g., OXYCONTIN® or PERCOCET®), oxymorphone hydrochloride (OPANA®), and fentanyl (e.g., DURAGESIC®) are also useful for moderate or severe pain.

Furthermore, cytoprotective agents (such as neuroprotectants, free-radical scavengers, cardioprotectors, anthracycline extravasation neutralizers, nutrients and the like) may be used as an adjunct therapy to protect normal cells from treatment toxicity and to limit organ toxicities. Suitable cytoprotective agents include amifostine (ETHYOL®), glutamine, dimesna (TAVOCEPT®), mesna (MESNEX®), dexrazoxane (ZINECARD® or TOTECT®), xaliproden (XAPRILA®), and leucovorin (also known as calcium leucovorin, citrovorum factor and folinic acid).

In yet another aspect, a compound of the present invention may be used in combination with known therapeutic processes, for example, with the administration of hormones or in radiation therapy. In certain instances, a compound of the present invention may be used as a radiosensitizer, especially for the treatment of tumors which exhibit poor sensitivity to radiotherapy.

In yet another aspect, the present invention provides kits comprising one or more compounds of the present invention and another therapeutic agent as described above. Representative kits include (a) compound of Formula (I) or sub-formulae thereof or a pharmaceutically acceptable salt thereof, and (b) at least one other therapeutic agent e.g., as indicated above; whereby such kit may further comprise a package insert or other labeling including directions for administration.

The kits of the invention may be used for administering different dosage forms, for example, oral and parenteral; for administering two or more separate pharmaceutical compositions at different dosage intervals; or for titrating the separate compositions against one another; wherein at least one pharmaceutical composition comprises a compound a Formula (I) or sub-formulae thereof.

EXAMPLES

Temperatures are given in degrees Celsius. The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Unless otherwise specified, starting materials are generally available from commercial sources.

The Examples herein merely illuminate the invention and does not limit the scope of the invention otherwise claimed. Further, the compounds of the present invention can be produced by organic synthesis methods known to one of ordinary skill in the art as shown in the following examples. Where desired, conventional protecting groups are used to protect reactive functional groups in accordance with standard practice, for example, see T. W. Greene and P. G. M. Wuts in "Protecting Groups in Organic Synthesis", John Wiley and Sons, 1991.

Abbreviations

Abbreviations as used herein, are defined as follows: "1×" for once, "2×" for twice, "3×" for thrice, "° C." for degrees Celsius, "aq" for aqueous, "FCC" for flash column chromatography, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" or "hrs" for hour or hours, "RT" for room temperature, "ON" for overnight, "atm" for atmosphere, "psi" for pounds per square inch, "conc." for concentrate, "sat" or "sat'd" for saturated, "MW" for molecular weight, "mw" or "μwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" or "LC-MS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, "ee" for "enantiomeric excess" and "α", "β", "R", "r", "S", "s", "E", and "Z" are stereochemical designations familiar to one skilled in the art.

The following abbreviations used herein below have the corresponding meanings:
Δ heat
Boc tert-butyloxycarbonyl
Boc$_2$O di-tert butyl dicarbonate
BPO benzoyl peroxide
BSA bovine serum albumin
CDCl$_3$ chloroform-d
CD$_3$OD methanol-d$_4$
dd doublet of doublets
DCM dichloromethane
DEAD Diethyl azodicarboxylate
DIAD diisopropyl azodicarboxylate
DIBAL-H di-isobutyl aluminum hydride
DIEA N,N-diisopropyl ethylamine
DMAP 4-dimethylaminopyridine
DMF dimethylformamide
DMF-DMA dimethylformamide dimethylacetal
DMHA N,O-dimethylhydroxyamine
DMSO dimethylsulfoxide
DTAD azodicarboxylic acid di-tert butyl ester
EA ethyl alcohol
EDC, EDC·HCl N-(3-dimethylaminopropyl)-N'-ethylcarbodiimide hydrochloride
EtI ethyl iodide
EtOAc ethyl acetate
EtOH ethanol
FBS fetal bovine serum HATU Hexafluorophosphate Azabenzotriazole Tetramethyl Uronium)
HOAc acetic acid
HOBt hydroxybenzotriazole
IPA isopropyl alcohol
ISCO in situ chemical oxidation
LAH lithium aluminum hydride
LDA lithium diisopropylamide
MeOH methanol
MsCl methane sulfonyl chloride
MTBE methyl tert-butyl ether
MHz megahertz
min minutes
m/z mass to charge ratio
NBS N-bromosuccinimide
NCS N-chlorosuccinimide
NMM N-methyl morpholine
PBu$_3$ tributylphosphine
PE petroleum ether
ppm parts per million
rac racemic
SFC Supercritical fluid chromatography
T3P® propylphosphonic anhydride solution
TBAF tetra-n-butylammonium fluoride
TBAI tetra-n-butyl ammonium iodide
TBDPSCl tert-butyl(chloro)diphenylsilane
TBSCl tert-butyl dimethylsilyl chloride
TEA triethylamine
TFA trifluoroacetic acid
THF tetrahydrofuran
TMSCl trimethylsilyl chloride
UV ultraviolet High performance liquid chromatography (HPLC) was performed using an Agilent 1260 HPLC System (Santa Clara, CA). The analytical column was reversed phase Phenomenex Kinetex C18-2.6 µm, 4.6×50 mm. A gradient elution was used (flow rate 2 mL/min), starting with 5% methanol/95% water and progressing to 95% methanol/5% water over a period of 10 minutes. All solvents contained 0.1% formic acid (FA). Compounds were detected by ultraviolet light (UV) absorption at 214, 254 and 300 nm. HPLC solvents were purchased from Sigma Aldrich (St. Louis, MO).

Mass spectrometric analysis was performed on an Agilent System (Agilent 1260 HPLC and an Agilent 6130 mass spectrometer detector; Column: Phenomenex Kinetex 2.6 um C18, column size 4.6×50 mm; column temperature 40° C.; gradient: 5 95% methanol in water with 0.1% FA over a 2 min period; flow rate 2 mL/min (or Polar gradient 5-50% over 2 min, or Non-Polar gradient 50-95% over 2 min); Mass Spectrometer molecular weight scan range 100 1000; or 100-1500; capillary voltage 4000 V. All masses were reported as those of the protonated parent ions, unless otherwise indicated.

Nuclear magnetic resonance (NMR) analysis was performed using a Bruker 400 MHz NMR. The spectral reference was either TMS or the known chemical shift of the solvent.

Chiral Preparative HPLC Methods Employed in Purification of Examples

SFC chiral screening was carried out on a Thar Instruments Investigator system. The Thar Investigator system consists of:
ALIAS autosampler
Thar Fluid Delivery Module (0 to 10 mL/min)
Thar SFC 10 position column oven
Waters 2998 PDA
Thar Automated Back Pressure Regulator All of the Thar components are part of the SuperPure Discovery Series line. The system flowed at 3 mL/min and kept at 38° C. The system back pressure was set to 100 bar. Each sample was screened through a battery of ten 5 μm columns:

5 μm 4.6×150 mm ChiralPak AD
5 μm 4.6×150 mm ChiralCel OD
5 μm 4.6×150 mm ChiralCel OJ
5 μm 4.6×150 mm ChiralPak AS
5 μm 4.6×250 mm ChiralPak AY
5 μm 4.6×250 mm ChiralCel OZ
5 μm 4.6×150 mm ChiralPak IC
5 μm 4.6×150 mm ChiralPak IG
5 μm 4.6×250 mm Regis Whelk-O1
5 μm 4.6×250 mm ChromegaChiral CC4

The system ran a gradient from 5% co-solvent to 50% co-solvent in 9 minutes followed by a 10 minutes hold at 50% co-solvent, a switch back to 5% co-solvent and a 0.5 minute hold at initial condition. In between each gradient there was a 4 minute equilibration method that flows 5% co-solvent through the next column to be screened. The typical solvents screened were, MeOH, EtOH, IPA, MeOH+ 0.5% $NH_3$, EtOH+0.5% $NH_3$, IPA+0.1% $NH_3$. Once separation was detected using one of the gradient methods, an isocratic method can be developed, and if necessary, scaled up for separation on the Thar Prep 80 system.

INTERMEDIATES

Intermediate A: 2,3-dichloro-6-hydroxybenzaldehyde

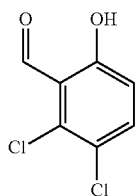 [SMILES: O=Cc1c(O)ccc(Cl)c1Cl]

Step 1. 3,4-dichlorophenyl diethylcarbamate (A-2)

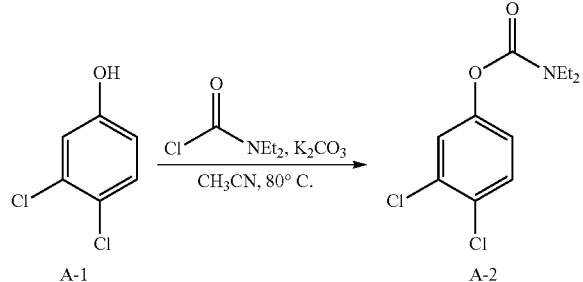

To a mixture of A-1 (500 g, 3.1 mol) and $K_2CO_3$ (847.9 g, 6.1 mol) in acetonitrile (2 L) was added diethylcarbamic chloride (623.8 g, 4.60 mol) at rt. The reaction mixture was then stirred at 80° C. for 2 h. Water (1 L) was added to the reaction and the reaction mixture was extracted with EtOAc. The organic layer was dried over $Na_2SO_4$ and filtered off. The filtrate was concentrated under vacuum to give the crude product. The crude residue was purified by flash chromatography to afford compound A-2 as a colorless oil. $^1$H NMR (400 MHz, $CDCl_3$): δ 7.41 (d, J=9.20 Hz, 1H), 7.28 (d, J=3.20 Hz, 1H), 7.01 (dd, J=8.60, 2.40 Hz, 1H), 3.40 (dq, J=7.20 Hz, 4H), 1.18-1.26 (m, 6H).

Step 2. 2,3-dichloro-6-hydroxybenzaldehyde (A)

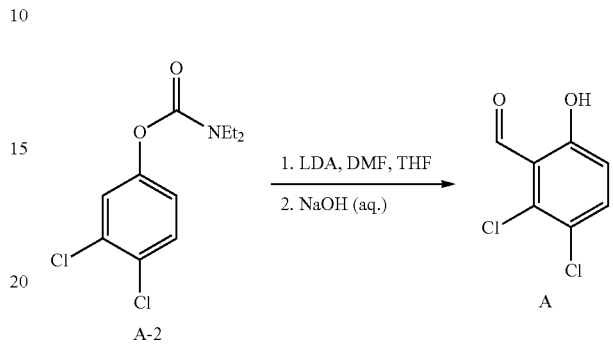

To a solution of A-2 (145 g, 553.2 mmol) in tetrahydrofuran (2 L) was added dropwise LDA (331.9 mL, 663.8 mmol) at −78° C. under $N_2$. After 1 h, dimethylformamide (86 mL, 1110 mmol) was added dropwise at −78° C. and the mixture was stirred for another 1.5 h before warming up to 0° C. The mixture was quenched with 1N NaOH (1 L). The mixture was stirred for another 1 h and then acidified with 1N HCl to pH=2. The mixture was extracted with EtOAc. The organic layer was dried over $Na_2SO_4$ and filtered off. The filtrate was concentrated under vacuum to give the crude residue. The crude product was purified by flash chromatography to afford Intermediate A as a yellow solid. $^1$H NMR (400 MHz, $CDCl_3$): δ 11.98 (s, 1H), 10.44 (s, 1H), 7.56 (d, J=9.20 Hz, 1H), 6.90 (d, J=9.20 Hz, 1H).

Intermediate B: tert-butyl (tert-butoxycarbonyl)(9H-purin-6-yl)carbamate

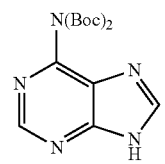

Step 1. 6-Chloro-5-iodopyrazine-2-amine

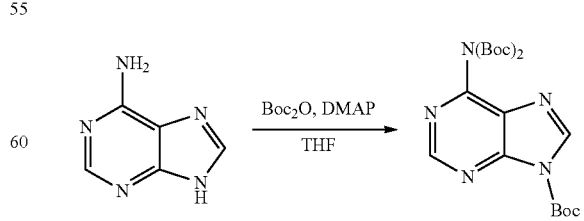

To a solution of 9H-purin-6-amine (100 g, 740 mmol) and DMAP (9.04 g, 74 mmol) in THF (2 L) were added dropwise $Boc_2O$ (647 g, 2.96 mol) and the reaction mixture was stirred at 10-15° C. for 16 hours. The mixture was concentrated under vacuum to give the crude product, which was directly used for the next step without further purification. ¹H NMR (400 MHz, CDCl₃): δ 9.01 (s, 1H) 8.51 (s, 1H), 1.71 (s, 9H), 1.43 (s, 18H).

Step 2. tert-butyl (tert-butoxycarbonyl)(9H-purin-6-yl)carbamate

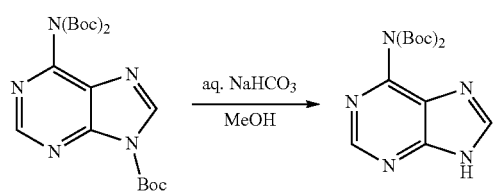

To a solution of 6-Chloro-5-iodopyrazine-2-amine (500 g, 1.15 mol) in MeOH (1.5 L) was added a saturated solution of NaHCO₃ (0.5 L) and the reaction mixture was stirred at 40-50° C. for 2 h. MeOH was removed under reduced pressure. Water (1 L) was added and the mixture was filtered off. The crude solid was washed with MTBE (0.5 L) and dried under vacuum to give tert-butyl (tert-butoxycarbonyl)(9H-purin-6-yl)carbamate as a white solid. ¹H NMR (400 MHz, DMSO-d₆): δ 8.85 (s, 1H), 8.41 (s, 1H), 1.52 (s, 18H).

Intermediate C: tert-butyl (R)-(tert-butoxycarbonyl) (9-(6-hydroxy-2,3-dichlorobenzyl)-9H-purin-6-yl) carbamate

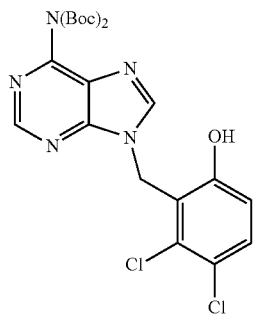

Step 1. 6-(allyloxy)-2,3-dichlorobenzaldehyde (C-2)

To a mixture of 2,3-dichloro-6-hydroxybenzaldehyde (Intermediate A) (11 g, 57.6 mmol), and K₂CO₃ (15.9 g, 115.2 mmol) in CH₃CN (200 mL) was added allyl bromide (13.9 g, 115.2 mmol) at rt. The reaction mixture was then stirred at 40° C. for 12 hours. After cooling down to rt, the reaction mixture was quenched with H₂O and extracted with EtOAc. The organic layer was dried over anhydrous Na₂SO₄, and concentrated under vacuum to give a crude mixture. The crude product was purified by flash chromatography to afford C-2 as a colorless solid. ¹H NMR (400 MHz, CDCl₃): δ 10.49 (s, 1H), 7.54 (d, J=8.8 Hz, 1H), 6.88 (d, J=9.2 Hz, 1H), 6.07-5.97 (m, 1H), 5.48-5.33 (m, 2H), 4.65-4.63 (m, 2H).

Step 2. (6-(allyloxy)-2,3-dichlorophenyl)methanol (C-3)

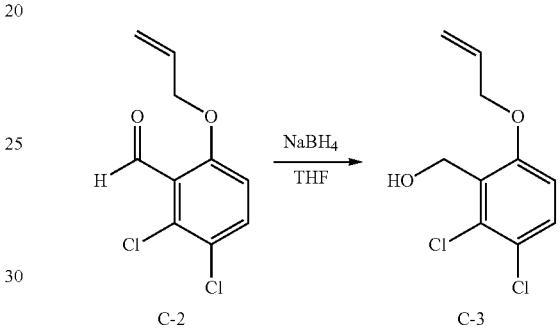

To a solution of C-2 (12 g, 51.9 mmol) in THF (200 mL) was added NaBH₄ (5.9 g, 155.8 mmol) in small portions. After addition, the reaction mixture was stirred at 8-10° C. for 2 hours. The reaction mixture was then quenched with saturated NH₄Cl (50 mL), and extracted with EtOAc. The organic layer was washed with brine, dried over anhydrous Na₂SO₄, filtered and concentrated to give C-3 as a colorless oil. ¹H NMR (400 MHz, CDCl₃): δ 7.35 (d, J=8.8 Hz, 1H), 6.78 (d, J=8.8 Hz, 1H), 6.08-6.00 (m, 1H), 5.44-5.40 (m, 1H), 5.33-5.35 (m, 1H), 4.93 (d, J=7.2 Hz, 2H), 4.60-4.59 (m, 2H), 2.36 (t, J=7.0 Hz, 1H)

Step 3. tert-butyl (R)-(tert-butoxycarbonyl)(9-(6-(allyloxy)-2,3-dichlorobenzyl)-9H-purin-6-yl)carbamate

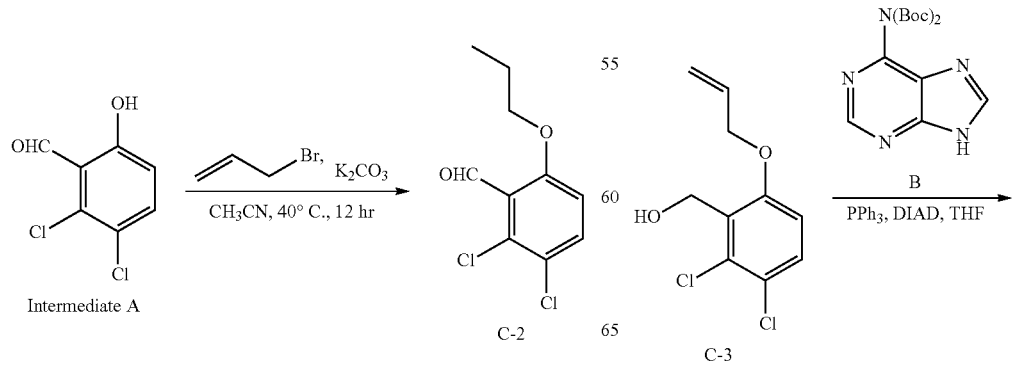

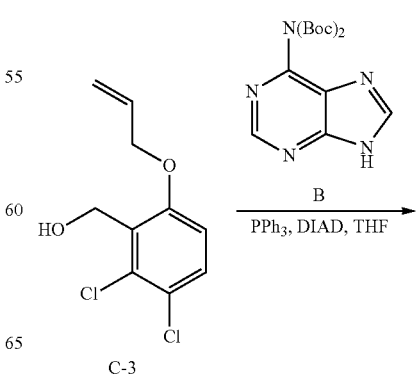

-continued

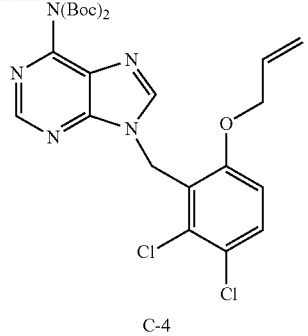

C-4

To a solution of C-3 (11 g, 47.2 mmol), intermediate B (16.6 g, 49.6 mmol) and PPh$_3$ (24.8 g, 17.2 mmol) in anhydrous THF (350 mL) was added DIAD (19.1 g, 17.2 mmol) dropwise at 0° C. After addition, the reaction mixture was stirred at 30° C. for 12 hours. The mixture was concentrated under vacuum to give a crude product. The residue was purified by flash chromatography to give C-4 as a yellow solid. $^1$H NMR (400 MHz, CDCl$_3$): δ 8.90 (s, 1H), 7.97 (s, 1H), 7.46 (d, J=9.2 Hz, 1H), 6.84 d, J=8.8 Hz, 1H), 5.93-5.85 (m, 1H), 5.34-5.26 (m, 2H), 4.56-4.55 (m, 2H), 4.15-4.10 (m, 2H), 1.44 (s, 18H).

Step 4. tert-butyl (R)-(tert-butoxycarbonyl)(9-(6-hydroxy-2,3-dichlorobenzyl)-9H-purin-6-yl)carbamate (C)

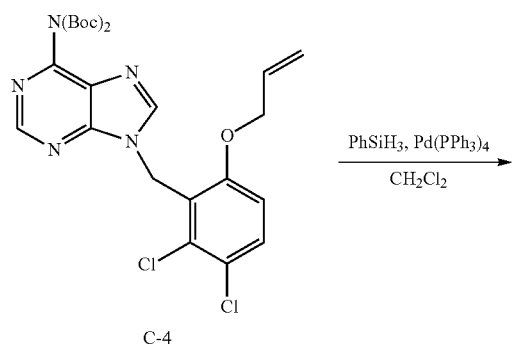

To a solution of C-4 (1.8 g, 3.3 mmol) and PhSiH$_3$ (1.1 g, 9.9 mmol) in DCM (30 mL) was added Pd(PPh$_3$)$_4$ (113.4 mg, 0.98 mmol) under N$_2$ at 3-8° C. The reaction mixture was stirred at 3-8° C. for 30 min, and the mixture was concentrated under vacuum to give the crude intermediate C (2.2 g, crude) as a brown oil. The crude was used for the next step without further purification. LC-MS: [M+H]$^+$=510.0.

Intermediate D: tert-butyl (R)-(5-iodo-1-methoxy-pentan-2-yl)carbamate

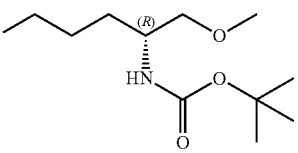

Step 1. (R)-tert-butyl 2-(tert-butoxycarbonylamino)-5-hydroxypentanoate (D-2)

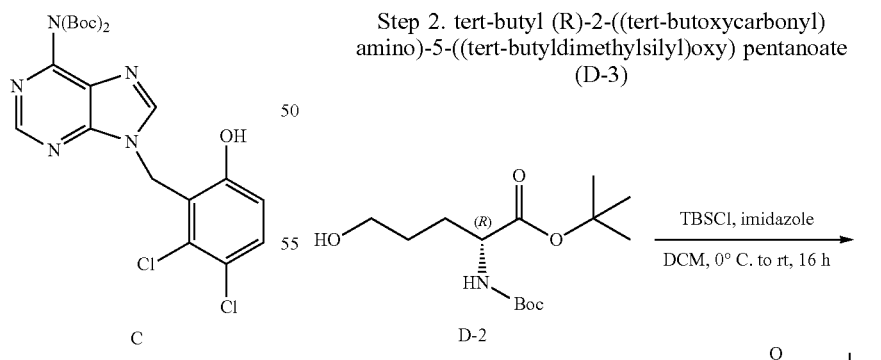

To a solution of D-1 (50 g, 0.16 mol) and NMM (33 g, 0.33 mol) in of THF (1 L) was added isobutyl carbonochloridate (36 g, 0.26 mol) at −10° C. and stirred for 1 h. The white solid was filtered off and the filtrate was added NaBH$_4$ (10 g, 0.26 mol) in portions at 0° C. The solution was stirred for another 1 hour. The resulting solution was added water (100 mL), stirred for 30 mins and adjusted to pH 4 with 1M HCl. The mixture was extracted with EtOAc (200 mL), washed with 1M NaOH, water and brine. The organic layer was dried over Na$_2$SO$_4$ and concentrated under vacuum to give D-2 as a colorless oil. LC-MS: [M+Na]$^+$=311.9.

Step 2. tert-butyl (R)-2-((tert-butoxycarbonyl)amino)-5-((tert-butyldimethylsilyl)oxy) pentanoate (D-3)

To a solution of D-2 (12.8 g, 76% purity, 34 mmol) and imidazole (4.5 g, 66 mmol) in DCM (100 mL) was added TBSCl (6.67 g, 44 mmol) at 0° C. and the solution was stirred for 16 hours.

The reaction was washed with water. The organic layer was dried over Na$_2$SO$_4$, filtered and concentrated under vacuum to give the crude product. The crude residue was purified by flash column to give D-3 as a colorless oil. $^1$H NMR (400 MHz, CDCl$_3$) δ 5.14-5.16 (m, 1H), 4.18-4.20 (m, 1H), 3.63-3.66 (m, 2H), 1.85-1.87 (m, 1H), 1.54-1.63 (m, 3H), 1.48 (s, 9H), 1.46 (s, 9H), 0.91 (s, 9H), 0.07 (s, 6H). LC-MS: [M+Na]$^+$=425.9.

Step 3. (R)-tert-butyl 5-(tert-butyldimethylsilyloxy)-1-hydroxypentan-2-ylcarbamate (D-4)

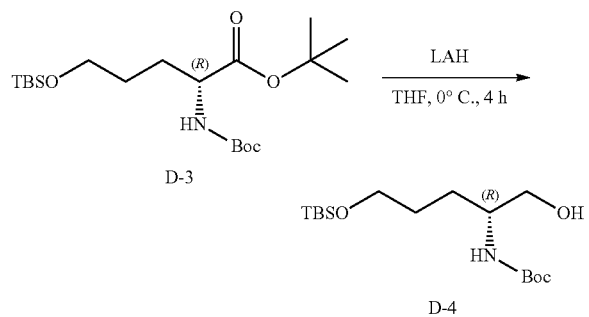

To a solution of D-3 (10.0 g, 25 mmol) in THF (200 mL) was added LAH (2.7 g, 71 mmol) in THF (100 mL) at −5° C. and stirred at 0° C. for 4 hours. The reaction mixture was carefully quenched with water (3 mL), followed by 15% NaOH (3 mL) and water (9 mL). The mixture was stirred for 20 mins, and filtered through a pad of celite. The filtrate was concentrated under vacuum and purified by flash chromatography to give D-4 as a colorless thick oil. $^1$H NMR (400 MHz, CDCl$_3$) δ 4.84 (m, 1H), 3.54-3.68 (m, 5H), 2.00 (bs, 1H), 1.48-1.65 (m, 4H), 1.45 (s, 9H), 0.90 (s, 9H), 0.06 (s, 6H). LC-MS: [M+Na]$^+$=355.9.

Step 4. tert-butyl (R)-(5-((tert-butyldimethylsilyl)oxy)-1-methoxypentan-2-yl)carbamate (D-5)

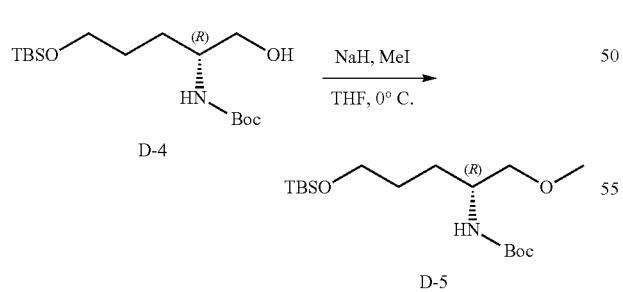

To a solution of D-4 (4.9 g, 15 mmol) and methyl iodide (2.5 g, 18 mmol) in THF (200 mL) was added NaH (1.1 g, 28 mmol) at 0° C. The mixture was stirred for 2 hrs at 0° C. The reaction was added H$_2$O (100 mL) and extracted with EtOAc. The organic layer was washed with brine, dried over Na$_2$SO$_4$, filtered and concentrated to give a residue. The residue was purified by flash chromatography to give D-5 as a colorless oil. $^1$H NMR (400 MHz, CDCl$_3$) δ 4.74 (s, 1H), 3.69 (s, 1H), 3.62 (t, J=6.0 Hz, 2H), 3.43-3.33 (m, 5H), 1.65-1.53 (m, 4H), 1.46-1.44 (m, 9H), 0.90 (s, 9H), 0.05 (s, 6H). LC-MS: [M+Na]$^+$=369.9.

Step 5. tert-butyl (R)-(5-hydroxy-1-methoxypentan-2-yl)carbamate (D-6)

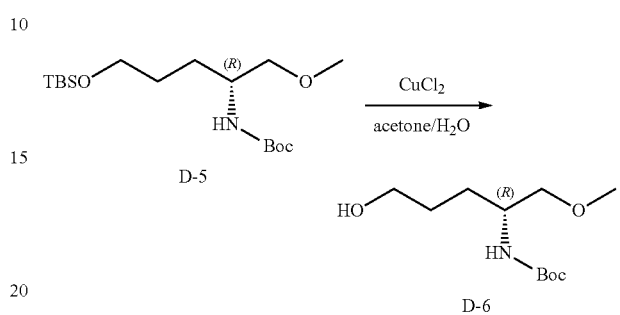

To a solution of D-5 (3.8 g, 11 mmol) in acetone (35 mL) and water (1.5 mL) was added CuCl$_2$ (0.25 g, 1.9 mmol). The mixture was stirred at 80° C. for 2 hours. The reaction mixture was directly concentrated to give the crude product. The crude residue was purified by flash chromatography to give D-6 as a brown thick oil. $^1$H NMR (400 MHz, CDCl$_3$) δ 4.76 (m, 1H), 3.69-3.3.67 (m, 3H), 3.35-3.39 (m, 5H), 1.59-1.65 (m, 5H), 1.44 (s, 9H). LC-MS: [M+Na]$^+$=256.0.

Step 6. tert-butyl (R)-(5-iodo-1-methoxypentan-2-yl)carbamate (D)

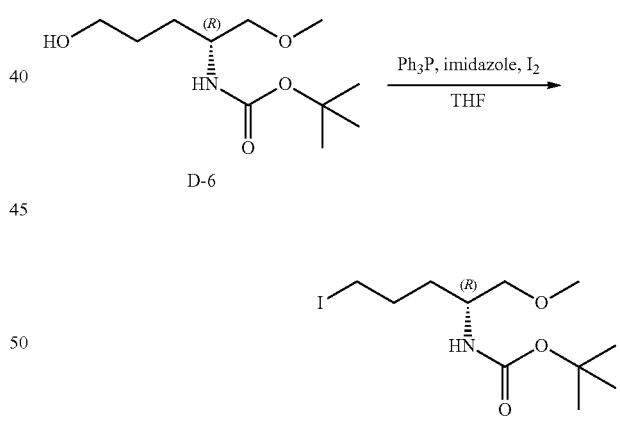

To a mixture of D-6 (2 g, 7.65 mmol), imidazole (625.2 mg, 9.2 mmol) and PPh$_3$ (2.4 g, 9.2 mmol) in THF (50 mL) was added I$_2$ (2.9 g, 11.5 mmol). The mixture was stirred at room temperature for 2 hours. The reaction mixture was quenched by saturated Na$_2$SO$_3$ and extracted with EtOAc. The organic extracts was dried over Na$_2$SO$_4$ and concentrated under vacuum to give a crude product. The crude residue was purified by flash chromatography to afford Intermediate D as an off-yellow oil. $^1$H NMR (400 MHz, CDCl$_3$): δ 4.73 (d, J=8.0 Hz, 1H), 3.72 (brs, 1H), 3.37-3.35 (m, 5H), 3.23-3.19 (m, 2H), 1.93-1.53 (m, 4H), 1.46 (s, 9H).

Intermediate E: tert-butyl (R)-2-((tert-butoxycarbonyl)amino)-5-iodopentanoate

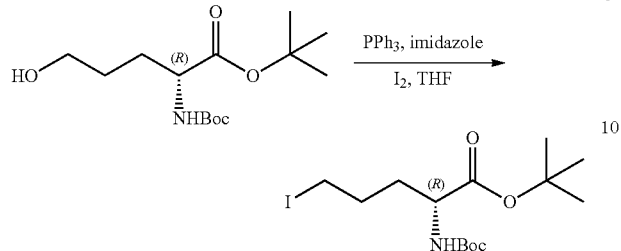

To tert-butyl (R)-2-((tert-butoxycarbonyl)amino)-5-hydroxypentanoate (20 g, 69.1 mmol, 1 eq), PPh$_3$ (21.7 g, 82.9 mmol, 1.2 eq) and imidazole (5.6 g, 82.9 mmol, 1.2 eq) in tetrahydrofuran (500 mL) were added portionwise iodine (21 g, 82.9 mmol, 1.2 eq) over 10 min at 5-11° C. The mixture was stirred for 12 h at 5-11° C. The mixture was filtered off and evaporated under vacuum. The crude was purified by column chromatography over silica gel (eluent: hexane:ethyl acetate=10:1) to afford tert-butyl (R)-2-((tert-butoxycarbonyl)amino)-5-iodopentanoate as a yellow oil. $^1$H NMR (CDCl$_3$ 400 MHz): δ 5.09-5.05 (m, 1H), 4.25-4.20 (m, 1H), 3.27-3.17 (m, 1H), 1.97-1.76 (m, 4H), 1.50 (s, 9H), 1.47 (s, 9H).

Intermediate F: (R)-2-((tert-butoxycarbonyl)amino)-5-(2-(((6-((tert-butoxycarbonyl)amino)-9H-purin-9-yl)methyl)-3,4-dichlorophenoxy)pentanoic acid

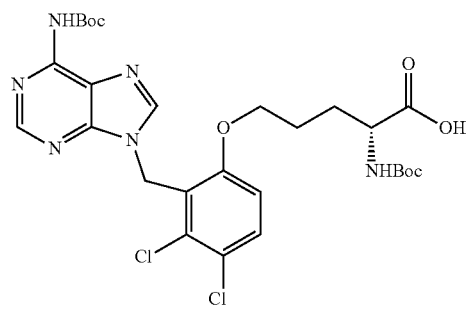 [SMILES: CC(C)(C)OC(=O)Nc1ncnc2c1ncn2Cc1c(OCCC[C@@H](NC(=O)OC(C)(C)C)C(=O)O)ccc(Cl)c1Cl]

Step 1: tert-butyl (R)-2-((tert-butoxycarbonyl)amino)-5-(3,4-dichloro-2-formylphenoxy)pentanoate (F-3)

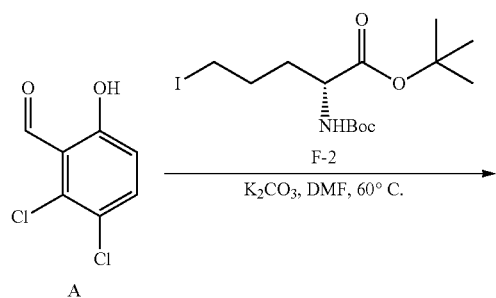

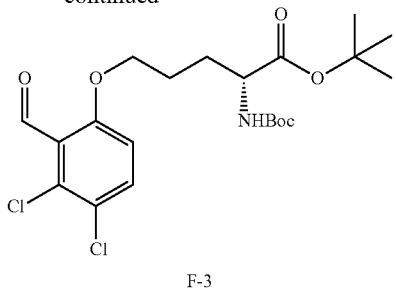

F-3

2,3-dichloro-6-hydroxybenzaldehyde (Intermediate A) (100 g, 1 mol), ((tert-butyl (R)-2-((tert-butoxycarbonyl)amino)-5-iodopentanoate (intermediate E) (230 g, 1.15 mol) and K$_2$CO$_3$ (150 g, 2.1 mol) in DMF (1.5 L) were stirred at 80° C. for 2 hrs. The reaction was quenched with H$_2$O and extracted with ethyl acetate. The organic layer was washed with brine, dried over Na$_2$SO$_4$ and filtered off. The filtrate was concentrated under vacuum to afford crude F-3 which was used for the next step without further purification. $^1$H NMR (400 MHz, CDCl$_3$): δ 10.46 (s, 1H), 7.55 (d, J=9.20 Hz, 1H), 6.88 (d, J=9.20 Hz, 1H), 5.07-5.22 (m, 1H), 4.19-4.29 (m, 1H), 4.06-4.12 (m, 2H), 1.81-2.01 (m, 4H), 1.47 (s, 9H), 1.45 (s, 9H).

Step 2: tert-butyl (R)-2-((tert-butoxycarbonyl)amino)-5-(3,4-dichloro-2-(hydroxymethyl)phenoxy)pentanoate (F-4)

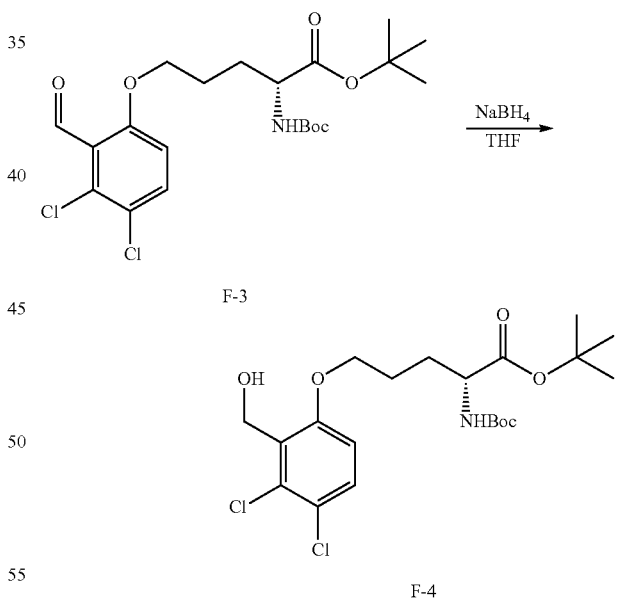

To a THF solution (1.5 L) of F-3 (270 g each, 1.2 mol) was added sodium borohydride (26.5 g, 1.4 mmol) in portion over 0.5 h at 0° C. The mixture was stirred for 1 h at 0° C. The mixture was quenched with 10% NH$_4$Cl and extracted with ethyl acetate. The organic layer was dried over Na$_2$SO$_4$ and filtered off. The filtrate was concentrated under vacuum and the crude was purified by column chromatography over silica gel (7% to 20% EA in Hex) to afford F-4 as a yellow oil. $^1$H NMR (400 MHz, CDCl$_3$): δ 7.31-7.37 (m, 1H), 6.75 (d, J=8.40 Hz, 1H), 5.18 (d, J=7.60 Hz, 1H), 4.89 (s, 2H), 4.26 (d, J=6.00 Hz, 1H), 4.05 (t, J=5.60 Hz, 2H), 2.50-2.74 (m, 1H), 1.75-2.02 (m, 4H), 1.47 (s, 9H), 1.43 (s, 9H).

Step 3: tert-butyl (R)-5-(2-((6-(bis(tert-butoxycarbonyl)amino)-9H-purin-9-yl)methyl)-3,4-dichlorophenoxy)-2-((tert-butoxycarbonyl)amino)pentanoate (F-5)

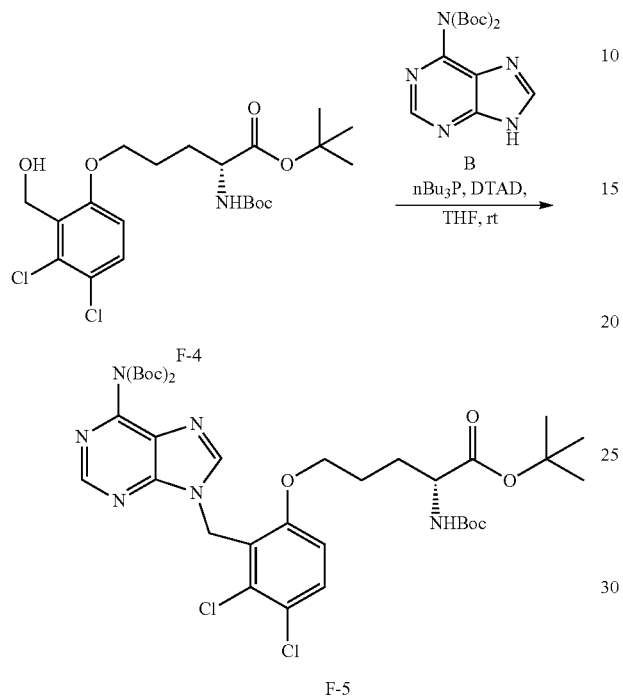

To a THF solution (1.5 L) of F-4 (120.0 g, 258.4 mmol) and intermediate B (104 g, 310.1 mmol) was added dropwise nBu₃P (140 mL, 516.8 mmol) and DTAD (120 g, 516.8 mmol). The mixture was stirred for 18 hrs at 7-14° C. The mixture was concentrated under vacuum and the crude was purified by column chromatography over silica gel (25% EA in hexanes) to afford tert-butyl (R)-5-(2-((6-(bis(tert-butoxycarbonyl)amino)-9H-purin-9-yl)methyl)-3,4-dichlorophenoxy)-2-((tert-butoxycarbonyl)amino)pentanoate F-5. ¹H NMR (400 MHz, CDCl₃): δ 8.91 (s, 1H), 7.97 (s, 1H), 7.45 (d, J=8.80 Hz, 1H), 6.82 (d, J=9.20 Hz, 1H), 5.65 (s, 2H), 5.20 (d, J=7.60 Hz, 1H), 4.18 (d, J=5.60 Hz, 1H), 4.01 (t, J=5.40 Hz, 2H), 1.89-1.99 (m, 1H), 1.70-1.82 (m, 3H), 1.43 (s, 36H).

Step 4: (R)-2-((tert-butoxycarbonyl)amino)-5-(2-((6-((tert-butoxycarbonyl)amino)-9H-purin-9-yl)methyl)-3,4-dichlorophenoxy)pentanoic acid (F)

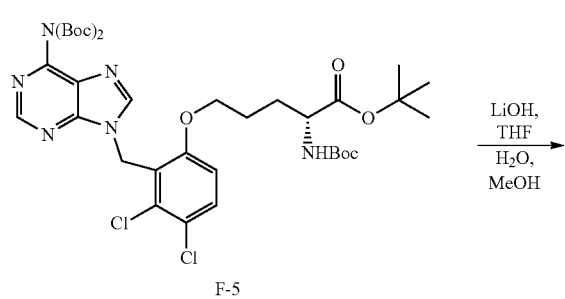

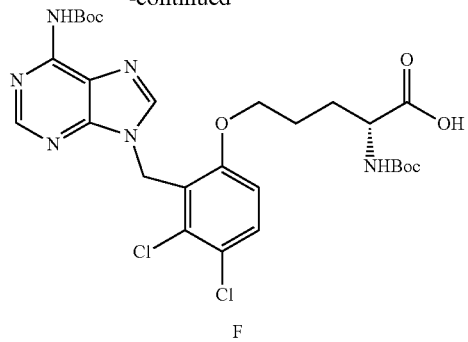

To a solution of MeOH and THF (200 mL, 1:1) of tert-butyl (R)-5-(2-((6-(bis(tert-butoxycarbonyl)amino)-9H-purin-9-yl)methyl)-3,4-dichlorophenoxy)-2-((tert-butoxycarbonyl)amino)pentanoate (F-5) (20 g, 25.6 mmol) was added LiOH (10.7 g, 255.8 mmol) in water (100 mL) at 9-14° C., and the solution was stirred for 60 hrs. The solvent was removed under vacuum. Ethyl acetate (500 mL) was added, and the mixture was adjusted to pH 7 using 6 N HCl. The organic layer was dried over Na₂SO₄ and concentrated under vacuum to afford intermediate F as a pink gum. ¹H NMR (400 MHz, DMSO-d₆): δ 10.07 (s, 1H), 8.57 (s, 1H), 8.28 (s, 1H), 7.61 (d, J=8.80 Hz, 1H), 7.08 (d, J=9.20 Hz, 1H), 6.23 (s, 1H), 5.57 (s, 2H), 4.06-4.01 (m, 3H), 3.65-3.58 (m, 1H), 1.99-1.67 (m, 4H), 1.47 (s, 9H), 1.36 (s, 9H).

Intermediate G: 7-bromo-4-(methylthio)imidazo[2,1-f][1,2,4]triazine

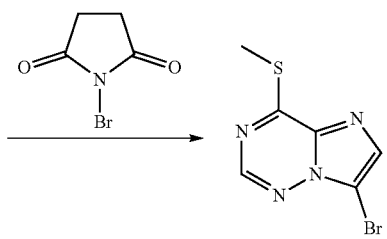

A mixture of 4-(methylthio)imidazo[2,1-j][1,2,4]triazine (3.5 g, 21.1 mmol) and NBS (5.6 g, 31.6 mmol) in DMF (60 mL) was stirred at r.t. for 2 hr. The reaction mixture was diluted with EtOAc, washed with sat. NaHCO₃ aq. solution and brine, dried, filtered and concentrated. ISCO (silica gel, 0-30% EtOAc in hexanes) to afford 7-bromo-4-(methylthio)imidazo[2,1-f][1,2,4]triazine as a white solid. LCMS ESI m/z M/M+2=245.0/247.0.

Intermediate H: Methyl (R)-2-((tert-butoxycarbonyl)amino)-5-(3,4-dichloro-2-formylphenoxy)pentanoate

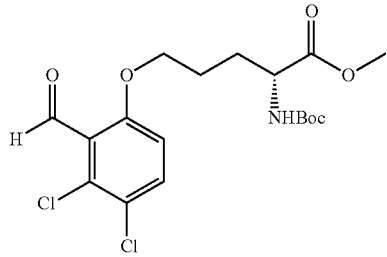 [SMILES: COC(=O)[C@@H](CCCOc1ccc(Cl)c(Cl)c1C=O)NC(=O)OC(C)(C)C]

Step 1. Methyl (R)-2-((tert-butoxycarbonyl)amino)-5-iodopentanoate

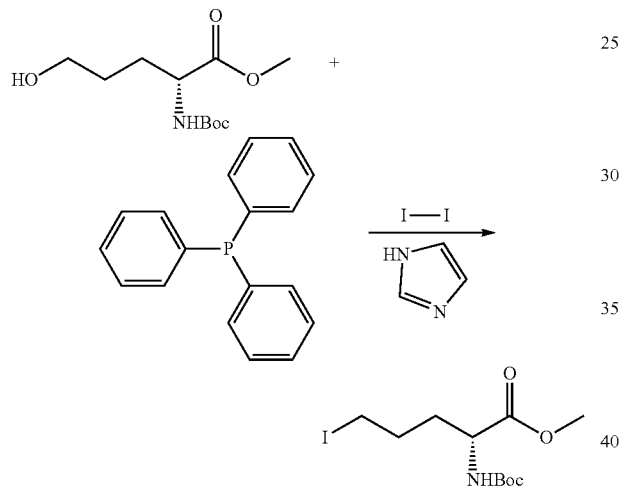

At 0° C., to a solution of triphenylphosphine (2.5 g, 9.7 mmol) and imidazole (0.66 g, 9.71 mmol) in DCM (25 mL) was added iodine (2.463 g, 9.71 mmol). The resulting mixture was stirred at r.t. for 15 min and cooled down to 0° C. A solution of methyl (R)-2-((tert-butoxycarbonyl)amino)-5-hydroxypentanoate (1.2 g, 4.85 mmol) in DCM (5 mL) was introduced and the reaction mixture was stirred at r.t. for 3 hr. The reaction mixture was diluted with ether, stirred at r.t. for 30 min, filtered. The filtrate was concentrated. ISCO (silica gel, 0-30% EtOAc in hexanes) to afford methyl (R)-2-((tert-butoxycarbonyl)amino)-5-iodopentanoate as a colorless oil. LCMS ESI m/z M+1 (−100)=257.9.

Step 2. Methyl (R)-2-((tert-butoxycarbonyl)amino)-5-(3,4-dichloro-2-formylphenoxy)pentanoate

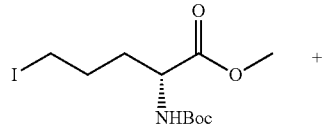

-continued

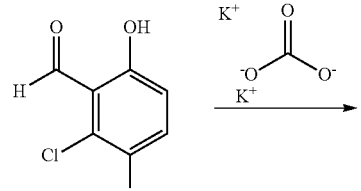

A mixture of methyl (R)-2-((tert-butoxycarbonyl)amino)-5-iodopentanoate (1.4 g, 3.8 mmol), potassium carbonate (1.1 g, 7.6 mmol) and 2,3-dichloro-6-hydroxybenzaldehyde (Intermediate A) (0.87 g, 4.6 mmol) in DMF (15 mL) was stirred at 60° C. overnight. The reaction mixture was diluted with EtOAc, washed with water and brine, dried, filtered and concentrated. ISCO (silica gel, 0-30% EtOAc in hexanes) to afford methyl (R)-2-((tert-butoxycarbonyl)amino)-5-(3,4-dichloro-2-formylphenoxy)pentanoate as a colorless oil. LCMS ESI m/z M/M+2=319.9/321.9.

Intermediate I: tert-butyl (R)-(5-((6-bromo-1-(hydroxymethyl)naphthalen-2-yl)oxy)-1-methoxypentan-2-yl)carbamate

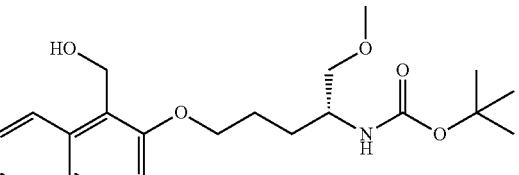

Step 1. 6-bromo-2-hydroxy-1-naphthaldehyde

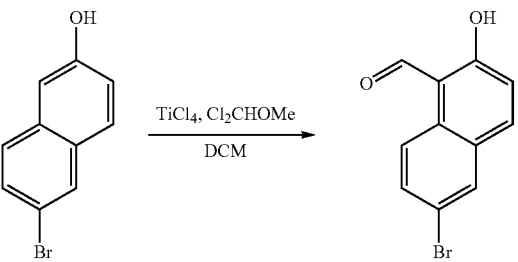 [SMILES: Oc1ccc2cc(Br)ccc2c1 ; O=Cc1c(O)ccc2cc(Br)ccc12]

The solution of TiCl$_4$ (1.2 mL, 10.5 mmol) and Cl$_2$CHOMe (575 mg, 5.5 mmol) in DCM (5 mL) was stirred at 0° C. for 15 min. Then the solution of 6-bromonaphthalen-2-ol (1.1 g, 5 mmol) in DCM (15 mL) was added dropwise at 0° C. The mixture was stirred for 12 h at 25° C. LCMS showed one main peak with desired MS was detected. HCl (30 mL, 1 N) was added. The mixture was extracted with EA (100 mL). The organic layer was dried over Na$_2$SO$_4$, filtered and concentrated to give 6-bromo-2-hydroxy-1-naphthaldehyde as a gray solid. LC-MS (ESI) m/z 251 [M+H]$^+$. $^1$H NMR (400 MHz, CDCl$_3$) δ 13.12 (s, 1H), 10.78 (s, 1H), 8.24 (d, J=8.8 Hz, 1H), 7.97 (d, J=2.0 Hz, 1H), 7.91 (d, J=8.8 Hz, 1H), 7.70 (dd, J=8.8, 2.0 Hz, 1H), 7.19 (d, J=9.2 Hz, 1H).

Step 2. tert-butyl (R)-(5-((6-bromo-1-formylnaphthalen-2-yl)oxy)-1-methoxypentan-2-yl) carbamate

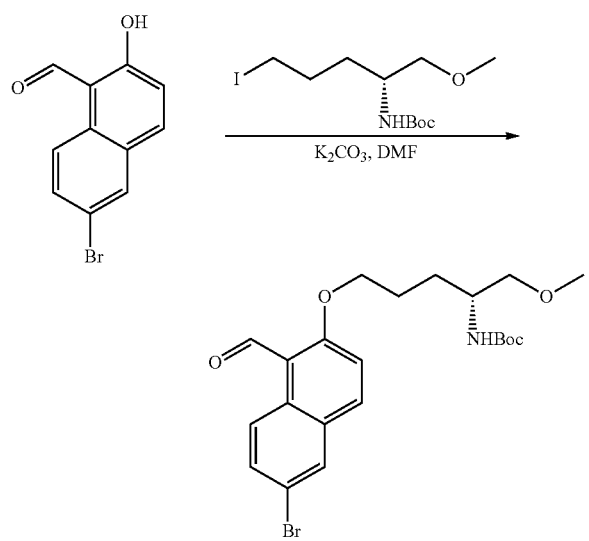

The mixture of 6-bromo-2-hydroxy-1-naphthaldehyde (0.11 g, 0.46 mmol), tert-butyl (R)-(5-iodo-1-methoxypentan-2-yl)carbamate (0.19 g, 0.55 mmol) and K$_2$CO$_3$ (0.19 g, 1.38 mmol) in DMF (2 mL) was stirred at 80° C. for 1 h. LCMS showed ~40% of desired MS was detected. The reaction was poured into EA (20 mL) and washed with H$_2$O (15 mL×2) and brine (15 mL×2). The organic layer was dried over Na$_2$SO$_4$, filtered and concentrated to give tert-butyl (R)-(5-((6-bromo-1-formylnaphthalen-2-yl)oxy)-1-methoxypentan-2-yl) carbamate as a brown oil. LC-MS (ESI) m/z 488.1 [M+H]$^+$.

Step 3. tert-butyl (R)-(5-((6-bromo-1-(hydroxymethyl)naphthalen-2-yl)oxy)-1-methoxypentan-2-yl) carbamate

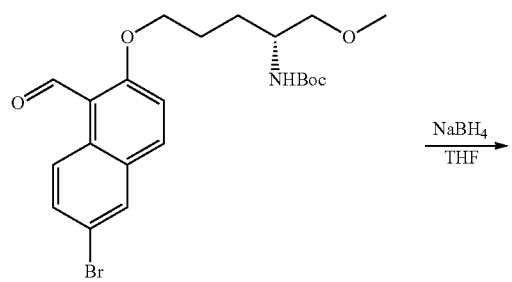

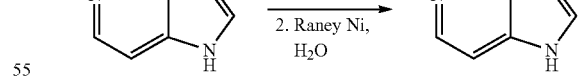

To the solution of tert-butyl (R)-(5-((6-bromo-1-formylnaphthalene-2-yl)oxy)-1-methoxypentan-2-yl) carbamate (0.16 g, 0.34 mmol) in THF (2 mL) was added NaBH$_4$ (16 mg, 0.41 mmol) at 28° C. The mixture was stirred at 28° C. for 3 h. LCMS showed ~35% of desired MS was detected. The reaction was quenched with NH$_4$Cl (aq, 5 mL), extracted with EA (10 mL×2). The organic layer was washed with brine (10 mL×2), dried over Na$_2$SO$_4$, filtered and concentrated to give a residue. The residue was purified by flash column to give tert-butyl (R)-(5-((6-bromo-1-(hydroxymethyl)naphthalen-2-yl)oxy)-1-methoxypentan-2-yl) carbamate as a colorless oil. LC-MS (ESI) m/z 492.0 [M+H]$^+$.

Intermediate J: tert-butyl (tert-butoxycarbonyl)(7-chloro-1H-imidazo[4,5-c]pyridin-4-yl)carbamate

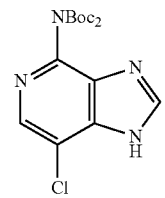

Step 1. 1H-imidazo[4,5-c]pyridin-4-amine

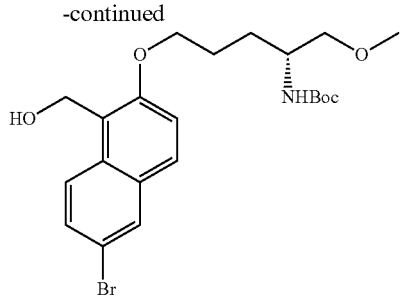

The solution of 4-chloro-1H-imidazo[4,5-c]pyridine (10 g, 65.1 mmol) in NH$_2$NH$_2$·H$_2$O (200 mL, 85%) and isopropanol (142.5 mL) was stirred and refluxed at 100° C. for 36 hrs. The solvent was removed under vacuum. Then the crude was added H$_2$O (400 mL) and Raney Ni (20.0 g) and stirred for 3 hrs at 100° C. The mixture was filtered over a pad of CELITE® and the filtrate was concentrated to afford 1H-imidazo[4,5-c]pyridin-4-amine. $^1$H NMR (400 MHz, D$_2$O): δ=8.07 (s, 1H), 7.34 (d, J=6.8 Hz, 1H), 6.87 (d, J=7.2 Hz, 1H).

Step 2. tert-butyl 4-(bis(tert-butoxycarbonyl)amino)-1H-imidazo[4,5-c]pyridine-1-carboxylate

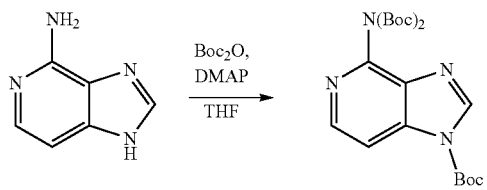

To a solution of compound 1H-imidazo[4,5-c]pyridin-4-amine (26 g, 111 mmol) in THF (280 mL) was added DMAP (5.42 g, 44.4 mmol), followed by additional of Boc$_2$O (242.3 g, 116.4 mol) slowly at 0° C. The mixture was stirred at 25° C. for 48 hrs. LCMS showed that the starting material was consumed completely and the desired MS was detected as main peak. The mixture was poured into 1 L water, extracted with MTBE (1 L×2). The combined organic phase was washed with brine (1 L), dried over anhydrous Na$_2$SO$_4$, concentrated under vacuum to give tert-butyl 4-(bis(tert-butoxycarbonyl)amino)-1H-imidazo[4,5-c]pyridine-1-carboxylate as a yellow oil. LC-MS (ESI) m/z 435.4 [M+H]$^+$.
$^1$H NMR (CDCl$_3$ 400 MHz): δ=8.47-8.41 (m, 2H), 7.87-7.82 (m, 1H), 1.40 (s, 18H), 1.26 (s, 9H).

Step 3. tert-butyl (tert-butoxycarbonyl)(1H-imidazo[4,5-c]pyridin-4-yl)carbamate

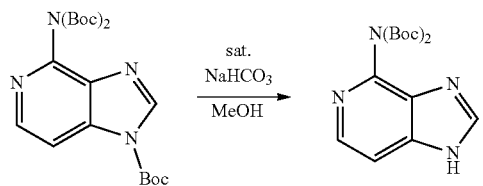

Aqueous NaHCO$_3$ (saturated, 500 mL) was added to a solution of tert-butyl 4-(bis(tert-butoxycarbonyl)amino)-1H-imidazo[4,5-c]pyridine-1-carboxylate (63 g, crude) in MeOH (1.5 L). The reaction mixture was stirred at 15° C. for 16 hrs. LCMS showed that the starting material was consumed completely and the desired MS was detected as main peak. The reaction mixture was concentrated to remove MeOH and the mixture was diluted with water (1.5 L). The mixture was filtered and the filter cake was washed with n-hexane (200 mL) to give tert-butyl (tert-butoxycarbonyl)(1H-imidazo[4,5-c]pyridin-4-yl)carbamate as a white solid LC-MS (ESI) m/z 335.4 [M+H]$^+$. $^1$H NMR (400 MHz, MeOD): δ=8.39 (s, 1H), 8.23 (d, J=5.6, 1H), 7.67 (d, J=5.6, 1H), 1.32 (s, 18H).

Step 4. tert-butyl (tert-butoxycarbonyl)(7-chloro-1H-imidazo[4,5-c]pyridin-4-yl)carbamate

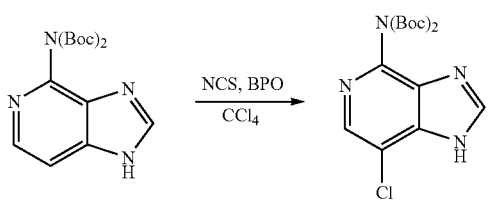

To a solution of tert-butyl (tert-butoxycarbonyl)(1H-imidazo[4,5-c]pyridin-4-yl)carbamate (42.6 g, 127.4 mmol) in DCM (852 mL) was added NCS (34 g, 254.8 mmol). The mixture was stirred at 60° C. for 16 hrs. LCMS showed 38% of desired mass was detected. The mixture was concentrated and was purified by flash column (PE/EA=1/1 to give tert-butyl (tert-butoxycarbonyl)(7-chloro-1H-imidazo[4,5-c]pyridin-4-yl)carbamate as a yellow solid. LC-MS (ESI) m/z 369.3 [M+H]$^+$.

Intermediate K: tert-butyl (2R)-2-((tert-butoxycarbonyl)amino)-5-iodohexanoate

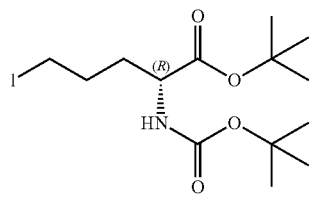

Step 1. tert-butyl N$^2$-(tert-butoxycarbonyl)-N$^5$-methoxy-N$^5$-methyl-D-glutaminate

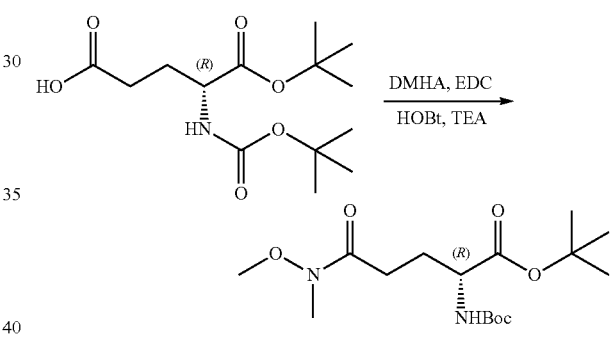

To a solution of (R)-5-(tert-butoxy)-4-((tert-butoxycarbonyl)amino)-5-oxopentanoic acid (5.0 g, 16.5 mmol, 1 eq.), HOBt (2.4 g, 18.1 mmol, 1.1 eq.), EDC·HCl (3.5 g, 18.1 mmol, 1.1 eq.) and TEA (6.9 mL, 49.4 mmol, 3 eq.) in dichloromethane (100 mL) was added DMHA (1.7 g, 18.1 mmol, 1.1 eq.). The reaction mixture was stirred at 22-26° C. for 18 hours. TLC (PE/EtOAc=1/1, Pf=0.8) showed the reaction was completed. The mixture was concentrated and the residue was purified by silica gel column (30% EtOAc in PE) to afford tert-butyl N$^2$-(tert-butoxycarbonyl)-N$^5$-methoxy-N$^5$-methyl-D-glutaminate as a colorless oil. $^1$H NMR (CDCl$_3$ 400 MHz): δ 5.18 (d, J=8.0 Hz, 1H), 4.15-4.25 (m, 1H), 3.67 (s, 3H), 3.17 (s, 3H), 2.41-2.63 (m, 2H), 2.08-2.22 (m, 1H), 1.88-1.97 (m, 1H), 1.46 (s, 9H), 1.44 (s, 9H).

Step 2 tert-butyl (R)-2-((tert-butoxycarbonyl)amino)-5-oxohexanoate

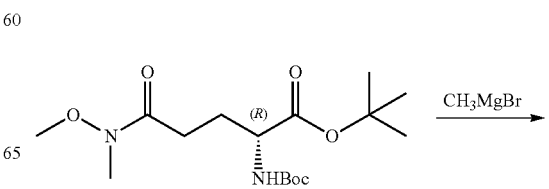

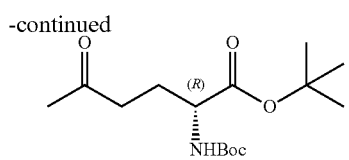

To a solution of tert-butyl N²-(tert-butoxycarbonyl)-N⁵-methoxy-N⁵-methyl-D-glutaminate (1 g, 2.9 mmol, 1 eq.) in toluene (15 mL) at −78° C. under N₂ was added methylmagnesium bromide (2.9 mL, 3M solution in hexenes, 8.7 mmol, 3 eq.) over 15 min. The reaction was warmed and stirred at −5-0° C. for 3.5 hours. TLC (30% EtOAc in PE, Rf=0.75) showed the reaction was completed. The reaction mixture was quenched with aq. HCl (1M) and extracted with ethyl acetate (3*50 mL). The organic layer was dried over sodium sulfate, filtered and concentrated. The residue was purified by column chromatography over silica gel (15% ethyl acetate in petroleum ether) to afford tert-butyl (R)-2-((tert-butoxycarbonyl)amino)-5-oxohexanoate as a colorless oil. ¹H NMR (CDCl₃ 400 MHz): δ 5.06 (d, J=7.6 Hz, 1H), 4.10-4.20 (m, 1H), 2.39-2.63 (m, 2H), 2.15 (s, 3H), 2.03-2.12 (m, 1H), 1.74-1.89 (m, 1H), 1.46 (s, 9H), 1.44 (s, 9H).

Step 3 tert-butyl (2R)-2-((tert-butoxycarbonyl)amino)-5-hydroxyhexanoate

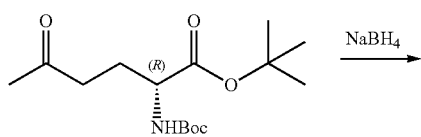

NaBH₄ (230 mg, 6.0 mmol, 1.5 eq) was added to a solution of tert-butyl (R)-2-((tert-butoxycarbonyl)amino)-5-oxohexanoate (1.2 g, 4 mmol, 1 eq) in THF (10 mL). The reaction mixture was warmed and stirred at 50° C. for 2.5 hours. TLC (30% EtOAc in PE, Rf=0.25) showed the reaction was completed. The resulting mixture was quenched with aq. NH₄Cl (30 mL) and extracted with ethyl acetate (3*50 mL). The organic layer was washed with brine (3*30 mL), dried over Na₂SO₄, filtered and concentrated to afford tert-butyl (2R)-2-((tert-butoxycarbonyl)amino)-5-hydroxyhexanoate as a colorless oil. ¹H NMR (CDCl₃ 400 MHz): δ 5.04-5.24 (m, 1H), 4.13-4.27 (m, 1H), 3.78-2.88 (m, 1H), 1.59-1.90 (m, 4H), 1.47 (s, 9H), 1.44 (s, 9H), 1.20 (dd, J=6.4, 2.0 Hz, 3H).

Step 4 tert-butyl (2R)-2-((tert-butoxycarbonyl)amino)-5-iodohexanoate

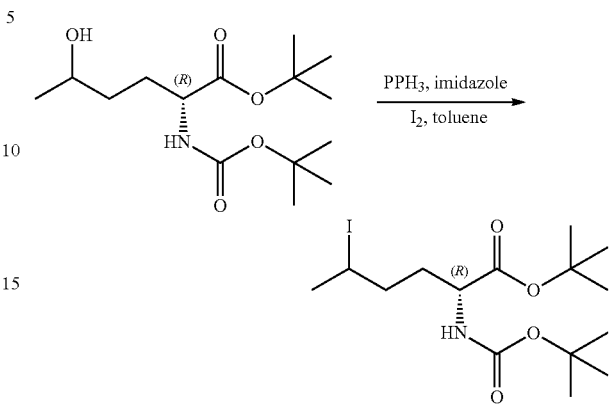

Iodine (502 mg, 2 mmol, 1.2 eq) was added to a solution of tert-butyl (2R)-2-((tert-butoxycarbonyl)amino)-5-hydroxyhexanoate (500 mg, 1.6 mmol, 1 eq), PPh₃ (518.7 mg, 2 mmol, 1.2 eq) and imidazole (224.4 mg, 3 mmol, 2 eq) in toluene (5 mL), which was purged with N₂. The reaction mixture was heated and stirred at 80° C. for 18 h. TLC (20% EtOAc in PE, Rf=0.7, I₂ fuming) showed the reaction was completed. The mixture was cooled to room temperature and concentrated. The residue was purified by pre-TLC (20% EtOAc in PE) to afford tert-butyl (2R)-2-((tert-butoxycarbonyl)amino)-5-iodohexanoate as a yellow oil. ¹H NMR (CDCl₃ 400 MHz): δ 5.06 (d, J=6.4 Hz, 1H), 4.08-4.29 (m, 2H), 1.67-2.06 (m, 7H), 1.48 (d, J=2.0 Hz, 9H), 1.44 (s, 9H).

Intermediate L. (R)-tert-butyl (5-(3-bromo-5-chloro-2-(hydroxymethyl)phenoxy)-1-methoxypentan-2-yl)carbamate

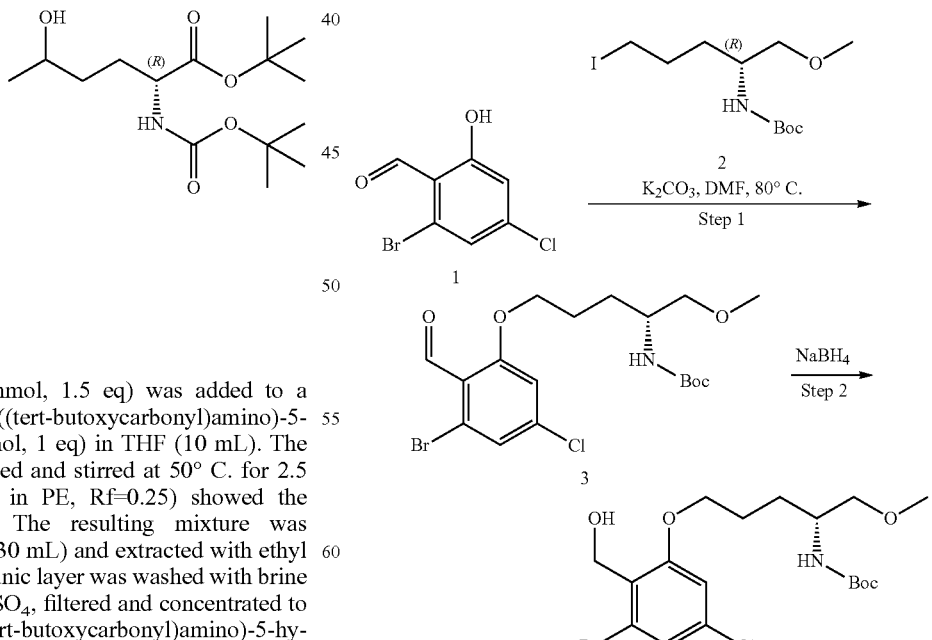

Step 1. To a solution of 2-bromo-4-chloro-6-hydroxybenzaldehyde (330 mg, 1.4 mmol) and tert-butyl (R)-(5-iodo- 1-methoxypentan-2-yl)carbamate (Intermediate D) (600 mg, 1.7 mmol) in DMF (10 mL) was added K$_2$CO$_3$ (580 mg, 4.2 mmol). The mixture was stirred at room temperature for 16 h. The solvent was removed in vacuo, and the residue was purified by silica gel column chromatography (eluting with PE:EA=2:1) to give (R)-tert-butyl (5-(3-bromo-5-chloro-2-formylphenoxy)-1-methoxypentan-2-yl)carbamate (3) as a colorless thick oil. MS (ESI) m/z: mass calcd for C$_{18}$H$_{25}$BrClNO$_5$ 449.06, found 471.6, 473.6, 475.7 [M+Na, Br, Cl]$^+$. $^1$H NMR (400 MHz, CDCl$_3$) δ 10.34 (s, 1H), 7.25 (s, 1H), 6.93 (s, 1H), 4.81 (d, J=8 Hz, 1H), 4.10-4.04 (m, 2H), 3.74 (s, 1H), 3.43-3.36 (m, 2H), 3.34 (s, 3H), 1.95-1.86 (m, 2H), 1.79-1.73 (m, 1H), 1.67-1.63 (m, 1H), 1.43 (s, 9H).

Step 2. To a solution of (R)-tert-butyl (5-(3-bromo-5-chloro-2-formylphenoxy)-1-methoxypentan-2-yl)carbamate (3) (360 mg, 0.8 mmol) in THF (10 mL) was added NaBH$_4$ (36 mg, 0.96 mmol) at room temperature. The mixture was stirred at room temperature for 3 h. The reaction was quenched with NH$_4$Cl (aq, 5 mL) and extracted with EA (30 mL×2). The combined organic layer was washed with brine (20 mL), dried over Na$_2$SO$_4$, filtered and concentrated to give (R)-tert-butyl (5-(3-bromo-5-chloro-2-(hydroxymethyl)phenoxy)-1-methoxypentan-2-yl)carbamate as a pale yellow solid. MS (ESI) m/z: mass calcd for C$_{18}$H$_{27}$BrClNO$_5$ 451.08, found 473.6, 475.7, 477.6 [M+Na, Br, Cl]$^+$. $^1$H NMR (400 MHz, CDCl$_3$) δ 7.28 (s, 1H), 7.21 (s, 1H), 6.82 (s, 1H), 4.81 (s, 2H), 4.12 (dd, J=12, 8 Hz, 1H), 4.06-3.99 (m, 2H), 3.82-3.73 (m, 1H), 3.45-3.33 (m, 5H), 1.92-1.85 (m, 2H), 1.79-1.62 (m, 2H), 1.43 (s, 9H).

Intermediate M. Methyl O-(2-((6-amino-9H-purin-9-yl)methyl)-3,4-difluorophenyl)-L-homoserinate

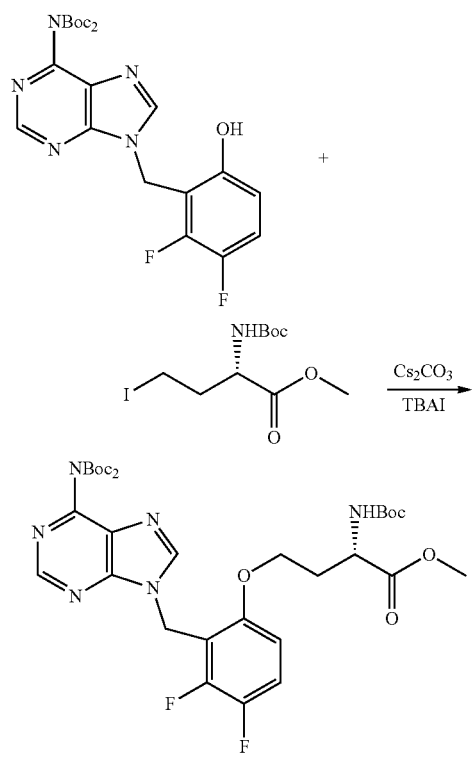

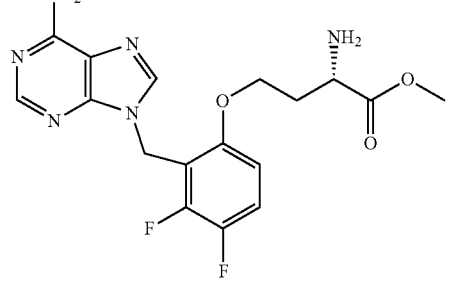

A solution of Cs$_2$CO$_3$ (123 mg, 0.377 mmol), tetra-n-butylammonium iodide (139 mg, 0.38 mmol), tert-butyl (tert-butoxycarbonyl)(9-(2,3-difluoro-6-hydroxybenzyl)-9H-purin-6-yl)carbamate (150 mg, 0.31 mmol), and methyl (S)-2-((tert-butoxycarbonyl)amino)-4-iodobutanoate (162 mg, 0.47 mmol) in acetone (3 mL) was heated to 50° C. for 3 hr. LC-MS indicated the reaction was completed. The mixture was cooled and concentrated. The mixture was treated with EA (20 ml) and H$_2$O (20 ml). The mixture was extracted with EA (10 ml*3). The combined organic layers were washed with brine, dried by Nas2SO4, filtered and evaporated to dryness. The residue was purified via biotage, eluting with EA in n-hexane (0 to 50%) to give methyl O-(2-((6-(bis(tert-butoxycarbonyl)amino)-9H-purin-9-yl)methyl)-3,4-difluorophenyl)-N-(tert-butoxycarbonyl)-L-homoserinate as a light yellow solid. LCMS ESI m/z M+1=692.7.

To the solution of methyl O-(2-((6-(bis(tert-butoxycarbonyl)amino)-9H-purin-9-yl)methyl)-3,4-difluorophenyl)-N-(tert-butoxycarbonyl)-L-homoserinate (167 mg, 0.43 mmol) in DCM (3 mL) was added TFA (0.66 mL, 8.5 mmol). The reaction mixture was stirred at room temperature for 1 hr, and the solvent was evaporated to afford a residue, which was used in the next step without purification. LCMS ESI m/z M+1=392.8.

EXAMPLES

Example 1. (R)-9-(6-((4-amino-5-methoxypentyl)oxy)-2,3-dichlorobenzyl)-9H-purin-6-amine

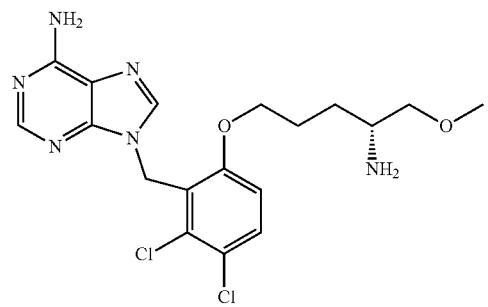 [SMILES: COC[C@H](N)CCCOc1ccc(Cl)c(Cl)c1Cn1cnc2c(N)ncnc21]

Step 1. tert-butyl (R)-(tert-butoxycarbonyl)(9-(6-((4-((tert-butoxycarbonyl)amino)-5-methoxypentyl)oxy)-2,3-dichlorobenzyl)-9H-purin-6-yl)carbamate (1-1)

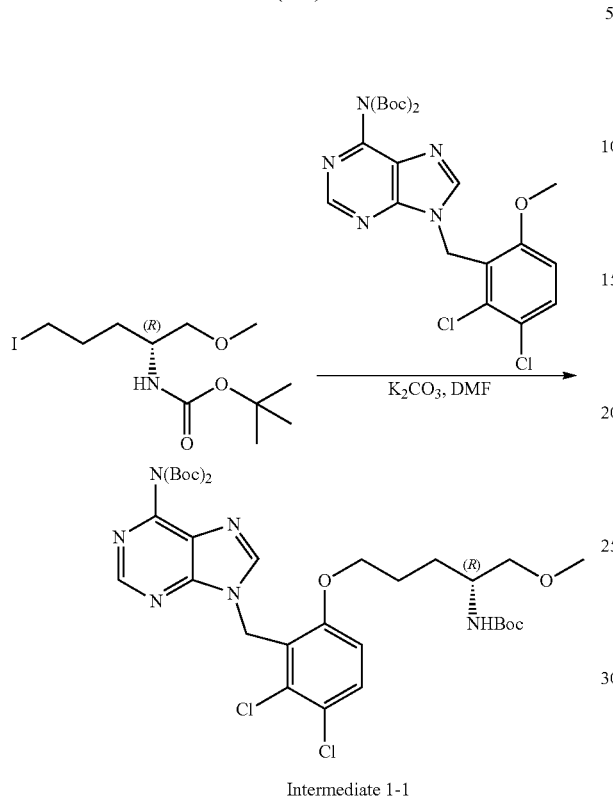

Intermediate 1-1

To a mixture of tert-butyl (R)-(5-iodo-1-methoxypentan-2-yl)carbamate (Intermediate D) (1.9 g, 5.5 mmol) and tert-butyl (R)-(tert-butoxycarbonyl)(9-(6-hydroxy-2,3-dichlorobenzyl)-9H-purin-6-yl)carbamate (Intermediate C) (2 g, 3.9 mmol) in DMF (20 mL) was added K$_2$CO$_3$ (1.5 g, 11.1 mmol). The mixture was stirred at room temperature for 12 hours. The reaction mixture was diluted with H$_2$O and extracted with EtOAc. The organic layer was dried over Na$_2$SO$_4$ and concentrated under reduced pressure to give the crude product. The crude product was purified by flash chromatography to afford tert-butyl (R)-(tert-butoxycarbonyl)(9-(6-((4-((tert-butoxycarbonyl)amino)-5-methoxypentyl)oxy)-2,3-dichlorobenzyl)-9H-purin-6-yl)carbamate (1-1) as an oil. LC-MS: [M+H]$^+$=725.3.

Step 2. (R)-9-(6-((4-amino-5-methoxypentyl)oxy)-2,3-dichlorobenzyl)-9H-purin-6-amine

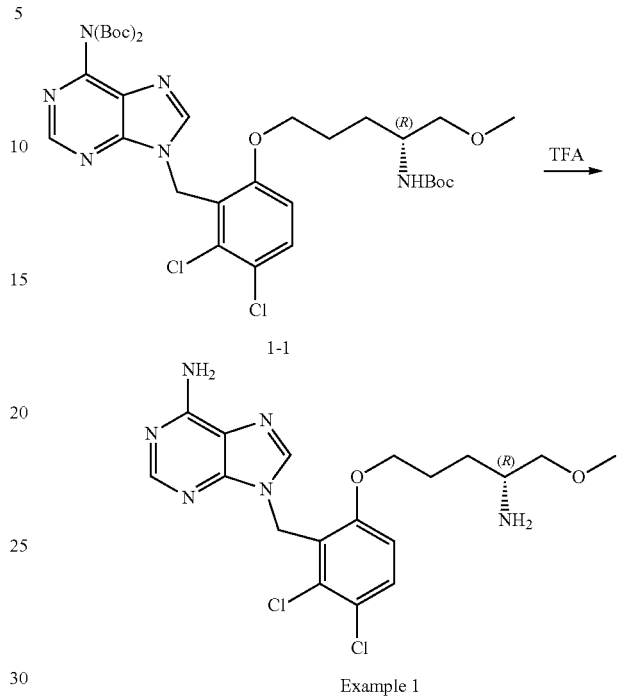

Example 1

To a solution of 1-1 (2.5 g, 4.1 mmol) in CH$_2$Cl$_2$ (20 mL) was added TFA (5 mL). The resulting mixture was stirred for 2 hours. The reaction mixture was concentrated under vacuum to give a crude product. The crude product was purified by prep-HPLC (column: Boston Green ODS 150*30 5u, gradient: 15-45% B (A=water (0.1% TFA), B=acetonitrile), flow rate: 30 mL/min) to afford a TFA solid, which was further purified by prep-HPLC (Column: Boston Green ODS 150*30 5u, gradient: 25-55% B (water (0.05% ammonia hydroxide v/v)-CH$_3$CN), flow rate: 25 mL/min) to afford Example 1 as a white powder. $^1$H NMR (400 MHz, MeOH-d$_4$): δ 8.25 (s, 1H), 7.78 (s, 1H), 7.56 (d, J=8.8 Hz, 1H), 7.06 (d, J=9.2 Hz, 1H), 5.58 (s, 2H), 4.04 (t, J=6.0 Hz, 2H), 3.31 (s, 3H), 3.27-3.24 (m, 1H), 3.13-3.08 (m, 1H), 2.87-2.85 (m, 1H), 1.82-1.63 (m, 2H), 1.44-1.35 (m, 2H). LC-MS: [M+H]$^+$=425.0.

The following examples were prepared from corresponding intermediates following procedures analogous to Example 1.

| Example No. | | |
|---|---|---|
| 2 | 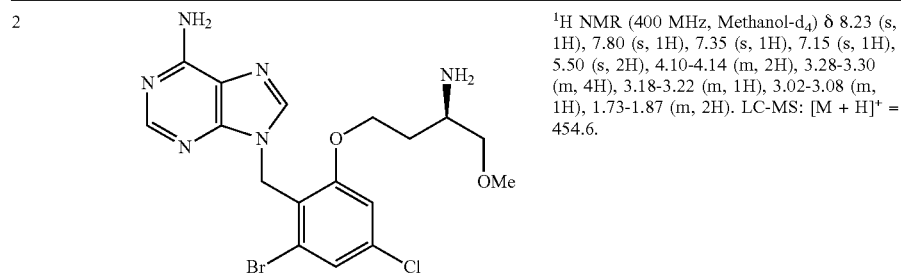 | $^1$H NMR (400 MHz, Methanol-d$_4$) δ 8.23 (s, 1H), 7.80 (s, 1H), 7.35 (s, 1H), 7.15 (s, 1H), 5.50 (s, 2H), 4.10-4.14 (m, 2H), 3.28-3.30 (m, 4H), 3.18-3.22 (m, 1H), 3.02-3.08 (m, 1H), 1.73-1.87 (m, 2H). LC-MS: [M + H]$^+$ = 454.6. |

| Example No. | | |
|---|---|---|
| 3 | 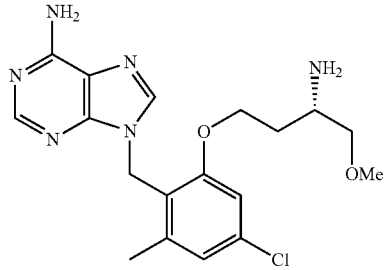 [SMILES: COC[C@@H](N)CCOc1cc(Cl)cc(C)c1Cn1cnc2c(N)ncnc21] | $^1$H NMR (400 MHz, Methanol-d$_4$) δ 8.22 (s, 1H), 7.79 (s, 1H), 6.95 (s, 1H), 6.91 (s, 1H), 5.37 (s, 2H), 4.18-4.02 (m, 2H), 3.31 (s, 3H), 3.28-3.22 (m, 1H), 3.21-3.12 (m, 1H), 3.01-2.87 (m, 1H), 2.45 (s, 3H), 1.92-1.76 (m, 1H), 1.75-1.59 (m, 1H). LC-MS: [M + H]$^+$ = 390.8. |
| 4 | 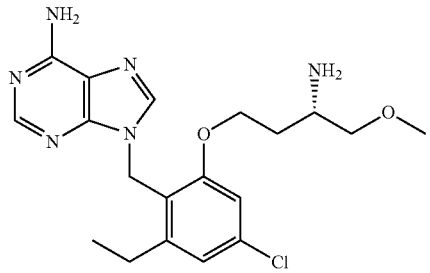 [SMILES: CCc1cc(Cl)cc(OCC[C@H](N)COC)c1Cn1cnc2c(N)ncnc21] | $^1$H-NMR (300 MHz, CD$_3$OD) δ 8.23 (s, 1H), 7.72 (s, 1H), 6.97 (s, 1H), 6.95 (s, 1H), 5.38 (s, 2H), 4.10 (t, J = 6.3 Hz, 2H), 3.31 (s, 3H), 3.27-3.23 (m, 1H), 3.20-3.13 (m, 1H), 3.00-2.95 (m, 1H), 2.86 (m, 2H), 1.90-1.76 (m, 1H), 1.75-1.60 (m, 1H), 1.12 (t, J = 7.5 Hz, 3H). LCMS (ESI) m/z: 404.8 [M + H]$^+$. |

Example 5. (R)-7-(6-((4-amino-5-methoxypentyl)oxy)-2,3-dichlorobenzyl)imidazo[2,1-f][1,2,4]triazin-4-amine

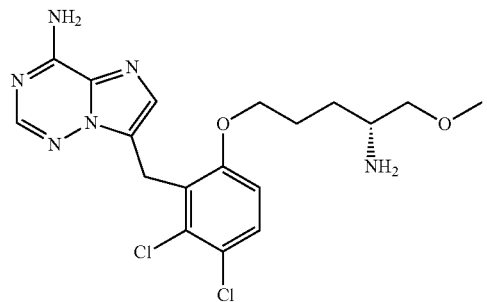 [SMILES: COC[C@H](N)CCCOc1ccc(Cl)c(Cl)c1Cc1cnc2c(N)ncnn12]

Step 1. tert-butyl (R)-5-(3,4-dichloro-2-formylphenoxy)-1-methoxypentan-2-yl)carbamate

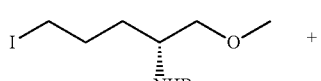

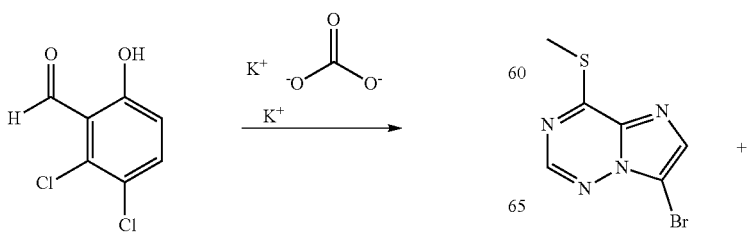

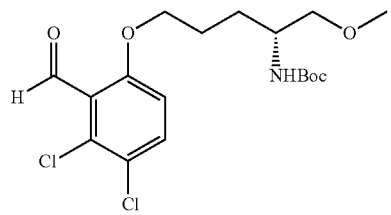

A mixture of tert-butyl (R)-(5-iodo-1-methoxypentan-2-yl)carbamate (Intermediate D) (620 mg, 1.8 mmol), 2,3-dichloro-6-hydroxybenzaldehyde (Intermediate A) (414 mg, 2.2 mmol) and potassium carbonate (499 mg, 3.6 mmol) in DMF (10 mL) was stirred at 60° C. overnight. The reaction mixture was diluted with EtOAc, washed with water and brine, dried, filtered and concentrated. ISCO (silica gel, 0-30% EtOAc in hexanes) to afford tert-butyl (R)-(5-(3,4-dichloro-2-formylphenoxy)-1-methoxypentan-2-yl)carbamate as a colorless oil. LCMS ESI m/z M/M+2 (−100)=306.0/308.0.

Step 2. tert-butyl ((2R)-5-(3,4-dichloro-2-(hydroxy(4-(methylthio)imidazo[2,1-f][1,2,4]triazin-7-yl)methyl)phenoxy)-1-methoxypentan-2-yl)carbamate

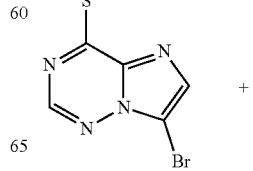

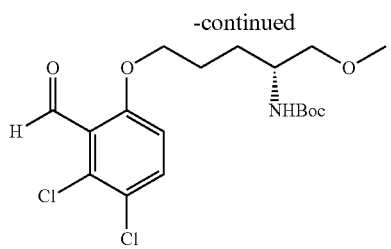

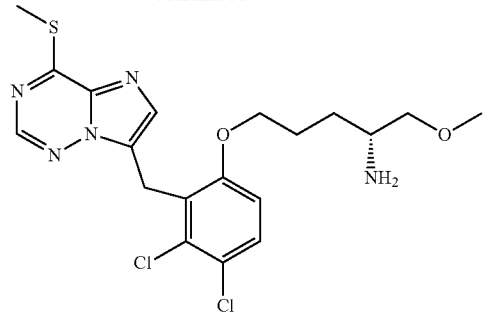

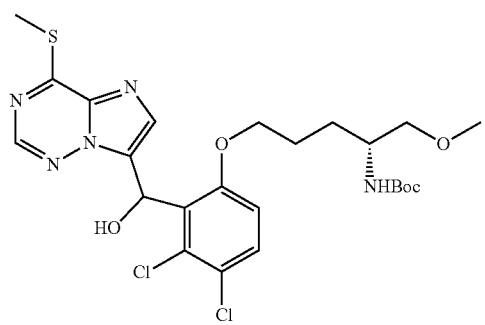

At −78° C., to a solution of 7-bromo-4-(methylthio)imidazo[2,1-f][1,2,4]triazine (Intermediate G) (121 mg, 0.49 mmol) in THF (4 mL) was added n-butyllithium (0.29 mL, 0.59 mmol) dropwise and the resulting mixture was stirred at −78° C. for 15 min. The carbon anion solution was quickly transferred to a pre-cooled solution of tert-butyl (R)-(5-(3,4-dichloro-2-formylphenoxy)-1-methoxypentan-2-yl)carbamate (100 mg, 0.25 mmol) in 2 mL THF at −78° C. The reaction mixture was stirred at −78° C. for 10 min and warmed up to r.t. and stirred for 15 min. The reaction mixture was quenched with sat. NH$_4$Cl aq. solution and extracted with EtOAc. The organic layer was washed with brine, dried, filtered and concentrated. ISCO (silica gel, 0-70% EtOAc in hexanes) to afford tert-butyl ((2R)-5-(3,4-dichloro-2-(hydroxy(4-(methylthio)imidazo[2,1-f][1,2,4]triazin-7-yl)methyl)phenoxy)-1-methoxypentan-2-yl)carbamate as a yellow oil. LCMS ESI m/z M/M+2=571.8/573.8.

Step 3. (R)-5-(3,4-dichloro-2-((4-(methylthio)imidazo[2,1-f][1,2,4]triazin-7-yl)methyl)phenoxy)-1-methoxypentan-2-amine

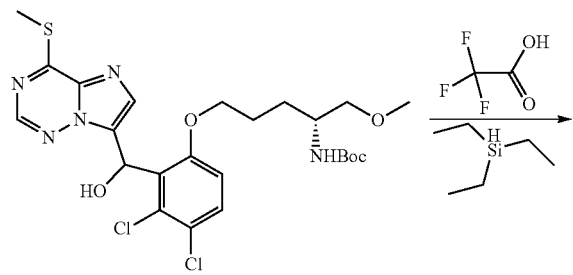

A mixture of tert-butyl ((2R)-5-(3,4-dichloro-2-(hydroxy(4-(methylthio)imidazo[2,1-f][1,2,4]triazin-7-yl)methyl)phenoxy)-1-methoxypentan-2-yl)carbamate (65 mg, 0.11 mmol), TFA (0.44 mL, 5.7 mmol) and triethylsilane (0.91 mL, 5.7 mmol) in CHCl$_3$ (3 mL) was stirred at 40° C. overnight. The reaction mixture was concentrated and the residue was partitioned between EtOAc and water. The organic layer was washed with brine, dried, filtered and concentrated. The crude product was used in the next step without purification. LCMS ESI m/z M/M+2=455.9/457.9.

Step 4. (R)-7-(6-((4-amino-5-methoxypentyl)oxy)-2,3-dichlorobenzyl)imidazo[2,1-f][1,2,4]triazin-4-amine

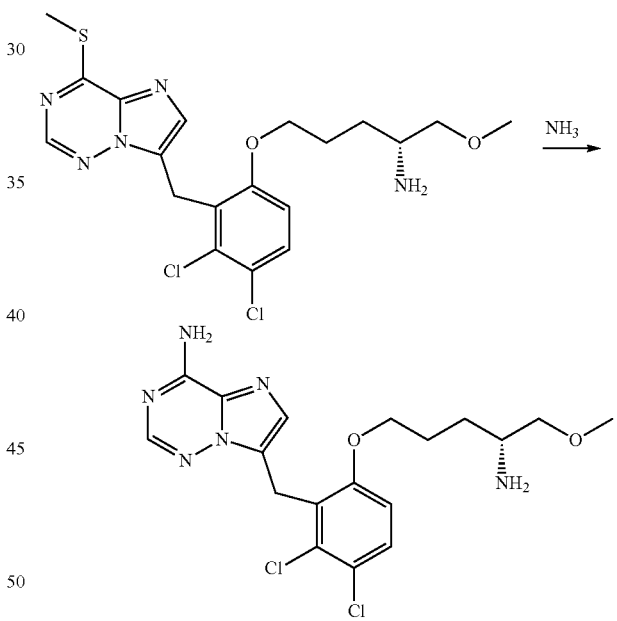

A mixture of (R)-5-(3,4-dichloro-2-((4-(methylthio)imidazo[2,1-f][1,2,4]triazin-7-yl)methyl)phenoxy)-1-methoxypentan-2-amine (51 mg, 0.095 mmol) in ammonia (2 mL in dioxane, 14 mmol) was sealed in microwave tube and heated at 100° C. for 2 hr. The reaction mixture was concentrated and the crude product was submitted to prep. HPLC to afford (R)-7-(6-((4-amino-5-methoxypentyl)oxy)-2,3-dichlorobenzyl)imidazo[2,1-f][1,2,4]triazin-4-amine. LCMS ESI m/z M/M+2=424.9/427.0. $^1$H NMR (400 MHz, Methanol-d4) δ 8.11 (s, 1H), 7.46 (d, J=8.9 Hz, 1H), 7.00 (d, J=8.6 Hz, 1H), 6.92 (s, 1H), 4.44 (s, 2H), 4.06-3.95 (m, 2H), 3.29 (s, 3H), 3.22-3.15 (m, 1H), 3.08-2.99 (m, 1H), 2.89-2.76 (m, 1H), 1.83-1.62 (m, 2H), 1.40-1.18 (m, 2H).

The following examples were prepared from corresponding intermediates following procedures analogous to Example 5.

| Example No. | | |
|---|---|---|
| 6 | 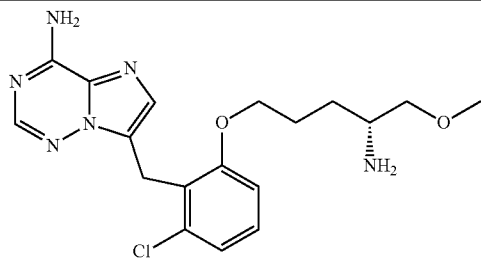 | ¹H NMR: (400 MHz, Methanol-d4) δ = 8.12 (s, 1H), 7.30-7.24 (m, 1H), 7.07 (d, J = 7.8 Hz, 1H), 6.97 (d, J = 8.2 Hz, 1H), 6.89 (s, 1H), 4.39 (s, 2H), 4.02-3.99 (m, 2H), 3.29 (s, 3H), 3.07-3.05 (m, 1H), 3.04-3.02 (m, 1H), 2.88-2.81 (m, 1H), 1.82-1.63 (m, 2H), 1.43-1.32 (m, 1H), 1.30-1.19 (m, 1H). LCMS ESI m/z M + 1 = 391.3. |
| 7 | 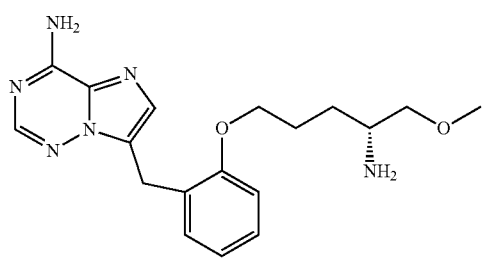 [SMILES: COC[C@H](N)CCCOc1ccccc1Cc1cnc2c(N)ncnn12] | ¹H NMR: (400 MHz, Methanol-d4) 8.07 (s, 1H), 7.27-7.17 (m, 2H), 7.14 (s, 1H), 6.95 (d, J = 7.8 Hz, 1H), 6.90-6.86 (m, 1H), 4.22 (s, 2H), 4.02-3.96 (m, 2H), 3.33 (s, 3H), 3.27 (dd, J = 4.0, 9.4 Hz, 1H), 3.12 (dd, J = 7.6, 9.3 Hz, 1H), 2.89-2.88 (m, 1H), 1.90-1.67 (m, 2H), 1.51-1.41 (m, 1H), 1.38-1.26 (m, 1H). LCMS ESI m/z M + 1 = 357.2. |

Example 8. (R)-8-(6-((4-amino-5-methoxypentyl)oxy)-2,3-dichlorobenzyl)pyrazolo[1,5-a][1,3,5]triazin-4-amine

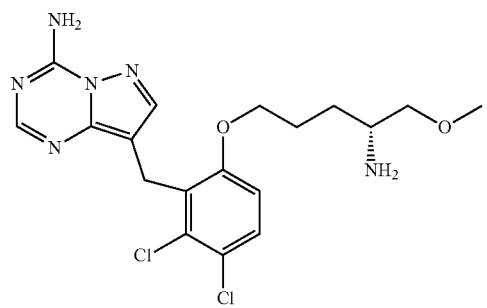 [SMILES: COC[C@H](N)CCCOc1ccc(Cl)c(Cl)c1Cc1cnn2c(N)ncnc12]

Step 1. tert-butyl ((2R)-5-(3,4-dichloro-2-(hydroxy(4-(methyl(phenyl)amino)pyrazolo[1,5-a][1,3,5]triazin-8-yl)methyl)phen oxy)-1-methoxypentan-2-yl)carbamate

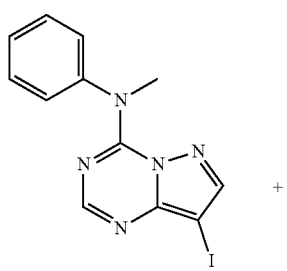 +

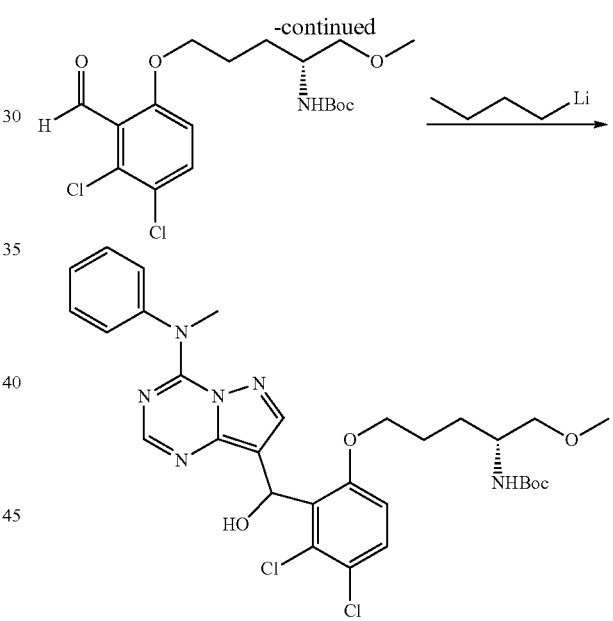

At −78° C., to a solution of 8-iodo-N-methyl-N-phenylpyrazolo[1,5-a][1,3,5]triazin-4-amine (519 mg, 1.5 mmol) in THF (12 mL) was added n-butyllithium (0.96 mL, 1.9 mmol). The resulting mixture was stirred at −78° C. for 15 min and the solution was transferred to a pre-cooled solution of tert-butyl (R)-(5-(3,4-dichloro-2-formylphenoxy)-1-methoxypentan-2-yl)carbamate (300 mg, 0.74 mmol) in 5 mL THF at −78° C. The reaction mixture was stirred at −78° C. for 10 min and warmed up to r.t. The reaction mixture was quenched with sat. NH₄Cl aq. solution and extracted with EtOAc. The organic layer was washed with brine, dried, filtered and concentrated. ISCO (silica gel, 0-70% EtOAc in hexanes) to afford tert-butyl ((2R)-5-(3,4-dichloro-2-(hydroxy(4-(methyl(phenyl)amino)pyrazolo[1,5-a][1,3,5]triazin-8-yl)methyl)phen oxy)-1-methoxypentan-2-yl)carbamate. LCMS ESI m/z M/M+2=631.9/633.9.

Step 2. (R)-8-(6-((4-amino-5-methoxypentyl)oxy)-2,3-dichlorobenzyl)-N-methyl-N-phenyl pyrazolo[1,5-a][1,3,5]triazin-4-amine Step 3. (R)-8-(6-((4-amino-5-methoxypentyl)oxy)-2,3-dichlorobenzyl)pyrazolo[1,5-a][1,3,5]triazin-4-amine

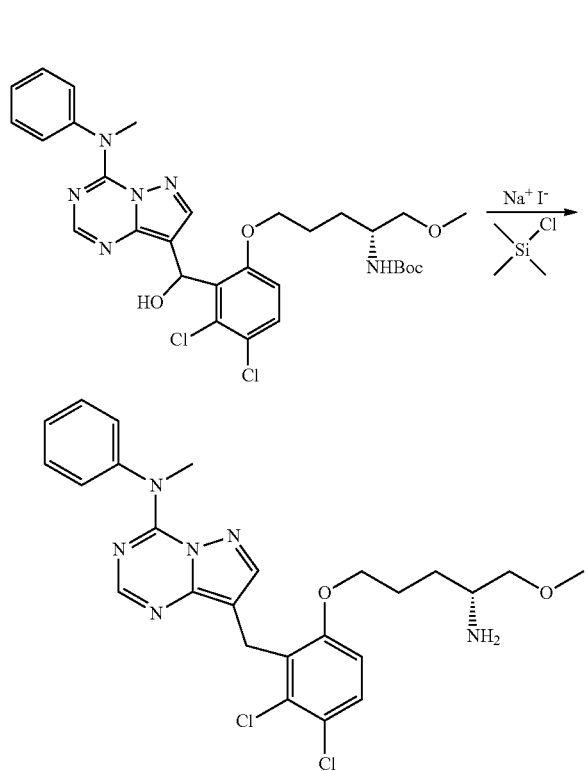

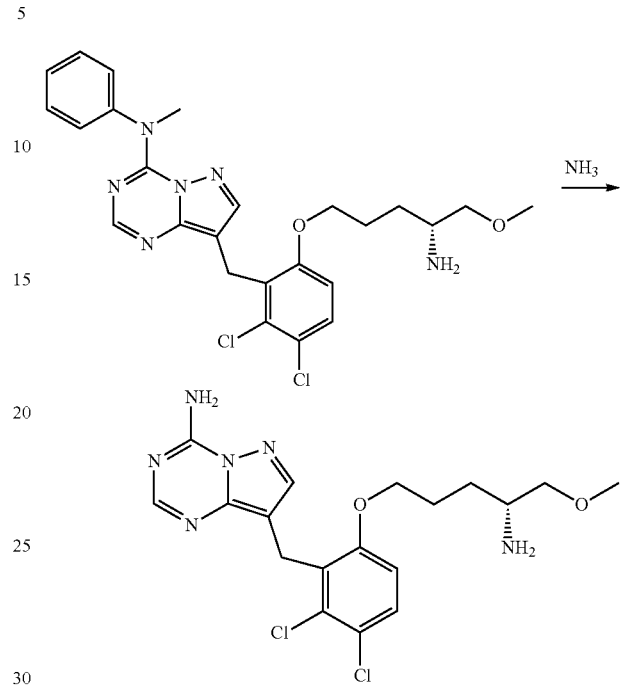

A mixture of sodium iodide (487 mg, 3.2 mmol) and TMSCl (0.41 mL, 3.2 mmol) in acetonitrile (10 mL) was stirred at r.t. for 15 min, followed by the addition of tert-butyl ((2R)-5-(3,4-dichloro-2-(hydroxy(4-(methyl(phenyl)amino)pyrazolo[1,5-a][1,3,5]triazin-8-yl)methyl)phenoxy)-1-methoxypentan-2-yl)carbamate (205 mg, 0.32 mmol) in 3 mL acetonitrile. The resulting mixture was stirred at r.t. for 2 hr. The reaction mixture was quenched with sat. Na₂SO₃ aq. solution and extracted with EtOAc. The organic layer was washed with brine, dried, filtered and concentrated. The crude product was used in the next step without purification. LCMS ESI m/z M/M+2=515.4/517.3

A mixture of (R)-8-(6-((4-amino-5-methoxypentyl)oxy)-2,3-dichlorobenzyl)-N-methyl-N-phenylpyrazolo[1,5-a][1,3,5]triazin-4-amine (167 mg, 0.32 mmol) in ammonia (3 mL, 21 mmol) (7N in MeOH) was heated at 100° C. in seal tube overnight. The reaction mixture was concentrated. The crude product was purified by prep. HPLC (C18, basic condition with ammonia) to afford (R)-8-(6-((4-amino-5-methoxypentyl)oxy)-2,3-dichlorobenzyl)pyrazolo[1,5-a][1,3,5] triazin-4-amine as a white powder. LCMS ESI m/z M/M+2=425.1/427.1. ¹H NMR (400 MHz, Methanol-d4) δ 8.07 (s, 1H), 7.60 (s, 1H), 7.39 (d, J=8.9 Hz, 1H), 6.96 (d, J=8.9 Hz, 1H), 4.23 (s, 2H), 4.03 (t, J=6.1 Hz, 2H), 3.31 (s, 3H), 3.28-3.24 (m, 1H), 3.13-3.06 (m, 1H), 2.93-2.87 (m, 1H), 1.90-1.71 (m, 2H), 1.49-1.30 (m, 2H).

The following examples were prepared from corresponding intermediates following procedures analogous to Example 8.

| Example No. | | |
|---|---|---|
| 9 | 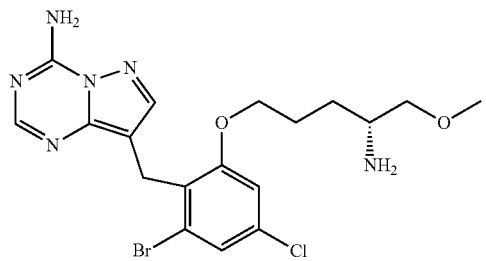 [SMILES: COC[C@H](N)CCCOc1cc(Cl)cc(Br)c1Cc1cnn2c(N)ncnc12] | ¹H NMR: (400 MHz, METHANOL-d4) δ = 8.14-8.00 (m, 1H), 7.72-7.50 (m, 1H), 7.28 (d, J = 1.8 Hz, 1H), 7.04 (d, J = 1.8 Hz, 1H), 4.18 (s, 2H), 4.03 (t, J = 5.8 Hz, 2H), 3.51-3.43 (m, 1H), 3.34 (s, 1H), 3.30-3.25 (m, 1H), 1.87-1.78 (m, 2H), 1.73-1.64 (m, 2H). LCMS ESI m/z M + 1 = 471.3. |

| Example No. | | |
|---|---|---|
| 10 | 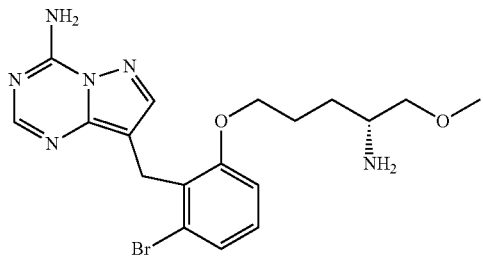 [SMILES: COC[C@H](N)CCCOc1cccc(Br)c1Cc1cnn2c(N)ncnc12] | ¹H NMR: (400 MHz, MeOD 400 MHz) δ 8.11-8.08 (m, 1H), 7.59 (s, 1H), 7.23-7.22 (m, 1H), 7.18-7.14 (m, 1H), 7.00-6.98 (d, J = 8.2 Hz, 1H), 4.23 (s, 2H), 4.03-4.01 (t, J = 5.6 Hz, 2H), 3.33 (s, 3H), 3.29-2.27 (dd, J = 3.9, 9.5 Hz, 1H), 3.16-3.12 (dd, J = 1.3, 9.5 Hz, 1H), 2.99-2.95 (m, 1H), 1.83-1.76 (m, 2H), 1.51-1.48 (m, 1H), 1.41-1.38 (m, 1H). LCMS ESI m/z M + 1 = 437.2. |
| 11 | 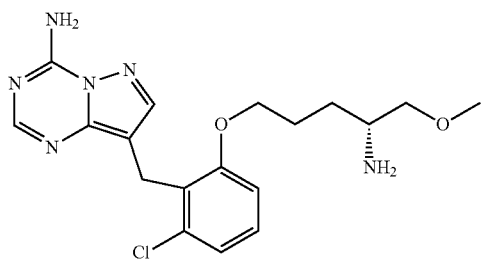 | ¹H NMR: (400 MHz, MeOD) δ 8.09 (s, 1H), 7.60 (s, 1H), 7.22-7.18 (t, J = 7.8 Hz, 1H), 7.05-7.03 (d, J = 4.4 Hz, 1H), 6.96-6.94 (d, J = 4.0 Hz, 1H), 4.20 (s, 2H), 4.08-4.01 (m, 2H), 3.33 (s, 3H), 3.30-3.26 (m, 1H), 3.15-3.13 (m, 1H), 2.96-2.94 (m, 1H), 1.86-1.76 (m, 2H), 1.51-1.39 (m, 2H). LCMS ESI m/z M + 1 = 391.3. |
| 12 | 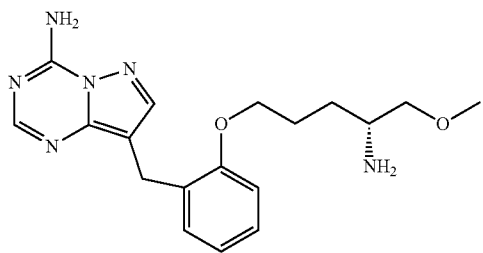 [SMILES: COC[C@H](N)CCCOc1ccccc1Cc1cnn2c(N)ncnc12] | ¹H NMR (400 MHz, MeOD) δ 8.06 (s, 1H), 7.79 (s, 1H), 7.20-7.16 (m, 2H), 6.94-6.83 (m, 2H), 4.01 (m, 4H), 3.35 (m, 4H), 3.19-3.15 (t, J = 8.3 Hz, 1H), 2.95 (m, 1H), 1.91-1.79 (m, 2H), 1.55-1.54 (m, 1H), 1.53-1.42 (m, 1H). LCMS ESI m/z M + 1 = 357.2. |
| 13 | 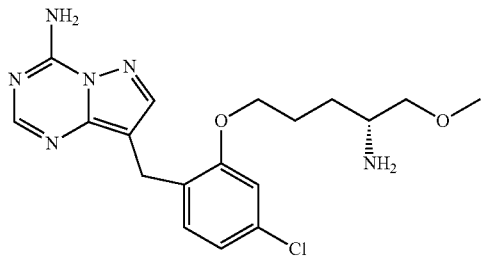 [SMILES: COC[C@H](N)CCCOc1cc(Cl)ccc1Cc1cnn2c(N)ncnc12] | ¹H NMR (400 MHz, Methanol-d4) δ 8.04 (s, 1H), 7.80 (s, 1H), 7.11 (d, J = 8.0 Hz, 1H), 6.94 (d, J = 2.0 Hz, 1H), 6.85 (dd, J = 8.0, 2.0 Hz, 1H), 4.00 (t, J = 6.1 Hz, 2H), 3.96 (s, 2H), 3.35-3.32 (m, 4H), 3.20-3.14 (m, 1H), 1.95-1.74 (m, 2H), 1.60-1.50 (m, 1H), 1.46-1.36 (m, 1H). LCMS ESI m/z M/M + 2 = 391.2/393.2. |
| 14 | 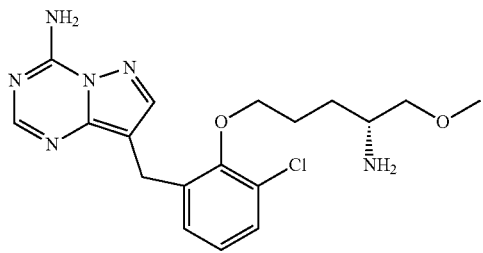 [SMILES: COC[C@H](N)CCCOc1c(Cl)cccc1Cc1cnn2c(N)ncnc12] | ¹H NMR (400 MHz, Methanol-d4) δ 8.05 (s, 1H), 7.84 (s, 1H), 7.26 (dd, J = 7.9, 1.7 Hz, 1H), 7.17-7.09 (m, 1H), 7.00 (t, J = 7.8 Hz, 1H), 4.08 (s, 2H), 4.01-3.95 (m, 2H), 3.40-3.36 (m, 1H), 3.35 (s, 3H), 3.24-3.18 (m, 1H), 3.02-2.95 (m, 1H), 1.98-1.81 (m, 2H), 1.72-1.62 (m, 1H), 1.56-1.46 (m, 1H). LCMS ESI m/z M/M + 2 = 391.2/393.2. |

| Example No. | | |
|---|---|---|
| 15 | (structure) | ¹H NMR (400 MHz, Methanol-d4) δ 8.07 (s, 1H), 7.61 (s, 1H), 7.39 (d, J = 8.9 Hz, 1H), 6.97 (d, J = 8.9 Hz, 1H), 4.23 (s, 2H), 4.07-4.01 (m, 2H), 3.20-3.12 (m, 3H), 2.94 (p, J = 6.6 Hz, 1H), 1.92-1.71 (m, 3H), 1.55 (ddt, J = 13.1, 10.8, 5.8 Hz, 1H), 1.45-1.36 (m, 1H), 0.86 (d, J = 6.7 Hz, 7H). LCMS ESI m/z M/M + 2 = 467.0/469.1. |
| 16 | (structure) | ¹H NMR (400 MHz, Methanol-d4) δ 8.07 (s, 1H), 7.61 (s, 1H), 7.40 (d, J = 8.9 Hz, 1H), 6.97 (d, J = 8.9 Hz, 1H), 4.23 (s, 2H), 4.04 (t, J = 6.0 Hz, 2H), 3.49-3.47 (m, 1H), 3.47-3.33 (m, 2H), 3.22-3.14 (m, 1H), 3.06-2.87 (m, 1H), 1.92-1.71 (m, 2H), 1.62-1.32 (m, 2H), 1.15 (t, J = 7.0 Hz, 3H). LCMS ESI m/z M/M + 2 = 439.0/441.0. |
| 17 | (structure) | ¹H NMR (400 MHz, Methanol-d4) δ 8.08 (s, 1H), 7.68 (s, 1H), 7.41 (d, J = 8.9 Hz, 1H), 6.98 (d, J = 8.9 Hz, 1H), 4.23 (s, 2H), 4.18-4.08 (m, 2H), 3.38-3.33 (m, 1H), 3.30 (s, 3H), 3.27-3.22 (m, 1H), 3.21-3.14 (m, 1H), 2.00-1.77 (m, 2H). LCMS ESI m/z M/M + 2 = 410.9/412.9. |

Example 18. (R)-1-(6-((4-amino-5-methoxypentyl)oxy)-2,3-dichlorobenzyl)-7-chloro-1H-imidazo[4,5-c]pyridin-4-amine Step 1. tert-butyl (R)-(1-(6-((4-amino-5-methoxypentyl)oxy)-2,3-dichlorobenzyl)-7-chloro-1H-imidazo[4,5-c]pyridin-4-yl)(tert-butoxycarbonyl)carbamate

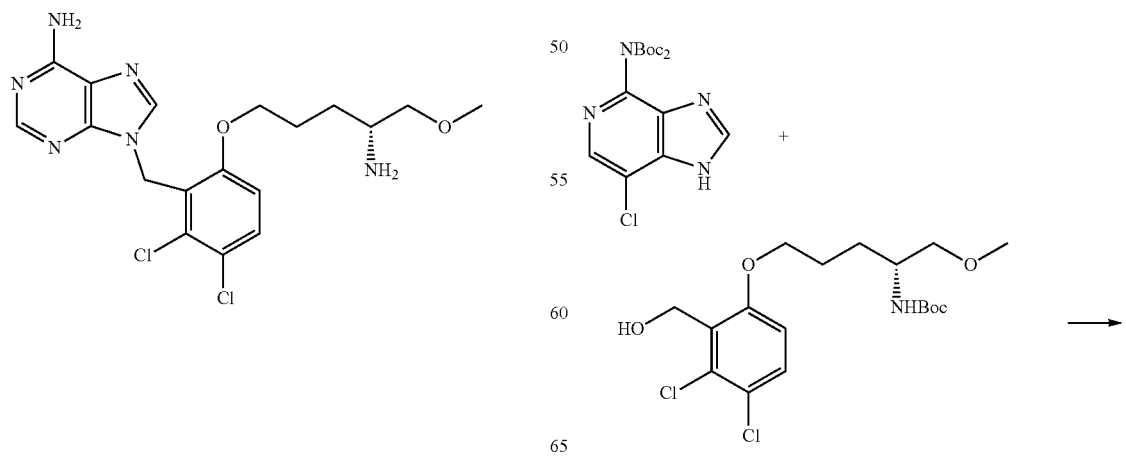

-continued

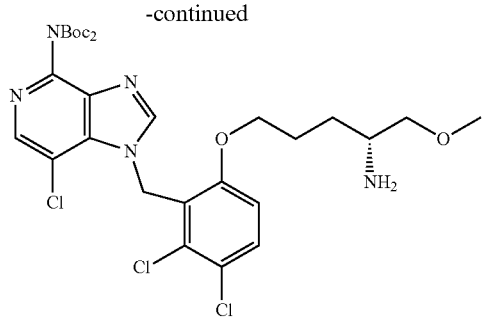

To a solution of tert-butyl (tert-butoxycarbonyl)(7-chloro-1H-imidazo[4,5-c]pyridin-4-yl)carbamate (Intermediate J) (400 mg, 0.98 mmol), tert-butyl (R)-(5-(3,4-dichloro-2-(hydroxymethyl)phenoxy)-1-methoxypentan-2-yl)carbamate (434 mg, 1.2 mmol) and DTAD (903 mg, 3.9 mmol) in THF (8 mL) was added Bu₃P (793 mg, 3.9 mmol) at 0° C. The mixture was stirred at 25° C. for 16 hours. LCMS (C-07037-068-1A) showed one main peak with desired MS was detected. The reaction was purified by flash column to give tert-butyl (R)-(1-(6-((4-amino-5-methoxypentyl)oxy)-2,3-dichlorobenzyl)-7-chloro-1H-imidazo[4,5-c]pyridin-4-yl)(tert-butoxycarbonyl)carbamate as a colorless oil. LCMS ESI m/z M+1=760.4.

Step 2. (R)-1-(6-((4-amino-5-methoxypentyl)oxy)-2,3-dichlorobenzyl)-7-chloro-1H-imidazo[4,5-c]pyridin-4-amine

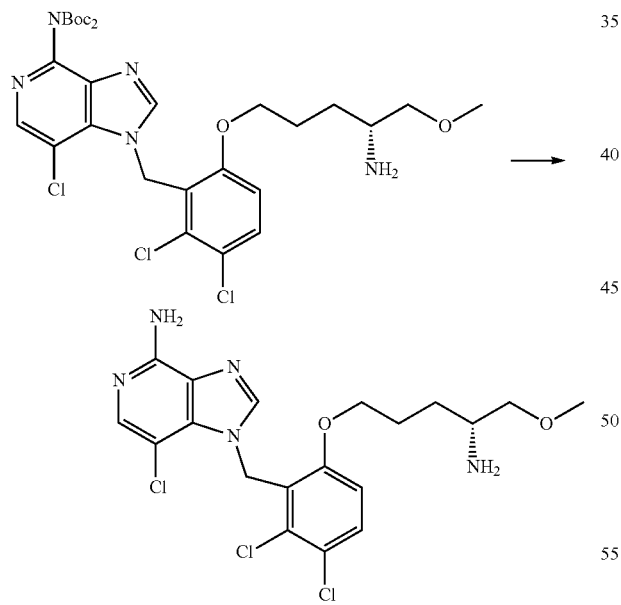

A solution of tert-butyl (R)-(1-(6-((4-amino-5-methoxypentyl)oxy)-2,3-dichlorobenzyl)-7-chloro-1H-imidazo[4,5-c]pyridin-4-yl)(tert-butoxycarbonyl)carbamate (580 mg, 0.76 mmol) in TFA/DCM (10 mL, $V_{TFA}/V_{DCM}=2/5$) was reacted at 25° C. for 4 hours. The reaction mixture was adjusted to pH=8 with NH₃·H₂O. The reaction mixture was concentrated to give a residue. The residue was purified by prep-HPLC to afford (R)-1-(6-((4-amino-5-methoxypentyl)oxy)-2,3-dichlorobenzyl)-7-chloro-1H-imidazo[4,5-c]pyridin-4-amine. LCMS ESI m/z M+1=460.3. ¹H NMR: (400 MHz, MeOD) δ=7.71 (s, 1H), 7.64-7.57 (m, 2H), 7.09 (d, J=9.0 Hz, 1H), 5.96 (s, 2H), 4.08-3.97 (m, 2H), 3.29 (s, 3H), 3.25-3.07 (m, 1H), 3.05-2.94 (m, 1H), 2.81-2.64 (m, 1H), 1.81-1.69 (m, 1H), 1.68-1.57 (m, 1H), 1.32-1.21 (m, 1H), 1.18-1.06 (m, 1H).

Example 19. (S)-9-((2-(2-amino-3-methoxypropoxy)naphthalen-1-yl)methyl)-9H-purin-6-amine

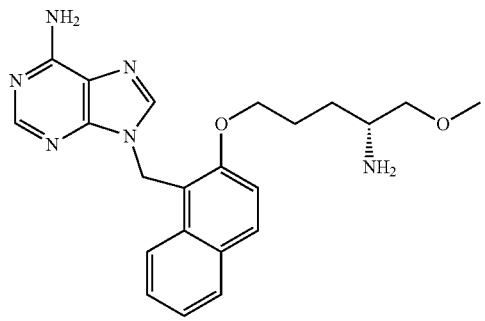 [SMILES: COC[C@H](N)CCCOc1ccc2ccccc2c1Cn1cnc2c(N)ncnc21]

Step 1. tert-Butyl (tert-butoxycarbonyl)(9-((2-(2-((tert-butoxycarbonyl)amino)-3-methoxy propoxy)naphthalen-1-yl)methyl)-9H-purin-6-yl)carbamate

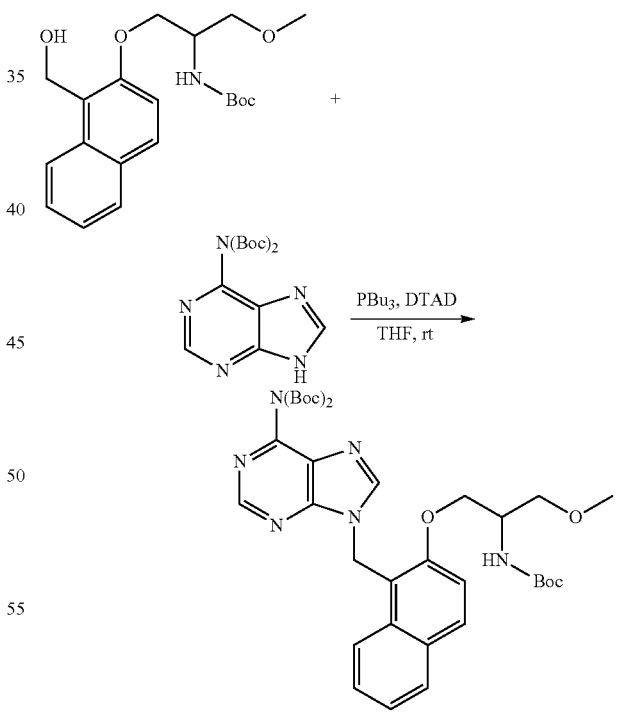

tert-butyl (1-((1-(hydroxymethyl)naphthalen-2-yl)oxy)-3-methoxypropan-2-yl)carbamate, prepared following procedures analogous to Intermediate I. ¹HNMR (400 MHz, CDCl₃) δ 8.17-8.14 (d, J=8.6 Hz, 1H), 7.85-7.81 (t, J=8.6 Hz, 2H), 7.56-7.53 (t, J=7.7 Hz, 1H), 7.41-7.37 (t, J=7.5 Hz, 1H), 7.32-7.30 (d, J=9.2 Hz. 1H), 5.21-5.18 (m, 3H), 4.29-4.24 (m, 3H), 3.73-3.69 (dd, J=9.5, 3.1 Hz, 1H), 3.63-3.59

(dd, J=9.4, 4.9 Hz, 1H), 3.42 (s, 3H), 1.75 (bs, 1H), 1.47 (s, 9H). MS (ESI) m/z: Calcd. for C$_{20}$H$_{27}$NO$_5$ 361.2; found 383.9 [M+Na]$^+$.

To a solution of tert-butyl (1-((1-(hydroxymethyl)naphthalen-2-yl)oxy)-3-methoxypropan-2-yl)carbamate, (0.35 g, 0.96 mmol), tert-butyl (tert-butoxycarbonyl)(9H-purin-6-yl)carbamate (Intermediate B) (0.39 g, 1.2 mmol) and DTAD (0.89 g, 3.8 mmol) in THF (20 mL) was added Bu$_3$P (0.78 g, 3.6 mmol) at 0° C. The mixture was stirred at room temperature for 16 h. The reaction was concentrated to give a residue, and the residue was purified by flash column to give tert-butyl (tert-butoxycarbonyl)(9-((2-(2-((tert-butoxycarbonyl)amino)-3-methoxy propoxy)naphthalen-1-yl)methyl)-9H-purin-6-yl)carbamate as a yellow oil. MS (ESI) m/z: Calcd. for C$_{35}$H$_{46}$N$_6$O$_8$ 678.3; found 678.8 [M+H]$^+$. $^1$HNMR (400 MHz, CDCl$_3$) δ 9.02 (s, 1H), 8.16-8.14 (d, J=8.3 Hz, 1H), 7.97-7.94 (d, J=9.1 Hz, 1H), 7.86-7.84 (d, J=8.1 Hz, 1H), 7.55-7.51 (m, 2H), 7.43-7.39 (t, J=8.0 Hz, 2H), 5.95 (s, 2H), 5.41-5.43 (m, 1H), 4.39-4.25 (m, 3H), 3.60-3.57 (dd, J=9.3, 3.2 Hz, 1H), 3.51-3.43 (m, 1H), 3.34 (s, 3H), 1.47 (s, 18H), 1.45 (s, 9H).

Step 2. 9-((2-(2-amino-3-methoxypropoxy)naphthalen-1-yl)methyl)-9H-purin-6-amine

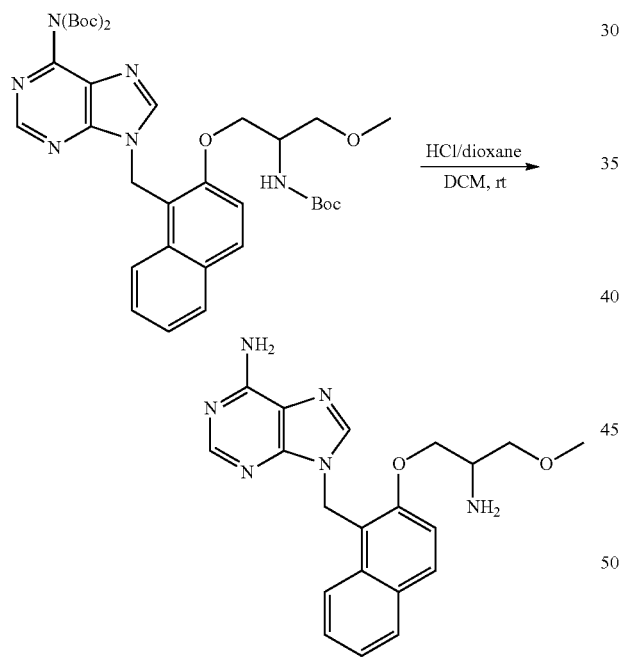

To a solution of tert-butyl (tert-butoxycarbonyl)(9-((2-(2-((tert-butoxycarbonyl)amino)-3-methoxypropoxy)naphthalen-1-yl)methyl)-9H-purin-6-yl)carbamate (0.22 g, 0.32 mmol) in DCM (7 mL) was added HCl/dioxane (7 mL) at room temperature. The mixture was stirred at room temperature for 16 h. The reaction mixture was concentrated to give a residue. The residue was purified by prep-HPLC to give 9-((2-(2-amino-3-methoxypropoxy)naphthalen-1-yl)methyl)-9H-purin-6-amine as a white solid. MS (ESI) m/z: Calcd. for C$_{20}$H$_{22}$N$_6$O$_2$ 378.2; found 378.9 [M+H]$^+$. $^1$HNMR (400 MHz, CDCl$_3$) δ 8.33 (s, 1H), 8.18-8.15 (d, J=8.7 Hz, 1H), 8.00-7.97 (d, J=9.3 Hz, 1H), 7.89-7.86 (d, J=8.2 Hz, 1H), 7.67 (s, 1H), 7.58-7.44 (m, 2H), 7.41-7.36 (t, J=7.5 Hz, 1H), 5.87 (s, 2H), 4.26-4.10 (m, 2H), 3.43-3.34 (m, 2H), 3.32-3.29 (m, 4H).

Step 3. (S)-9-((2-(2-amino-3-methoxypropoxy)naphthalen-1-yl)methyl)-9H-purin-6-amine

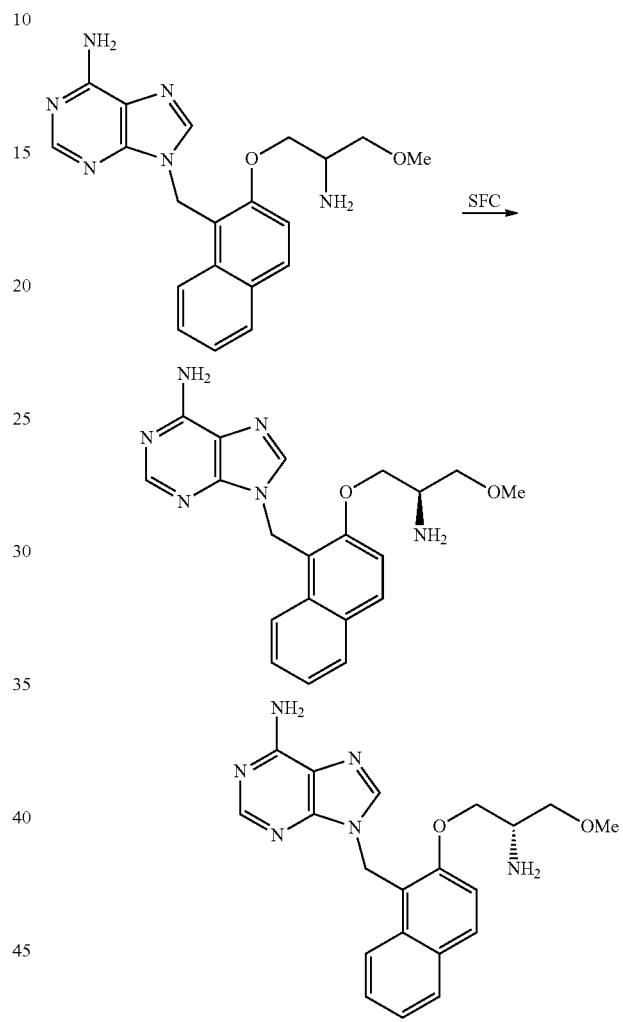

The mixture of enantiomers were separated by chiral SFC to afford both products. LCMS ESI m/z M+1=379.2. $^1$H NMR (400 MHz, METHANOL-d4) δ ppm 3.30 (s, 3H) 3.35-3.41 (m, 2H) 4.13-4.26 (m, 2H) 5.89 (s, 2H) 7.40 (ddd, J=8.04, 6.97, 0.88 Hz, 1H) 7.48 (d, J=9.13 Hz, 1H) 7.54 (ddd, J=8.51, 6.94, 1.31 Hz, 1H) 7.67 (s, 1H) 7.88 (d, J=8.13 Hz, 1H) 8.00 (d, J=9.13 Hz, 1H) 8.18 (d, J=8.63 Hz, 1H) 8.32-8.36 (m, 1H).

The following examples were prepared from corresponding intermediates (e.g., from tert-butyl (R)-(5-((6-bromo-1-(hydroxymethyl)naphthalen-2-yl)oxy)-1-methoxypentan-2-yl)carbamate (Intermediate I for Example 20) following procedures analogous to Example 19.

| Example No. | | |
|---|---|---|
| 20 | 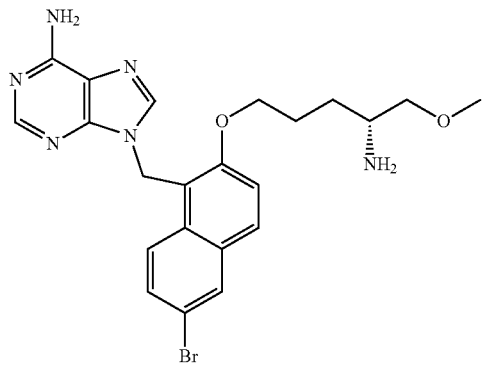 [SMILES: COC[C@H](N)CCCOc1ccc2cc(Br)ccc2c1Cn1cnc2c(N)ncnc21] | ¹H NMR (400 MHz, MeOD) δ 8.48 (s, 1H), 8.20 (d, J = 9.20 Hz, 1H), 8.16 (s, 1H), 8.06 (d, J = 2.0 Hz, 1H), 7.95 (d, J = 9.20 Hz, 1H), 7.61 (dd, J = 9.20, 2.0 Hz, 1H), 7.55 (d, J = 9.2 Hz, 1H), 5.95 (s, 2H), 4.34 (t, J = 6.0 Hz, 2H), 3.65-3.62 (m, 1H), 3.54-3.45 (m, 2H), 3.42 (s, 3H), 2.03-1.80 (m, 4H). LC-MS (ESI) m/z 487.0 [M + H]⁺. |
| 21 | 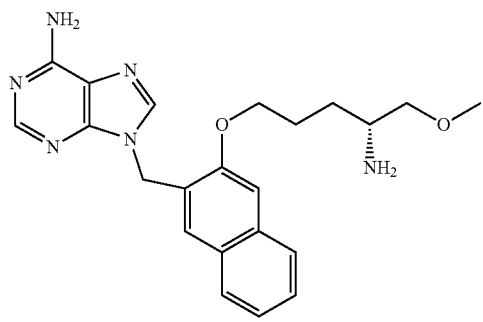 [SMILES: COC[C@H](N)CCCOc1cc2ccccc2cc1Cn1cnc2c(N)ncnc21] | ¹H-NMR (400 MHz, d4-MeOH) δ 8.38 (s, 1H), 8.34 (s, 1H), 7.78-7.74 (m, 3H), 7.44 (t, J = 7.2 Hz, 1H), 7.36-7.30 (m, 2H), 5.64 (s, 2H), 4.18 (t, J = 6.0 Hz, 2H), 3.65-3.62 (m, 1H), 3.51-3.44 (m, 5H), 1.97-1.81 (m, 4H). LCMS ESI m/z M + 1 = 407.1. |

Example 22. (R)-9-(2-bromo-4-chloro-6-((5-methoxy-4-(methylamino)pentyl)oxy)benzyl)-9H-purin-6-amine

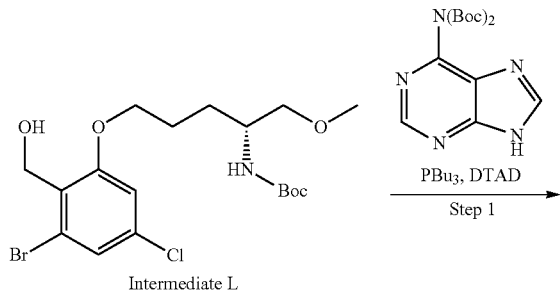

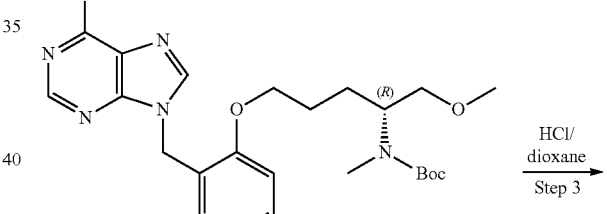

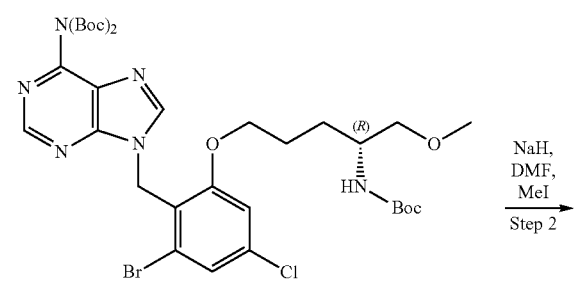

Step 1. (R)-tert-butyl (9-(2-bromo-6-((4-((tert-butoxycarbonyl)amino)-5-methoxypentyl)oxy)-4-chlorobenzyl)-9H-purin-6-yl)(tert-butoxycarbonyl)carbamate To a solution of (R)-tert-butyl (5-(3-bromo-5-chloro-2-(hydroxymethyl)phenoxy)-1-methoxypentan-2-yl)carbamate (Intermediate L) (300 mg, 0.66 mmol), tert-butyl (tert-butoxycarbonyl)(9H-purin-6-yl)carbamate (Intermediate B) (270 mg, 0.79 mmol) and DEAD (350 mg, 2 mmol) in THF (15 mL) was added PPh₃ (520 mg, 2 mmol) at 0° C. The mixture was stirred at 30° C. for 16 h. The reaction mixture was concentrated to give a residue. The residue was purified by silica gel column chromatography (PE/EA=10/1 to 5/1) to give (R)-tert-butyl (9-(2-bromo-6-((4-((tert-butoxycarbonyl)amino)-5-methoxypentyl)oxy)-4-chlorobenzyl)-9H-purin-6-yl)(tert-butoxycarbonyl)carbamate as a colorless thick oil. MS (ESI) m/z: mass calcd for $C_{33}H_{46}BrClN_6O_8$ 768.22, found 768.7 $[M+H]^+$.

Step 2. tert-butyl (R)-(9-(2-bromo-6-((4-((tert-butoxycarbonyl)(methyl)amino)-5-methoxypentyl)oxy)-4-chlorobenzyl)-9H-purin-6-yl)(tert-butoxycarbonyl)carbamate To a solution of (R)-tert-butyl (9-(2-bromo-6-((4-((tert-butoxycarbonyl)amino)-5-methoxypentyl)oxy)-4-chlorobenzyl)-9H-purin-6-yl)(tert-butoxycarbonyl)carbamate (135 mg, 0.18 mmol) in DMSO (10 mL) at 5° C. was added NaH (22 mg, 0.53 mmol). The reaction mixture was stirred at 5° C. for 0.5 h, and then MeI (50 mg, 0.35 mmol) was added. The mixture was allowed to warm to room temperature slowly, and stirred for 2 h at room temperature. The mixture was diluted with EA (20 mL) and water (10 mL), the separated organic layer was dried over anhydrous $Na_2SO_4$, filtered and concentrated to give a residue. The residue was purified by silica gel column chromatography (DCM/MeOH=10:1) to give tert-butyl (R)-(9-(2-bromo-6-((4-((tert-butoxycarbonyl)(methyl)amino)-5-methoxypentyl)oxy)-4-chlorobenzyl)-9H-purin-6-yl)(tert-butoxycarbonyl)carbamate as a colorless oil. MS (ESI) m/z: mass calcd. for $C_{34}H_{48}BrClN_6O_8$ 782.24, found 782.5 $[M+H]^+$.

Step 3. (R)-9-(2-bromo-4-chloro-6-((5-methoxy-4-(methylamino)pentyl)oxy)benzyl)-9H-purin-6-amine To a solution of tert-butyl (R)-(9-(2-bromo-6-((4-((tert-butoxycarbonyl)(methyl)amino)-5-methoxypentyl)oxy)-4-chlorobenzyl)-9H-purin-6-yl)(tert-butoxycarbonyl)carbamate (93 mg, 0.12 mmol) in DCM (5 mL) was added HCl/dioxane (4 M, 0.6 mL) at 0° C. The mixture was stirred at 30° C. for 3 h. The reaction mixture was concentrated to give a residue, and the residue was purified by Prep-HPLC (Gemin-$C_{18}$×21.2 mm, 5 μm, $CH_3CN$ % in mobile phase ($CH_3$ $CN/H_2O$ with 0.5% $NH_3·H_2O$) from 10% to 50% over 0.5 h) and neutralized with saturated aqueous $NaHCO_3/H_2O$ to give (R)-9-(2-bromo-4-chloro-6-((5-methoxy-4-(methylamino)pentyl)oxy)benzyl)-9H-purin-6-amine as a white solid. $^1H$ NMR (400 MHz, $CD_3OD$) δ 8.27 (s, 1H), 7.77 (s, 1H), 7.39 (s, 1H), 7.17 (s, 1H), 5.54 (s, 2H), 4.04 (t, J=5.5 Hz, 2H), 3.33 (s, 3H), 3.28-3.21 (m, 2H), 2.66-2.55 (m, 1H), 2.32 (s, 3H), 1.73-1.63 (m, 2H), 1.52-1.32 (m, 2H). MS (ESI) m/z: Calcd. for $C_{19}H_{24}BrClN_6O_2$ 482.08; Found 482.6 484.7 $[M+H, Br]^+$.

Example 23. (R)-2-amino-5-(2-((6-amino-9H-purin-9-yl)methyl)-3,4-dichlorophenoxy)pentanoic acid

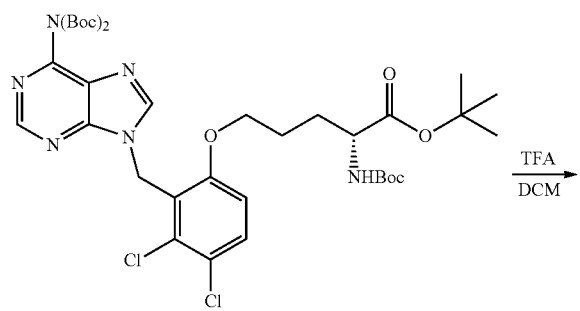

-continued

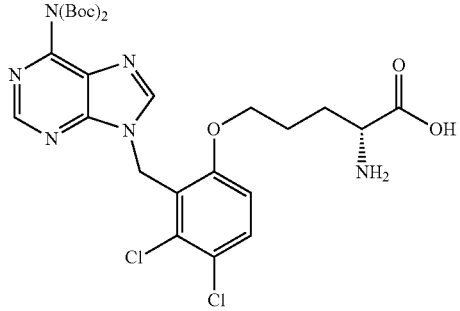

To tert-butyl (R)-5-(2-((6-(bis(tert-butoxycarbonyl)amino)-9H-purin-9-yl)methyl)-3,4-dichlorophenoxy)-2-((tert-butoxycarbonyl)amino)pentanoate (Intermediate F-5) (0.26 g, 0.41 mmol) in dichloromethane (5 mL) was added dropwise trifluoroacetic acid (5 mL) and the mixture was stirred for 18 hrs at 1-5° C. The mixture was concentrated and purified by prep-HPLC [column: Boston Green ODS: 150*30 mm*5 um, gradient 11%-41% B (A: water (0.1% TFA), B (acetonitrile))] to afford (R)-2-amino-5-(2-((6-amino-9H-purin-9-yl)methyl)-3,4-dichlorophenoxy)pentanoic acid as a white solid (TFA salt). $^1H$ NMR (400 MHz, MeOH-$d_4$): δ 8.34 (s, 1H), 8.05 (brs., 1H), 7.58 (d, J=9.20 Hz, 1H), 7.09 (d, J=9.20 Hz, 1H), 5.66 (s, 2H), 4.14 (brs., 2H), 4.00 (brs., 1H), 1.85-2.09 (m, 4H). LC-MS: $[M+H]^+$=424.9. LCMS ESI m/z M+1=459.0.

Example 24. (R)-2-amino-5-(2-((4-aminoimidazo[2,1-f][1,2,4]triazin-7-yl)methyl)-3,4-dichloro henoxy) pentanoic acid

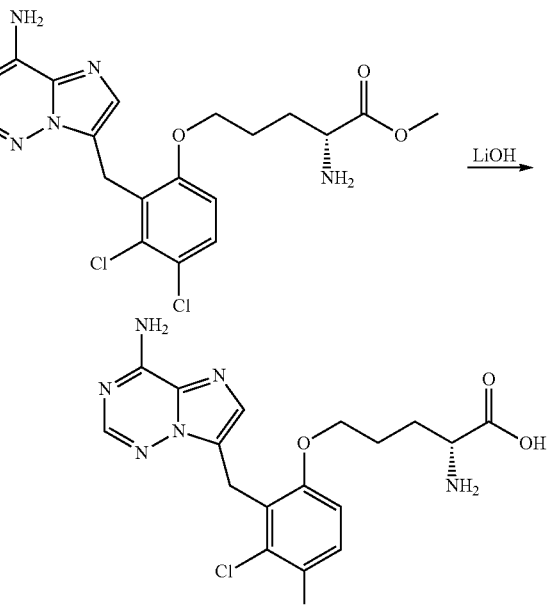

A mixture of methyl (R)-2-amino-5-(2-((4-aminoimidazo[2,1-f][1,2,4]triazin-7-yl)methyl)-3,4-dichlorophenoxy)pentanoate (25 mg, 0.057 mmol) in lithium hydroxide (0.28 mL, 0.28 mmol) and THF (2 mL) was stirred at r.t. for 2 hr. The reaction mixture was neutralized with 1N HCl and concentrated to remove THF. The crude mixture in water was diluted with MeOH and submitted to prep. HPLC to afford (R)-2-amino-5-(2-((4-aminoimidazo[2,1-f][1,2,4]triazin-7-yl)methyl)-3,4-dichloro phenoxy)pentanoic acid as a white powder. LCMS ESI m/z M/M+2=424.9/426.9. ¹H NMR (400 MHz, Methanol-d4) δ 8.11 (s, 1H), 7.45 (d, J=8.9 Hz, 1H), 7.03 (d, J=9.0 Hz, 1H), 6.96 (s, 1H), 4.45 (s, 2H), 4.09-4.00 (m, 2H), 3.42-3.35 (m, 1H), 1.87-1.73 (m, 4H).

The following examples were prepared from corresponding intermediates following procedures analogous to Example 24.

| Example No. | | |
|---|---|---|
| 25 | 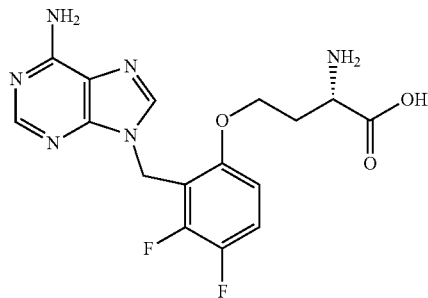 [SMILES: Nc1ncnc2c1ncn2Cc1c(OCC[C@H](N)C(=O)O)ccc(F)c1F] | ¹H NMR (400 MHz, Methanol-d₄) δ 8.38 (s, 1H), 8.32 (s, 1H), 7.29 (q, J = 9.5 Hz, 1H), 6.87 (d, J = 9.4 Hz, 1H), 5.58 (s, 2H), 3.61 (q, J = 7.1 Hz, 1H), 2.54-2.37 (m, 2H), 1.18 (t, J = 7.1 Hz, 2H). LCMS ESI m/z M + 1 = 378.8. |
| 26 | 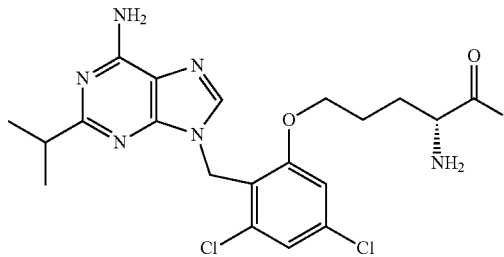 | ¹H-NMR (400 MHz, Methanol-d₄) δ 8.15 (s, 1H), 7.18 (d, J = 1.6 Hz, 1H), 7.11 (d, J = 1.6 Hz, 1H), 5.60 (s, 2H), 4.14 (m, 2H), 3.92 (m, 1H), 3.11 (m, 1H), 2.00 (m, 4H), 1.34 (d, J = 7.2 Hz, 6H). LCMS ESI m/z M/M + 2 = 466.7/468.7. |
| 27 | 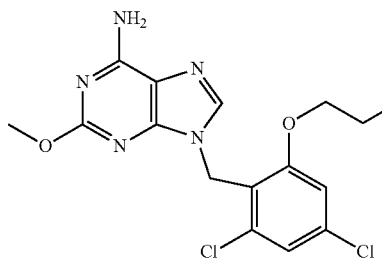 | ¹H-NMR (400 MHz, Methanol-d₄) δ 7.85 (s, 1H), 7.22 (d, J = 1.6 Hz, 1H), 7.11 (d, J = 1.6 Hz, 1H), 4.49-4.48 (m, 2H), 4.88-4.02 (m, 3H), 4.00 (s, 3H), 2.08-1.91 (m, 4H). LCMS ESI m/z M/M + 2 = 454.6/456.6. |
| 28 | 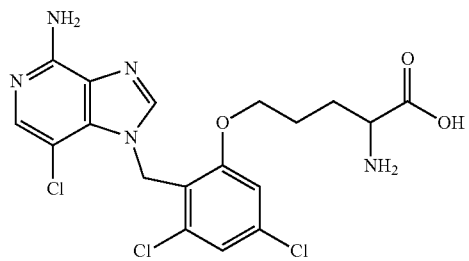 [SMILES: Nc1ncc(Cl)c2c1ncn2Cc1c(Cl)cc(Cl)cc1OCCCC(N)C(=O)O] | ¹H NMR (400 MHz, DMSO-d₆) δ 7.69 (s, 1H), 7.65 (s, 1H), 7.30 (d, J = 1.9 Hz, 1H), 7.26 (d, J = 1.9 Hz, 1H), 6.41 (s, 2H), 5.73 (s, 2H), 4.07 (t, J = 6.1 Hz, 2H), 3.13 (t, J = 5.8 Hz, 1H), 1.85-1.60 (m, 4H). LCMS ESI m/z M/M + 2 = 458.0/460.0. |

Example 29. Ethyl (R)-2-amino-5-(2-((6-amino-9H-purin-9-yl)methyl)-3,4-dichlorophenoxy)pentonate

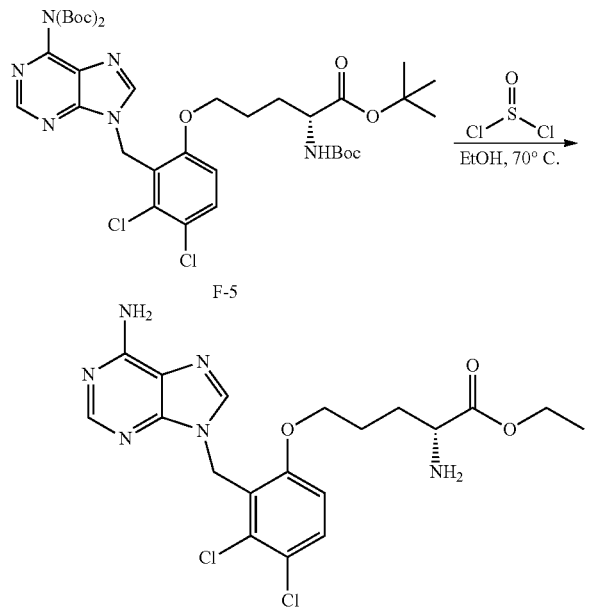

F-5

To an EtOH solution (1.2 L) of tert-butyl (R)-5-(2-((6-(bis(tert-butoxycarbonyl)amino)-9H-purin-9-yl)methyl)-3,4-dichlorophenoxy)-2-((tert-butoxycarbonyl)amino)pentanoate (Intermediate F-5) (120 g, 153.5 mmol) was added dropwise thionyl chloride (120 mL, 1.5 mol) and the mixture was stirred for 24 hrs at 70° C. The mixture was concentrated and the crude was dissolved in water (500 mL). The mixture was basified to pH 8 with saturated NaHCO$_3$ solution. The suspension was filtered off and the solid was dissolved in DCM/TFA solution (10:1 v/v). The reaction mixture was concentrated under vacuum and the crude was purified by prep-HPLC [column: Phenomenex synery: Max-Rp 250*80 mm 10 um, gradient 20%-50% B (A: water (0.1% TFA), B (acetonitrile))] to afford ethyl (R)-2-amino-5-(2-((6-amino-9H-purin-9-yl)methyl)-3,4-dichlorophenoxy)pentanoate as a white solid (TFA salt). $^1$H NMR (400 MHz, MeOH-d$_4$): δ 8.41 (s, 1H), 8.17 (s, 1H), 7.59 (d, J=8.8 Hz, 1H), 7.11 (d, J=8.80 Hz, 1H), 5.71 (s, 2H), 4.33-4.27 (m, 2H), 4.16 (t, J=6.0 Hz, 2H), 4.11 (t, J=6.2 Hz, 2H), 2.12-1.90 (m, 4H), 1.29 (t, J=7.2 Hz, 3H). LC-MS: [M+H]$^+$=453.1.

Example 30. Ethyl (2R)-2-amino-5-(2-((6-amino-9H-purin-9-yl)methyl)-3,4-dichlorophenoxy)hexanoate

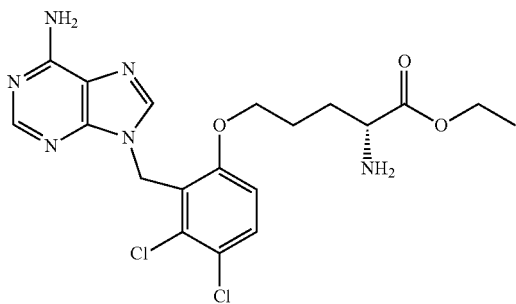 [SMILES: CCOC(=O)[C@H](N)CCCOc1ccc(Cl)c(Cl)c1Cn1cnc2c(N)ncnc21]

Step 1. tert-butyl (2R)-5-(2-((6-(bis(tert-butoxycarbonyl)amino)-9H-purin-9-yl)methyl)-3,4-dichlorophenoxy)-2-((tert-butoxycarbonyl)amino)hexanoate

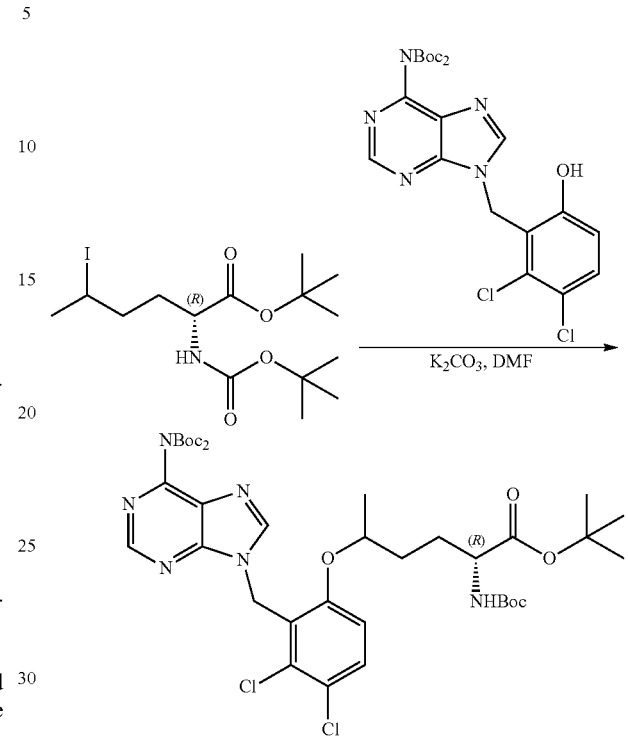

Potassium carbonate (135.4 mg, 979 μmol, 2.5 eq.) was added to a solution of tert-butyl (2R)-2-((tert-butoxycarbonyl)amino)-5-iodohexanoate (Intermediate K) (200 mg, 392 μmol, 1 eq.) and tert-butyl (tert-butoxycarbonyl)(9-(2,3-dichloro-6-hydroxybenzyl)-9H-purin-6-yl)carbamate (162 mg, 392 μmol, 1 eq.) in DMF (15 mL). The reaction mixture was stirred at 40° C. for 18 hours. LCMS showed the desired product was observed. The mixture was diluted with water (20 mL) and extracted with ethyl acetate (3*20 mL). The organic layer was washed with brine (3*50 mL), dried over Na$_2$SO$_4$, filtered and concentrated under vacuum to afford tert-butyl (2R)-5-(2-((6-(bis(tert-butoxycarbonyl)amino)-9H-purin-9-yl)methyl)-3,4-dichlorophenoxy)-2-((tert-butoxycarbonyl)amino)hexanoate as yellow gum. LCMS (ESI) m/z 795.3 [M+H]$^+$.

Step 2. (2R)-2-((tert-butoxycarbonyl)amino)-5-(2-((6-((tert-butoxycarbonyl)amino)-9H-purin-9-yl)methyl)-3,4-dichlorophenoxy)hexanoic acid

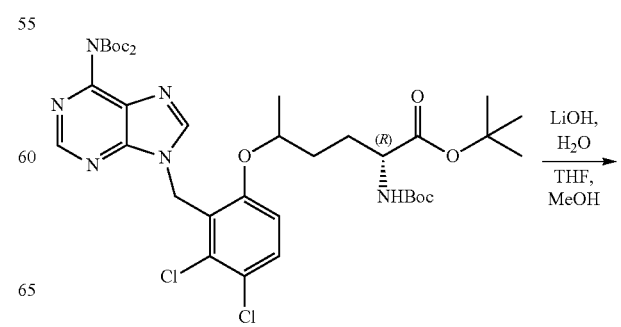

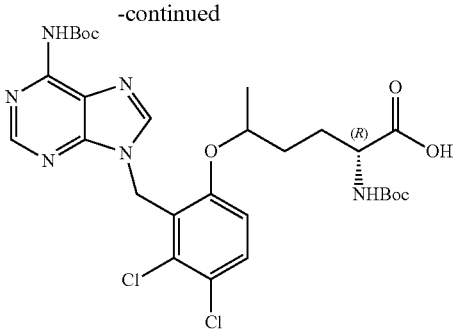

To tert-butyl (2R)-5-(2-((6-(bis(tert-butoxycarbonyl)amino)-9H-purin-9-yl)methyl)-3,4-dichlorophenoxy)-2-((tert-butoxycarbonyl)amino)hexanoate (250 mg, 314 μmol, 1 eq) in THF (5 ml) was added LiOH (0.2 g, 8.35 mmol), MeOH (5 ml) and H₂O (5 ml). The mixture was stirred for 14 h at 24-31° C. LCMS show the reaction was completed. The solution was adjust to pH=3 using 1M hydrochloride. Water (10 ml) was added and extracted with dichloromethane (2*10 ml). The organic layer was washed with brine (10 ml) dried over Na₂SO₄ and filtrated. The mixture was concentrated under vacuum to afford (2R)-2-((tert-butoxycarbonyl)amino)-5-(2-((6-((tert-butoxycarbonyl)amino)-9H-purin-9-yl)methyl)-3,4-dichlorophenoxy)hexanoic acid as a white solid. LC-MS (ESI) m/z 639.0 [M+H]⁺.

Step 3. Ethyl (2R)-2-((tert-butoxycarbonyl)amino)-5-(2-((6-((tert-butoxycarbonyl)amino)-9H-purin-9-yl)methyl)-3,4-dichlorophenoxy)hexanoate

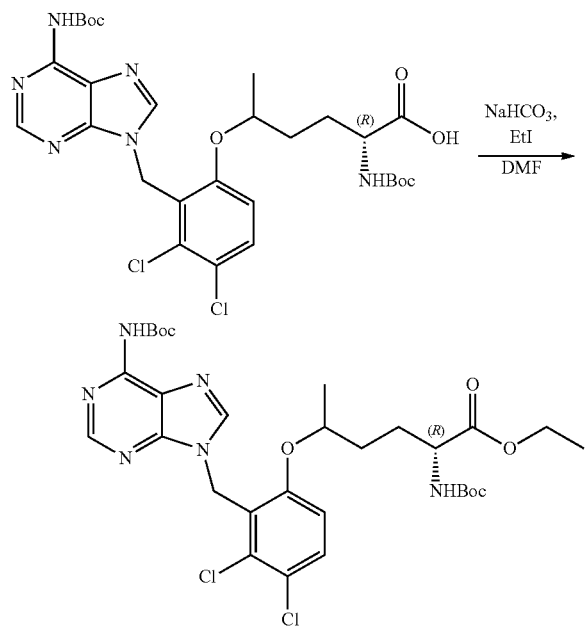

To (2R)-2-((tert-butoxycarbonyl)amino)-5-(2-((6-((tert-butoxycarbonyl)amino)-9H-purin-9-yl)methyl)-3,4-dichlorophenoxy)hexanoic acid (200 mg, 270.4 μmol, 1 eq) in DMF (10 ml) was added NaHCO₃ (68.15 mg 811.2 umol, 3 eq) and EtI (46.39 mg, 297.44 umol, 1.1 eq). The mixture was stirred for 14 h at 24-31° C. LCMS show the reaction was completed. The mixture was quenched with water (10 ml) and extracted with ethyl acetate (3*10 ml). The organic layer was washed with brine (10 ml) dried over Na₂SO₄ and filtrated. The mixture was concentrated under vacuum to afford crude product. The residue was purified by column chromatography on silica gel (petroleum ether:ethyl acetate=2:3) to afford ethyl (2R)-2-((tert-butoxycarbonyl)amino)-5-(2-((6-(((tert-butoxycarbonyl)amino)-9H-purin-9-yl)methyl)-3,4-dichlorophenoxy)hexanoate as a colorless oil. LC-MS (ESI) m/z 667.1 [M+H]⁺.

Step 4. Ethyl (2R)-2-amino-5-(2-((6-amino-9H-purin-9-yl)methyl)-3,4-dichlorophenoxy) hexanoate

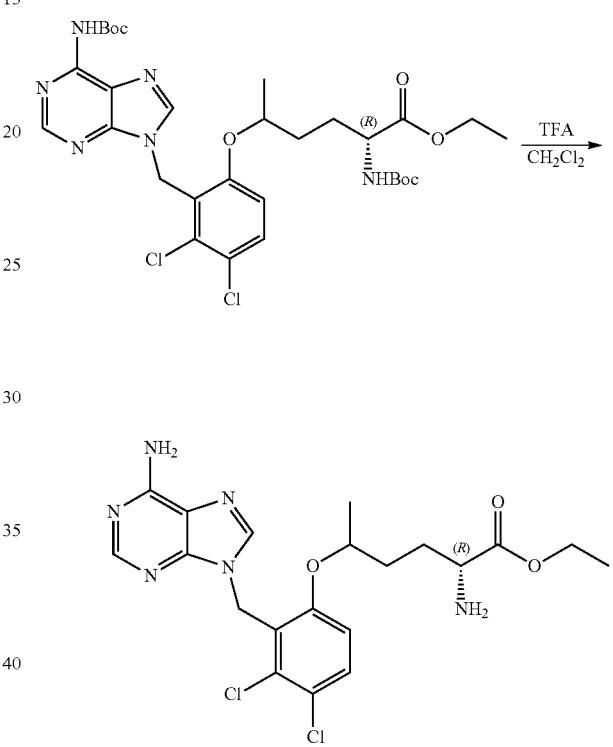

To ethyl (2R)-2-((tert-butoxycarbonyl)amino)-5-(2-((6-((tert-butoxycarbonyl)amino)-9H-purin-9-yl)methyl)-3,4-dichlorophenoxy)hexanoate (200 mg, 270.4 μmol, 1 eq) in dichloromethane (5 ml) was added TFA (5 ml) and stirred for 4 h at 25-31° C. LCMS show the reaction was completed. The mixture was purified by pre-HPLC (column: Boston Green ODS150*30 5u. Gradient 26-36% B (A: water (0.1% TFA), B: CH₃CN)) to give ethyl (2R)-2-amino-5-(2-((6-amino-9H-purin-9-yl)methyl)-3,4-dichlorophenoxy) hexanoate as a white solid. ¹H NMR (MeOD 400 MHz): 8.38 (s, 1H), 8.09 (s, 1H), 7.57 (d, J=9.20 Hz, 1H), 7.09 (d, J=9.20 Hz, 1H), 5.67 (s, 2H), 4.59-4.67 (m, 1H), 4.22-4.31 (m, 2H), 4.01-4.07 (m, 1H), 1.68-2.03 (m, 4H), 1.2-1.3 (m, 3H), 1.19 (d, J=5.60 Hz, 3H). LC-MS (ESI) m/z 467.1.0 [M+H]⁺.

The following examples were prepared from corresponding intermediates following procedures analogous to Example 31.

| Example No. | | |
|---|---|---|
| 31 | 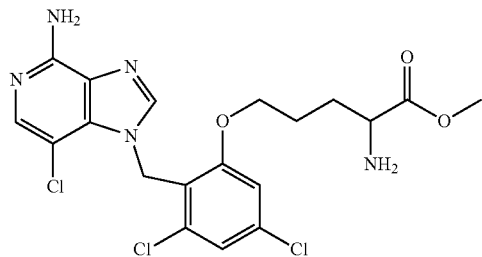 [SMILES: COC(=O)C(N)CCCOc1cc(Cl)cc(Cl)c1Cn1cnc2c(N)ncc(Cl)c21] | $^1$H NMR (400 MHz, DMSO-d$_6$) δ 7.65 (s, 1H), 7.64 (s, 1H), 7.32 (d, J = 1.9 Hz, 1H), 7.23 (d, J = 1.9 Hz, 1H), 6.39 (s, 2H), 5.73 (s, 2H), 4.04 (t, J = 6.2 Hz, 2H), 3.55 (s, 3H), 3.27-3.23 (m, 1H), 1.70-1.32 (m, 4H). LCMS ESI m/z M/M + 2 = 472.0/474.0. |
| 32 | 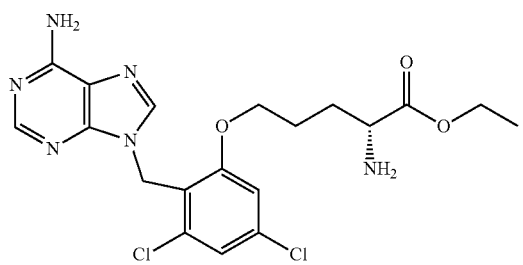 [SMILES: CCOC(=O)[C@H](N)CCCOc1cc(Cl)cc(Cl)c1Cn1cnc2c(N)ncnc21] | $^1$H NMR (400 MHz, MeOD): δ 8.27 (s, 1H), 7.83 (s, 1H), 7.21 (s, 1H), 7.12 (s, 1H), 5.54 (s, 1H), 4.16-4.12 (m, 2H), 4.08 (t, J = 4.8 Hz, 2H), 3.41-3.33 (m, 1H), 1.78-1.61 (m, 4H), 1.21 (t, J = 5.6 Hz, 3H). LC-MS (ESI) m/z 453.1/455.1 [M/M + 2]$^+$. |
| 33 | 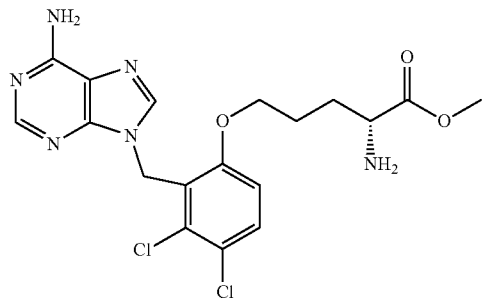 [SMILES: COC(=O)[C@H](N)CCCOc1ccc(Cl)c(Cl)c1Cn1cnc2c(N)ncnc21] | $^1$H NMR (400 MHz, MeOH-d$_4$): δ 8.27 (s, 1H), 7.81 (s, 1H), 7.58 (d, J = 9.2 Hz, 1H), 7.08 (d, J = 9.2 Hz, 1H), 5.61 (s, 2H), 4.08 (t, J = 5.6 Hz, 2H), 3.69 (s, 3H), 3.51-3.48 (m, 1H), 1.79-1.64 (m, 4H). LCMS ESI m/z M/M + 2 = 439.0/441.0. |

Example 34. Methyl (R)-2-amino-5-(2-((4-amino-imidazo[2,1-f][1,2,4]triazin-7-yl)methyl)-3,4-dichlorophenoxy)pentanoate

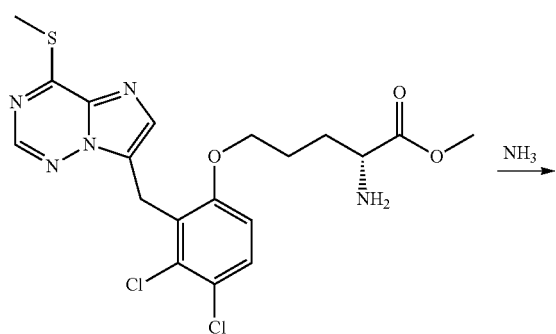 →NH$_3$ 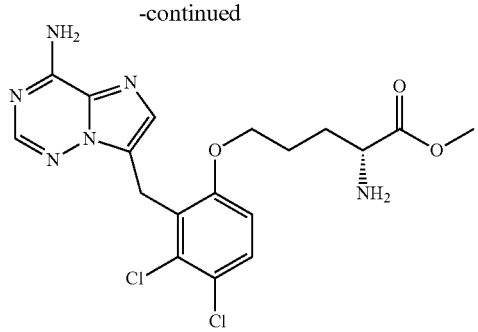

A mixture of methyl (R)-2-amino-5-(3,4-dichloro-2-((4-(methylthio)imidazo[2,1-f][1,2,4]triazin-7-yl)methyl)phenoxy)pentanoate (35 mg, 0.074 mmol) in ammonia (2 mL, 14 mmol) (7N in MeOH) was sealed in microwave tube and heated at 100° C. for 2 hr. The reaction mixture was concentrated. The crude product was purified by ISCO (silica gel, 0-15% MeOH in DCM) to remove the primary amide by-product and then submitted to prep. HPLC to afford methyl (R)-2-amino-5-(2-((4-aminoimidazo[2,1-f][1,2,4]triazin-7-yl)methyl)-3,4-dichlorophenoxy)pentanoate.
1H NMR (400 MHz, Methanol-d4) δ 8.11 (s, 1H), 7.46 (d, J=8.9 Hz, 1H), 7.00 (d, J=9.0 Hz, 1H), 6.94 (s, 1H), 4.45 (s, 2H), 4.01 (t, J=5.8 Hz, 2H), 3.63 (s, 3H), 3.38-3.32 (m, 1H), 1.81-1.60 (m, 3H), 1.60-1.47 (m, 1H). LCMS ESI m/z M/M+2=438.9/440.9.

Example 35. (R)-2-amino-5-(2-((4-aminoimidazo[2,1-f][1,2,4]triazin-7-yl)methyl)-3,4-dichlorophenoxy)pentanamide

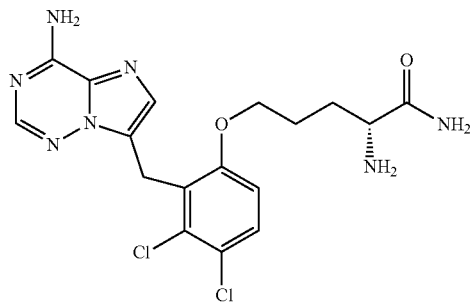 [SMILES: NC(=O)[C@H](N)CCCOc1ccc(Cl)c(Cl)c1Cc1cnc2c(N)ncnn12]

Step 1. Methyl (2R)-2-((tert-butoxycarbonyl)amino)-5-(3,4-dichloro-2-(hydroxy(4-(methylthio)imidazo[2,1-f][1,2,4]triazin-7-yl)methyl)phenoxy)pentanoate

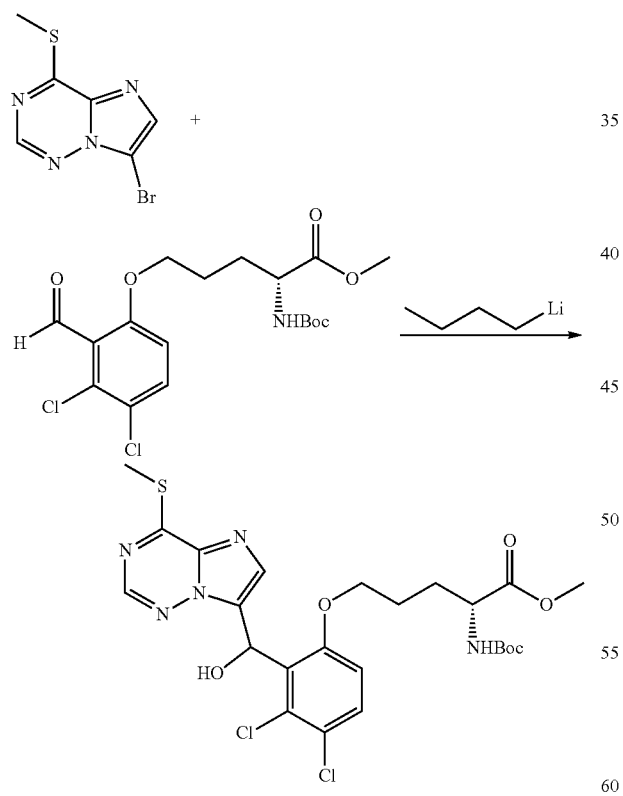

At −78° C., to a solution of 7-bromo-4-(methylthio)imidazo[2,1-f][1,2,4]triazine (Intermediate G) (467 mg, 1.9 mmol) in THF (15 mL) was added n-butyllithium (1.1 mL, 2.3 mmol) dropwise and the resulting mixture was stirred at −78° C. for 15 min. The carbon anion solution was quickly transferred to a pre-cooled solution of methyl (R)-2-((tert-butoxycarbonyl)amino)-5-(3,4-dichloro-2-formylphenoxy)pentanoate (Intermediate H) (400 mg, 0.95 mmol) in 5 mL THF at −78° C. The reaction mixture was stirred at −78° C. for 10 min and warmed up to r.t. and stirred for 15 min. The reaction mixture was quenched with sat. NH₄Cl aq. solution and extracted with EtOAc. The organic layer was washed with brine, dried, filtered and concentrated. ISCO (silica gel, 0-70% EtOAc in hexanes) to afford methyl (2R)-2-((tert-butoxycarbonyl)amino)-5-(3,4-dichloro-2-(hydroxy(4-(methylthio)imidazo[2,1-f][1,2,4]triazin-7-yl)methyl)phenoxy)pentanoate as a yellow oil. LCMS ESI m/z M/M+2=585.8/587.8.

Step 2. Methyl (R)-2-amino-5-(3,4-dichloro-2-((4-(methylthio)imidazo[2,1-f][1,2,4]triazin-7-yl)methyl)phenoxy)pentanoate

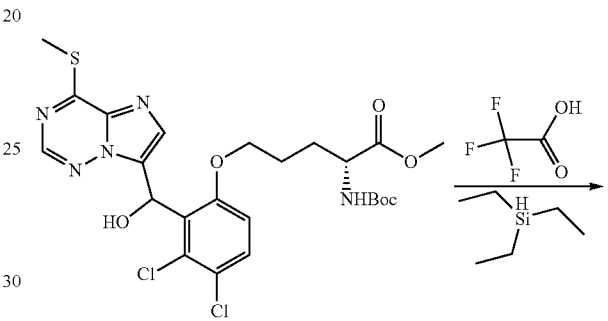

A mixture of methyl (2R)-2-((tert-butoxycarbonyl)amino)-5-(3,4-dichloro-2-(hydroxy(4-(methylthio)imidazo[2,1-f][1,2,4]triazin-7-yl)methyl)phenoxy)pentanoate (315 mg, 0.54 mmol), TFA (2.2 mL, 26.9 mmol) and triethylsilane (4.3 mL, 26.9 mmol) in CHCl₃ (8 mL) was stirred at 40° C. overnight. The reaction mixture was concentrated and the residue was diluted with EtOAc, washed with sat. NaHCO₃ aq. solution and brine, dried, filtered and concentrated. The crude product was used in the next step without purification. LCMS ESI m/z M/M+2=467.8/469.8.

Step 3. (R)-2-amino-5-(2-((4-aminoimidazo[2,1-f][1,2,4]triazin-7-yl)methyl)-3,4-dichloro phenoxy)pentanamide

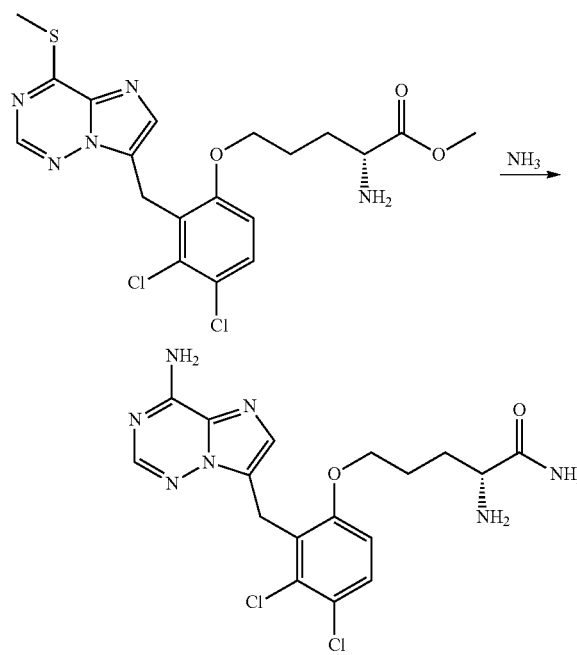

MeOH in DCM) and then submitted to prep. HPLC to afford (R)-2-amino-5-(2-((4-aminoimidazo[2,1-f][1,2,4]triazin-7-yl)methyl)-3,4-dichloro phenoxy)pentanamide as a white powder. 1H NMR (400 MHz, Methanol-d4) δ 8.11 (s, 1H), 7.45 (d, J=8.9 Hz, 1H), 7.01 (d, J=9.0 Hz, 1H), 6.96 (s, 1H), 4.45 (s, 2H), 4.02 (t, J=6.1 Hz, 2H), 3.28-3.24 (m, 1H), 1.82-1.61 (m, 3H), 1.61-1.49 (m, 1H). LCMS ESI m/z M/M+2=423.9/425.9.

Example 36. (R)-2-amino-5-(2-((4-aminoimidazo[2,1-f][1,2,4]triazin-7-yl)methyl)-3,4-dichlorophenoxy)-N-cyclopropylpentanamide

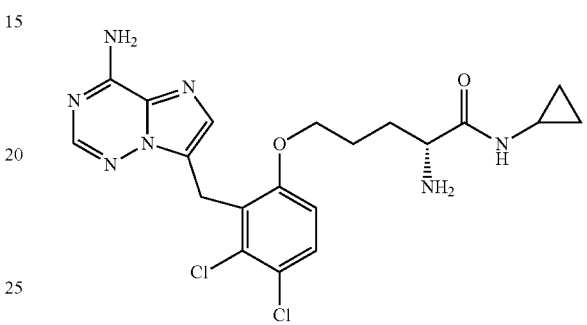

Step 1. tert-butyl ((2R)-1-(cyclopropylamino)-5-(3,4-dichloro-2-(hydroxy(4-(methylthio) imidazo[2,1-f][1,2,4]triazin-7-yl)methyl)phenoxy)-1-oxopentan-2-yl)carbamate

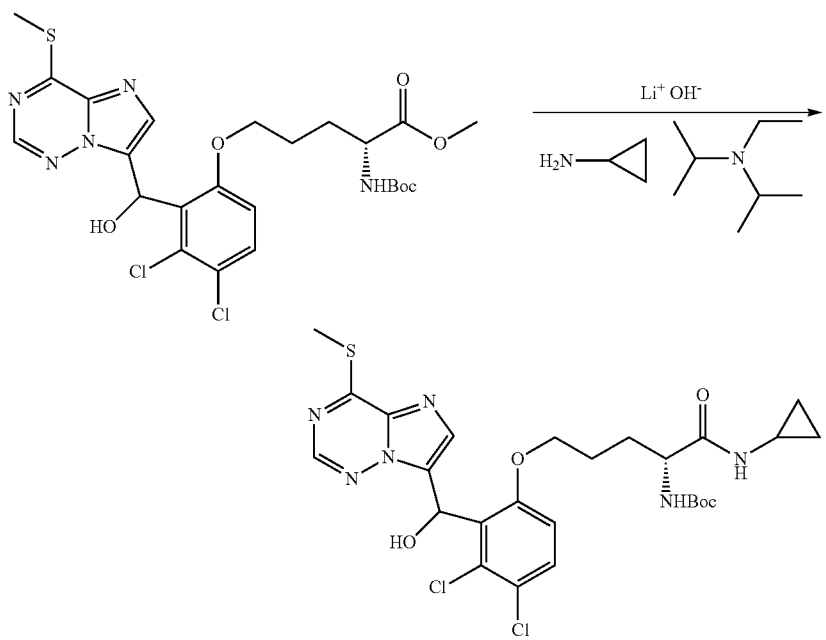

A mixture of methyl (R)-2-amino-5-(3,4-dichloro-2-((4-(methylthio)imidazo[2,1-f][1,2,4]triazin-7-yl)methyl)phenoxy)pentanoate (50 mg, 0.11 mmol) in ammonia (2 mL, 14 mmol) was sealed in microwave tube and heated at 100° C. overnight. The reaction mixture was concentrated. The crude product was purified by ISCO (silica gel, 0-20%

A mixture of methyl (2R)-2-((tert-butoxycarbonyl)amino)-5-(3,4-dichloro-2-(hydroxy(4-(methylthio)imidazo[2,1-f][1,2,4]triazin-7-yl)methyl)phenoxy)pentanoate (90 mg, 0.15 mmol) in lithium hydroxide (3 mL, 3 mmol) and THF (5 mL) was stirred at r.t. for 2 hr. The reaction mixture was acidified to pH 3-4 with 1N HCl and extracted with EtOAc. The organic layer was washed with brine, dried, filtered and concentrated. The residue was mixed with cyclopropylamine (0.016 mL, 0.23 mmol), DIEA (0.080 mL, 0.46 mmol) and propylphosphonic anhydride solution (T3P®) (195 mg, 0.31 mmol) in EtOAc (5 mL) and stirred at r.t. for 3 hr. The reaction mixture diluted with EtOAc, washed with sat. NaHCO$_3$ aq. solution, citric acid aq. solution and brine, dried, filtered and concentrated. The crude product was used in the next step without purification. LCMS ESI m/z M/M+2=610.9/612.9.

Step 2. (R)-2-amino-N-cyclopropyl-5-(3,4-dichloro-2-((4-(methylthio)imidazo[2,1-f][1,2,4]triazin-7-yl)methyl)phenoxy)pentanamide

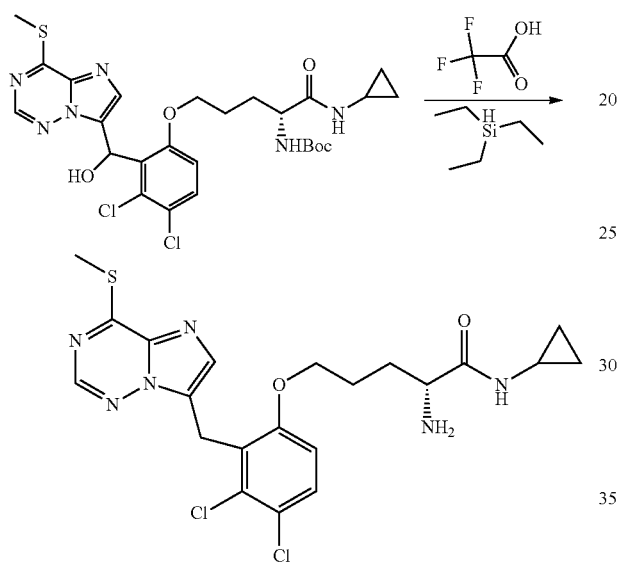

A mixture of tert-butyl ((2R)-1-(cyclopropylamino)-5-(3,4-dichloro-2-(hydroxy(4-(methylthio)imidazo[2,1-f][1,2,4]triazin-7-yl)methyl)phenoxy)-1-oxopentan-2-yl)carbamate (80 mg, 0.13 mmol), TFA (0.50 mL, 6.5 mmol) and triethylsilane (1 mL, 6.5 mmol) in CHCl$_3$ (2 mL) was stirred at 40° C. overnight. The reaction mixture was concentrated and the residue was partitioned between EtOAc and water. The organic layer was washed with brine, dried, filtered and concentrated. The crude product was used in the next step without purification. LCMS ESI m/z M/M+2=494.9/496.9.

Step 3. (R)-2-amino-5-(2-((4-aminoimidazo[2,1-f][1,2,4]triazin-7-yl)methyl)-3,4-dichlorophen oxy)-N-cyclopropylpentanamide

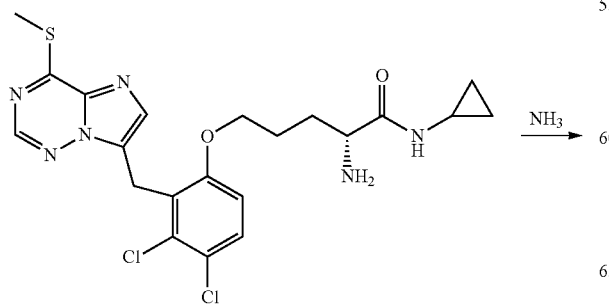

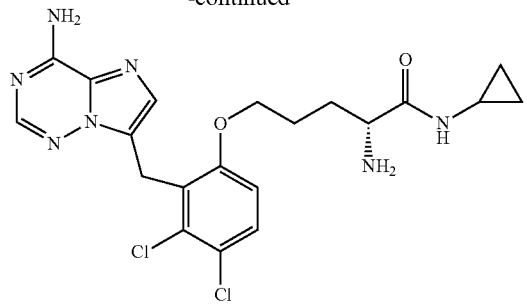

A mixture of (R)-2-amino-N-cyclopropyl-5-(3,4-dichloro-2-((4-(methylthio)imidazo[2,1-f][1,2,4]triazin-7-yl)methyl)phenoxy)pentanamide (60 mg, 0.10 mmol) in ammonia (2 mL, 14 mmol) was sealed in microwave tube and heated at 100° C. for 2 hr. The reaction mixture was concentrated. The crude product was submitted to prep. HPLC to afford (R)-2-amino-5-(2-((4-aminoimidazo[2,1-f][1,2,4]triazin-7-yl)methyl)-3,4-dichlorophen oxy)-N-cyclopropylpentanamide. LCMS ESI m/z M/M+2=463.9/465.9. $^1$H NMR (400 MHz, Methanol-d4) δ 8.11 (s, 1H), 7.45 (d, J=8.9 Hz, 1H), 7.00 (d, J=9.0 Hz, 1H), 6.94 (s, 1H), 4.44 (s, 2H), 4.01 (t, J=6.0 Hz, 2H), 3.16 (t, J=6.3 Hz, 1H), 2.64-2.57 (m, 1H), 1.77-1.60 (m, 3H), 1.59-1.48 (m, 1H), 0.72-0.63 (m, 2H), 0.50-0.35 (m, 2H).

Example 37. (R)-2-amino-5-(2-((4-aminopyrazolo[1,5-a][1,3,5]triazin-8-yl)methyl)-3,4-dichlorophenoxy)-N-cyclopropylpentanamide

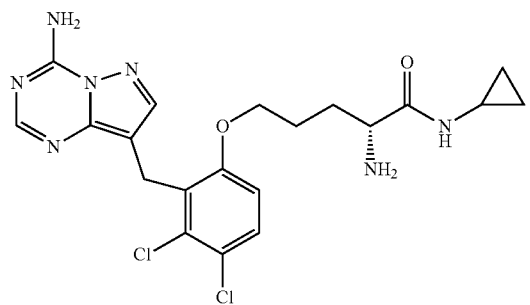 [SMILES: Nc1ncnc2c(Cc3c(OCCC[C@@H](N)C(=O)NC4CC4)ccc(Cl)c3Cl)cnn12]

Step 1. N-methy-N-phenylpyrazolo[1,5-a][1,3,5]triazin-4-amine

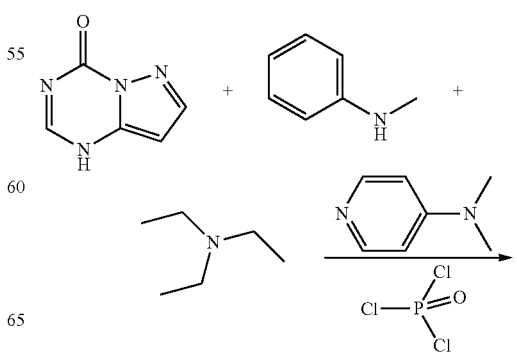

-continued

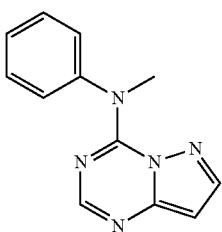

A mixture of pyrazolo[1,5-a][1,3,5]triazin-4(1H)-one (2 g, 14.7 mmol), DMAP (5.4 g, 44.1 mmol) and POCl₃ (15.1 mL, 162 mmol) was stirred at 120° C. for 4 hr. The resulting mixture was concentrated and the residue was dissolved in DCM (50 mL) and treated with N-methylaniline (6.4 mL, 58.8 mmol) and TEA (12.3 mL, 88 mmol). The reaction mixture was stirred at r.t. for 2 hr. The reaction mixture was diluted with DCM, washed with water and brine, dried, filtered and concentrated (filtered through Celite pad if there was insoluble materials). ISCO (0-50% EtOAc in hexanes) to afford N-methyl-N-phenylpyrazolo[1,5-a][1,3,5]triazin-4-amine as a white solid. LCMS ESI m/z M+1=226.0.

Step 2. 8-Iodo-N-methyl-N-phenylpyrazolo[1,5-a][1,3,5]triazin-4-amine

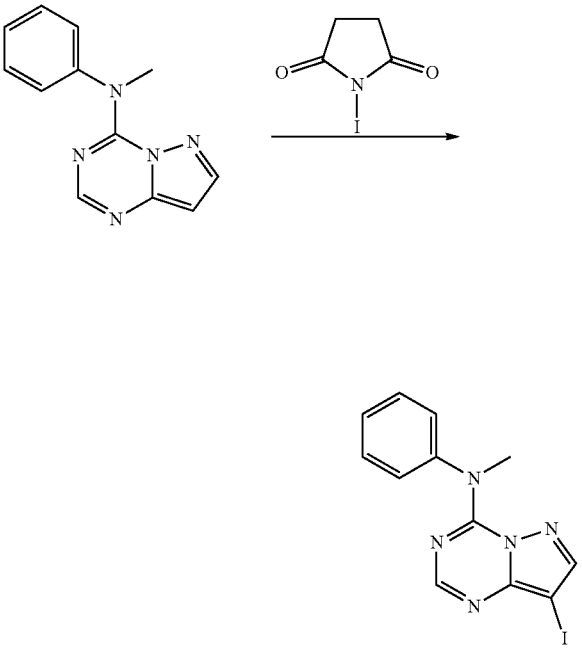

A mixture of N-methyl-N-phenylpyrazolo[1,5-a][1,3,5]triazin-4-amine (1.5 g, 6.7 mmol) and NIS (1.9 g, 8.7 mmol) in chloroform (30 mL) was stirred at 80° C. for 1 hr. The reaction mixture was quenched with 1N Na₂S₂O₃ aq. solution and extracted with DCM. The organic layer was washed with brine, dried, filtered and concentrated. ISCO (silica gel, 0-30% EtOAc in hexanes) to afford 8-iodo-N-methyl-N-phenylpyrazolo[1,5-a][1,3,5]triazin-4-amine as a light brown solid. LCMS ESI m/z M+1=351.9.

Step 3. Methyl (2R)-2-((tert-butoxycarbonyl)amino)-5-(3,4-dichloro-2-(hydroxy(4-(methyl (phenyl)amino)pyrazolo[1,5-a][1,3,5]triazin-8-yl)methyl)phenoxy)pentanoate

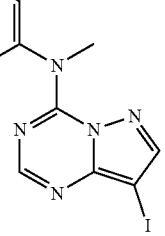

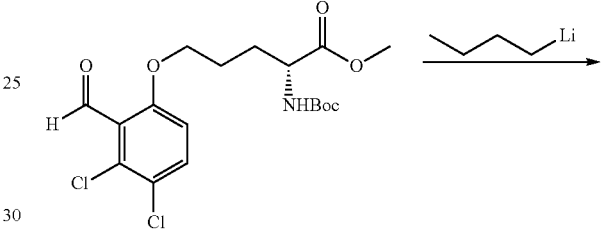

At −78° C., to a solution of 8-iodo-N-methyl-N-phenylpyrazolo[1,5-a][1,3,5]triazin-4-amine (284 mg, 0.81 mmol) in THF (10 mL) was added n-butyllithium (0.61 mL, 1.2 mmol). The resulting mixture was stirred at −78° C. for 15 min and the solution was transferred to a pre-cooled solution of methyl (R)-2-((tert-butoxycarbonyl)amino)-5-(3,4-dichloro-2-formylphenoxy) pentanoate (Intermediate H) (170 mg, 0.404 mmol) in 4 mL THF at −78° C. The reaction mixture was stirred at −78° C. for 10 min and warmed up to r.t. The reaction mixture was quenched with sat. NH₄Cl aq. solution and extracted with EtOAc. The organic layer was washed with brine, dried, filtered and concentrated. ISCO (silica gel, 0-50% EtOAc in hexanes) to afford methyl (2R)-2-((tert-butoxycarbonyl)amino)-5-(3,4-dichloro-2-(hydroxy(4-(methyl (phenyl)amino)pyrazolo[1,5-a][1,3,5]triazin-8-yl)methyl)phenoxy)pentanoate. LCMS ESI m/z M/M+2=644.9/646.9.

Step 4. tert-Butyl ((2R)-1-(cyclopropylamino)-5-(3,4-dichloro-2-(hydroxy(4-(methyl(phenyl)amino)pyrazolo[1,5-a][1,3,5]triazin-8-yl)methyl)phenoxy)-1-oxopentan-2-yl)carbamate

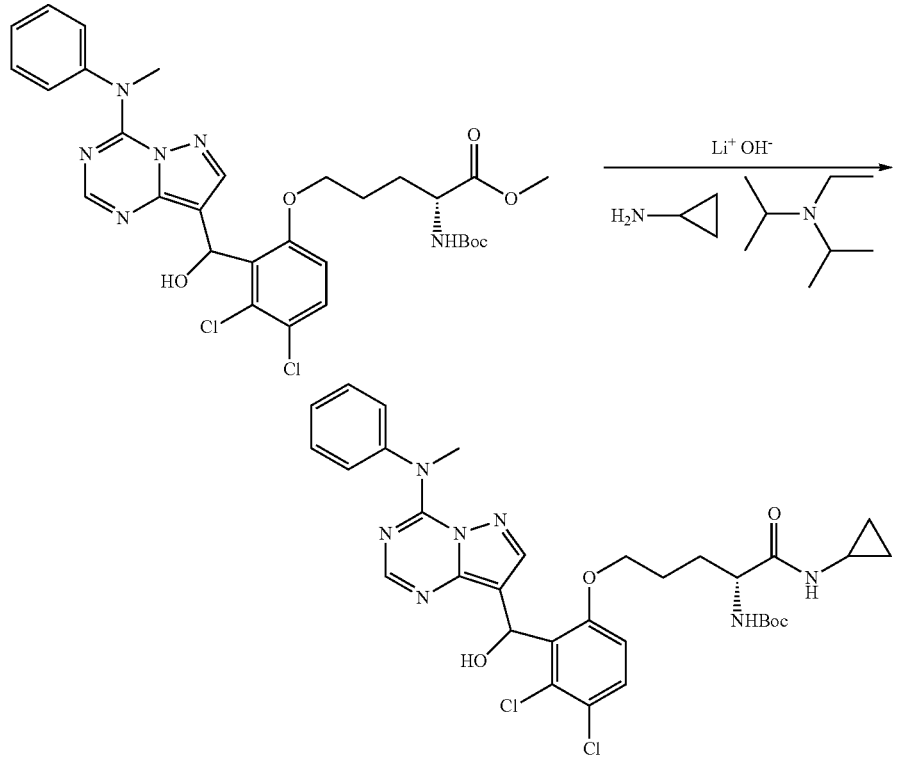

A mixture of methyl (2R)-2-((tert-butoxycarbonyl)amino)-5-(3,4-dichloro-2-(hydroxy(4-(methyl(phenyl)amino)pyrazolo[1,5-a][1,3,5]triazin-8-yl)methyl)phenoxy)pentanoate (86 mg, 0.13 mmol) in lithium hydroxide (4 mL, 4 mmol) and THF (6 mL) was stirred at r.t. for 2 hr. The reaction mixture was acidified to pH 3-4 with 1N HCl and extracted with EtOAc. The organic layer was washed with brine, dried, filtered and concentrated. The residue was mixed with cyclopropylamine (0.014 mL, 0.20 mmol), DIEA (0.14 mL, 0.80 mmol) and propylphosphonic anhydride solution (T3P®) (170 mg, 0.27 mmol) in EtOAc (6 mL) was stirred at r.t. for 3 hr. The reaction mixture diluted with EtOAc, washed with sat. NaHCO₃ aq. solution, citric acid aq. solution and brine, dried, filtered and concentrated. The crude product was used in the next step without purification. LCMS ESI m/z M/M+2=669.9/671.9.

Step 5. (R)-2-amino-N-cyclopropyl-5-(3,4-dichloro-2-((4-(methyl(phenyl)amino)pyrazolo[1,5-a][1,3,5]triazin-8-yl)methyl)phenoxy)pentanamide

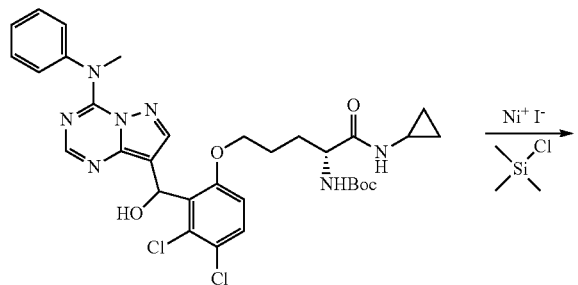

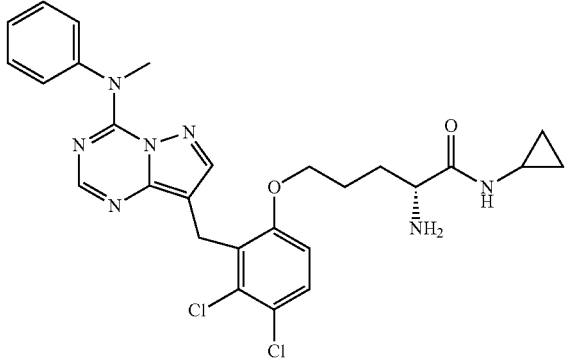

A mixture of sodium iodide (268 mg, 1.8 mmol) and sodium iodide (268 mg, 1.8 mmol) in acetonitrile (2 mL) was stirred at r.t. for 15 min before the addition of tert-butyl ((2R)-1-(cyclopropylamino)-5-(3,4-dichloro-2-(hydroxy(4-(methyl(phenyl)amino)pyrazolo[1,5-a][1,3,5]triazin-8-yl)methyl)phenoxy)-1-oxopentan-2-yl)carbamate in acetonitrile (~1 mL). The resulting mixture was stirred at r.t. for 1 hr. The reaction was quenched with sat. Na₂SO₃ aq. solution and extracted with EtOAc. The organic layer was washed with brine, dried, filtered and concentrated. ISCO (silica gel, 0-10% MeOH in DCM) to afford (R)-2-amino-N-cyclopropyl-5-(3,4-dichloro-2-((4-(methyl(phenyl)amino)pyrazolo[1,5-a][1,3,5]triazin-8-yl)methyl)phenoxy)pentanamide. LCMS ESI m/z M/M+2=553.9/555.9.

Step 6. (R)-2-amino-5-(2-((4-aminopyrazolo[1,5-a][1,3,5]triazin-8-yl)methyl)-3,4-dichloro phenoxy)-N-cyclopropylpentanamide

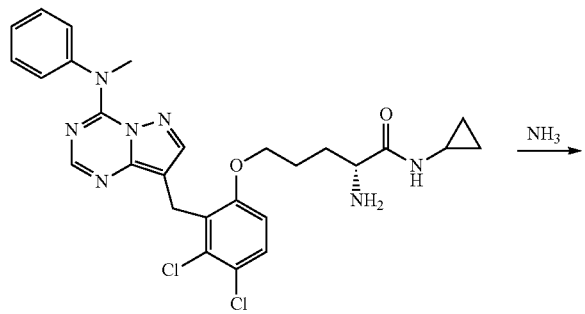

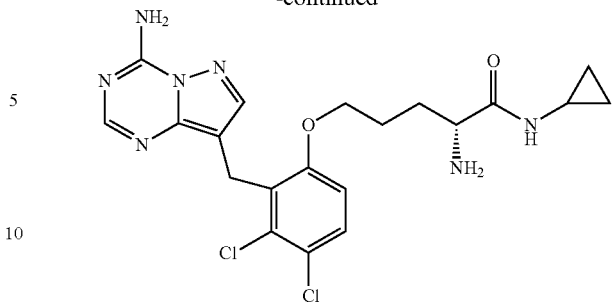

A mixture of (R)-2-amino-N-cyclopropyl-5-(3,4-dichloro-2-((4-(methyl(phenyl)amino)pyrazolo [1,5-a][1,3,5]triazin-8-yl)methyl)phenoxy)pentanamide (60 mg, 0.11 mmol) in ammonia (2 mL, 14 mmol) was sealed in microwave tube and heated at 100° C. overnight. The reaction mixture was concentrated. The crude product was purified by prep. HPLC to afford (R)-2-amino-5-(2-((4-aminopyrazolo[1,5-a][1,3,5]triazin-8-yl)methyl)-3,4-dichloro phenoxy)-N-cyclopropylpentanamide as a white powder. LCMS ESI m/z M/M+2=463.9/465.9. $^1$H NMR (400 MHz, Methanol-d4) δ 8.08 (s, 1H), 7.62 (s, 1H), 7.39 (d, J=9.6 Hz, 1H), 6.96 (d, J=8.9 Hz, 1H), 4.23 (s, 2H), 4.03 (t, J=5.6 Hz, 2H), 3.22 (t, J=6.3 Hz, 1H), 2.65-2.57 (m, 1H), 1.84-1.67 (m, 3H), 1.67-1.57 (m, 1H), 0.75-0.64 (m, 2H), 0.49-0.36 (m, 2H).

The following examples were prepared from corresponding intermediates following procedures analogous to Example 37.

| Example No. | | |
|---|---|---|
| 38 | 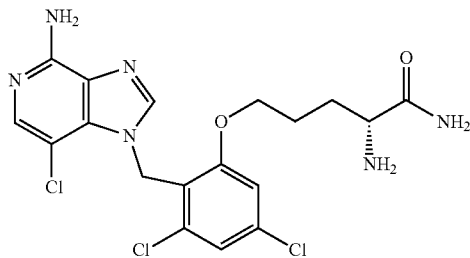 [SMILES: NC(=O)[C@H](N)CCCOc1cc(Cl)cc(Cl)c1Cn1cnc2c(N)ncc(Cl)c21] | $^1$H NMR (400 MHz, Methanol-d$_4$) δ 7.82 (s, 1H), 7.78 (s, 1H), 7.26 (d, J = 1.9 Hz, 1H), 7.18 (d, J = 1.9 Hz, 1H), 5.94 (s, 2H), 4.12 (t, J = 5.8 Hz, 2H), 3.86 (t, J = 6.0 Hz, 1H), 1.96-1.75 (m, 4H). LCMS ESI m/z M + 1 = 459.0. |
| 39 | 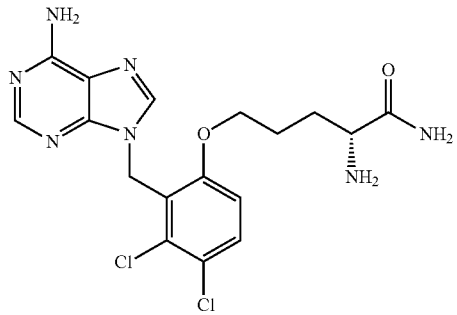 [SMILES: NC(=O)[C@H](N)CCCOc1ccc(Cl)c(Cl)c1Cn1cnc2c(N)ncnc21] | $^1$H NMR (400 MHz, Methanol-d$_4$) δ 8.37 (s, 1H), 8.07 (br s, 1H), 7.59 (d, J = 9.0 Hz, 1H), 7.10 (d, J = 9.0 Hz, 1H), 5.68 (s, 2H), 4.14-4.17 (m, 2H), 3.92-3.94 (m, 1H), 1.88-2.07 (m, 4H); LC-MS: [M + H]$^+$ = 424.0. |

| Example No. | | |
|---|---|---|
| 40 | 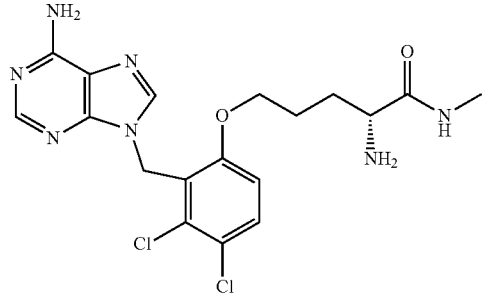 [SMILES: CNC(=O)[C@H](N)CCCOc1ccc(Cl)c(Cl)c1Cn1cnc2c(N)ncnc21] | ¹H NMR (MeOD 400 MHz): δ 8.39 (s, 1H), 8.10 (s, 1H), 7.59 (d, J = 7.6 Hz, 1H), 7.11-7.08 (m, 1H), 5.69 (s, 2H), 4.16-4.12 (m, 2H), 3.85 (t, J = 5.2 Hz, 1H), 2.80 (s, 3H), 2.06-2.81 (m, 4H). LC-MS (ESI) m/z 438.1/440.1 [M/M + 2]⁺. |
| 41 | 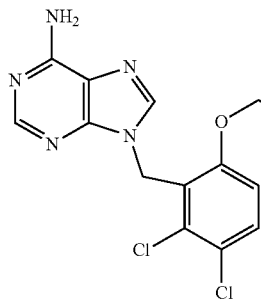 | ¹H NMR (400 MHz, MeOH-d₄): δ 8.27 (s, 1H), 7.83 (s, 1H), 7.58 (d, J = 9.2 Hz, 1H), 7.08 (d, J = 9.2 Hz, 1H), 5.63-5.55 (m, 2H), 4.12-4.08 (m, 2H), 3.86 (t, J = 6.8 Hz, 1H), 3.45-3.39 (m, 4H), 3.28 (s, 3H), 2.01-1.82 (m, 4H). LCMS ESI m/z M/M + 2 = 482.1/484.2. |
| 42 | 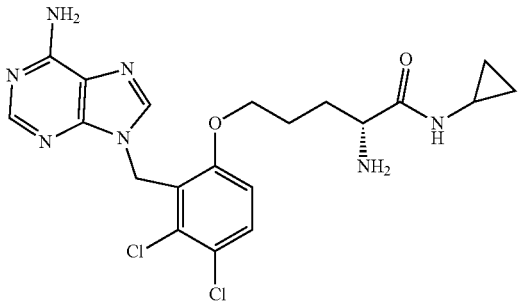 [SMILES: Nc1ncnc2c1ncn2Cc1c(OCCC[C@@H](N)C(=O)NC2CC2)ccc(Cl)c1Cl] | ¹H NMR (400 MHz, Methanol-d₄) δ 8.37 (s, 1H), 8.05 (d, J = 5.2 Hz, 1H), 7.61-7.54 (m, 1H), 7.07 (d, J = 9.0 Hz, 1H), 5.66 (s, 2H), 4.12 (t, J = 6.0 Hz, 2H), 3.77 (t, J = 6.7 Hz, 1H), 2.69 (dt, J = 7.3, 3.7 Hz, 1H), 1.96 (dp, J = 13.4, 6.9, 5.9 Hz, 2H), 1.83 (q, J = 7.3 Hz, 2H), 0.74 (d, J = 7.2 Hz, 2H), 0.50 (d, J = 11.9 Hz, 1H), 0.47-0.39 (m, 1H). LC-MS: [M + H]⁺ = 464.2. |
| 43 | 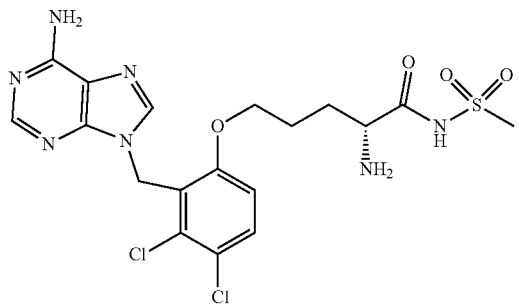 [SMILES: CS(=O)(=O)NC(=O)[C@H](N)CCCOc1ccc(Cl)c(Cl)c1Cn1cnc2c(N)ncnc21] | ¹H NMR (400 MHz, Methanol-d₄) δ 8.37 (s, 1H), 8.12 (d, J = 2.5 Hz, 1H), 7.57 (d, J = 9.0 Hz, 1H), 7.08 (d, J = 9.0 Hz, 1H), 5.68 (d, J = 2.1 Hz, 2H), 4.13 (t, J = 5.9 Hz, 2H), 3.92 (d, J = 6.4 Hz, 1H), 3.25-3.19 (m, 3H), 2.07 (tt, J = 14.2, 6.3 Hz, 2H), 1.91 (tq, J = 12.5, 6.8 Hz, 2H). LC-MS: [M + H]⁺ = 501.8. |

Example 44. (R)-2-amino-5-(2-((4-aminopyrazolo[1,5-a][1,3,5]triazin-8-yl)methyl)-3,4-dichlorophenoxy)pentan-1-ol

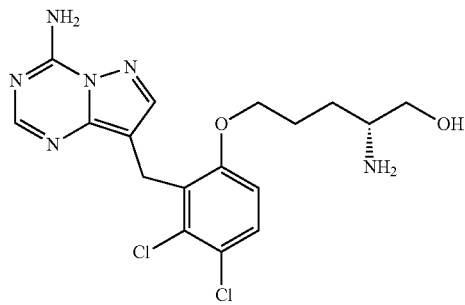 [SMILES: Nc1ncnc2c(Cc3c(OCCC[C@@H](N)CO)ccc(Cl)c3Cl)cnn12]

Step 1. Methyl (2R)-2-((tert-butoxycarbonyl)amino)-5-(3,4-dichloro-2-(hydroxy(4-(methyl(phenyl) amino)pyrazolo[1,5-a][1,3,5]triazin-8-yl)methyl)phenoxy)pentanoate

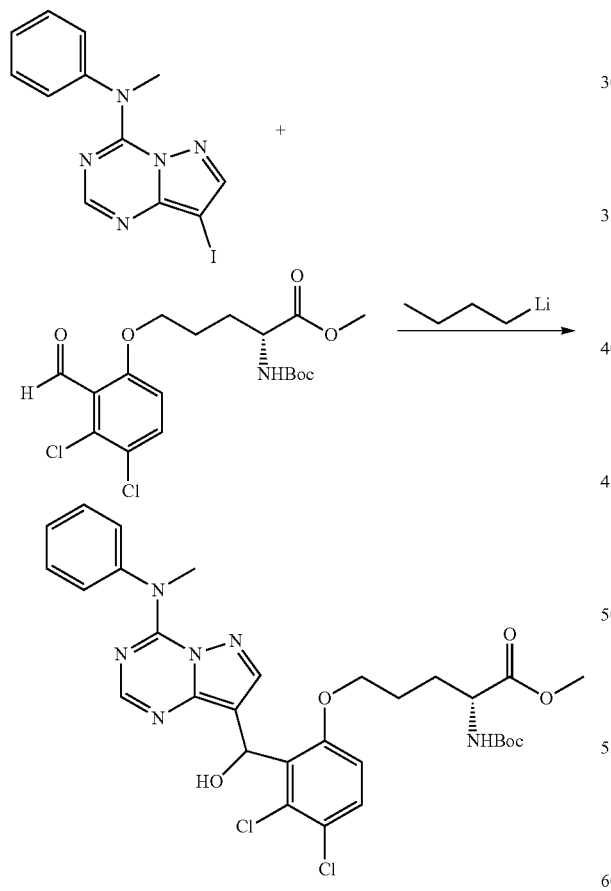

At −78° C., to a solution of 8-iodo-N-methyl-N-phenylpyrazolo[1,5-a][1,3,5]triazin-4-amine (167 mg, 0.48 mmol) in THF (4 mL) was added n-butyllithium (0.31 mL, 0.62 mmol). The resulting mixture was stirred at −78° C. for 15 min and the solution was transferred to a pre-cooled solution of methyl (R)-2-((tert-butoxycarbonyl)amino)-5-(3, 4-dichloro-2-formylphenoxy) pentanoate (100 mg, 0.24 mmol) in 2 mL THF at −78° C. The reaction mixture was stirred at −78° C. for 10 min and warmed up to r.t. The reaction mixture was quenched with sat. NH₄Cl aq. solution and extracted with EtOAc. The organic layer was washed with brine, dried, filtered and concentrated. ISCO (silica gel, 0-70% EtOAc in hexanes) to afford methyl (2R)-2-((tert-butoxycarbonyl)amino)-5-(3,4-dichloro-2-(hydroxy(4-(methyl(phenyl) amino)pyrazolo[1,5-a][1,3,5]triazin-8-yl)methyl)phenoxy)pentanoate. LCMS ESI m/z M/M+2=645.1/647.1.

Step 2. Methyl (R)-2-amino-5-(3,4-dichloro-2-((4-(methyl(phenyl)amino)pyrazolo[1,5-a][1,3,5] triazin-8-yl)methyl)phenoxy)pentanoate

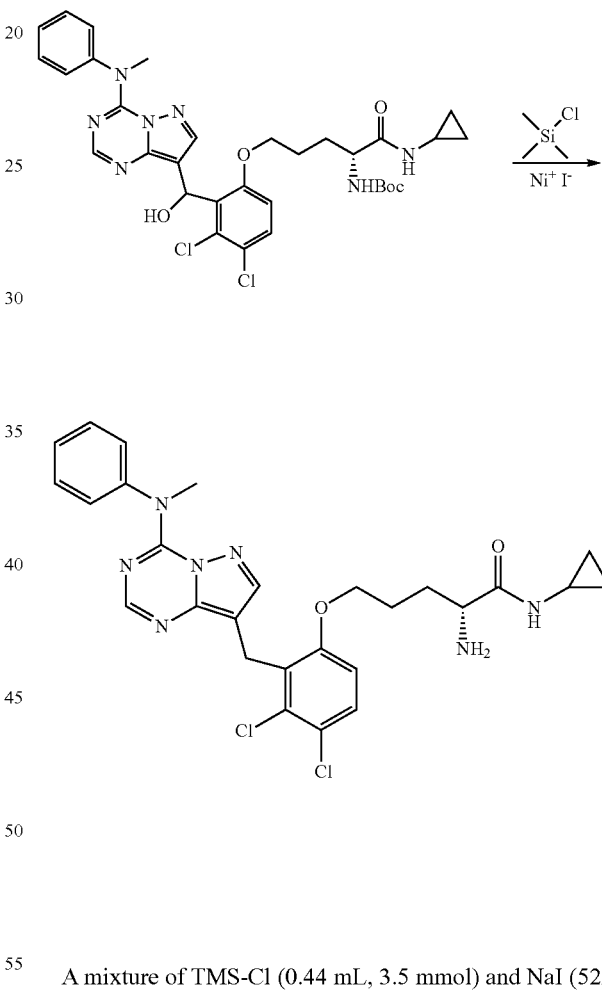

A mixture of TMS-Cl (0.44 mL, 3.5 mmol) and NaI (522 mg, 3.5 mmol) in acetonitrile (5 mL) was stirred at r.t. for 10 min, followed by the addition of methyl (2R)-2-((tert-butoxycarbonyl)amino)-5-(3,4-dichloro-2-(hydroxy(4-(methyl(phenyl)amino)pyrazolo[1,5-a][1,3,5]triazin-8-yl)methyl)phenoxy)pentanoate (225 mg, 0.35 mmol) in 2 mL acetonitrile. The reaction mixture was stirred at r.t. for 3 hr. The reaction mixture was quenched with sat. Na₂SO₃ aq. solution and extracted with EtOAc. The organic layer was washed with brine, dried, filtered and concentrated. The crude product was used in the next step without purification. LCMS ESI m/z M/M+2=529.1/531.1.

Step 3. Methyl (R)-2-((tert-butoxycarbonyl)amino)-5-(3,4-dichloro-2-((4-(methyl(phenyl)amino) pyrazolo[1,5-a][1,3,5]triazin-8-yl)methyl)phenoxy)pentanoate

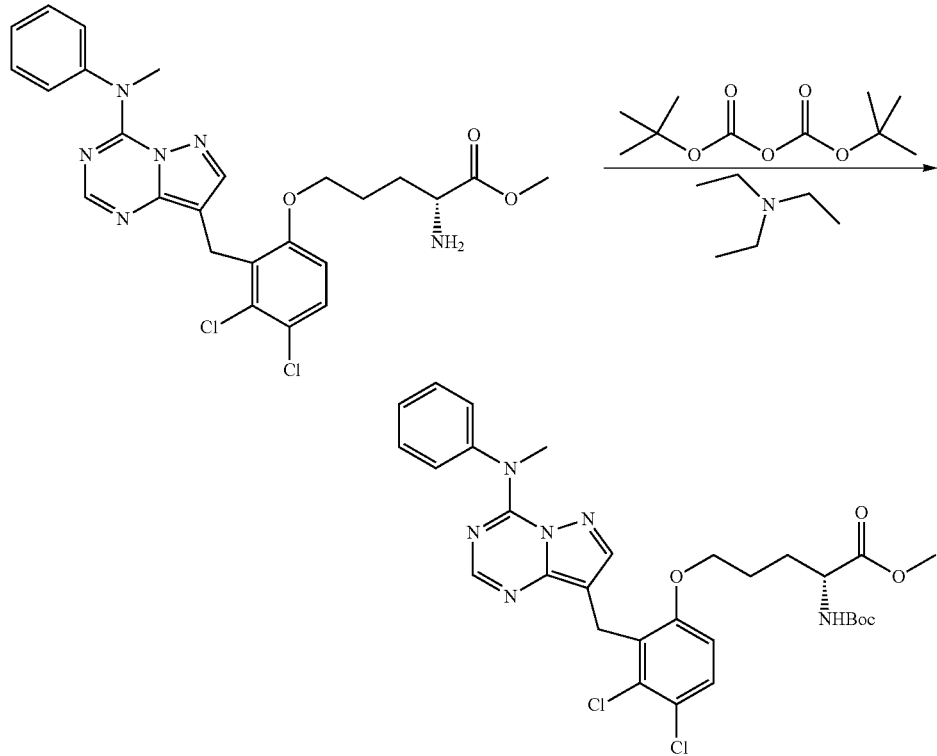

A mixture of methyl (R)-2-amino-5-(3,4-dichloro-2-((4-(methyl(phenyl)amino)pyrazolo[1,5-a][1,3,5]triazin-8-yl) methyl)phenoxy)pentanoate (185 mg, 0.35 mmol), Boc-Anhydride (203 μl, 0.87 mmol) and TEA (146 μl, 1 mmol) in DCM was stirred at r.t. for 2 hr. The reaction mixture was diluted with DCM, washed with water and brine, dried, filtered and concentrated. ISCO (silica gel, 0-50% EtOAc in hexanes) to afford methyl (R)-2-((tert-butoxycarbonyl) amino)-5-(3,4-dichloro-2-((4-(methyl(phenyl)amino) pyrazolo[1,5-a][1,3,5]triazin-8-yl)methyl)phenoxy)pentanoate. LCMS ESI m/z M/M+2=629.1/631.2.

Step 4. tert-Butyl (R)-(5-(3,4-dichloro-2-((4-(methyl (phenyl)amino)pyrazolo[1,5-a][1,3,5]triazin-8-yl) methyl)phenoxy)-1-hydroxypentan-2-yl)carbamate

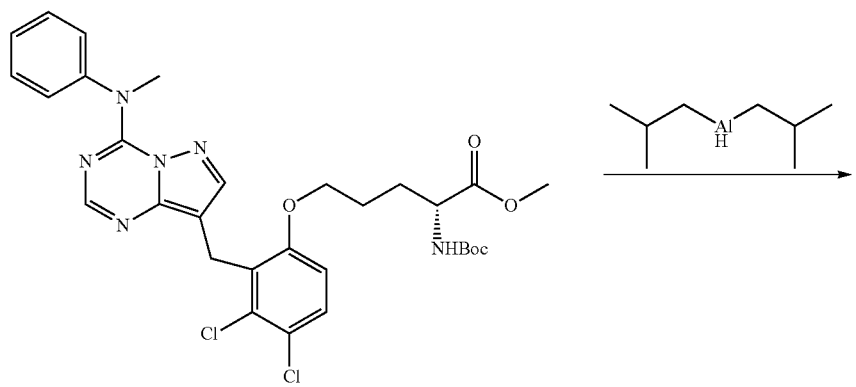

-continued

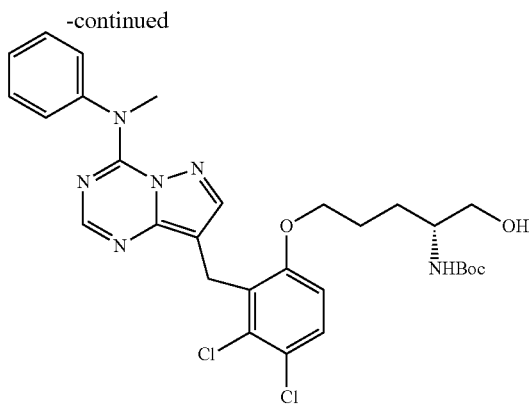

At 0° C., to a solution of methyl (R)-2-((tert-butoxycarbonyl)amino)-5-(3,4-dichloro-2-((4-(methyl(phenyl)amino)pyrazolo[1,5-a][1,3,5]triazin-8-yl)methyl)phenoxy)pentanoate (150 mg, 0.24 mmol) in DCM (5 mL) was added DIBAL-H (1.2 mL, 1.2 mmol) and the reaction mixture was stirred at 0° C. for 15 min. The reaction mixture was quenched with sat. Na₂CO₃ aq. solution and extracted with EtOAc. The organic layer was washed with brine, dried, filtered and concentrated. ISCO (silica gel, 0-70% EtOAc in hexanes) to afford tert-butyl (R)-(5-(3,4-dichloro-2-((4-(methyl(phenyl)amino)pyrazolo[1,5-a][1,3,5]triazin-8-yl)methyl)phenoxy)-1-hydroxypentan-2-yl)carbamate. LCMS ESI m/z M/M+2=601.1/603.1.

Step 5. (R)-2-amino-5-(2-((4-aminopyrazolo[1,5-a][1,3,5]triazin-8-yl)methyl)-3,4-dichlorophen oxy)pentan-1-ol

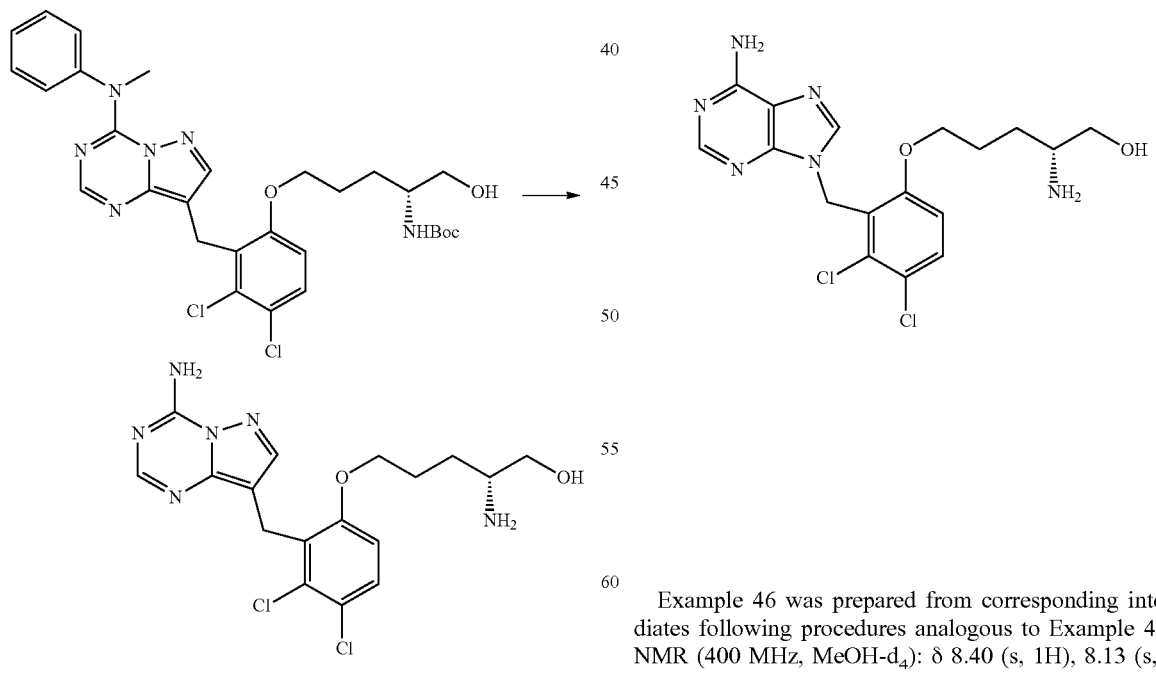

A mixture of tert-butyl (R)-(5-(3,4-dichloro-2-((4-(methyl(phenyl)amino)pyrazolo[1,5-a][1,3,5]triazin-8-yl)methyl)phenoxy)-1-hydroxypentan-2-yl)carbamate (25 mg, 0.042 mmol) in TFA (2 mL, 26 mmol) and DCM (5 mL) was stirred at r.t. for 2 hr and the resulting mixture was concentrated. The residue was dissolved in ammonia (2 mL, 14 mmol) and heated at 100° C. in microwave tube overnight. The reaction mixture was concentrated. The crude product was purified by prep. HPLC (basic condition with ammonia) to afford (R)-2-amino-5-(2-((4-aminopyrazolo[1,5-a][1,3,5]triazin-8-yl)methyl)-3,4-dichlorophen oxy)pentan-1-ol. LCMS ESI m/z M/M+2=411.1/413.1. $^1$H NMR (400 MHz, Methanol-d4) δ 8.07 (s, 1H), 7.62 (s, 1H), 7.39 (d, J=8.9 Hz, 1H), 6.97 (d, J=8.9 Hz, 1H), 4.23 (s, 2H), 4.03 (t, J=6.1 Hz, 2H), 3.52-3.47 (m, 1H), 3.30-3.26 (m, 1H), 2.85-2.77 (m, 1H), 1.93-1.72 (m, 2H), 1.60-1.50 (m, 1H), 1.42-1.33 (m, 1H).

Example 45. (R)-2-amino-5-(2-((6-amino-9H-purin-9-yl)methyl)-3,4-dichlorophenoxy)pentan-1-ol Example 46 was prepared from corresponding intermediates following procedures analogous to Example 45. $^1$H NMR (400 MHz, MeOH-d₄): δ 8.40 (s, 1H), 8.13 (s, 1H), 7.59 (d, J=7.2 Hz, 1H), 7.10 (d, J=7.2 Hz, 1H), 5.69 (s, 2H), 4.14 (t, J=4.4 Hz, 2H), 3.78-3.75 (m, 1H), 3.58-3.56 (m, 1H), 3.28-3.24 (m, 1H), 1.89-1.71 (m, 4H). LCMS ESI m/z M/M+2=411.1/423.1.

Example 46. 1-(2-(4-aminobutoxy)-4,6-dichlorobenzyl)-1H-imidazo[4,5-c]pyridin-4-amine

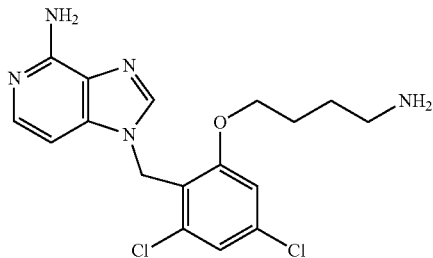 [SMILES: NCCCCOc1cc(Cl)cc(Cl)c1Cn1cnc2c(N)nccc21]

Step 1. tert-Butyl (1-(2-(allyloxy)-4,6-dichlorobenzyl)-1H-imidazo[4,5-c]pyridin-4-yl)(tert-butoxycarbonyl)carbamate

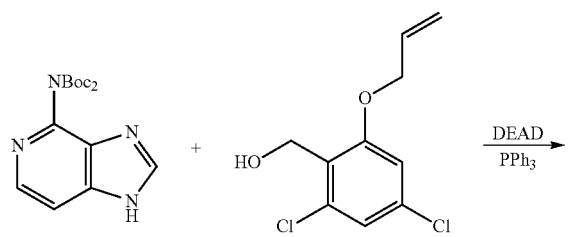

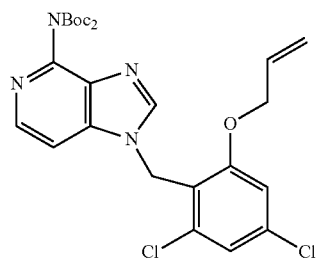

To a solution of (2-(allyloxy)-4,6-dichlorophenyl)methanol (500 mg, 2.1 mmol), tert-butyl (tert-butoxycarbonyl)(1H-imidazo[4,5-c]pyridin-4-yl)carbamate (719 mg, 2.1 mmol), Ph₃P (1125 mg, 4.3 mmol) in THF (10 mL) was added dropwise DEAD (0.849 mL, 4.29 mmol) at 0° C. under N₂. The mixture was allowed to warmed to rt for 12 hrs, LC-MS indicated the reaction was completed. The mixture was treated with EA (30 ml) and H₂O (50 ml). The layers were separated and the aqueous layer was extracted with EA (30 mL*3). The combined organic layers were washed with brine, dried over Na₂SO₄ and filtered. The filtrate was concentrated. The residue was purified via biotage, eluting with EA in n-hexane (20% to 50%) to give 1-(2-(4-aminobutoxy)-4,6-dichlorobenzyl)-1H-imidazo[4,5-c]pyridin-4-amine as a light yellow syrup. LCMS ESI m/z M/M+2=549.7/551.7.

Step 2. tert-Butyl (tert-butoxycarbonyl)(1-(2,4-dichloro-6-hydroxybenzyl)-1H-imidazo[4,5-c]pyridin-4-yl)carbamate

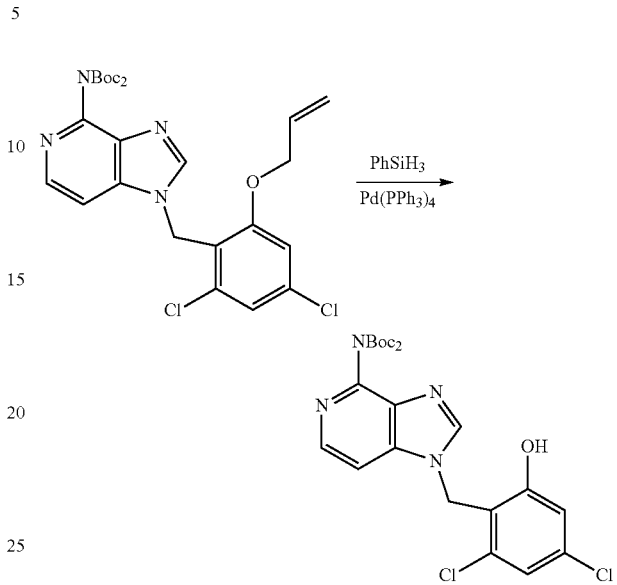

To a solution of tert-butyl (1-(2-(allyloxy)-4,6-dichlorobenzyl)-1H-imidazo[4,5-c]pyridin-4-yl)(tert-butoxycarbonyl)carbamate (992 mg, 1.8 mmol) and PhSiH₃ (390 mg, 3.6 mmol) in DCM (5 mL) was added Pd(Ph₃P)₄ (208 mg, 0.180 mmol) under N₂. The mixture was stirred at 25° C. under N₂ for 1 hrs. LC-MS indicated the reaction was completed. The mixture was treated with H₂O (20 ml) and DCM (20 ml). The layers were separated and the aqueous layer was extracted with DCM (20 ml*2). The combined organic layers were washed with brine, dried over Na₂SO₄ and filtered. The filtrate was concentrated. The residue was purified via biotage, eluting with EA in n-hexane 0 to 70% to give tert-butyl (tert-butoxycarbonyl)(1-(2,4-dichloro-6-hydroxybenzyl)-1H-imidazo[4,5-c]pyridin-4-yl)carbamate as a light yellow solid. LCMS ESI m/z m/M+2=509.7/511.7.

Step 3. tert-Butyl (tert-butoxycarbonyl)(1-(2-(4-((tert-butoxycarbonyl)amino)butoxy)-4,6-dichlorobenzyl)-1H-imidazo[4,5-c]pyridin-4-yl)carbamate

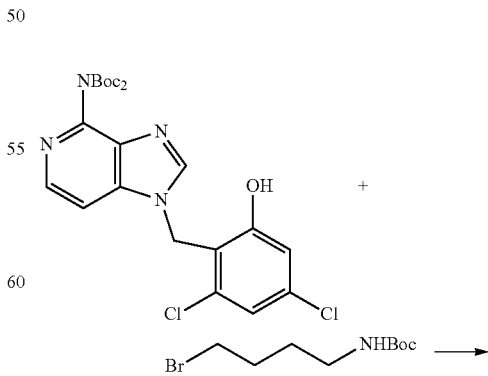

-continued

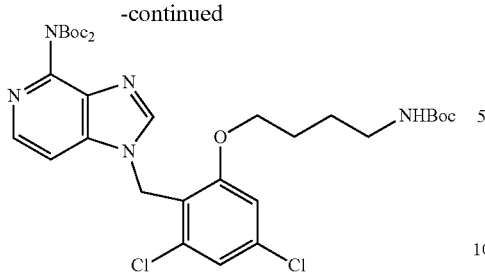

A mixture of tert-butyl (tert-butoxycarbonyl)(1-(2,4-dichloro-6-hydroxybenzyl)-1H-imidazo[4,5-c]pyridin-4-yl)carbamate (0.36 g, 0.71 mmol), tert-butyl (4-bromobutyl) carbamate (0.27 g, 1.1 mmol), NaI (0.21 g, 1.4 mmol) and $K_2CO_3$ (0.20 g, 1.4 mmol) in acetonitrile (3 mL) was heated to 50° C. for 24 hr. LC-MS indicated the reaction was complete. The mixture was cooled to rt. The mixture was treated with EA (20 ml) and $H_2O$ (20 ml). The layers were separated and the aqueous layer was extracted with EA (20 ml*3). The combined organic layers were washed with brine, dried over $Na_2SO_4$ and filtered. The filtrate was taken to next step without purification. LCMS ESI m/z M/M+1=681.3/683.3.

Step 4. 1-(2-(4-aminobutoxy)-4,6-dichlorobenzyl)-1H-imidazo[4,5-c]pyridin-4-amine

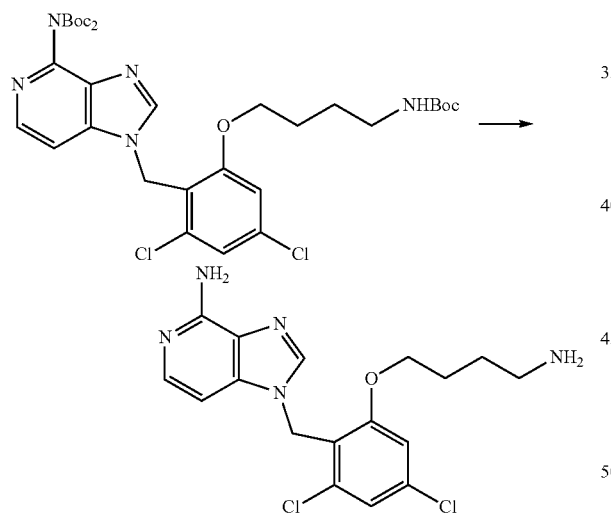

To the solution of tert-butyl (tert-butoxycarbonyl)(1-(2-(4-((tert-butoxycarbonyl)amino)butoxy)-4,6-dichlorobenzyl)-1H-imidazo[4,5-c]pyridin-4-yl)carbamate (485 mg, 0.71 mmol) in THF (5 mL) and water (0.5 mL) was added TFA (1.1 mL, 14.3 mmol). The reaction mixture was stirred at room temperature for 1 hr at 25° C., evaporate the solvent. LCMS shows product produced. The residue mixture was purified through HPLC to give 1-(2-(4-aminobutoxy)-4,6-dichlorobenzyl)-1H-imidazo[4,5-c]pyridin-4-amine. LCMS ESI m/z M/M+2=381.1/383.1. $^1$H NMR (400 MHz, Methanol-$d_4$) δ 8.36 (s, 1H), 8.10 (s, 1H), 7.20 (d, J=1.9 Hz, 1H), 7.12 (d, J=2.0 Hz, 1H), 5.60 (s, 2H), 4.29-4.06 (m, 3H), 2.98 (t, J=7.1 Hz, 2H), 1.87-1.73 (m, 4H), 1.30 (dd, J=7.8, 5.7 Hz, 1H).

Example 47. (R)-9-(6-((4-amino-5-(2-methoxyethoxy)pentyl)oxy)-2,3-dichlorobenzyl)-9H-purin-6-amine

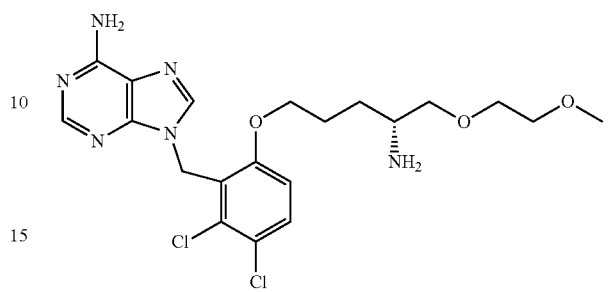

Step 1. tert-Butyl (9-(6-(allyloxy)-2,3-dichlorobenzyl)-9H-purin-6-yl)(tert-butoxycarbonyl) carbamate

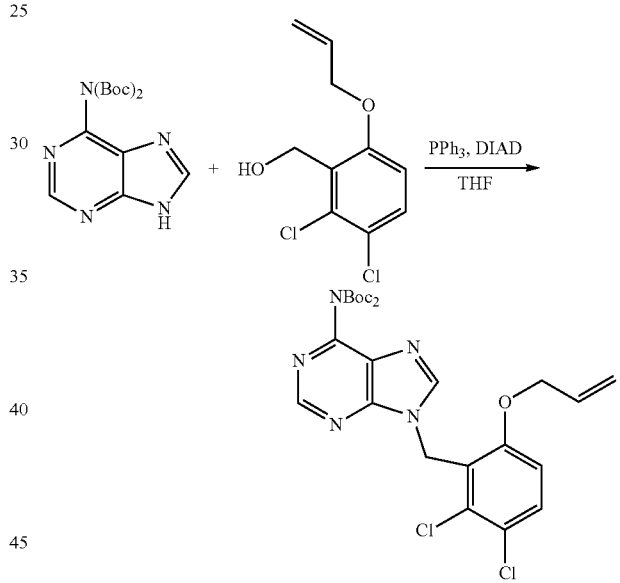

To a solution of (6-(allyloxy)-2,3-dichlorophenyl)methanol (11 g, 47.2 mmol, 1 eq), tert-butyl (tert-butoxycarbonyl)(9H-purin-6-yl)carbamate (Intermediate B) (16.6 g, 49.5 mmol, 1.1 eq) and $PPh_3$ (24.8 g, 17.2 mmol, 2 eq) in anhydrous THF (350 mL) was cooled to 0° C., DIAD (19.1 g, 17.2 mmol, 2 eq) was added dropwise, after additional, the reaction mixture was stirred at 30° C. for 12 hours. LCMS showed the starting material was consumed completely, and then the mixture was concentrated in vacuum. The crude was purified by silica gel column chromatography (column: petroleum ether:EtOAc from: 0% to 35%) to give tert-butyl (9-(6-(allyloxy)-2,3-dichlorobenzyl)-9H-purin-6-yl)(tert-butoxycarbonyl) carbamate as a yellow solid. $^1$H NMR ($CDCl_3$ 400 MHz): δ 8.90 (s, 1H), 7.97 (s, 1H), 7.46 (d, J=9.2 Hz, 1H), 6.84 d, J=8.8 Hz, 1H), 5.93-5.85 (m, 1H), 5.34-5.26 (m, 2H), 4.56-4.55 (m, 2H), 4.15-4.10 (m, 2H), 1.44 (s, 18H).

Step 2. tert-Butyl (tert-butoxycarbonyl)(9-(2,3-dichloro-6-hydroxybenzyl)-9H-purin-6-yl)carbamate

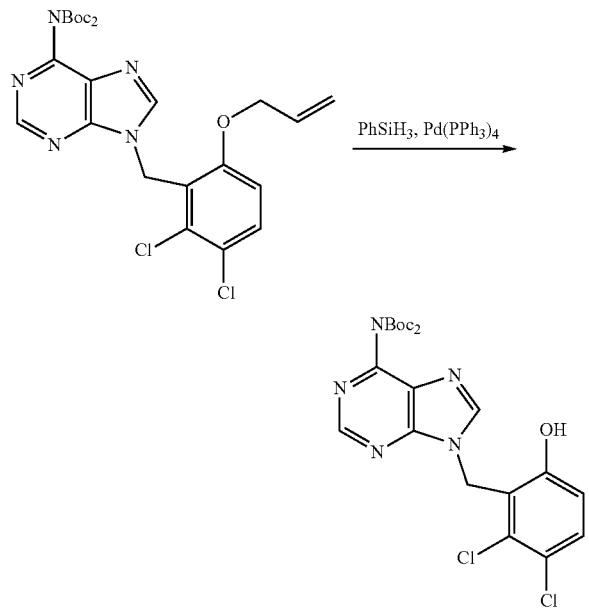

To a solution of tert-butyl (9-(6-(allyloxy)-2,3-dichlorobenzyl)-9H-purin-6-yl)(tert-butoxycarbonyl) carbamate (23 g, 41.2 mmol, 1 eq) and PhSiH₃ (13.53 g, 126.2 mmol, 3 eq) in DCM (300 mL), the reaction mixture was stirred at 9-15° C. for 5 min protected with N₂ gas, Pd(PPh₃)₄ (1.4 g, 1.2 mmol, 0.03 eq) was added, the reaction mixture was stirred at 9-15° C. for 30 min, LCMS showed the starting material was consumed completely, then the mixture was concentrated in vacuum to give tert-butyl (tert-butoxycarbonyl)(9-(2,3-dichloro-6-hydroxybenzyl)-9H-purin-6-yl) carbamate as a brown oil, which was used for the next step without further purification.

Step 3. tert-Butyl (R)-5-(2-((6-(bis(tert-butoxycarbonyl)amino)-9H-purin-9-yl)methyl)-3,4-dichlorophenoxy)-2-((tert-butoxycarbonyl)amino)pentanoate

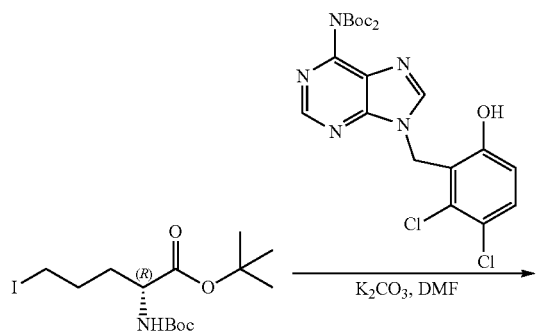

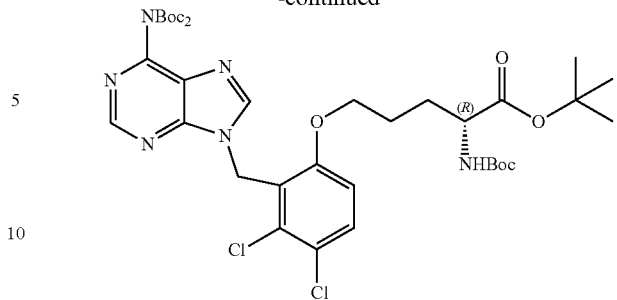

tert-butyl (tert-butoxycarbonyl)(9-(2,3-dichloro-6-hydroxybenzyl)-9H-purin-6-yl)carbamate (23 g, 47 mmol, 1 eq), tert-butyl (R)-2-((tert-butoxycarbonyl)amino)-5-iodopentanoate (Intermediate E) (18 g, 47 mmol, 1 eq) and K₂CO₃ (12.5 g, 2.7 mmol, 2 eq) in DMF (250 mL) were stirred at 9-15° C. for 12 hours. H₂O (200 mL) was added and extracted with ethyl acetate (3*200 mL). The organic layers were dried over Na₂SO₄ and filtered off. The filtrate was evaporated under vacuum. The crude was purified by column chromatography on silica gel (eluent: hexane:ethyl acetate=4:1) to afford tert-butyl (R)-5-(2-((6-(bis(tert-butoxycarbonyl)amino)-9H-purin-9-yl)methyl)-3,4-dichlorophenoxy)-2-((tert-butoxycarbonyl)amino)pentanoate as a yellow oil. $^1$H NMR (CDCl₃ 400 MHz): δ 8.94 (s, 1H), 7.99 (s, 1H), 7.48 (d, J=8.80 Hz, 1H), 6.85 (d, J=9.20 Hz, 1H), 5.67 (s, 2H), 5.23-5.21 (m, 1H), 4.22-4.20 (m, 1H), 4.05-4.02 (m, 2H), 1.99-1.71 (m, 4H), 1.46 (s, 36H).

Step 4. (R)-2-((tert-butoxycarbonyl)amino)-5-(2-((6-((tert-butoxycarbonyl)amino)-9H-purin-9-yl)methyl)-3,4-dichlorophenoxy)pentanoic acid

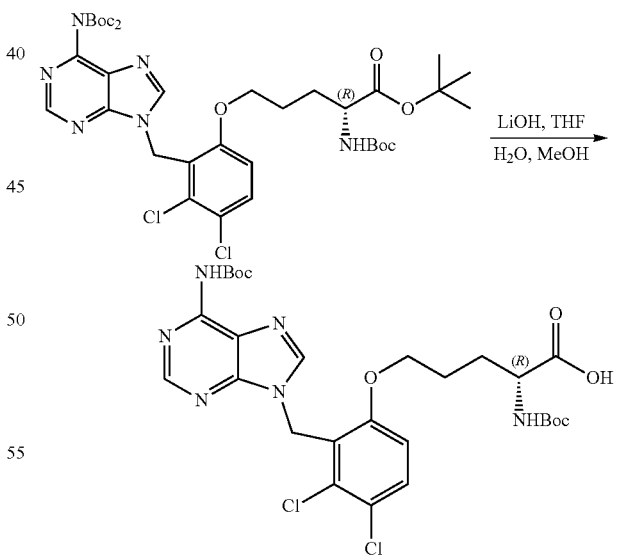

tert-butyl (R)-5-(2-((6-(bis(tert-butoxycarbonyl)amino)-9H-purin-9-yl)methyl)-3,4-dichloro phenoxy)-2-((tert-butoxycarbonyl)amino)pentanoate (20 g, 25.6 mmol, 1 eq) and lithium hydroxide (10.7 g, 256 mmol, 10 eq) in water (100 mL), THF (100 mL) and MeOH (100 mL) were stirred at 9-14° C. for 60 hour. The solvent was removed under vacuum. Ethyl acetate (500 mL) was added, and the mixture was adjusted to pH=7 using HCl (6N). The organic layers were separated and the aqueous was extracted with ethyl acetate (3*500 mL), dried over Na₂SO₄ and evaporated under vacuum to afford (R)-2-((tert-butoxycarbonyl)amino)-5-(2-((6-(((tert-butoxycarbonyl)amino)-9H-purin-9-yl)methyl)-3,4-dichlorophenoxy)pentanoic acid as a pink gum. ¹H NMR (DMSO 400 MHz): δ 10.07 (s, 1H), 8.57 (s, 1H), 6.28 (s, 1H), 7.61 (d, J=8.80 Hz, 1H), 7.08 (d, J=9.20 Hz, 1H), 6.23 (s, 1H), 5.57 (s, 2H), 4.06-4.01 (m, 3H), 3.65-3.58 (m, 1H), 1.99-1.67 (m, 4H), 1.47 (s, 9H), 1.36 (s, 9H).

Step 5. tert-Butyl (R)-(9-(6-((4-(((tert-butoxycarbonyl)amino)-5-hydroxypentyl)oxy)-2,3-dichlorobenzyl)-9H-purin-6-yl)carbamate

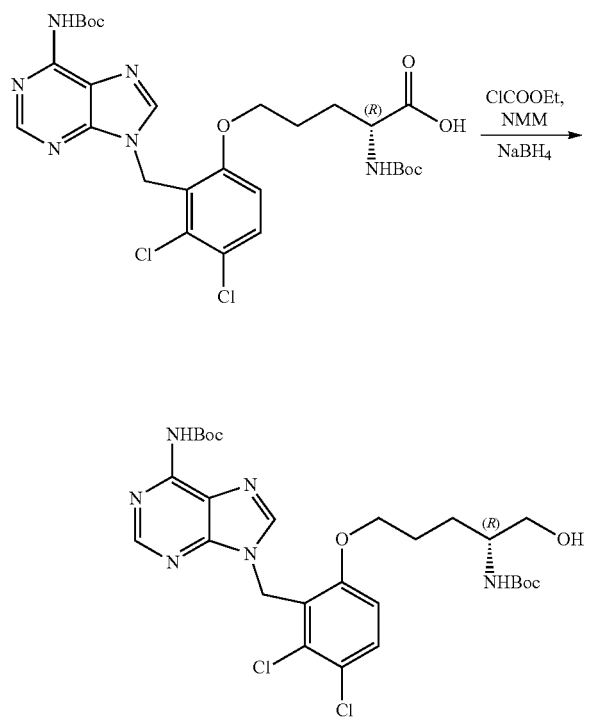

To (R)-2-((tert-butoxycarbonyl)amino)-5-(2-((6-(((tert-butoxycarbonyl)amino)-9H-purin-9-yl)methyl)-3,4-dichlorophenoxy)pentanoic acid (0.66 g, 0.91 mmol, 1 eq) and TEA (0.28 g, 2.7 mmol, 3 eq) in THF (20 mL) were added dropwise ClCOOEt (0.15 g, 1.4 mmol, 1.5 eq) at 0° C. The mixture was stirred for 10 min and filtered off. To the filtrate was added NaBH₄ (52 mg, 1.36 mmol, 1.5 eq) in water (0.5 mL) at 0° C. The mixture was stirred for 1 h at 5-10° C. EtOAc (50 mL) was added and washed with 10% NaHCO₃ (20 mL), 1M NaOH (10 mL) and brine (20 mL). The organic layer was dried over sodium sulfate and filtered off. The filtrate was evaporated under vacuum. The crude was purified by column chromatography over silica gel (EtOAc) to afford tert-butyl (R)-(9-(6-((4-(((tert-butoxycarbonyl)amino)-5-hydroxypentyl)oxy)-2,3-dichlorobenzyl)-9H-purin-6-yl)carbamate as a colorless oil. ¹H NMR (CDCl 400 MHz): δ 8.81 (s, 1H), 8.01 (brs., 1H), 7.80 (s, 1H), 7.47 (d, J=9.20 Hz, 1H), 6.81 (d, J=9.20 Hz, 1H), 5.55-5.69 (m, 2H), 4.81 (brs., 1H), 3.97 (d, J=8.40 Hz, 2H), 3.51-3.62 (m, 3H), 2.78 (brs., 1H), 1.72 (d, J=5.60 Hz, 4H), 1.56 (s, 9H), 1.43 (s, 9H).

Step 6. tert-Butyl (4R)-4-(3-(2-((6-(((tert-butoxycarbonyl)amino)-9H-purin-9-yl)methyl)-3,4-dichlorophenoxy)propyl)-1,2,3-oxathiazolidine-3-carboxylate 2-oxide

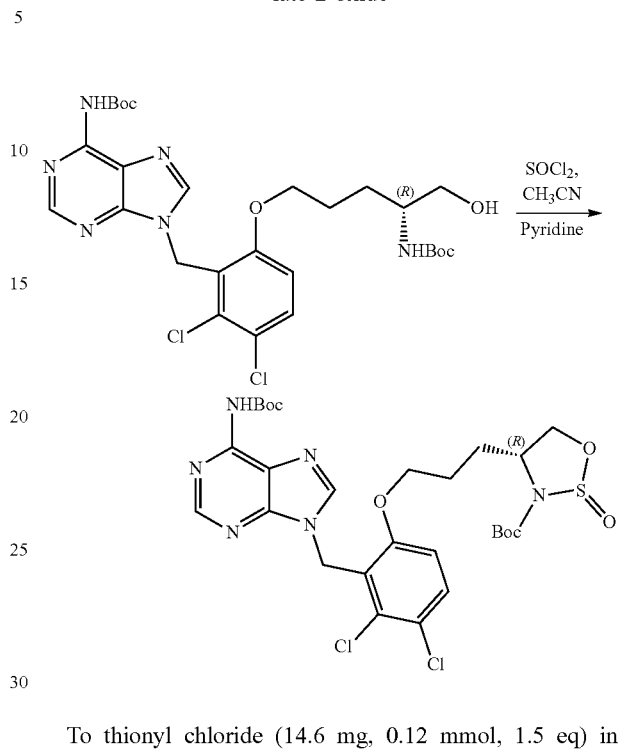

To thionyl chloride (14.6 mg, 0.12 mmol, 1.5 eq) in acetonitrile (1 mL) was added tert-butyl (R)-(9-(6-((4-(((tert-butoxycarbonyl)amino)-5-hydroxypentyl)oxy)-2,3-dichlorobenzyl)-9H-purin-6-yl)carbamate (50 mg, 0.08 mmol, 1 eq) in acetonitrile (1 mL) dropwise at 10° C. Pyridine (19.4 mg, 0.24 mmol, 3 eq) was added dropwise at 5-11° C. The mixture was stirred for 0.5 h at 5-11° C. 10% NaHCO₃ (2 mL) was added and the solvent was removed. The aqueous was extracted with DCM (2*5 mL). The organic layer was dried over sodium sulfate and filtered off. The filtrate was evaporated under vacuum to afford tert-butyl (4R)-4-(3-(2-((6-(((tert-butoxycarbonyl)amino)-9H-purin-9-yl)methyl)-3,4-dichlorophenoxy)propyl)-1,2,3-oxathiazolidine-3-carboxylate 2-oxide as a yellow oil. LC-MS (ESI) m/z 657 [M+H]⁺.

Step 7. tert-Butyl (R)-4-(3-(2-((6-(bis(tert-butoxycarbonyl)amino)-9H-purin-9-yl)methyl)-3,4-dichlorophenoxy)propyl)-1,2,3-oxathiazolidine-3-carboxylate 2,2-dioxide

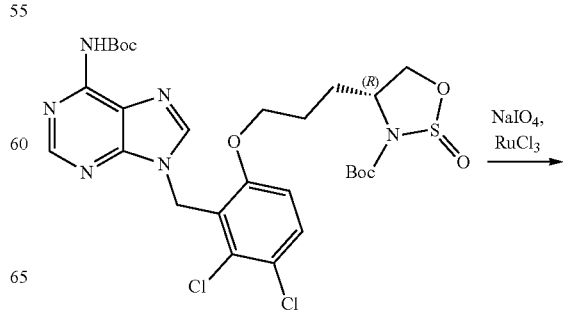

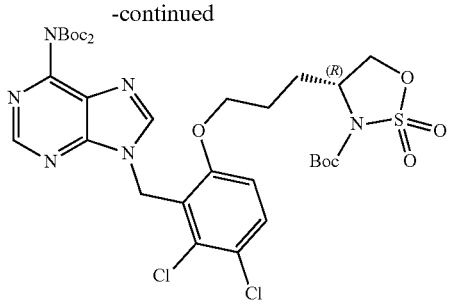

To tert-butyl (4R)-4-(3-(2-((6-((tert-butoxycarbonyl)amino)-9H-purin-9-yl)methyl)-3,4-dichloro phenoxy)propyl)-1,2,3-oxathiazolidine-3-carboxylate 2-oxide (50 mg, 0.076 mmol, 1 eq) in and NaIO$_4$ (17.9 mg, 0.084 mmol, 1.1 eq) in acetonitrile (1 mL) were added RuCl$_3$ (0.16 mg, 0.008 mmol, 0.1 eq) at 8-16° C. The mixture was stirred for 2 h at 8-16° C. Water (5 mL) was added and extracted with ethyl acetate (2*5 mL). The organic layer was dried over sodium sulfate and filtered off. The filtrate was evaporated under vacuum. The crude was purified by column chromatography over silica gel to afford tert-butyl (R)-4-(3-(2-((6-(bis(tert-butoxycarbonyl)amino)-9H-purin-9-yl)methyl)-3,4-dichlorophenoxy)propyl)-1,2,3-oxathiazolidine-3-carboxylate 2,2-dioxide as a brown oil. $^1$H NMR (CDCl$_3$ 400 MHz): δ 8.80 (s, 1H), 7.81 (s, 1H), 7.50 (d, J=8.80 Hz, 1H), 6.83 (d, J=8.80 Hz, 1H), 5.63 (s, 2H), 4.69-4.65 (m, 1H), 4.36-4.34 (m, 1H), 4.28 (d, J=9.20 Hz, 1H), 4.01 (t, J=6.00 Hz, 2H), 1.87-1.95 (m, 2H), 1.79-1.76 (m, 2H), 1.58 (s, 9H), 1.54 (s, 9H).

Step 8. (R)-(5-(2-((6-(bis(tert-butoxycarbonyl)amino)-9H-purin-9-yl)methyl)-3,4-dichloro phenoxy)-1-(2-methoxyethoxy)pentan-2-yl)(tert-butoxycarbonyl)sulfamic acid

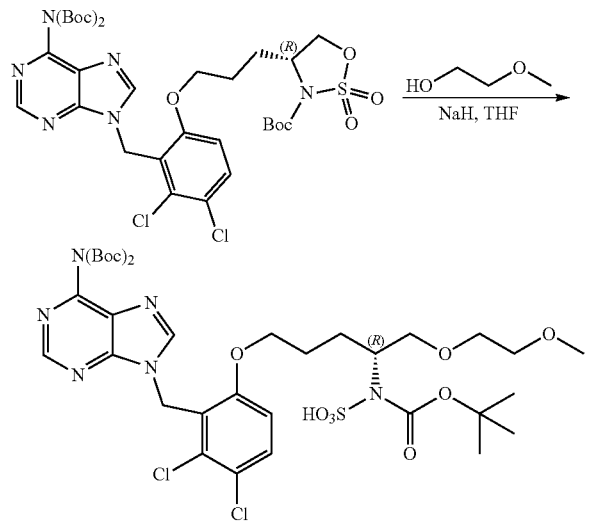

To tert-butyl (R)-4-(3-(2-((6-(bis(tert-butoxycarbonyl)amino)-9H-purin-9-yl)methyl)-3,4-dichlorophenoxy)propyl)-1,2,3-oxathiazolidine-3-carboxylate 2,2-dioxide (26 mg, 0.3 mmol, 2 eq) in tetrahydrofuran (2 mL) was added sodium hydride (11 mg, 0.45 mmol, 3 eq) and the mixture was stirred for 30 min at 16-20° C. 2-methoxyethan-1-ol (0.15 mmol, 1 eq) was added and the mixture was stirred for another 12 h at 16-20° C. The mixture was quenched with 10% NH$_4$Cl (5 mL) and extracted with ethyl acetate (2*10 mL). The aqueous layer was collected and used for the next step without further purification. LC-MS (ESI) m/z 649.1 [M+H]$^+$.

Step 9. (R)-9-(6-((4-amino-5-(2-methoxyethoxy)pentyl)oxy)-2,3-dichlorobenzyl)-9H-purin-6-amine

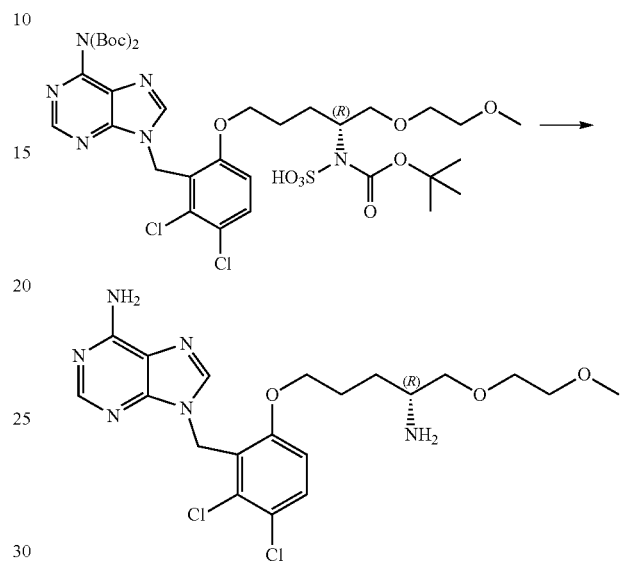

(R)-(5-(2-((6-(bis(tert-butoxycarbonyl)amino)-9H-purin-9-yl)methyl)-3,4-dichlorophenoxy)-1-(2-methoxyethoxy)pentan-2-yl)(tert-butoxycarbonyl)sulfamic acid (mother solution, 0.15 mmol, 1 eq) in conc. HCl (2 mL) and water (2 mL) were stirred for 4 h at 80° C. The mixture was evaporated under vacuum and purified by pre-HPLC to (R)-9-(6-((4-amino-5-(2-methoxyethoxy)pentyl)oxy)-2,3-dichlorobenzyl)-9H-purin-6-amine as a white solid. LC-MS (ESI) m/z 491.1 [M+Na]$^+$. $^1$H NMR (METHANOL-d$_4$ varian 400): δ 8.36 (s, 1H), 8.08 (s, 1H), 7.58 (d, J=9.20 Hz, 1H), 7.09 (d, J=9.20 Hz, 1H), 5.67 (s, 2H) 4.12 (t, J=5.60 Hz, 2H), 3.65 (dd, J=6.00, 3.20 Hz, 3H), 3.48-3.58 (m, 3H), 3.39 (brs., 1H), 3.37 (s, 3H), 1.70-1.92 (m, 4H).

Example 48. (R)-9-(6-(4-amino-4-(1H-1,2,4-triazol-3-yl)butoxy)-2,3-dichlorobenzyl)-9H-purin-6-amine

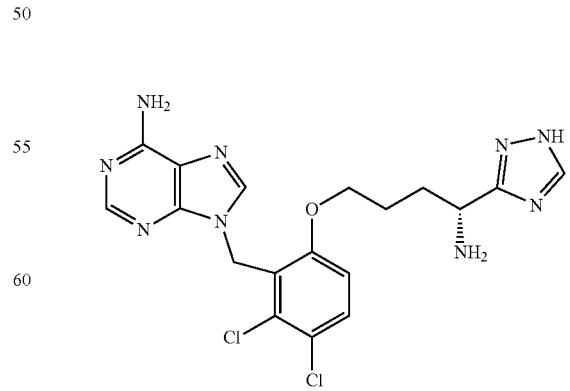

Step 1. tert-Butyl (R)-(9-(6-((5-amino-4-((tert-butoxycarbonyl)amino)-5-oxopentyl)oxy)-2,3-dichlorobenzyl)-9H-purin-6-yl)carbamate

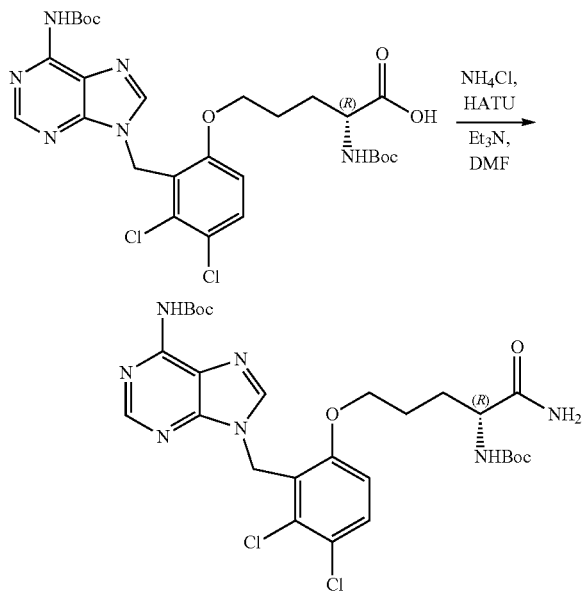

To (R)-2-((tert-butoxycarbonyl)amino)-5-(2-((6-((tert-butoxycarbonyl)amino)-9H-purin-9-yl)methyl)-3,4-dichlorophenoxy)pentanoic acid (500 mg, 799 μmol, 1 eq), NH₄Cl (214 mg, 4.0 mmol, 5 eq), HATU (608 mg, 1.6 mmol, 2 eq) and Et₃N (162 mg, 1.6 mmol, 3 eq) in DMF (20 mL) were stirred at 14-22° C. for 1 h. LCMS showed the starting material was consumed completely. The reaction mixture was diluted with H₂O (200 mL) and extracted with EtOAc (100 mL*3). The extracts were combined, dried (NaSO₄), and the solvent was removed under crude product which was purified by column chromatography on silica gel (eluent: hexane:ethyl acetate=5:1) to afford tert-butyl (R)-(9-(6-((5-amino-4-((tert-butoxycarbonyl)amino)-5-oxopentyl)oxy)-2,3-dichlorobenzyl)-9H-purin-6-yl)carbamate. LC-MS (ESI) m/z 624.1 [M+H]⁺.

Step 2. tert-Butyl (R,E)-(9-(6-((4-((tert-butoxycarbonyl)amino)-5-(((dimethylamino)methylene)amino)-5-oxopentyl)oxy)-2,3-dichlorobenzyl)-9H-purin-6-yl)carbamate

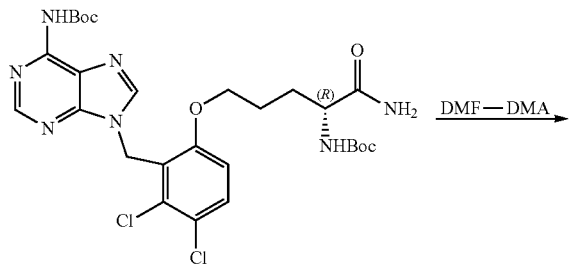

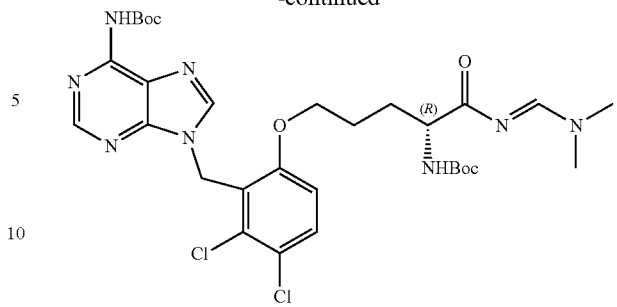

To tert-butyl (R)-(9-(6-((5-amino-4-((tert-butoxycarbonyl)amino)-5-oxopentyl)oxy)-2,3-dichlorobenzyl)-9H-purin-6-yl)carbama (100 mg, 160.1 μmol, 1 eq) and DMF-DMA (57.2 mg, 480 μmol, 3 eq) in CH₂Cl₁₋₂ (15 mL) were stirred at 40° C. for 2 h. LCMS showed the starting material was consumed completely. The reaction mixture was concentrated under vacuum to give tert-butyl (R,E)-(9-(6-((4-((tert-butoxycarbonyl)amino)-5-(((dimethylamino)methylene)amino)-5-oxopentyl)oxy)-2,3-dichlorobenzyl)-9H-purin-6-yl)carbamate as a colorless oil. LC-MS (ESI) m/z 701.2 [M+Na]⁺.

Step 3. tert-Butyl (R)-(9-(6-(4-((tert-butoxycarbonyl)amino)-4-(1H-1,2,4-triazol-3-yl)butoxy)-2,3-dichlorobenzyl)-9H-purin-6-yl)carbamate

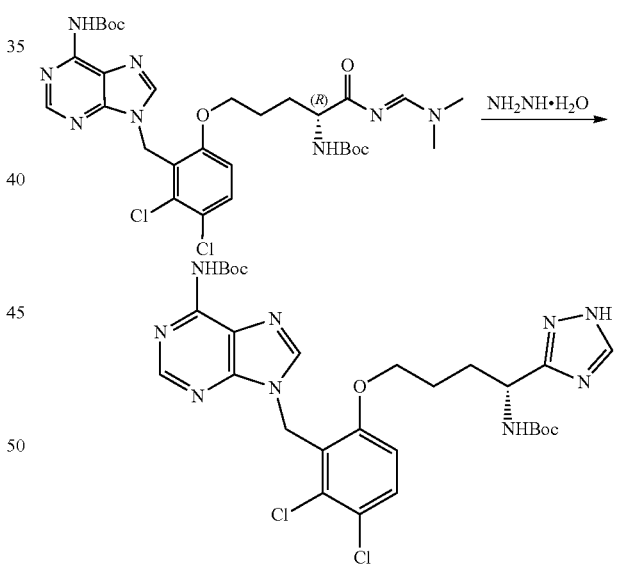

To tert-butyl (R,E)-(9-(6-((4-((tert-butoxycarbonyl)amino)-5-(((dimethylamino)methylene)amino)-5-oxopentyl)oxy)-2,3-dichlorobenzyl)-9H-purin-6-yl)carbamate (108 mg, 159 μmol, 1 eq) in HOAc (2 mL) was added NH₂NH₂·H₂O slowly. The mixture was stirred at 90-100° C. for 2 h. LCMS showed the starting material was consumed completely. The reaction mixture was concentrated under vacuum to give tert-butyl (R)-(9-(6-(4-((tert-butoxycarbonyl)amino)-4-(1H-1,2,4-triazol-3-yl)butoxy)-2,3-dichlorobenzyl)-9H-purin-6-yl)carbamate as a colorless oil. LC-MS (ESI) m/z 548.1 [M+H]⁺.

Step 4. (R)-9-(6-(4-amino-4-(1H-1,2,4-triazol-3-yl)butoxy)-2,3-dichlorobenzyl)-9H-purin-6-amine

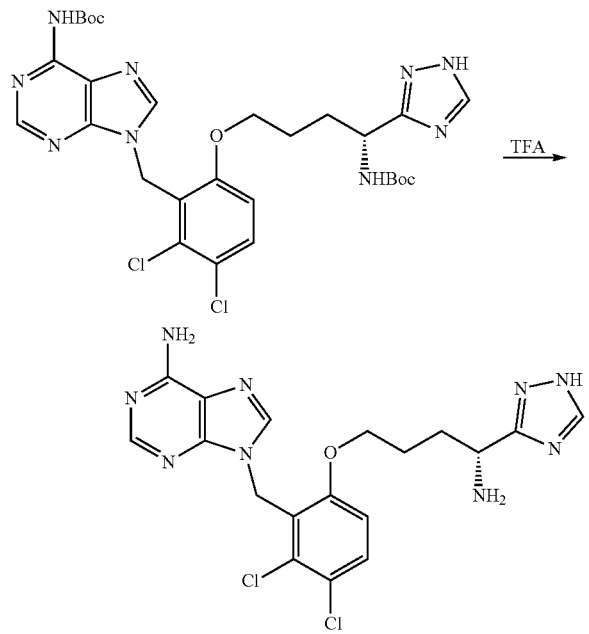

To tert-butyl (R)-(9-(6-(4-((tert-butoxycarbonyl)amino)-4-(1H-1,2,4-triazol-3-yl)butoxy)-2,3-dichlorobenzyl)-9H-purin-6-yl)carbamate (100 mg, 154 μmol, 1 eq) in TFA/DCM (4 mL) were stirred at 8-15° C. for 2 h. LCMS showed the starting material was consumed completely.

The reaction mixture was concentrated under vacuum to give crude product (100 mg) as oil which was dissolved in MeOH (3 mL), the mixture was adjusted to Ph=7 and purified by prep-HPLC to afford (R)-9-(6-(4-amino-4-(1H-1,2,4-triazol-3-yl)butoxy)-2,3-dichlorobenzyl)-9H-purin-6-amine as a white solid. LC-MS (ESI) m/z 448.0 [M+H]$^+$. $^1$H NMR (MeOH 400 MHz): δ 8.24 (s, 1H), 8.22 (s, 1H), 7.57 (d, J=9.2 Hz, 1H), 7.06 (d, J=9.2 Hz, 1H), 5.60 (s, 2H), 4.08-4.04 (m, 3H), 1.94-1.66 (m, 4H).

Example 49. (R)-9-(6-((4-amino-5-(1H-pyrazol-1-yl)pentyl)oxy)-2,3-dichlorobenzyl)-9H-purin-6-amine

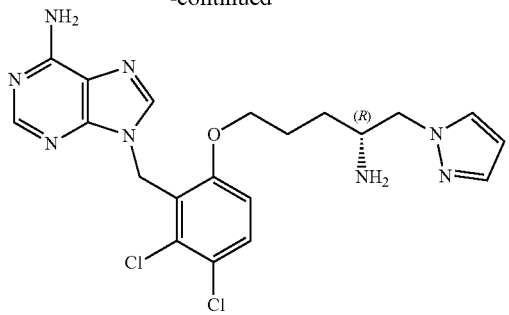

tert-butyl (R)-4-(3-(2-((6-(bis(tert-butoxycarbonyl)amino)-9H-purin-9-yl)methyl)-3,4-dichloro phenoxy)propyl)-1,2,3-oxathiazolidine-3-carboxylate 2,2-dioxide (60 mg, 0.089 mmol, 1 eq) and 1H-pyrazole (24 mg, 0.36 mmol, 4 eq) in tetrahydrofuran (5 mL) were stirred and refluxed for 2 h. The mixture was evaporated under vacuum to afford crude intermediate (80 mg). To crude intermediate (80 mg, 0.089 mmol, 1 eq) in dichloromethane (1 mL) was added trifluoroacetic acid (1 mL) at 17-26° C. The mixture was stirred for 2 h at 17-26° C. The mixture was evaporated under vacuum. The crude was purified by pre-HPLC to afford (R)-9-(6-((4-amino-5-(1H-pyrazol-1-yl)pentyl)oxy)-2,3-dichlorobenzyl)-9H-purin-6-amine as a white solid. LC-MS (ESI) m/z 461.1 [M+H]$^+$. $^1$H NMR (METHANOL-d$_4$ varian 400): δ 8.26 (s, 1H), 7.77 (s, 1H), 7.49-7.65, (m, 2H), 7.44 (d, J=1.6 Hz, 1H), 7.06 (d, J=9.20 Hz, 1H), 6.21 (d, J=2.00 Hz, 1H), 5.49-5.60 (m, 2H), 3.89-4.11 (m, 4H), 3.10-3.21 (m, 1H), 1.66-1.90 (m, 2H), 1.25-1.47 (m, 2H).

Example 50. (R)-9-(6-(4-amino-4-(5-methyl-1,3,4-thiadiazol-2-yl)butoxy)-2,3-dichlorobenzyl)-9H-purin-6-amine

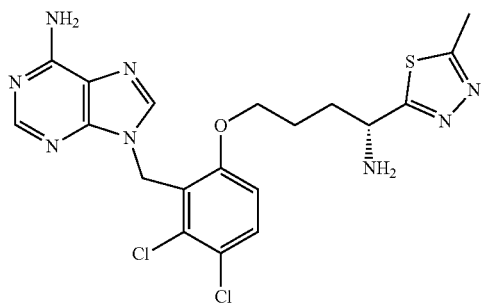 [SMILES: Cc1nnc([C@H](N)CCCOc2ccc(Cl)c(Cl)c2Cn2cnc3c(N)ncnc32)s1]

Step 1: tert-butyl (R)-(9-(6-((5-(2-acetylhydrazinyl)-4-((tert-butoxycarbonyl)amino)-5-oxopentyl)oxy)-2,3-dichlorobenzyl)-9H-purin-6-yl)carbamate

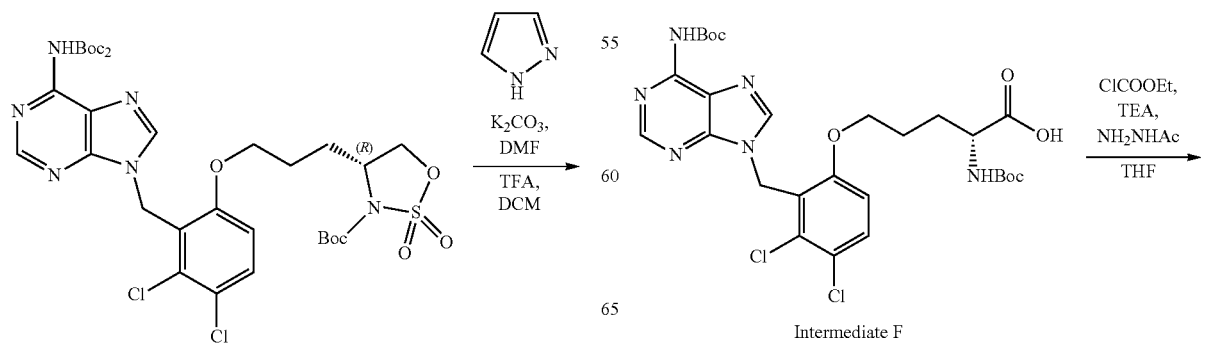

Intermediate F

-continued

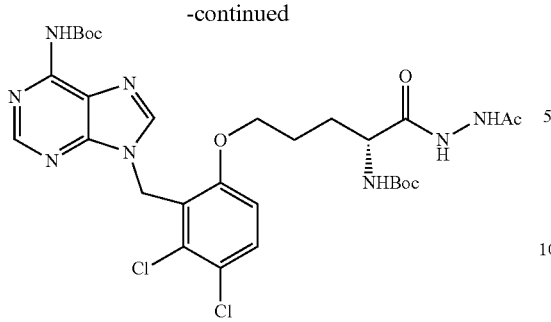

To a THF solution (2 mL) of (R)-2-((tert-butoxycarbonyl)amino)-5-(2-((6-((tert-butoxycarbonyl)amino)-9H-purin-9-yl)methyl)-3,4-dichlorophenoxy)pentanoic acid (Intermediate F) (250 mg, 0.4 mmol) was slowly added TEA (121 mg, 1.2 mmol). 10 mins later, the resulting mixture was slowly added to a solution of ClCOOEt (87 mg, 0.8 mmol) in dry THF (2 mL) at 0° C. After filtering off the salts, the filtrate was slowly added to a solution of NH$_2$NHAc (148 mg, 2 mmol) in dry THF (2 mL) at 0° C. The mixture was allowed to warm up to rt and stirred for 2 hrs. The solvent was removed under vacuum to give crude tert-butyl (R)-(9-(6-((5-(2-acetylhydrazinyl)-4-((tert-butoxycarbonyl)amino)-5-oxopentyl)oxy)-2,3-dichlorobenzyl)-9H-purin-6-yl)carbamate as a colorless oil. LC-MS: [M+H]$^+$=681.1.

Step 2: tert-butyl (R)-(9-(6-(4-((tert-butoxycarbonyl)amino)-4-(5-methyl-1,3,4-thiadiazol-2-yl)butoxy)-2,3-dichlorobenzyl)-9H-purin-6-yl)carbamate

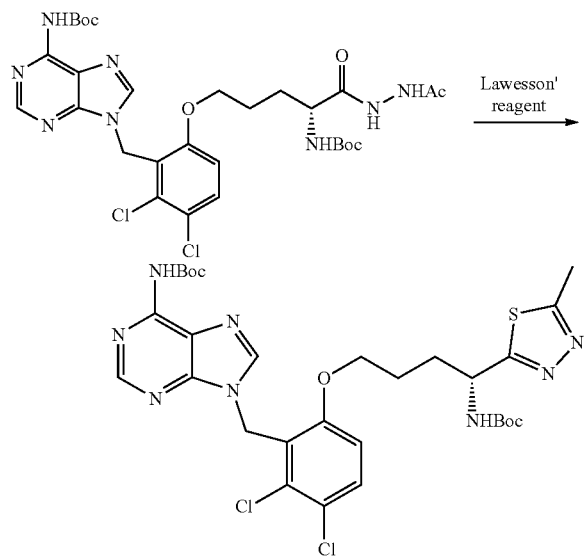

To a solution of tert-butyl (R)-(9-(6-((5-(2-acetylhydrazinyl)-4-((tert-butoxycarbonyl)amino)-5-oxopentyl)oxy)-2,3-dichlorobenzyl)-9H-purin-6-yl)carbamate (0.1 g, 0.15 mmol) in dry THF (10 mL) was added Lawesson' reagent and the reaction mixture was refluxed for 12 hrs. After the solvent was removed, the residue was purified by column chromatography on silica gel to give crude tert-butyl (R)-(9-(6-(4-((tert-butoxycarbonyl)amino)-4-(5-methyl-1,3,4-thiadiazol-2-yl)butoxy)-2,3-dichlorobenzyl)-9H-purin-6-yl)carbamate (80 mg) as a solid. LC-MS: [M+H]$^+$=679.0.

Step 3: (R)-9-(6-(4-amino-4-(5-methyl-1,3,4-thiadiazol-2-yl)butoxy)-2,3-dichlorobenzyl)-9H-purin-6-amine

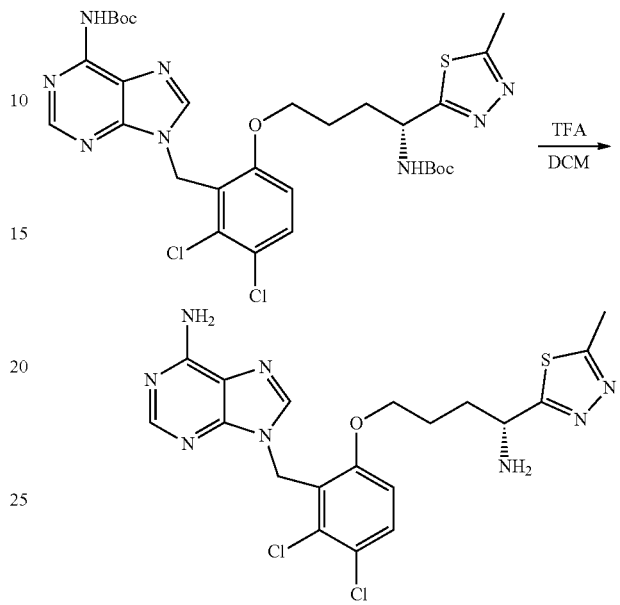

To a solution of tert-butyl (R)-(9-(6-(4-((tert-butoxycarbonyl)amino)-4-(5-methyl-1,3,4-thiadiazol-2-yl)butoxy)-2,3-dichlorobenzyl)-9H-purin-6-yl)carbamate (100 mg, 0.14 mmol) in CH$_2$Cl$_2$ (5 mL) was added TFA (1 mL). The resulting mixture was stirred at 0° C. for 2 hrs. After the reaction was complete, TEA was added to neutralize the reaction. The reaction mixture was concentrated under vacuum to give the crude product, which was purified by prep-HPLC (Column: Waters Xbridge 150*25 5u, gradient: 20-50% B (A=water/10 mM NH$_4$HCO$_3$, B=acetonitrile), flow rate: 25 mL/min) to afford (R)-9-(6-(4-amino-4-(5-methyl-1,3,4-thiadiazol-2-yl)butoxy)-2,3-dichlorobenzyl)-9H-purin-6-amine as a white solid. $^1$H NMR (400 MHz, MeOH-d$_4$): δ 8.23 (s, 1H), 7.78 (s, 1H), 7.56 (d, J=9.2 Hz, 1H), 7.05 (d, J=9.2 Hz, 1H), 5.58 (s, 2H), 4.31 (t, J=6.4 Hz, 1H), 4.08 (t, J=5.6 Hz, 2H), 1.89-1.73 (m, 4H). LC-MS: [M+H]$^+$=479.0.

Example 51. (R)-9-(6-(4-amino-4-(1,3,4-oxadiazol-2-yl)butoxy)-2,3-dichlorobenzyl)-9H-purin-6-amine

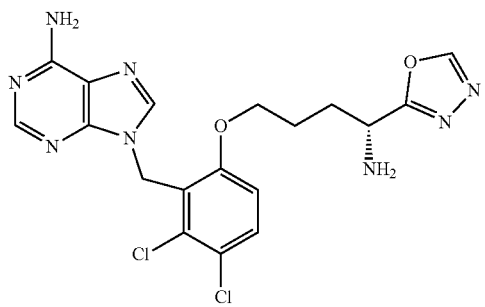 [SMILES: Nc1ncnc2c1ncn2Cc1c(OCCC[C@@H](N)c2nnco2)ccc(Cl)c1Cl]

Step 1. tert-Butyl (R)-(9-(6-((4-((tert-butoxycarbonyl)amino)-5-hydrazinyl-5-oxopentyl)oxy)-2,3-dichlorobenzyl)-9H-purin-6-yl)carbamate

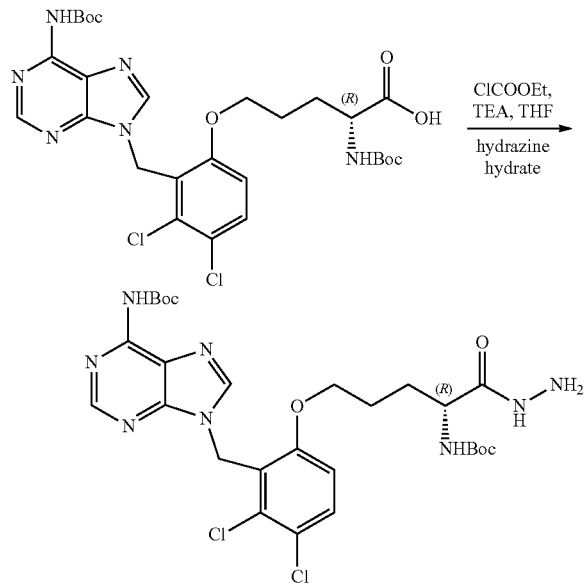

To a stirred solution of the (R)-2-((tert-butoxycarbonyl)amino)-5-(2-((6-((tert-butoxycarbonyl)amino)-9H-purin-9-yl)methyl)-3,4-dichlorophenoxy)pentanoic acid (500 mg, 0.8 mmol, 1 eq) in dry THF (10 mL) was slowly added TEA (121 mg, 1.2 mmol, 1.5 eq). After 10 minutes, the resulting mixture was slowly added to a solution of ClCOOEt (113 mg, 1 mmol, 1.3 eq) in dry THF (10 mL) at 0° C. Then Et₃N·HCl formed was filtered off and the filtrate was slowly added to a solution of hydrazine hydrate (1 mL) at 0° C. The mixture was allowed to warm up to rt and stirred for 2 hours. The reaction mixture was directly concentrated under reduced pressure to furnish oil, which on purification by prep-HPLC to tert-butyl (R)-(9-(6-((4-((tert-butoxycarbonyl)amino)-5-hydrazinyl-5-oxopentyl)oxy)-2,3-dichlorobenzyl)-9H-purin-6-yl)carbamate as a white solid. ¹H NMR (MeOD 400 MHz): δ 8.60 (s, 1H), 8.07 (s, 1H), 7.55 (d, J=8.8 Hz, 1H), 7.04 (d, J=9.2 Hz, 1H), 5.68 (s, 2H), 4.05-3.98 (m, 3H), 1.75-1.62 (m, 4H), 1.58 (s, 9H), 1.41 (s, 9H).

Step 2. tert-Butyl (R)-(9-(6-(4-((tert-butoxycarbonyl)amino)-4-(1,3,4-oxadiazol-2-yl)butoxy)-2,3-dichlorobenzyl)-9H-purin-6-yl)carbamate

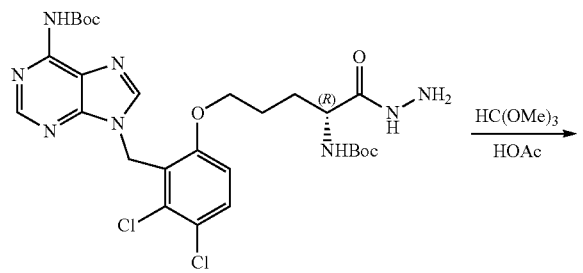

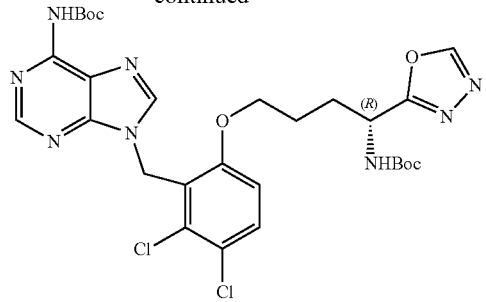

To a stirred solution of tert-butyl (R)-(9-(6-((4-((tert-butoxycarbonyl)amino)-5-hydrazineyl-5-oxopentyl)oxy)-2,3-dichlorobenzyl)-9H-purin-6-yl)carbamate (60 mg, 0.09 mmol, 1 eq) in HC(OMe)₃ (2 mL) was added HOAc (0.1 mL). Then the mixture was stirred at 90° C. for 2 hours. The reaction mixture was directly concentrated under reduced pressure to afford tert-butyl (R)-(9-(6-(4-((tert-butoxycarbonyl)amino)-4-(1,3,4-oxadiazol-2-yl)butoxy)-2,3-dichlorobenzyl)-9H-purin-6-yl)carbamate as a colorless oil. LC-MS (ESI) m/z 549.1 [M+H]⁺.

Step 3. (R)-9-(6-(4-amino-4-(1,3,4-oxadiazol-2-yl)butoxy)-2,3-dichlorobenzyl)-9H-purin-6-amine

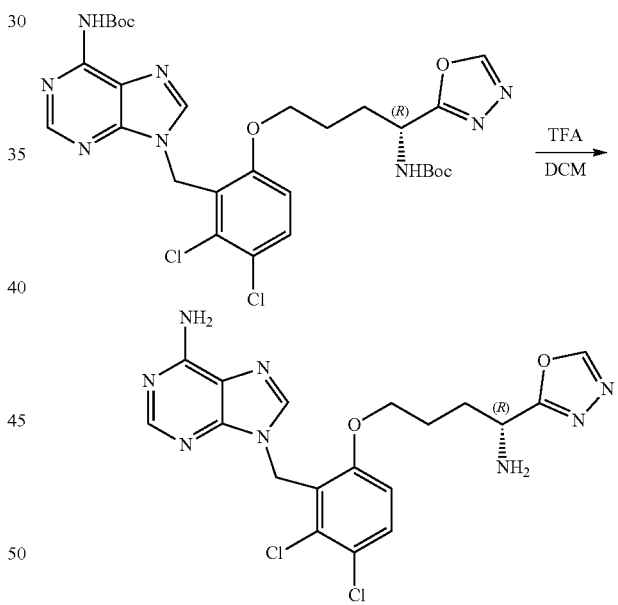

To a solution of tert-butyl (R)-(9-(6-(4-((tert-butoxycarbonyl)amino)-4-(1,3,4-oxadiazol-2-yl)butoxy)-2,3-dichlorobenzyl)-9H-purin-6-yl)carbamate (40 mg, 0.06 mmol, 1 eq) in CH₂Cl₂ (1 mL) was added TFA (1 mL). The resulting mixture was stirred at 0° C. for 2 hours. LCMS showed the starting material was consumed completely. TEA was added until the pH=8. Then the mixture was concentrated in vacuum. The crude was purified by prep-HPLC to afford (R)-9-(6-(4-amino-4-(1,3,4-oxadiazol-2-yl)butoxy)-2,3-dichlorobenzyl)-9H-purin-6-amine as a white solid. LC-MS (ESI) m/z 448.9 [M+H]⁺. ¹H NMR (MeOD 400 MHz): δ 8.87 (s, 1H), 8.24 (s, 1H), 7.80 (s, 1H), 7.56 (d, J=8.8 Hz, 1H), 7.06 (d, J=9.2 Hz, 1H), 5.59 (s, 2H), 4.15 (t, J=6.4 Hz, 1H), 4.08 (t, J=6.0 Hz, 2H), 1.91-1.72 (m, 4H).

Example 52. (R)-9-(6-((4-amino-5-(methylthio)pentyl)oxy)-2,3-dichlorobenzyl)-9H-purin-6-amine

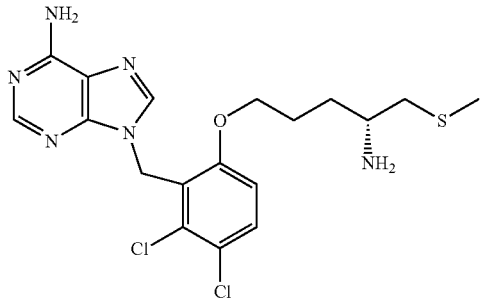

Step 1. tert-Butyl (R)-2-((tert-butoxycarbonyl)amino)-5-((tert-butyldiphenylsilyl)oxy) pentanoate

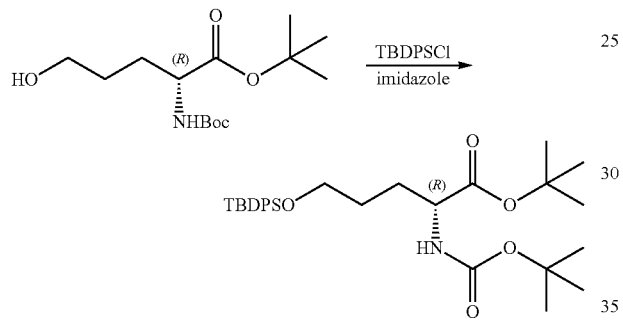

To a solution of tert-butyl (R)-2-((tert-butoxycarbonyl)amino)-5-hydroxypentanoate (2 g, 6.9 mmol, 1 eq) in $CH_2Cl_2$ (40 mL), were added imidazole (1.1 g, 15 mmol, 2.2 eq.) and TBDPSCl (3.72 g, 13.53 mmol, 1.96 eq.) after additional, the reaction mixture was stirred at 18° C. for 11 hours. LCMS showed the starting material was consumed completely. The reaction mixture was then quenched with water (40 mL), the mixture was separated and the organic layer was dried over anhydrous sodium sulfate, filtered and concentrated to give the crude product, which was purified by prep-HPLC to afford tert-butyl (R)-2-((tert-butoxycarbonyl)amino)-5-((tert-butyldiphenylsilyl)oxy)pentanoate as a white solid. $^1$H NMR (CDCl$_3$ 400 MHz): δ 7.66-7.64 (m, 4H), 7.45-7.36 (m, 6H), 5.08 (d, J=8.0 Hz, 1H), 4.22-4.15 (m, 1H), 3.67 (t, J=6.0 Hz, 2H), 1.96-1.90 (1H, m), 1.77-1.63 (1H, m), 1.62-1.55 (m, 2H), 1.46 (s, 9H), 1.44 (s, 9H), 1.05 (s, 9H).

Step 2. tert-Butyl (R)-(5-((tert-butyldiphenylsilyl)oxy)-1-hydroxypentan-2-yl)carbamate

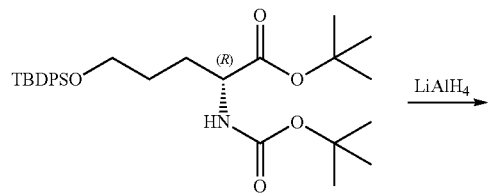

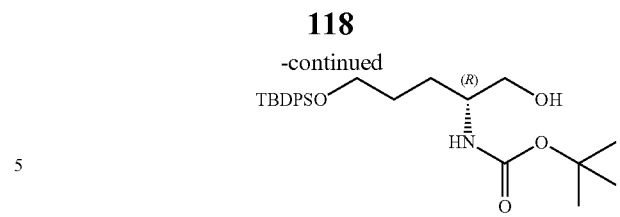

A solution of the tert-butyl (R)-2-((tert-butoxycarbonyl)amino)-5-((tert-butyldiphenylsilyl) oxy)pentanoate (2.3 g, 4.4 mmol, 1 eq) in dry THF (50 mL) was added dropwise to a slurry of LiAlH$_4$ (0.66 g, 17.4 mmol, 4 eq) in dry THF (100 mL) at 0° C. under a nitrogen atmosphere. When the addition was complete, the cooling bath was removed and the mixture was stirred at ambient temperature. After 16 hours, TLC showed the starting material was consumed completely. The mixture was cooled to 0° C., and the reaction was carefully quenched with water (3 mL), 15% aqueous sodium hydroxide (3 mL), and water (9 mL). After being stirred for 30 min, the mixture was diluted with EtOAc (100 mL), filtered through CELITE®, and concentrated under reduced pressure to furnish oil, which on purification by flash chromatography afforded tert-butyl (R)-(5-((tert-butyldiphenylsilyl)oxy)-1-hydroxypentan-2-yl)carbamate as a colourless oil. $^1$H NMR (CDCl$_3$ 400 MHz): δ 7.70-7.61 (m, 4H), 7.44-7.36 (m, 6H), 4.71 (brs, 1H), 3.69-3.53 (m, 5H), 2.45 (brs, 1H), 1.65-1.57 (m, 3H), 1.51-1.47 (m, 1H), 1.44 (s, 9H), 1.05 (s, 9H).

Step 3. (R)-2-((tert-Butoxycarbonyl)amino)-5-((tert-butyldiphenylsilyl)oxy)pentyl methane sulfonate

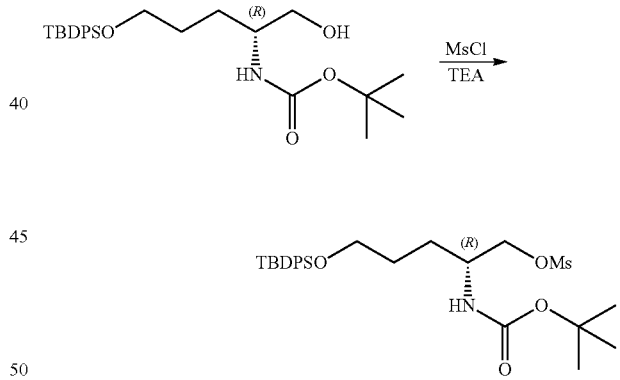

To a solution of the tert-butyl (R)-(5-((tert-butyldiphenylsilyl)oxy)-1-hydroxypentan-2-yl)carbamate (1.7 g, 3.7 mmol, 1 eq) in dry DCM (50 mL) was added MsCl (510.6 mg, 4.5 mmol, 1.2 eq) and TEA (564 mg, 5.6 mmol, 1.5 eq) at 0° C. under a nitrogen atmosphere. Then the mixture was stirred at room temperature for 12 hours. TLC showed the starting material was consumed completely. The reaction mixture was concentrated under reduced pressure to furnish oil, which on purification by flash chromatography afforded (R)-2-((tert-butoxycarbonyl)amino)-5-((tert-butyldiphenylsilyl)oxy)pentyl methane sulfonate as a colorless oil. $^1$H NMR (CDCl$_3$ 400 MHz): δ 7.66-7.64 (m, 4H), 7.43-7.37 (m, 6H), 4.67 (d, J=7.2 Hz, 1H), 4.26-4.09 (m, 2H), 3.90-3.82 (m, 1H), 3.68 (t, J=5.6 Hz, 2H), 3.01 (s, 3H), 1.63-1.59 (m, 4H), 1.44 (s, 9H), 1.05 (s, 9H).

Step 4. tert-Butyl (R)-(5-((tert-butyldiphenylsilyl)oxy)-1-(methylthio)pentan-2-yl)carbamate

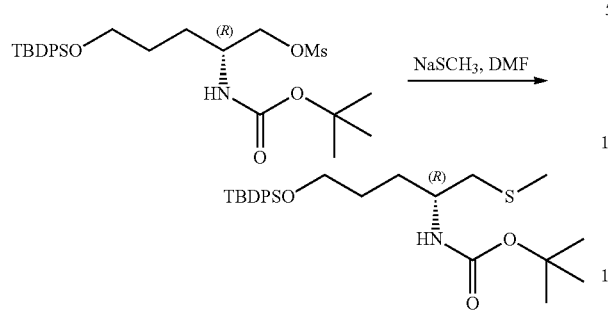

(R)-2-((tert-butoxycarbonyl)amino)-5-((tert-butyldiphenylsilyl)oxy)pentyl methanesulfonate (800 mg, 1.5 mmol, 1 eq.) was dissolved in DMF (10 mL). Then NaSCH$_3$ (420 mg, 4 eq.) was added and the mixture was stirred at 5-15° C. for 2.5 hours. TLC showed the reaction was completed. The mixture was treated with water (20 mL) and extracted with EtOAc (3*30 mL). The organic layer was washed with brine (3*30 mL), dried over anhydrous sodium sulfate, filtered and concentrated under vacuum to afford tert-butyl (R)-(5-((tert-butyldiphenylsilyl)oxy)-1-(methylthio)pentan-2-yl)carbamate as a colorless gum. LC-MS (ESI) m/z 510.6 [M+Na]$^+$. $^1$H NMR (CDCl$_3$ 400 MHz): δ 7.66 (dd, J=8.0, 1.6 Hz, 4H), 7.46-7.35 (m, 6H), 4.65 (d, J=7.6 Hz, 1H), 3.74 (br. s., 1H), 3.67 (t, J=6.2 Hz, 2H), 2.70-2.55 (m, 2H), 2.14 (s, 3H), 1.82-1.70 (m, 1H), 1.67-1.52 (m, 3H), 1.44 (s, 9H), 1.05 (s, 9H).

Step 5. tert-Butyl (R)-(5-hydroxy-1-(methylthio)pentan-2-yl)carbamate

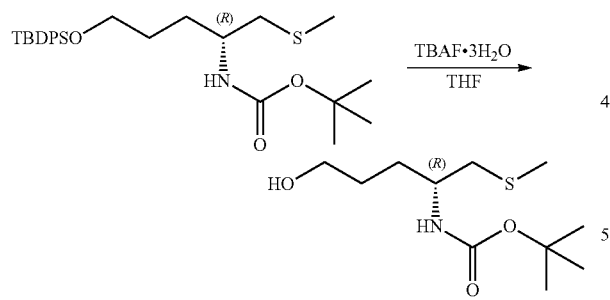

TBAF·3H$_2$O (1.9 g, 4 eq.) was added to a solution of tert-butyl (R)-(5-((tert-butyldiphenylsilyl)oxy)-1-(methylthio)pentan-2-yl)carbamate (750 mg, 1.5 mmol, 1 eq) and acetic acid (0.18 mL, 3.1 mmol, 2 eq.) in THF (15 mL). The mixture was stirred at 10-20° C. for 18 hours. TLC showed the reaction was completed. The reaction mixture was concentrated under vacuum. The residue was purified by column chromatography on silica gel (PE/EtOAc=1/1) to afford tert-butyl (R)-(5-hydroxy-1-(methylthio)pentan-2-yl)carbamate as a colourless gum. $^1$H NMR (CDCl$_3$ 400 MHz): δ 4.71 (d, J=8.4 Hz, 1H), 3.79 (brs., 1H), 3.66 (t, J=6.0 Hz, 2H), 2.70-2.53 (m, 2H) 2.13 (s, 3H), 1.79-1.48 (m, 4H), 1.43 (s, 9H).

Step 6. tert-Butyl (R)-(tert-butoxycarbonyl)(9-(6-((4-((tert-butoxycarbonyl)amino)-5-(methylthio)pentyl)oxy)-2,3-dichlorobenzyl)-9H-purin-6-yl)carbamate

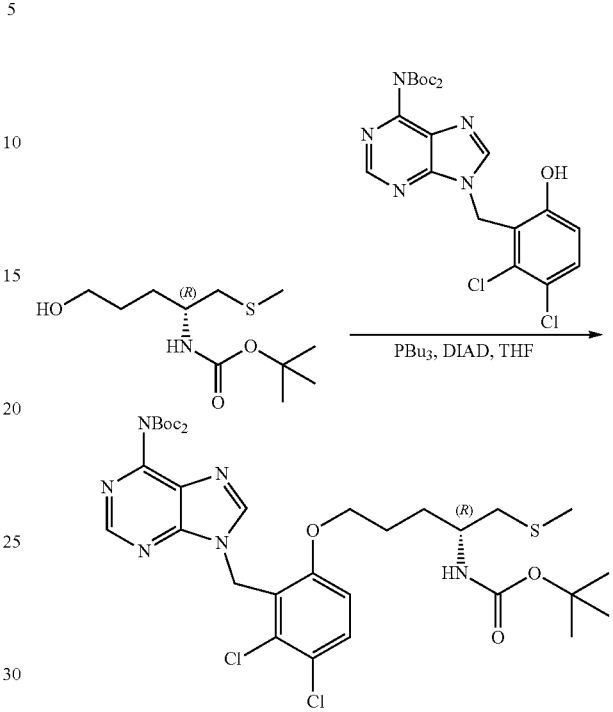

A solution of DIAD (600 mg, 5 eq.) in THF (1 mL) was added dropwise to a solution of tert-butyl (R)-(5-hydroxy-1-(methylthio)pentan-2-yl)carbamate (300 mg, 0.6 mmol, 1 eq.), PBu$_3$ (600 mg, 5 eq.) and tert-butyl (tert-butoxycarbonyl)(9-(2,3-dichloro-6-hydroxybenzyl)-9H-purin-6-yl)carbamate (150 mg, 1 eq.) in THF (15 mL) under ice-water bath. The mixture was warmed and stirred at 30° C. for 19 hours. LCMS showed the reaction was completed. The solvent was evaporated and the residue was dissolved in CH$_2$Cl$_2$ (30 mL). The organic layer was washed with water (2*20 mL) and brine (1*20 mL), dried over anhydrous sodium sulfate, filtered and concentrated in vacuo. The crude product was purified by column chromatography on silica gel (PE/EtOAc=5/1~1/1) to afford tert-butyl (R)-(tert-butoxycarbonyl)(9-(6-((4-((tert-butoxycarbonyl)amino)-5-(methylthio)pentyl)oxy)-2,3-dichlorobenzyl)-9H-purin-6-yl)carbamate as a white solid. LC-MS (ESI) m/z 763.2 [M+Na]$^+$.

Step 7. (R)-9-(6-((4-amino-5-(methylthio)pentyl)oxy)-2,3-dichlorobenzyl)-9H-purin-6-amine

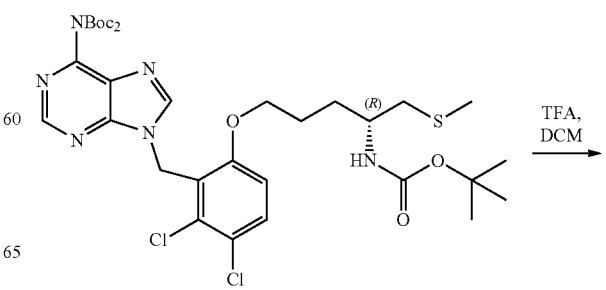

121
-continued

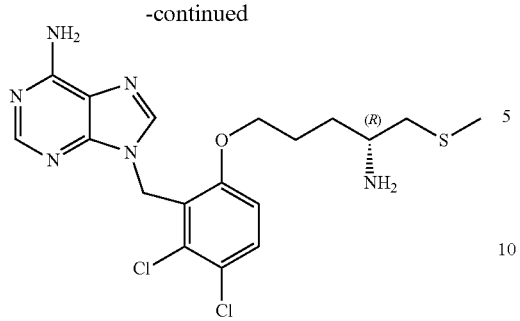

TFA (4 mL) was added slowly to a solution of tert-butyl (R)-(tert-butoxycarbonyl)(9-(6-(((4-((tert-butoxycarbonyl)amino)-5-(methylthio)pentyl)oxy)-2,3-dichlorobenzyl)-9H-purin-6-yl)carbamate (90 mg, 0.12 mmol, 1 eq) in $CH_2Cl_2$ (4 mL). The resulting mixture was stirred at 5-15° C. for 2.5 hours. LCMS showed the reaction was completed. The mixture was diluted with $CH_2Cl_2$ (15 mL), basified with saturated $NaHCO_3$. The resulting mixture was partitioned. The organic layer was washed with water (2*20 mL) and brine (1*20 mL), dried over $Na_2SO_4$, filtered and concentrated under vacuum. The residue was purified by pre-HPLC to afford (R)-9-(6-(((4-amino-5-(methylthio)pentyl)oxy)-2,3-dichlorobenzyl)-9H-purin-6-amine as a white solid. LC-MS (ESI) m/z 441.1 $[M+H]^+$. $^1H$ NMR (MeOD varian 400): δ 8.25 (s, 1H), 7.78 (s, 1H), 7.57 (d, J=8.8 Hz, 1H), 7.07 (d, J=9.2 Hz, 1H), 5.59 (s, 2H) 4.06 (t, J=6.2 Hz, 2H) 2.92-2.77 (m, 1H), 2.55 (dd, J=13.6, 4.8 Hz, 1H), 2.33 (dd, J=13.6, 8.0 Hz, 1H), 2.05 (s, 3H), 1.86-1.64 (m, 2H), 1.41-1.57 (m, 1H), 1.29-1.37 (m, 1H).

Example 53. (R)-5-(2-(((6-amino-9H-purin-9-yl)methyl)-3,4-dichlorophenoxy)-$N^1$,$N^1$-dimethylpentane-1,2-diamine

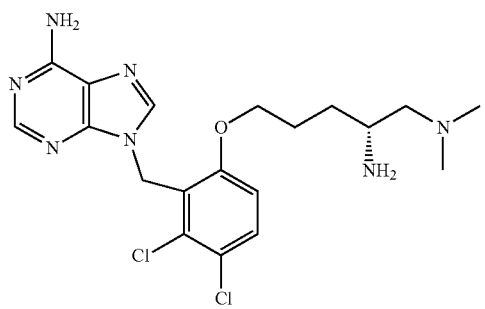 [SMILES: CN(C)C[C@H](N)CCCOc1ccc(Cl)c(Cl)c1Cn1cnc2c(N)ncnc21]

Step 1. (R)-(5-(2-(((6-(bis(tert-butoxycarbonyl)amino)-9H-purin-9-yl)methyl)-3,4-dichlorophenoxy)-1-(dimethylamino)pentan-2-yl)(tert-butoxycarbonyl)sulfamic acid

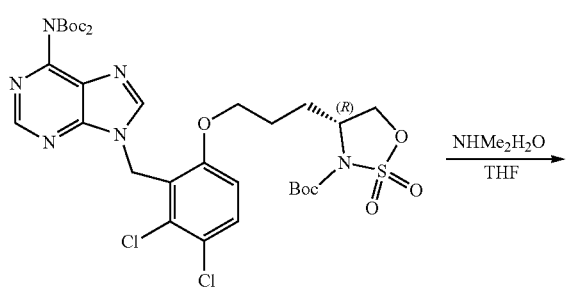

122
-continued

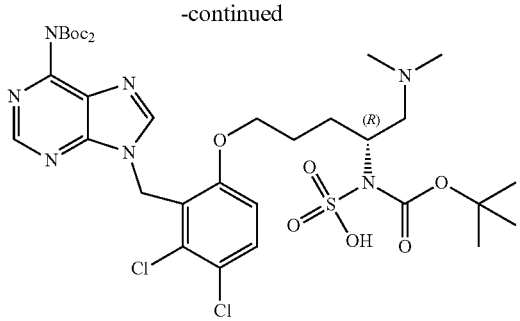

tert-butyl (R)-4-(3-(2-(((6-(bis(tert-butoxycarbonyl)amino)-9H-purin-9-yl)methyl)-3,4-dichloro phenoxy)propyl)-1,2,3-oxathiazolidine-3-carboxylate 2,2-dioxide (200 mg, 0.26 mmol, 1 eq) in methylamine monohydrate (2 mL) and tetrahydrofuran (2 mL) were stirred for 2 hours at 3-11° C. The organic layer was evaporated under vacuum to afford (R)-(5-(2-(((6-(bis(tert-butoxycarbonyl)amino)-9H-purin-9-yl)methyl)-3,4-dichlorophen oxy)-1-(dimethylamino)pentan-2-yl)(tert-butoxycarbonyl)sulfamic acid, which was used in the next step without further purification. LC-MS (ESI) m/z 738.2$[M+H]^+$.

Step 2. (R)-5-(2-(((6-amino-9H-purin-9-yl)methyl)-3,4-dichlorophenoxy)-$N^1$,$N^1$-dimethypentane-1,2-diamine

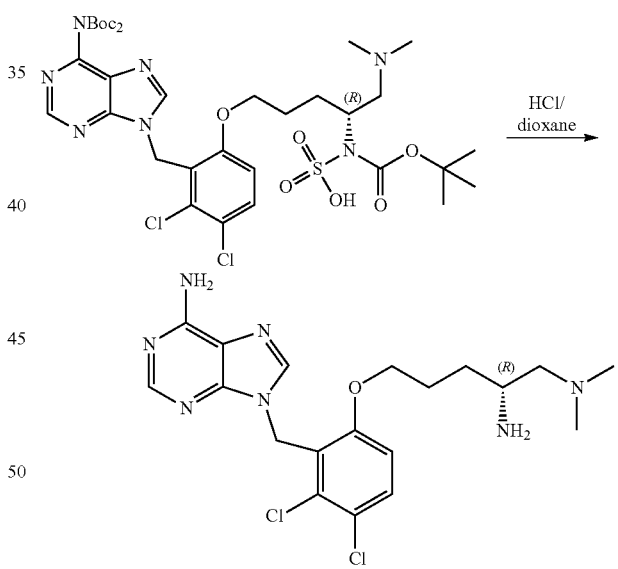

(R)-(5-(2-(((6-(bis(tert-butoxycarbonyl)amino)-9H-purin-9-yl)methyl)-3,4-dichlorophenoxy)-1-(dimethylamino)pentan-2-yl)(tert-butoxycarbonyl)sulfamic acid (200 mg, 0.28 mmol, 1 eq) in HCl/dioxane (4 M, 2 mL) was stirred for 2 h at 3-11° C. The mixture was evaporated under vacuum, dissolved in acetonitrile (5 mL) and basified with $NH_3H_2O$. The mixture was purified by pre-HPLC to afford (R)-5-(2-(((6-amino-9H-purin-9-yl)methyl)-3,4-dichlorophenoxy)-$N^1$,$N^1$-dimethylpentane-1,2-diamine as a white solid. LC-MS (ESI) m/z 438.1 $[M+H]^+$. $^1H$ NMR (METHANOL-$d_4$ varian 400): δ 8.26 (s., 1H), 7.77 (s., 1H), 7.56 (d, J=9.2 Hz, 1H), 7.06 (d, J=8.80 Hz, 1H), 5.58 (s., 1H), 4.04 (t, J=6.4 Hz, 1H), 2.77-2.81 (m, 1H), 2.20 (s., 6H), 2.01-2.16 (m, 2H), 1.67-1.78 (m, 2H), 1.19-1.32 (m, 2H).

Biological Assays

The compounds of the present invention may be evaluated for their ability to inhibit mixed lineage leukemia 1 (MLL1) using assays described below, as well as other assays known in the art.

MLL1 LC-MS Assay

The compounds of the present disclosure were serially and separately diluted 3-fold in DMSO to obtain a total of eight or twelve concentrations. Then the test compounds at each concentration (120 nL of each) were transferred by Mosquito into white Proxiplate plus 384-well microplate (PerkinElmer). Solutions (6 µL) of 60 nM wild type MLL1 four-member complex (MLL1-4C) and 5 µM SAM in the reaction buffer (20 mM Tris-HCl, pH8.0, 0.01% Tween 20, 1 mM DTT, 10 mM $MgCl_2$, 0.01% BSA) were added to the wells that were then incubated with the test compound for 20 min. A 6 µL solution of 20 µM of the peptide substrate H3K4me0 (histone H3[1-21]-Biotin) in the reaction buffer was added to initiate each reaction. The final components in the reaction solution include 30 nM MLL1-4C, 2.5 µM SAM, and 10 µM H3K4me0 with varying concentration of the compounds. A positive control consisted of 30 nM MLL1-4C, 2.5 µM SAM, and 10 µM substrate in the absence of the test compound, and a negative control consisted of 2.5 µM SAM, and 10 µM substrate only. Each reaction was incubated at rt for 120 min, then stopped by addition of 3 µL per of quench solution (2.5% TFA with 320 nM d4-SAH). The reaction mixture was centrifuged (Eppendorf centrifuge 5810, Rotor A-4-62) for 2 min at 2000 rmp. The SAH production from the enzymatic assays were monitored by LC-MS/MS on an API 4000 triple quadrupole mass spec with TurboIon Spray (Applied Biosystem) coupled with Prominenece UFLC(Shimazu). The level of SAH production were then normalized based on the values coming from the positive and negative controls to give percent enzyme activities. The data were then fit to a dose response equation using the program Helios (Novartis) to get the IC50 values of the test compounds.

MLL1 Flashplate Assay

To assess the compound potency in MLL1 Flashplate assay, compounds were serially diluted 3-fold in DMSO to obtain a total of twelve concentrations. Then the test compounds at each concentration (250 nL of each) were transferred by Mosquito into Corning #3675 384-well plate. Solutions (15 µL) of 4.2 nM wild type MLL1 five-member complex (MLL1-5C) in the assay buffer (20 mM Tris-HCl, pH8.0, 0.01% Tween 20, 1 mM DTT, 0.01% BSA) were added to the wells. A 10 µL solution of 2.5 µM of the peptide substrate H3K4me0 (histone H3[1-21]-Biotin) and 1.25 µM $^3$H-SAM in the reaction buffer was then added to initiate each reaction. The final components in the reaction solution include 2.5 nM MLL1-5C, 0.5 µM $^3$H-SAM, and 1 µM H3K4me0 with varying concentration of the compounds. A positive control consisted of 2.5 nM MLL1-5C, 0.5 µM $^3$H-SAM, and 1 µM substrate in the absence of the test compound, and a negative control consisted of 0.5 µM $^3$H-SAM, and 1 µM substrate only. Each reaction was incubated at rt for 90 min, then stopped by addition of 5 µL per of quench solution (0.5 mM SAM in assay buffer).

25 µL of each reaction solution was transferred to FlashPlate streptavidin 384-well microplate (PerkinElmer). After at least 1 h incubation at rt, the wells were washed three times with 0.1% Tween-20 in $dH_2O$ using the BioTek plate washer. The plates were then read in MicroBeta (PerkinElmer). The radioactive readouts were then normalized based on the values coming from the positive and negative controls to give percent enzyme activities. The data were then fit to a dose response equation using the program Helios to get the IC50 values of the test compounds.

MV4-11H3K4Me3 Cellular ELISA Assay

MV4-11 (ATCC® CRL-9591™) was cultured with RPMI1640 medium (Thermo Fisher Scientific, cat #11875) supplemented with 10% FBS (Thermo Fisher Scientific, cat #10099141) and 50 U/ml Penicillin-Streptomycin (Thermo Fisher Scientific, cat #10378016) in humidified incubator at 37° C., 5% $CO_2$.

200 nL compounds dissolved in DMSO were serially diluted at 1:3 ratio for 12 points starting from 10 mM and dispensed into each wells of cell culture plates (PDL-coated ViewPlate-384 Black, FTC, PerkinElmer, #6007710). 3,750 MV4-11 cells in 40 µL culture medium were seeded into each well and treated with desired concentration for 48 hours. After treatment, wash cells with cold phosphate based buffer (PBS, pH 7.4) and aspirate the remaining PBS buffer. Crude histone lysate was extracted by 40 µL 0.5M HCl for 1 hour in 4° C. following neutralization by adding 32 µL neutralization buffer (0.5M Sodium phosphate dibasic, pH~12.5, 1.25 mM Dithiothreitol, Promega #V3151, Protease Inhibitor Cocktail, Sigma #8340) for each well. 5 µL and 20 µL of histone lysate was loaded to ELISA plate (384 Well Plates, PE HB, White, 6005620) for detection of total H3 and H3K4me3, respectively. Shake the plates gently in 4° C. for overnight. After histone binding, plates were washed with 80 µL PBS/T (PBS with 0.05% Tween-20) and blocked with 50 µL 3% BSA diluted in PBS/T per well for 1 hour. Incubate wells with primary antibody for 1 hour at room temperature using anti-H3K4me3 (CST #9727) and anti-total H3 (CST #9715) diluted 1:2000 in 3% BSA. Plates were then washed with PBS/T for 3 times and incubated with horseradish peroxidase (HRP) conjugated secondary antibody (CST #7074, 1:5000) for 1 hour at room temperature. The abundance of H3K4me3 and total H3 were measured by ECL substrates chemiluminesce (Pierce, #34080) on a plate reader (PerkinElmer EnVison 2104 Mutilable Reader). Percentage inhibition was calculated against DMSO control after normalization of H3K4me3 signal to H3 signal for individual samples. The data were then fit to a dose response curve using GraphPad Prism for IC50 calculation.

MV4-11 6-Day Cell Growth CTG (CellTiter-Glo) Assay

Acute myeloid leukemia cell MV4-11 (ATCC® CRL-9591™) was cultured with RPMI 1640 medium (Thermo Fisher Scientific, cat #11875) supplemented with 10% FBS (Thermo Fisher Scientific, cat #10099141) in humidified incubator at 37° C., 5% $CO_2$. To assess the effect of MLL1 inhibition on cell growth, the compound of the present invention was dissolved in DMSO and serially diluted at 1:3 for 12 points starting from 10 mM then 200 nL for the replicate of each dose per well was dispensed to Viewplate-384 Black (Perkin Elmer). Exponentially growing MV4-11 cells were seeded at the density of 300 cells per well in 40 µL to the plate, so the final compound working concentration starts from 50 µM. After 6 days, 40 µL CellTiter-Glo (Promega, cat #G7573) was added into the cell culture well and luminescence was read with Envision (Perkin Elmer) to determine the viable cells. The percentage inhibition was calculated against the samples treated with DMSO only and the data were used for dose response curve fitting in GraphPad Prism to get the IC50 of representative compound of present invention, which reflects the inhibition of MLL1 activity.

The activity of the compounds of the present invention in different assay formats and cell lines are summarized in Table 1.

TABLE 1

| Ex. No. | Compound name | MLL1 LCMS | MV4-11 ELISA | MV4-11 CTG | MLL1 flash plate |
|---|---|---|---|---|---|
| 1 | (R)-9-(6-((4-amino-5-methoxypentyl)oxy)-2,3-dichlorobenzyl)-9H-purin-6-amine | +++ | + | ++ | +++ |
| 2 | (R)-9-(2-(3-amino-4-methoxybutoxy)-6-bromo-4-chlorobenzyl)-9H-purin-6-amine | + | − | − | + |
| 3 | (S)-9-(2-(3-amino-4-methoxybutoxy)-4-chloro-6-methylbenzyl)-9H-purin-6-amine | + | + | − | − |
| 4 | (S)-9-(2-(3-amino-4-methoxybutoxy)-4-chloro-6-ethylbenzyl)-9H-purin-6-amine | + | + | − | − |
| 5 | (R)-7-(6-((4-amino-5-methoxypentyl)oxy)-2,3-dichlorobenzyl)imidazo[2,1-f][1,2,4]triazin-4-amine | + | + | − | + |
| 6 | (R)-7-(2-((4-amino-5-methoxypentyl)oxy)-6-chlorobenzyl)imidazo[2,1-f][1,2,4]triazin-4-amine | + | − | − | − |
| 7 | (R)-7-(2-(((4-amino-5-methoxypentyl)oxy)benzyl)imidazo[2,1-f][1,2,4]triazin-4-amine | + | − | − | − |
| 8 | (R)-8-(6-((4-amino-5-methoxypentyl)oxy)-2,3-dichlorobenzyl)pyrazolo[1,5-a][1,3,5]triazin-4-amine | + | + | − | + |
| 9 | (R)-8-(2-((4-amino-5-methoxypentyl)oxy)-6-bromo-4-chlorobenzyl)pyrazolo[1,5-a][1,3,5] triazin-4-amine | + | + | − | − |
| 10 | (R)-8-(2-((4-amino-5-methoxypentyl)oxy)-6-bromobenzyl)pyrazolo[1,5-a][1,3,5]triazin-4-amine | + | − | − | − |
| 11 | (R)-8-(2-((4-amino-5-methoxypentyl)oxy)-6-chlorobenzyl)pyrazolo[1,5-a][1,3,5]triazin-4-amine | + | + | − | − |
| 12 | (R)-8-(2-(((4-amino-5-methoxypentyl)oxy)benzyl)pyrazolo[1,5-a][1,3,5]triazin-4-amine | + | − | − | − |
| 13 | (R)-8-(2-((4-amino-5-methoxypentyl)oxy)-4-chlorobenzyl)pyrazolo[1,5-a][1,3,5]triazin-4-amine | + | − | − | − |
| 14 | (R)-8-(2-((4-amino-5-methoxypentyl)oxy)-3-chlorobenzyl)pyrazolo[1,5-a][1,3,5]triazin-4-amine | + | − | − | − |
| 15 | (R)-8-(6-((4-amino-5-isobutoxypentyl)oxy)-2,3-dichlorobenzyl)pyrazolo[1,5-a][1,3,5]triazin-4-amine | + | − | − | + |
| 16 | (R)-8-(6-((4-amino-5-ethoxypentyl)oxy)-2,3-dichlorobenzyl)pyrazolo[1,5-a][1,3,5]triazin-4-amine | + | + | − | + |
| 17 | (S)-8-(6-(3-amino-4-methoxybutoxy)-2,3-dichlorobenzyl)pyrazolo[1,5-a][1,3,5]triazin-4-amine | + | − | − | + |
| 18 | (R)-1-(6-((4-amino-5-methoxypentyl)oxy)-2,3-dichlorobenzyl)-7-chloro-1H-imidazo[4,5-c]pyridin-4-amine | ++ | + | − | − |
| 19 | (S)-9-((2-(2-amino-3-methoxypropoxy)naphthalen-1-yl)methyl)-9H-purin-6-amine | ++ | ++ | +++ | − |
| 20 | (R)-9-((2-((4-amino-5-methoxypentyl)oxy)-6-bromonaphthalen-1-yl)methyl)-9H-purin-6-amine | ++ | + | + | +++ |
| 21 | (R)-9-((3-((4-amino-5-methoxypentyl)oxy)naphthalen-2-yl)methyl)-9H-purin-6-amine | ++ | + | − | + |
| 22 | (R)-9-(2-bromo-4-chloro-6-((5-methoxy-4-(methylamino)pentyl)oxy)benzyl)-9H-purin-6-amine | + | − | − | + |
| 23 | (R)-2-amino-5-(2-((6-amino-9H-purin-9-yl)methyl)-3,4-dichlorophenoxy)pentanoic acid | +++ | +++ | ++ | +++ |
| 24 | (R)-2-amino-5-(2-((4-aminoimidazo[2,1-f][1,2,4]triazin-7-yl)methyl)-3,4-dichlorophenoxy) pentanoic acid | ++ | + | − | − |
| 25 | O-(2-((6-amino-9H-purin-9-yl)methyl)-3,4-difluorophenyl)-L-homoserine | + | − | − | − |
| 26 | (R)-2-amino-5-(2-((6-amino-2-isopropyl-9H-purin-9-yl)methyl)-3,5-dichlorophenoxy)pentanoic acid | + | − | − | − |
| 27 | (R)-2-amino-5-(2-((6-amino-2-methoxy-9H-purin-9-yl)methyl)-3,5-dichlorophenoxy)pentanoic acid | ++ | − | + | − |

TABLE 1-continued

| Ex. No. | Compound name | MLL1 LCMS | MV4-11 ELISA | MV4-11 CTG | MLL1 flash plate |
|---|---|---|---|---|---|
| 28 | 2-amino-5-(2-((4-amino-7-chloro-1H-imidazo[4,5-c]pyridin-1-yl)methyl)-3,5-dichlorophenoxy) pentanoic acid | + | − | − | − |
| 29 | Ethyl (R)-2-amino-5-(2-((6-amino-9H-purin-9-yl)methyl)-3,4-dichlorophenoxy)pentanoate | +++ | +++ | +++ | +++ |
| 30 | Ethyl (2R)-2-amino-5-(2-((6-amino-9H-purin-9-yl)methyl)-3,4-dichlorophenoxy)hexanoate | ++ | ++ | +++ | − |
| 31 | Methyl 2-amino-5-(2-((4-amino-7-chloro-1H-imidazo[4,5-c]pyridin-1-yl)methyl)-3,5-dichloro phenoxy)pentanoate | +++ | − | +++ | − |
| 32 | ethyl (R)-2-amino-5-(2-((6-amino-9H-purin-9-yl)methyl)-3,5-dichlorophenoxy)pentanoate | ++ | − | +++ | − |
| 33 | methyl (R)-2-amino-5-(2-((6-amino-9H-purin-9-yl)methyl)-3,4-dichlorophenoxy)pentanoate | +++ | − | − | − |
| 34 | Methyl (R)-2-amino-5-(2-((4-aminoimidazo[2,1-f][1,2,4]triazin-7-yl)methyl)-3,4-dichlorophenoxy)pentanoate | ++ | +++ | +++ | − |
| 35 | (R)-2-amino-5-(2-((4-aminoimidazo[2,1-f][1,2,4]triazin-7-yl)methyl)-3,4-dichlorophenoxy)pentanamide | + | + | − | − |
| 36 | (R)-2-amino-5-(2-((4-aminoimidazo[2,1-f][1,2,4]triazin-7-yl)methyl)-3,4-dichlorophenoxy)-N-cyclopropylpentanamide | +++ | + | − | +++ |
| 37 | (R)-2-amino-5-(2-((4-aminopyrazolo[1,5-a][1,3,5]triazin-8-yl)methyl)-3,4-dichlorophenoxy)-N-cyclopropylpentanamide | ++ | + | − | + |
| 38 | (R)-2-amino-5-(2-((4-amino-7-chloro-1H-imidazo[4,5-c]pyridin-1-yl)methyl)-3,5-dichlorophenoxy)pentanamide | + | − | − | − |
| 39 | (R)-2-amino-5-(2-((6-amino-9H-purin-9-yl)methyl)-3,4-dichlorophenoxy)pentanamide | ++ | − | +++ | − |
| 40 | (R)-2-amino-5-(2-((6-amino-9H-purin-9-yl)methyl)-3,4-dichlorophenoxy)-N-methylpentanamide | + | − | − | − |
| 41 | (R)-2-amino-5-(2-((6-amino-9H-purin-9-yl)methyl)-3,4-dichlorophenoxy)-N-(2-methoxyethyl) pentanamide | ++ | +++ | +++ | − |
| 42 | (R)-2-amino-5-(2-((6-amino-9H-purin-9-yl)methyl)-3,4-dichlorophenoxy)-N-cyclopropylpentanamide | +++ | +++ | +++ | +++ |
| 43 | (R)-2-amino-5-(2-((6-amino-9H-purin-9-yl)methyl)-3,4-dichlorophenoxy)-N-(methylsulfonyl)pentanamide | +++ | +++ | +++ | +++ |
| 44 | (R)-2-amino-5-(2-((4-aminopyrazolo[1,5-a][1,3,5]triazin-8-yl)methyl)-3,4-dichlorophen oxy)pentan-1-ol | + | + | − | + |
| 45 | (R)-2-amino-5-(2-((6-amino-9H-purin-9-yl)methyl)-3,4-dichlorophenoxy)pentan-1-ol | ++ | − | ++ | ++ |
| 46 | 1-(2-(4-aminobutoxy)-4,6-dichlorobenzyl)-1H-imidazo[4,5-c]pyridin-4-amine | + | − | − | − |
| 47 | (R)-9-(6-((4-amino-5-(2-methoxyethoxy)pentyl)oxy)-2,3-dichlorobenzyl)-9H-purin-6-amine | + | − | + | + |
| 48 | (R)-9-(6-(4-amino-4-(1H-1,2,4-triazol-3-yl)butoxy)-2,3-dichlorobenzyl)-9H-purin-6-amine | +++ | +++ | +++ | +++ |
| 49 | (R)-9-(6-((4-amino-5-(1H-pyrazol-1-yl)pentyl)oxy)-2,3-dichlorobenzyl)-9H-purin-6-amine | ++ | − | + | − |
| 50 | (R)-9-(6-(4-amino-4-(5-methyl-1,3,4-thiadiazol-2-yl)butoxy)-2,3-dichlorobenzyl)-9H-purin-6-amine | +++ | + | + | +++ |
| 51 | (R)-9-(6-(4-amino-4-(1,3,4-oxadiazol-2-yl)butoxy)-2,3-dichlorobenzyl)-9H-purin-6-amine | + | − | + | ++ |

TABLE 1-continued

| Ex. No. | Compound name | MLL1 LCMS | MV4-11 ELISA | MV4-11 CTG | MLL1 flash plate |
|---|---|---|---|---|---|
| 52 | (R)-9-(6-((4-amino-5-(methylthio)pentyl)oxy)-2,3-dichlorobenzyl)-9H-purin-6-amine | ++ | − | + | + |
| 53 | (R)-5-(2-((6-amino-9H-purin-9-yl)methyl)-3,4-dichlorophenoxy)-$N^1,N^1$-dimethylpentane-1,2-diamine | + | + | + | + |

| Legend: | "+++" | "++" | "+" |
|---|---|---|---|
| LCMS | <0.05M | 0.05-0.10M | >0.10M |
| MLL1 flash plate | <0.06M | 0.06-0.10M | >0.10M |
| ELISA | <1.9M | 1.9-3.0M | >3.0M |
| CTG MV4:11 | <2.0M | 2.0-3.0M | >3.0M |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A compound of Formula (I)

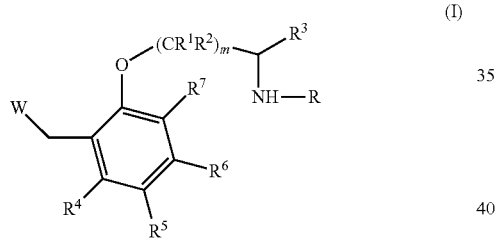

(I)

or an enantiomer, an enantiomeric mixture, or a pharmaceutically acceptable salt thereof, wherein:

W is selected from:

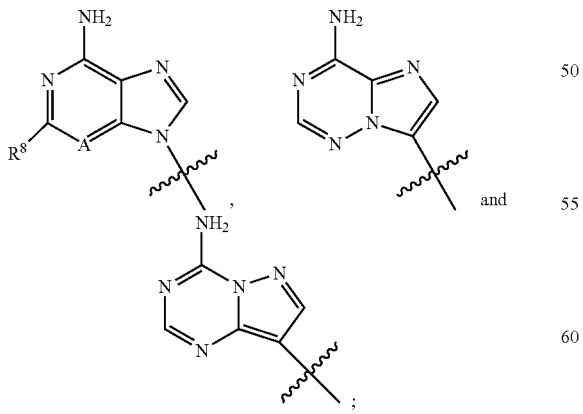

;

A is N or $CR^9$ wherein $R^9$ is hydrogen or halo;
R, $R^1$ and $R^2$ are independently H or $C_{1-4}$ alkyl;
$R^3$ is hydrogen or selected from the group consisting of:

(i) —$C_{1-6}$ alkyl, -halo$C_{1-6}$ alkyl, -hydroxy$C_{1-6}$ alkyl, —$C_{1-6}$alkoxy$C_{1-6}$alkyl, —$C_{3-8}$cycloalkoxy($C_{1-6}$ alkyl), cyano, -cyano$C_{1-6}$ alkyl, —$C_{1-6}$ alkylthio$C_{1-6}$alkyl, —$C_{2-6}$ alkenyl, -halo$C_{2-6}$ alkenyl, —$C_{2-6}$ alkynyl, —$C_{1-4}$ alkyl-S—$C_{1-4}$alkyl, —$C_{1-4}$ alkylSO$_2$C$_{1-4}$alkyl, —SO$_2$(C$_{1-4}$ alkyl), or —C(C$_{1-4}$ alkyl)=N—O(C$_{1-4}$ alkyl);

(ii) —$C_{1-4}$alkylcarbonyl, —$(CR^aR^b)_p$—C(=O)—OR$^{10a}$, or —C(=O)—$(CR^aR^b)_q$R$^{11}$;
wherein R$^{11}$ is —$C_{3-7}$ cycloalkyl, 5-6 membered heterocyclyl or 5-6 membered heteroaryl, each of which is independently unsubstituted or substituted with —$C_{1-6}$ alkyl or —$C_{1-6}$ alkoxy; and said 5-6 membered heterocyclyl or 5-6 membered heteroaryl independently comprises 1-3 heteroatoms selected from nitrogen, oxygen and sulfur;

(iii) —$(CR^aR^b)_r$—C(=O)—NR$^{12}$R$^{13}$, —$(CR^aR^b)_s$—NR$^{12}$R$^{13}$, —$(CR^aR^b)_{1-4}$—O—$(CR^aR^b)_{1-4}$—OR$^{10a}$ or —$(CR^aR^b)_{1-4}$—O—$(CR^aR^b)_{1-4}$—C(=O)—NR$^{12}$R$^{13}$;
wherein R$^{12}$ is hydrogen or —$C_{1-6}$ alkyl;
R$^{13}$ is hydrogen, —$C_{1-6}$ alkyl, —$C_{1-6}$alkoxy$C_{1-6}$alkyl, -cyano$C_{1-6}$ alkyl; —$C_{0-4}$ alkylSO$_2$R$^{10b}$ wherein R$^{10b}$ is —$C_{1-6}$ alkyl or phenyl; $C_{3-10}$ monocyclic or bicyclic cycloalkyl$C_{0-6}$alkyl, phenyl, 5-10 membered monocyclic or bicyclic heterocyclic ring or 5-9 membered heteroaryl$C_{0-6}$alkyl;
said 5-10 membered monocyclic or bicyclic heterocyclic ring or 5-9 membered heteroaryl radical independently comprises 1-4 heteroatoms selected from nitrogen, oxygen and sulfur; and
said $C_{3-10}$ monocyclic or bicyclic cycloalkyl, phenyl, 5-10 membered monocyclic or bicyclic heterocyclic ring or 5-9 membered heteroaryl radical are independently unsubstituted or substituted with 1-2 —$C_{1-4}$ alkyl, -hydroxy$C_{1-6}$ alkyl, —$C_{1-4}$ alkoxy, halo, hydroxyl, phenyl or —S($C_{1-4}$ alkyl);
or R$^{12}$ and R$^{13}$ together form a 5-10 membered monocyclic or bicyclic heterocyclic ring comprising 1-4 heteroatoms selected from nitrogen, oxygen and sulfur; and is unsubstituted or substituted with —$C_{1-4}$ alkyl, hydroxyl, cyano, -cyano$C_{1-6}$ alkyl, —SO$_2$ or —$C_{2-4}$alkenylcarbonyl;

(v) 5-6 membered heterocyclyl$C_{0-6}$alkyl or 5-6 membered heterocyclyl(halo$C_{1-4}$ alkyl), wherein each said heterocyclyl radical is unsubstituted or substituted with oxo; and wherein each said heterocyclyl radical comprises 1-3 heteroatoms selected from nitrogen, oxygen and sulfur; and (vi) phenyl, 5-9 membered heteroaryl$C_{0-6}$alkyl or 5-9 membered heteroaryl(halo$C_{1-4}$alkyl), wherein each said phenyl or heteroaryl radical is independently unsubstituted or substituted by —$C_{1-4}$ alkyl, -halo$C_{1-4}$ alkyl, -hydroxy$C_{1-4}$ alkyl, —$C_{1-4}$ alkoxy, -halo$C_{1-4}$ alkoxy, halo, hydroxy, cyano, oxido, amino, —$C_{1-4}$ alkylamino, —$C_{1-4}$ dialkylamino, -aminocarbonyl$C_{0-6}$alkyl, —$C_{1-4}$alkylaminocarbonyl$C_{0-6}$alkyl, -di$C_{1-4}$alkylaminocarbonyl$C_{0-6}$alkyl or $C_{3-7}$ cycloalkyl;

wherein each said heteroaryl radical comprises 1-4 heteroatoms selected from nitrogen, oxygen and sulfur;

$R^4$, $R^5$, $R^6$ and $R^7$ are independently hydrogen, halo, —$C_{1-4}$ alkyl, -halo$C_{1-6}$ alkyl, -hydroxy$C_{1-6}$ alkyl, cyano, -cyano$C_{1-6}$ alkyl, —$C_{2-6}$ alkenyl, —$C_{2-6}$ alkynyl, —$C_{1-6}$ alkylthio, —$(CR^aR^b)_{1-4}$—$NR^{14}R^{15}$, —$(CR^aR^b)_{1-4}NR^{14}$—$C(O)$—$OR^{15}$, —$(CR^aR^b)_{1-4}$—$OR^{16}$, $C_{3-8}$cycloalkyl, phenyl or 5-6 membered heteroaryl comprising 1-3 heteroatoms selected from nitrogen, oxygen and sulfur; wherein said $C_{3-8}$cycloalkyl, phenyl or 5-6 membered heteroaryl is independently substituted with 1-2 $R^{17}$;

alternatively, $R^4$ and $R^5$, $R^5$ and $R^6$, and $R^6$ and $R^7$ together with the phenyl ring to which they are attached form a 9-10 membered benzo-fused carbocycle or benzo-fused heterocycle comprising 1-3 heteroatoms selected from nitrogen, oxygen and sulfur; wherein said benzo-fused carbocycle or benzo-fused heterocycle is independently unsubstituted or substituted with 1-2 halo or $C_{1-4}$ alkyl;

$R^8$ is hydrogen, —$C_{1-4}$ alkyl or —$C_{1-4}$ alkoxy;

$R^a$, $R^b$, $R^c$, $R^{10a}$ and $R^{14}$ are independently hydrogen or —$C_{1-4}$ alkyl;

$R^{15}$ is hydrogen, —$C_{1-4}$ alkyl, -halo$C_{1-6}$ alkyl or —$C_{3-6}$ cycloalkyl;

alternatively, $R^{14}$ and $R^{15}$ together with N in the —$NR^{14}R^{15}$ moiety form a 4-10 membered monocyclic or bicyclic heterocyclic ring comprising 1-3 heteroatoms selected from nitrogen, oxygen and sulfur; wherein said 4-10 membered monocyclic or bicyclic heterocyclic ring is unsubstituted or substituted with 1-2 halo or —$C_{1-4}$ alkyl;

$R^{16}$ is hydrogen, —$C_{1-4}$ alkyl, -halo$C_{1-6}$ alkyl, —$C_{3-6}$ cycloalkyl, phenyl, 5-6 membered heterocyclyl or 5-6 membered heteroaryl; wherein said 5-6 membered heterocyclyl or 5-6 membered heteroaryl independently comprises 1-3 heteroatoms selected from nitrogen, oxygen and sulfur;

$R^{17}$ is —$C_{1-4}$ alkyl, halo or —$C_{3-6}$ cycloalkyl; or two $R^{20}$ together form a 5-6 membered ring;

m is 1, 2, 3 or 4; and p, q, r and s are independently 0, 1, 2, 3 or 4.

2. The compound of Formula (I) in claim 1, wherein said compound is of Formula (II):

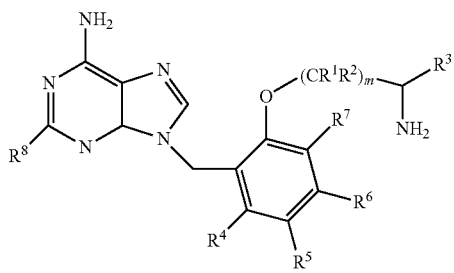

(II)

or an enantiomer, an enantiomeric mixture, or a pharmaceutically acceptable salt thereof.

3. The compound of Formula (I) in claim 1, wherein said compound is of Formula (III):

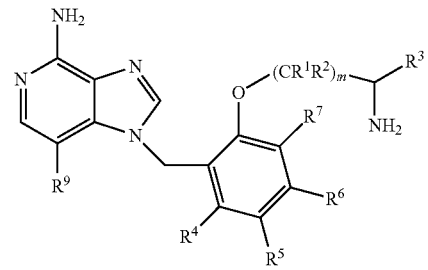

(III)

or an enantiomer, an enantiomeric mixture, or a pharmaceutically acceptable salt thereof.

4. The compound of Formula (I) in claim 1, wherein said compound is of Formula (IV):

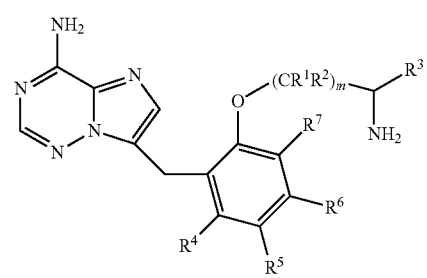

(IV)

or an enantiomer, an enantiomeric mixture, or a pharmaceutically acceptable salt thereof.

5. The compound of Formula (I) in claim 1, wherein said compound is of Formula (V):

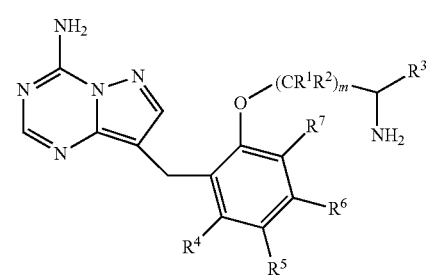

(V)

or an enantiomer, an enantiomeric mixture, or a pharmaceutically acceptable salt thereof.

6. The compound according to claim 1, or an enantiomer, an enantiomeric mixture, or a pharmaceutically acceptable salt thereof, wherein $R^3$ is hydrogen, -hydroxy$C_{1-6}$ alkyl, —$C_{1-6}$alkoxy$C_{1-6}$alkyl, —$C_{1-4}$ alkyl-S—$C_{1-4}$alkyl, —$C(=O)$—$OR^{10a}$, —$C(=O)$—$NR^{12}R^{13}$, —$(CR^aR^b)$—$NR^{12}R^{13}$, —$(CR^aR^b)$—$O$—$(CR^aR^b)_2$—$O$—$_{1-6}$ alkyl or 5-9 membered heteroaryl$C_{0-6}$alkyl wherein said heteroaryl radical is unsubstituted or substituted by —$C_{1-4}$ alkyl;

wherein $R^a$, $R^b$, $R^{10a}$ and $R^{12}$ are independently hydrogen or $C_{1-4}$ alkyl;

R¹³ is hydrogen, —C₁₋₆ alkyl, —C₁₋₆alkoxyC₁₋₆alkyl, —SO₂—(C₁₋₄ alkyl) or -cyclopropyl; and
m is 1, 2, 3 or 4.

7. The compound according to claim 1, or an enantiomer, an enantiomeric mixture, or a pharmaceutically acceptable salt thereof; wherein R³ is —C₁₋₆alkoxyC₁₋₆alkyl, —C(═O)—OR¹⁰ᵃ, —C(═O)—NR¹²R¹³, triazolyl or thiadiazolyl unsubstituted or substituted by —C₁₋₄ alkyl;
wherein Rᵃ, Rᵇ, R¹⁰ᵃ and R¹² are independently hydrogen or C₁₋₄ alkyl;
R¹³ is hydrogen, —C₁₋₆alkoxyC₁₋₆alkyl, —SO₂—(C₁₋₄ alkyl) or -cyclopropyl; and
m is 1, 2 or 3.

8. The compound according to claim 1, or an enantiomer, an enantiomeric mixture, or a pharmaceutically acceptable salt thereof; wherein:
R⁴ and R⁵ are halo; and
R⁶ and R⁷ are hydrogen.

9. The compound according to claim 1, or an enantiomer, an enantiomeric mixture, or a pharmaceutically acceptable salt thereof; wherein:
R⁴ is halo or —C₁₋₄ alkyl;
R⁶ is halo; and
R⁵ and R⁷ are hydrogen.

10. The compound according to claim 1, or an enantiomer, an enantiomeric mixture, or a pharmaceutically acceptable salt thereof, wherein R⁴ and R⁵ together with the phenyl ring to which they are attached form a 9-10 membered benzo-fused carbocycle; wherein said benzo-fused carbocycle is unsubstituted or substituted with halo; and
R⁶ and R⁷ are hydrogen.

11. The compound according to claim 1, or an enantiomer, an enantiomeric mixture, or a pharmaceutically acceptable salt thereof, wherein:
R⁴ and R⁷ are hydrogen; and
R⁵ and R⁶ together with the phenyl ring to which they are attached form a 9-10 membered benzo-fused carbocycle.

12. The compound according to claim 1, or an enantiomer, an enantiomeric mixture, or a pharmaceutically acceptable salt thereof, wherein R⁴, R⁵, R⁶ and R⁷ are hydrogen; or wherein one of R⁴, R⁵, R⁶ and R⁷ is halo and the others are hydrogen.

13. The compound according to claim 1, wherein the compound is selected from the group consisting of:
(R)-9-(6-((4-amino-5-methoxypentyl)oxy)-2,3-dichlorobenzyl)-9H-purin-6-amine;
(R)-9-(2-(3-amino-4-methoxybutoxy)-6-bromo-4-chlorobenzyl)-9H-purin-6-amine;
(S)-9-(2-(3-amino-4-methoxybutoxy)-4-chloro-6-methylbenzyl)-9H-purin-6-amine;
(S)-9-(2-(3-amino-4-methoxybutoxy)-4-chloro-6-ethylbenzyl)-9H-purin-6-amine;
(R)-7-(6-((4-amino-5-methoxypentyl)oxy)-2,3-dichlorobenzyl)imidazo[2,1-f][1,2,4]triazin-4-amine;
(R)-7-(2-((4-amino-5-methoxypentyl)oxy)-6-chlorobenzyl)imidazo[2,1-f][1,2,4]triazin-4-amine;
(R)-7-(2-((4-amino-5-methoxypentyl)oxy)benzyl)imidazo[2,1-f][1,2,4]triazin-4-amine;
(R)-8-(6-((4-amino-5-methoxypentyl)oxy)-2,3-dichlorobenzyl)pyrazolo[1,5-a][1,3,5]triazin-4-amine;
(R)-8-(2-((4-amino-5-methoxypentyl)oxy)-6-bromo-4-chlorobenzyl)pyrazolo[1,5-a][1,3,5]triazin-4-amine;
(R)-8-(2-((4-amino-5-methoxypentyl)oxy)-6-bromobenzyl)pyrazolo[1,5-a][1,3,5]triazin-4-amine;
(R)-8-(2-((4-amino-5-methoxypentyl)oxy)-6-chlorobenzyl)pyrazolo[1,5-a][1,3,5]triazin-4-amine;
(R)-8-(2-((4-amino-5-methoxypentyl)oxy)benzyl)pyrazolo[1,5-a][1,3,5]triazin-4-amine;
(R)-8-(2-((4-amino-5-methoxypentyl)oxy)-4-chlorobenzyl)pyrazolo[1,5-a][1,3,5]triazin-4-amine;
(R)-8-(2-((4-amino-5-methoxypentyl)oxy)-3-chlorobenzyl)pyrazolo[1,5-a][1,3,5]triazin-4-amine;
(R)-8-(6-((4-amino-5-isobutoxypentyl)oxy)-2,3-dichlorobenzyl)pyrazolo[1,5-a][1,3,5]triazin-4-amine;
(R)-8-(6-((4-amino-5-ethoxypentyl)oxy)-2,3-dichlorobenzyl)pyrazolo[1,5-a][1,3,5]triazin-4-amine;
(S)-8-(6-(3-amino-4-methoxybutoxy)-2,3-dichlorobenzyl)pyrazolo[1,5-a][1,3,5]triazin-4-amine;
(R)-1-(6-((4-amino-5-methoxypentyl)oxy)-2,3-dichlorobenzyl)-7-chloro-1H-imidazo[4,5-c]pyridin-4-amine;
(S)-9-((2-(2-amino-3-methoxypropoxy)naphthalen-1-yl)methyl)-9H-purin-6-amine;
(R)-9-((2-((4-amino-5-methoxypentyl)oxy)-6-bromonaphthalen-1-yl)methyl)-9H-purin-6-amine;
(R)-9-((3-((4-amino-5-methoxypentyl)oxy)naphthalen-2-yl)methyl)-9H-purin-6-amine;
(R)-9-(2-bromo-4-chloro-6-((5-methoxy-4-(methylamino)pentyl)oxy)benzyl)-9H-purin-6-amine;
(R)-2-amino-5-(2-((6-amino-9H-purin-9-yl)methyl)-3,4-dichlorophenoxy)pentanoic acid;
(R)-2-amino-5-(2-((4-aminoimidazo[2,1-f][1,2,4]triazin-7-yl)methyl)-3,4-dichlorophenoxy) pentanoic acid;
O-(2-((6-amino-9H-purin-9-yl)methyl)-3,4-difluorophenyl)-L-homoserine;
(R)-2-amino-5-(2-((6-amino-2-isopropyl-9H-purin-9-yl)methyl)-3,5-dichlorophenoxy)pentanoic acid;
(R)-2-amino-5-(2-((6-amino-2-methoxy-9H-purin-9-yl)methyl)-3,5-dichlorophenoxy)pentanoic acid;
2-amino-5-(2-((4-amino-7-chloro-1H-imidazo[4,5-c]pyridin-1-yl)methyl)-3,5-dichlorophenoxy) pentanoic acid;
Ethyl (R)-2-amino-5-(2-((6-amino-9H-purin-9-yl)methyl)-3,4-dichlorophenoxy)pentanoate;
Ethyl (2R)-2-amino-5-(2-((6-amino-9H-purin-9-yl)methyl)-3,4-dichlorophenoxy)hexanoate;
Methyl 2-amino-5-(2-((4-amino-7-chloro-1H-imidazo[4,5-c]pyridin-1-yl)methyl)-3,5-dichloro phenoxy)pentanoate;
Ethyl (R)-2-amino-5-(2-((6-amino-9H-purin-9-yl)methyl)-3,5-dichlorophenoxy)pentanoate;
Methyl (R)-2-amino-5-(2-((6-amino-9H-purin-9-yl)methyl)-3,4-dichlorophenoxy)pentanoate;
Methyl (R)-2-amino-5-(2-((4-aminoimidazo[2,1-f][1,2,4]triazin-7-yl)methyl)-3,4-dichlorophenoxy)pentanoate;
(R)-2-amino-5-(2-((4-aminoimidazo[2,1-f][1,2,4]triazin-7-yl)methyl)-3,4-dichlorophenoxy)pentanamide;
(R)-2-amino-5-(2-((4-aminoimidazo[2,1-f][1,2,4]triazin-7-yl)methyl)-3,4-dichlorophenoxy)-N-cyclopropylpentanamide;
(R)-2-amino-5-(2-((4-aminopyrazolo[1,5-a][1,3,5]triazin-8-yl)methyl)-3,4-dichlorophenoxy)-N-cyclopropylpentanamide;
(R)-2-amino-5-(2-((4-amino-7-chloro-1H-imidazo[4,5-c]pyridin-1-yl)methyl)-3,5-dichlorophenoxy)pentanamide;
(R)-2-amino-5-(2-((6-amino-9H-purin-9-yl)methyl)-3,4-dichlorophenoxy)pentanamide;
(R)-2-amino-5-(2-((6-amino-9H-purin-9-yl)methyl)-3,4-dichlorophenoxy)-N-methylpentanamide;

(R)-2-amino-5-(2-((6-amino-9H-purin-9-yl)methyl)-3,4-dichlorophenoxy)-N-(2-methoxyethyl) pentanamide;
(R)-2-amino-5-(2-((6-amino-9H-purin-9-yl)methyl)-3,4-dichlorophenoxy)-N-cyclopropylpentanamide;
(R)-2-amino-5-(2-((6-amino-9H-purin-9-yl)methyl)-3,4-dichlorophenoxy)-N-(methylsulfonyl)pentanamide;
(R)-2-amino-5-(2-((4-aminopyrazolo[1,5-a][1,3,5]triazin-8-yl)methyl)-3,4-dichlorophenoxy)pentan-1-ol;
(R)-2-amino-5-(2-((6-amino-9H-purin-9-yl)methyl)-3,4-dichlorophenoxy)pentan-1-ol;
1-(2-(4-aminobutoxy)-4,6-dichlorobenzyl)-1H-imidazo[4,5-c]pyridin-4-amine;
(R)-9-(6-((4-amino-5-(2-methoxyethoxy)pentyl)oxy)-2,3-dichlorobenzyl)-9H-purin-6-amine;
(R)-9-(6-(4-amino-4-(1H-1,2,4-triazol-3-yl)butoxy)-2,3-dichlorobenzyl)-9H-purin-6-amine;
(R)-9-(6-((4-amino-5-(1H-pyrazol-1-yl)pentyl)oxy)-2,3-dichlorobenzyl)-9H-purin-6-amine;
(R)-9-(6-(4-amino-4-(5-methyl-1,3,4-thiadiazol-2-yl)butoxy)-2,3-dichlorobenzyl)-9H-purin-6-amine;
(R)-9-(6-(4-amino-4-(1,3,4-oxadiazol-2-yl)butoxy)-2,3-dichlorobenzyl)-9H-purin-6-amine;
(R)-9-(6-((4-amino-5-(methylthio)pentyl)oxy)-2,3-dichlorobenzyl)-9H-purin-6-amine; and
(R)-5-(2-((6-amino-9H-purin-9-yl)methyl)-3,4-dichlorophenoxy)-N,N-dimethylpentane-1,2-diamine;

or a pharmaceutically acceptable salt thereof.

14. A pharmaceutical composition comprising a compound according to claim 1, and one or more pharmaceutically acceptable carrier.

15. A combination comprising a compound according to claim 1, and one or more therapeutically active agent.

16. A method for treating a disease or condition that benefits from or is treatable by inhibition of mixed lineage leukemia 1 (MLL1), comprising administering to a subject in need of such treatment a therapeutically effective amount of a compound according to claim 1.

17. The method of claim 16, wherein said disease or condition that benefit from or is treatable by inhibition of MLL1 is selected from solid tumors, leukemia, myeloma, lymphoma and hypertension.

18. The method of claim 16, wherein said disease or condition that benefit from or is treatable by inhibition of MLL1 is breast cancer, cervical cancer, skin cancer skin squamous cell carcinoma, ovarian cancer, gastric cancer, prostate cancer, pancreatic cancer, lung cancer, hepatocellular carcinoma, head and neck cancer, peripheral nerve A sheath tumor, osteosarcoma, multiple myeloma, neuroblastoma, leukemia acute lymphoblastic leukemia, non-Hodgkin's lymphoma mantle cell lymphoma or pulmonary arterial hypertension.

19. The method of claim 18, wherein said disease or condition that benefit from or is treatable by inhibition of MLL1 is acute lymphoblastic leukaemia, skin squamous cell carcinoma or mantle cell lymphoma.

* * * * *

UNITED STATES PATENT AND TRADEMARK OFFICE
CERTIFICATE OF CORRECTION

| | | |
|---|---|---|
| PATENT NO. | : 12,371,434 B2 | Page 1 of 1 |
| APPLICATION NO. | : 17/772888 | |
| DATED | : July 29, 2025 | |
| INVENTOR(S) | : Gao et al. | |

It is certified that error appears in the above-identified patent and that said Letters Patent is hereby corrected as shown below:

On the Title Page

Item (73) Assignee, change "CHINA NOVARTIS INSTITUTES FOR BIOMEDICAL RESEARCH CO., LTD., Shanghai, (CN)" to --NOVARTIS AG, Basel (CH)--.

Signed and Sealed this
Sixteenth Day of September, 2025

Coke Morgan Stewart
*Acting Director of the United States Patent and Trademark Office*